US011236168B2

(12) United States Patent
Igawa et al.

(10) Patent No.: US 11,236,168 B2
(45) Date of Patent: Feb. 1, 2022

(54) MOUSE FCγAMMARII-SPECIFIC FC ANTIBODY

(71) Applicant: Chugai Seiyaku Kabushiki Kaisha, Tokyo (JP)

(72) Inventors: Tomoyuki Igawa, Shizuoka (JP); Eriko Murata, Shizuoka (JP); Futa Mimoto, Shizuoka (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 14/422,207

(22) PCT Filed: Aug. 23, 2013

(86) PCT No.: PCT/JP2013/072598
§ 371 (c)(1),
(2) Date: Feb. 18, 2015

(87) PCT Pub. No.: WO2014/030750
PCT Pub. Date: Feb. 27, 2014

(65) Prior Publication Data
US 2015/0203577 A1 Jul. 23, 2015

(30) Foreign Application Priority Data
Aug. 24, 2012 (JP) .............. JP2012-185865

(51) Int. Cl.
*C07K 16/28* (2006.01)
*G01N 33/564* (2006.01)
*A61K 39/395* (2006.01)
*G01N 33/68* (2006.01)
*A61K 49/00* (2006.01)

(52) U.S. Cl.
CPC ........ *C07K 16/283* (2013.01); *A61K 49/0004* (2013.01); *A61K 49/0008* (2013.01); *C07K 16/2866* (2013.01); *G01N 33/564* (2013.01); *G01N 33/6857* (2013.01); *C07K 2317/52* (2013.01); *C07K 2317/72* (2013.01); *C07K 2317/92* (2013.01); *G01N 2800/52* (2013.01)

(58) Field of Classification Search
None
See application file for complete search history.

(56) References Cited

U.S. PATENT DOCUMENTS

| | | | |
|---|---|---|---|
| 5,827,733 A | 10/1998 | Lee et al. |
| 5,994,524 A | 11/1999 | Matsushima et al. |
| 6,024,956 A | 2/2000 | Matsushima et al. |
| 6,025,158 A | 2/2000 | Gonzalez et al. |
| 6,096,506 A | 8/2000 | Lee et al. |
| 6,165,745 A | 12/2000 | Ward et al. |
| 6,245,894 B1 | 6/2001 | Matsushima et al. |
| 6,458,355 B1 | 10/2002 | Hsei et al. |
| 6,737,056 B1 | 5/2004 | Presta |
| 6,821,505 B2 | 11/2004 | Ward |
| 7,247,302 B1 | 7/2007 | Rosok et al. |
| 7,261,893 B2 | 8/2007 | Geertruida et al. |
| 7,282,568 B2 | 10/2007 | Teeling et al. |
| 7,320,789 B2 | 1/2008 | Aghajanian et al. |
| 7,371,826 B2 | 5/2008 | Presta |
| 7,632,499 B2 | 12/2009 | Davies et al. |
| 7,662,925 B2 | 2/2010 | Lazar et al. |
| 7,670,600 B2 | 3/2010 | Dall Acqua et al. |
| 7,785,791 B2 | 8/2010 | Presta |
| 7,807,159 B2 | 10/2010 | Chin et al. |
| 7,888,486 B2 | 2/2011 | Walsh et al. |
| 7,951,917 B1 | 5/2011 | Arathoon et al. |
| 8,147,829 B2 | 4/2012 | Hariharan et al. |
| 8,188,231 B2 | 5/2012 | Lazar et al. |
| 8,323,962 B2 | 12/2012 | Dall Acqua et al. |
| 8,388,955 B2 | 3/2013 | Lazar et al. |
| 8,415,459 B2 | 4/2013 | La Vallie et al. |
| 8,524,867 B2 | 9/2013 | Bernett et al. |
| 8,604,174 B2 | 12/2013 | Babcook et al. |
| 8,637,641 B2 | 1/2014 | Dahiyat et al. |
| 8,753,629 B2 | 6/2014 | Lazar et al. |
| 9,029,515 B2 | 5/2015 | Pons et al. |
| 9,051,373 B2 | 6/2015 | Lazar et al. |
| 9,605,061 B2 | 3/2017 | Lazar et al. |
| 9,890,218 B2 | 2/2018 | Mimoto et al. |
| 10,519,229 B2 | 12/2019 | Igawa et al. |
| 10,738,111 B2 | 8/2020 | Ruike et al. |
| 11,053,308 B2 | 7/2021 | Kakiuchi et al. |

(Continued)

FOREIGN PATENT DOCUMENTS

| | | |
|---|---|---|
| AU | 2010/206050 | 8/2010 |
| AU | 2011/244851 | 11/2011 |

(Continued)

OTHER PUBLICATIONS

Shields et al, High Resolution Mapping of the Binding Site on Human IgG1 for FcgRI, FcgRII, Fcg RIII, and FcRn and Design of IgG1 Variants with Improved Binding to the FcgR, 2001, The Journal of Biological Chemistry, vol. 276, No. 9, Issue of March 2, pp. 6591-6604.*

Lazar et al., "Engineered antibody Fc variants with enhanced effector function," *Proc Natl Acad Sci U S A.*, Mar. 14, 2006;103(11):4005-10. Epub Mar. 6, 2006.

Amigorena et al., "Fc gamma RII expression in resting and activated B lymphocytes," *Eur J Immunol.*, Aug. 1989;19(8):1379-85.

Amigorena et al., "Cytoplasmic domain heterogeneity and functions of IgG Fc receptors in B lymphocytes," *Science*, Jun. 26, 1992;256(5065):1808-12.

Blank et al., Decreased transcription of the human FCGR2B gene mediated by the -343 G/C promoter polymorphism and association with systemic lupus erythematosus. *Hum Genet.*, Jul. 2005;117(2-3):220-7. Epub May 14, 2005.

(Continued)

*Primary Examiner* — Maria Marvich
(74) *Attorney, Agent, or Firm* — Fish & Richardson P.C.

(57) ABSTRACT

The present inventors have successfully found a large number of Fc variants with remarkably increased binding activity against and/or binding selectivity for mouse FcγRII by introducing amino acid alteration(s) to the Fc region.

18 Claims, 24 Drawing Sheets

Specification includes a Sequence Listing.

(56) References Cited

U.S. PATENT DOCUMENTS

| | | |
|---|---|---|
| 2002/0082396 A1 | 6/2002 | Matsushima et al. |
| 2003/0077283 A1 | 4/2003 | Ye |
| 2004/0110226 A1 | 6/2004 | Lazar et al. |
| 2004/0132101 A1 | 7/2004 | Lazar et al. |
| 2006/0140934 A1 | 6/2006 | Gegg et al. |
| 2006/0275283 A1 | 12/2006 | Van Vlijmen et al. |
| 2007/0009523 A1 | 1/2007 | Presta |
| 2007/0190056 A1 | 8/2007 | Kambadur et al. |
| 2007/0237767 A1 | 10/2007 | Lazar et al. |
| 2008/0050370 A1 | 2/2008 | Glaser et al. |
| 2008/0206867 A1 | 8/2008 | Desjarlais et al. |
| 2009/0053240 A1 | 2/2009 | Lazar et al. |
| 2009/0136485 A1 | 5/2009 | Chu et al. |
| 2009/0324589 A1 | 12/2009 | Igawa et al. |
| 2010/0099147 A1 | 4/2010 | Hariharan et al. |
| 2010/0129365 A1 | 5/2010 | Kim et al. |
| 2010/0286374 A1 | 11/2010 | Kannan et al. |
| 2010/0316641 A1 | 12/2010 | Dmitrov |
| 2011/0027276 A1* | 2/2011 | Bernett ............ C07K 16/2878 424/133.1 |
| 2011/0059093 A1 | 3/2011 | Bohrmann et al. |
| 2011/0105724 A1 | 5/2011 | Clegg et al. |
| 2011/0111406 A1 | 5/2011 | Igawa et al. |
| 2011/0135662 A1 | 6/2011 | Finney et al. |
| 2011/0229489 A1 | 9/2011 | Pons et al. |
| 2012/0149876 A1 | 6/2012 | Kreudenstein et al. |
| 2012/0189639 A1 | 7/2012 | Schebye et al. |
| 2012/0244578 A1 | 9/2012 | Kannan et al. |
| 2012/0301488 A1 | 11/2012 | Zhang et al. |
| 2013/0085074 A1 | 4/2013 | Walker et al. |
| 2013/0209489 A1 | 8/2013 | Han et al. |
| 2013/0302399 A1 | 11/2013 | Feldhaus et al. |
| 2014/0105889 A1* | 4/2014 | Igawa ................. C07K 16/303 424/133.1 |
| 2014/0112926 A1 | 4/2014 | Liu et al. |
| 2014/0127209 A1 | 5/2014 | Grabstein et al. |
| 2014/0199294 A1* | 7/2014 | Mimoto ............... C07K 16/00 424/133.1 |
| 2014/0227292 A1 | 8/2014 | Flanagan et al. |
| 2014/0271459 A1 | 9/2014 | Dutzar et al. |
| 2014/0294833 A1 | 10/2014 | Desjarlais et al. |
| 2014/0363426 A1 | 12/2014 | Moore et al. |
| 2015/0079088 A1 | 3/2015 | Lowman et al. |
| 2015/0166636 A1* | 6/2015 | Igawa .................. C07K 16/22 424/133.1 |
| 2015/0166654 A1 | 6/2015 | Igawa et al. |
| 2015/0203577 A1 | 7/2015 | Igawa et al. |
| 2015/0299296 A1 | 10/2015 | Katada et al. |
| 2015/0344570 A1* | 12/2015 | Igawa .................. C07K 16/00 424/133.1 |
| 2015/0353630 A1 | 12/2015 | Igawa et al. |
| 2016/0039912 A1 | 2/2016 | Mimoto et al. |
| 2016/0046693 A1 | 2/2016 | Igawa et al. |
| 2016/0053023 A1 | 2/2016 | Rosenthal et al. |
| 2016/0200807 A1 | 7/2016 | Ruike et al. |
| 2016/0229908 A1 | 8/2016 | Igawa et al. |
| 2016/0229915 A1 | 8/2016 | Igawa et al. |
| 2016/0326237 A1 | 11/2016 | Rosenthal et al. |
| 2017/0181987 A1 | 6/2017 | Camilla et al. |
| 2018/0258163 A1 | 9/2018 | Igawa et al. |

FOREIGN PATENT DOCUMENTS

| | | |
|---|---|---|
| AU | 2014/250434 | 10/2015 |
| AU | 2015/227424 | 10/2015 |
| CN | 1156460 | 8/1997 |
| CN | 101230102 | 7/2008 |
| CN | 101277976 | 10/2008 |
| CN | 101282992 | 10/2008 |
| CN | 100455598 | 1/2009 |
| CN | 101479381 | 7/2009 |
| CN | 101511871 | 8/2009 |
| CN | 102325793 | 1/2012 |
| CN | 102918057 | 2/2013 |
| CN | 102993304 | 3/2013 |
| CN | 103097415 | 5/2013 |
| CN | 103221426 | 7/2013 |
| CN | 103492565 | 1/2014 |
| CN | 103975060 | 8/2014 |
| CO | 07124506 | 11/2007 |
| CO | 11080753 | 6/2011 |
| CO | 13047993 | 3/2013 |
| CO | 15075851 | 4/2015 |
| EA | 2008/01027 | 10/2008 |
| EP | 0 770 628 | 9/2006 |
| EP | 2 006 381 | 12/2008 |
| EP | 2 202 245 | 6/2010 |
| EP | 2 275 443 A | 1/2011 |
| EP | 2 431 393 | 3/2012 |
| EP | 2 471 813 A | 7/2012 |
| EP | 2 679 681 | 1/2014 |
| EP | 1 509 770 B | 7/2014 |
| EP | 2 762 166 | 8/2014 |
| EP | 2 762 493 | 8/2014 |
| EP | 2 762 564 | 8/2014 |
| EP | 2 818 183 | 12/2014 |
| EP | 2 853 898 | 4/2015 |
| EP | 2 889 377 | 7/2015 |
| EP | 2 940 043 | 11/2015 |
| EP | 3 240 804 | 11/2017 |
| JP | 2005-510212 | 4/2005 |
| JP | 2006-517525 | 7/2006 |
| JP | 2006-519583 | 8/2006 |
| JP | 3865418 | 1/2007 |
| JP | 2008-505174 | 2/2008 |
| JP | 2009-541352 | 11/2009 |
| JP | 2010-500020 | 1/2010 |
| JP | 2010-514460 | 5/2010 |
| JP | 2011-504096 | 2/2011 |
| JP | 2012-512641 | 6/2012 |
| JP | 4961501 | 6/2012 |
| JP | 5048866 | 10/2012 |
| JP | 2013-518606 | 5/2013 |
| JP | 2013-513486 | 8/2013 |
| JP | 2013-531486 | 8/2013 |
| JP | 2013-537425 | 10/2013 |
| JP | 2014-055145 | 3/2014 |
| JP | 2016-026190 | 2/2016 |
| JP | 2019-523295 | 8/2019 |
| KR | 2011/0103431 | 9/2011 |
| KR | 2012-003 5192 | 4/2012 |
| KR | 2014/0005864 | 1/2014 |
| RU | 2360925 | 7/2009 |
| RU | 2009/112723 | 10/2010 |
| RU | 2422460 | 6/2011 |
| RU | 2010/150931 | 6/2012 |
| TW | 416960 | 1/2001 |
| TW | 2016/38107 | 11/2016 |
| TW | 2016/43190 | 12/2016 |
| TW | 2017/12032 | 4/2017 |
| TW | 2017/26718 | 8/2017 |
| TW | I605057 | 11/2017 |
| TW | 2018/08331 | 3/2018 |
| TW | 2018/08992 | 3/2018 |
| TW | 2018/19409 | 6/2018 |
| TW | I656133 | 4/2019 |
| TW | 2020/39553 | 11/2020 |
| WO | WO 91/13631 | 9/1991 |
| WO | WO 94/21681 | 9/1994 |
| WO | WO 96/02576 | 2/1996 |
| WO | WO 98/05787 | 2/1998 |
| WO | WO 99/51642 | 10/1999 |
| WO | WO 00/42072 | 7/2000 |
| WO | WO 02/09641 | 2/2002 |
| WO | WO 02/060919 | 8/2002 |
| WO | WO 03/027248 | 4/2003 |
| WO | WO 03/074679 | 9/2003 |
| WO | WO 2004/024890 | 3/2004 |
| WO | WO 2004/029207 | 4/2004 |
| WO | WO 2004/037861 | 5/2004 |
| WO | WO 2004/058797 | 7/2004 |
| WO | WO 2004/099249 | 11/2004 |
| WO | WO 2004/108157 | 12/2004 |

(56) References Cited

FOREIGN PATENT DOCUMENTS

| | | |
|---|---|---|
| WO | WO 2005/023193 | 3/2005 |
| WO | WO 2005/047307 | 5/2005 |
| WO | WO 2005/047327 | 5/2005 |
| WO | WO 2005/056759 | 6/2005 |
| WO | WO 2005/066204 | 7/2005 |
| WO | WO 2005/077981 | 8/2005 |
| WO | WO 2005/092925 | 10/2005 |
| WO | WO 2005/094446 | 10/2005 |
| WO | WO 2006/004663 | 1/2006 |
| WO | WO 2006/019447 | 2/2006 |
| WO | WO 2006/020114 | 2/2006 |
| WO | WO 2006/031370 | 3/2006 |
| WO | WO 2006/047350 | 5/2006 |
| WO | WO 2006/050166 | 5/2006 |
| WO | WO 2006/053301 | 5/2006 |
| WO | WO 2006/071877 | 7/2006 |
| WO | WO 2006/083182 | 8/2006 |
| WO | WO 2006/083183 | 8/2006 |
| WO | WO 2006/085967 | 8/2006 |
| WO | WO 2006/102095 | 9/2006 |
| WO | WO 2006/105338 | 10/2006 |
| WO | WO 2006/113643 | 10/2006 |
| WO | WO 2006/116269 | 11/2006 |
| WO | WO 2006/130834 | 12/2006 |
| WO | WO 2007/001422 | 1/2007 |
| WO | WO 2007/008943 | 1/2007 |
| WO | WO 2007/024535 | 3/2007 |
| WO | WO 2007/041635 | 4/2007 |
| WO | WO 2007/044411 | 4/2007 |
| WO | WO 2007/044616 | 4/2007 |
| WO | WO 2007/047112 | 4/2007 |
| WO | WO 2007/114319 | 10/2007 |
| WO | WO 2007/150015 | 12/2007 |
| WO | WO 2007/150016 | 12/2007 |
| WO | WO 2008/017963 | 2/2008 |
| WO | WO 2008/022152 | 2/2008 |
| WO | WO 2008/030706 | 3/2008 |
| WO | WO 2008/036688 | 3/2008 |
| WO | WO 2008/091798 | 7/2008 |
| WO | WO 2008/091954 | 7/2008 |
| WO | WO 2008/092117 | 7/2008 |
| WO | WO 2007/092772 | 8/2008 |
| WO | WO 2008/098115 | 8/2008 |
| WO | WO 2008/031056 | 10/2008 |
| WO | WO 2008/121160 | 10/2008 |
| WO | WO 2008/130969 | 10/2008 |
| WO | WO 2008/150494 | 12/2008 |
| WO | WO 2009/000098 | 12/2008 |
| WO | WO 2009/000099 | 12/2008 |
| WO | WO 2009/026117 | 2/2009 |
| WO | WO 2009/032145 | 3/2009 |
| WO | WO 2009/032782 | 3/2009 |
| WO | WO 2009/041643 | 4/2009 |
| WO | WO 2009/058346 | 5/2009 |
| WO | WO 2009/058492 | 5/2009 |
| WO | WO 2009/086320 | 7/2009 |
| WO | WO 2009/125825 | 10/2009 |
| WO | WO 2009/137880 | 11/2009 |
| WO | WO 2010/033736 | 3/2010 |
| WO | WO 2010/045193 | 4/2010 |
| WO | WO 2010/070094 | 6/2010 |
| WO | WO 2010/136831 | 12/2010 |
| WO | WO 2010/151338 | 12/2010 |
| WO | WO 2011/021009 | 2/2011 |
| WO | WO 2011/100271 | 8/2011 |
| WO | WO 2011/111007 | 9/2011 |
| WO | WO 2011/122011 | 10/2011 |
| WO | WO 2011/150008 | 12/2011 |
| WO | WO 2011/151432 | 12/2011 |
| WO | WO 2012/016227 | 2/2012 |
| WO | WO 2012/024242 | 2/2012 |
| WO | WO 2012/073992 | 6/2012 |
| WO | WO 2012/093704 | 7/2012 |
| WO | WO 2012/115241 | 8/2012 |
| WO | WO 2012/151481 | 11/2012 |
| WO | WO 2013/012733 | 1/2013 |
| WO | WO 2013/046704 | 4/2013 |
| WO | WO 2013/046722 | 4/2013 |
| WO | WO 2013/047748 | 4/2013 |
| WO | WO 2013/047752 | 4/2013 |
| WO | WO 2013/081143 | 6/2013 |
| WO | WO 2013/125667 | 8/2013 |
| WO | WO 2013/138680 | 9/2013 |
| WO | WO 2013/152001 | 10/2013 |
| WO | WO 2013/166099 | 11/2013 |
| WO | WO 2013/180200 | 12/2013 |
| WO | WO 2013/186719 | 12/2013 |
| WO | WO 2013/192240 | 12/2013 |
| WO | WO 2014/006217 | 1/2014 |
| WO | WO 2014/028354 | 2/2014 |
| WO | WO 2014/030728 | 2/2014 |
| WO | WO 2014/030750 | 2/2014 |
| WO | WO 2014/043344 | 3/2014 |
| WO | WO 2014/066744 | 5/2014 |
| WO | WO 2014/071206 | 5/2014 |
| WO | WO 2014/074532 | 5/2014 |
| WO | WO 2014/100689 | 6/2014 |
| WO | WO 2014/114651 | 7/2014 |
| WO | WO 2014/144903 | 9/2014 |
| WO | WO 2014/145159 | 9/2014 |
| WO | WO 2014/145806 | 9/2014 |
| WO | WO 2014/163101 | 10/2014 |
| WO | WO 2014/182676 | 11/2014 |
| WO | WO 2014/184384 | 11/2014 |
| WO | WO 2014/186599 | 11/2014 |
| WO | WO 2014/190441 | 12/2014 |
| WO | WO 2015/022658 | 2/2015 |
| WO | WO 2015/111008 | 7/2015 |
| WO | WO 2015/162590 | 10/2015 |
| WO | WO 2016/073853 | 5/2016 |
| WO | WO 2016/073879 | 5/2016 |
| WO | WO 2016/073906 | 5/2016 |
| WO | WO 2016/092439 | 6/2016 |
| WO | WO 2016/098357 | 6/2016 |
| WO | WO 2016/125495 | 8/2016 |
| WO | WO 2016/164358 | 10/2016 |
| WO | WO 2016/168613 | 10/2016 |
| WO | WO 2017/046994 | 3/2017 |
| WO | WO 2017/049011 | 3/2017 |
| WO | WO 2017/091719 | 6/2017 |
| WO | WO 2017/110981 | 6/2017 |
| WO | WO 2017/120523 | 7/2017 |
| WO | WO 2017/217525 | 12/2017 |
| WO | WO 2017/218592 | 12/2017 |
| WO | WO 2018/025982 | 2/2018 |
| WO | WO 2019/098212 | 5/2019 |
| WO | WO 2019/198807 | 10/2019 |

OTHER PUBLICATIONS

Boumpas et al., "A short course of BG9588 (anti-CD40 ligand antibody) improves serologic activity and decreases hematuria in patients with proliferative lupus glomerulonephritis," *Arthritis Rheum.*, Mar. 2003;48(3):719-27.

Bruhns et al., "Specificity and affinity of human Fcgamma receptors and their polymorphic variants for human IgG subclasses," *Blood*, Apr. 16, 2009;113(16):3716-25. doi: 10.1182/blood-2008-09-179754. Epub Nov. 18, 2008.

Bruhns, "Properties of mouse and human IgG receptors and their contribution to disease models," *Blood*, Jun. 14, 2012;119(24):5640-9. doi: 10.1182/blood-2012-01-380121. Epub Apr. 25, 2012.

Cemerski et al., "Suppression of mast cell degranulation through a dual-targeting tandem IgE-IgG Fc domain biologic engineered to bind with high affinity to FcγRIIb," *Immunol Lett.*, Mar. 30, 2012;143(1):34-43. doi: 10.1016/j.imlet.2012.01.008. Epub Jan. 25, 2012.

Chen et al., "Association of a transmembrane polymorphism of Fcgamma receptor IIb (FCGR2B) with systemic lupus erythematosus in Taiwanese patients," *Arthritis Rheum.*, Dec. 2006;54(12):3908-17.

Chu et al., "Inhibition of B cell receptor-mediated activation of primary human B cells by coengagement of CD19 and Fcgam-

(56) References Cited

OTHER PUBLICATIONS maRIIb with Fc-engineered antibodies," *Mol Immunol.*, Sep. 2008;45(15):3926-33. doi: 10/1016.j.molimm.2008.06.027. Epub Aug. 8, 2008.
Chu et al., "Reduction of total IgE by targeted coengagement of IgE B-cell receptor and FcγRIIb with Fc-engineered antibody," *J Allergy Clin Immunol.*, Apr. 2012;129(4):1102-15. doi: 10.1016/j.jaci.2011. 11.029. Epub Jan. 16, 2012.
Chuntharapai et al., "Isotype-dependent inhibition of tumor growth in vivo by monoclonal antibodies to death receptor 4," *J Immunol.*, Apr. 15, 2001;166(8):4891-8.
Clark, "IgG effector mechanisms," *Chem Immunol.*, 1997;65:88-110.
Duffau et al., "Platelet CD154 potentiates interferon-alpha secretion by plasmacytoid dendritic cells in systemic lupus erythematosus," *Sci Transl Med.*, Sep. 1, 2010;2(47):47ra63. doi: 10.1126/scitranslmed. 3001001.
Floto et al., "Loss of function of a lupus-associated FcgammaRIIb polymorphism through exclusion from lipid rafts," *Nat Med.*, Oct. 2005;11(10):1056-8. Epub Sep. 18, 2005.
Fournier et al., "Activation of human peripheral IgM+ B cells is transiently inhibited by BCR-independent aggregation of Fc gammaRIIB," *J Immunol.*, Oct. 15, 2008;181(8):5350-9.
Greenwood et al., "Structural motifs involved in human IgG antibody effector functions," *Eur J Immunol.*, May 1993;23(5):1098-104.
Heyman, "Feedback regulation by IgG antibodies," *Immunol Lett.*, Aug. 5, 2003;88(2):157-61.
Hjelm et al., "Antibody-mediated regulation of the immune response," *Scand J Immunol.*, Sep. 2006;64(3):177-84.
Jefferis et al., "Interaction sites on human IgG-Fc for Fc gamma R: current models," *Immunol Lett.*, Jun. 3, 2002;82(1-2):57-65.
Kohrt et al., "Stimulation of natural killer cells with a CD137-specific antibody enhances trastuzumab efficacy in xenotransplant models of breast cancer," *J Clin Invest.*, Mar. 1, 2012;122(3):1066-75. doi: 10.1172/JCI61226. Epub Feb. 13, 2012.
Li et al., "Inhibitory Fcγ receptor engagement drives adjuvant and anti-tumor activities of agonistic CD40 antibodies," *Science*, Aug. 19, 2011;333(6045):1030-4. doi: 10.1126/science.1206954.
Li et al., "CD72 down-modulates BCR-induced signal transduction and diminishes survival in primary mature B lymphocytes," *J Immunol.*, May 1, 2006;176(9):5321-8.
Lund et al., "Multiple binding sites on the CH2 domain of IgG for mouse Fc gamma R11," *Mol Immunol.*, Jan. 1992;29(1):53-9.
Mackay et al., "Selective dysregulation of the FcgammaIIB receptor on memory B cells in SLE," *J Exp Med.*, Sep. 4, 2006;203(9):2157-64. Epub Aug. 21, 2006.
Meyer et al., "Bevacizumab immune complexes activate platelets and induce thrombosis in FCGR2A transgenic mice," *J Thromb Haemost.*, Jan. 2009;7(1):171-81. doi: 10.1111/j.1538-7836.2008. 03212.x. Epub Oct. 30, 2008.
Morgan et al., "The N-terminal end of the CH2 domain of chimeric human IgG1 anti-HLA-DR is necessary for C1q, Fc gamma RI and Fc gamma RIII binding," *Immunology*, Oct. 1995; 86(2):319-24.
Muta et al., "A 13-amino-acid motif in the cytoplasmic domain of Fc gamma RIIB modulates B-cell receptor signaling," *Nature*, Mar. 3, 1994;368(6466):70-3.
Nakamura et al., "Fcgamma receptor IIB-deficient mice develop Goodpasture's syndrome upon immunization with type IV collagen: a novel murine model for autoimmune glomerular basement membrane disease," *J Exp Med.*, Mar. 6, 2000;191(5):899-906.
Nicholas et al., "Regulation of the immune response. I. Reduction in ability of specific antibody to inhibit long-lasting IgG immunological priming after removal of the Fc fragment," *J Exp Med.*, Jun. 1, 1969;129(6):1183-201.
Nimmerjahn et al.. "Fcgamma receptors as regulators of immune responses," *Nat Rev Immunol.*, Jan. 2008;8(1):34-47.
Olferiev et al., "The role of activating protein 1 in the transcriptional regulation of the human FCGR2B promoter mediated by the -343

G -> C polymorphism associated with systemic lupus erythematosus," *J Biol Chem.*, Jan. 19, 2007;282(3):173 8-46. Epub Nov. 27, 2006.
Pavlou et al., "The therapeutic antibodies market to 2008," *Eur J Pharm Biopharm.*, Apr. 2005;59(3):389-96.
Radaev et al., "The role of Fc glycosylation and the binding of peptide inhibitors," *J Biol Chem.*, May 11, 2001:276(19):16478-83. Epub Jan. 31, 2001.
Ravetch et al., "Immune inhibitory receptors," *Science*, Oct. 6, 2000;290(5489):84-9.
Reichert et al., "Monoclonal antibody successes in the clinic," *Nat Biotechnol.*, Sep. 2005;23(9):1073-8.
Robles-Carrillo et al., "Anti-CD40L immune complexes potently activate platelets in vitro and cause thrombosis in FCGR2A transgenic mice," *J Immunol.*, Aug. 1, 2010;185(3):1577-83. doi: 10.4049/jimmunol.0903888. Epub Jun. 28, 2010.
Scappaticci et al., "Arterial thromboembolic events in patients with metastatic carcinoma treated with chemotherapy and bevacizumab," *J Natl Cancer Inst.*, Aug. 15, 2007;99(16):1232-9. Epub Aug. 8, 2007.
Smith et al., "FcgammaRIIB in autoimmunity and infection: evolutionary and therapeutic implications," *Nat Rev Immunol.*, May 2010;10(5):328-43. doi: 10.1038/nri2762.
Su et al., Expression profile of FcgammaRIIb on leukocytes and its dysregulation in systemic lupus erythematosus, *J Immunol.*, Mar. 1, 2007;178(5):3272-80.
Veri et al., "Therapeutic control of B cell activation via recruitment of Fcgamma receptor IIb (CD32B) inhibitory function with a novel bispecific antibody scaffold," *Arthritis Rheum.*, Jul. 2010;62(7):1933-43. doi: 10.1002/art.27477.
Wernersson et al., "IgG-mediated enhancement of antibody responses is low in Fc receptor gamma chain-deficient mice and increased in Fc gamma RII-deficient mice," *J Immunol.*, Jul. 15, 1999;163(2):618-22.
Wilson et al., "An Fcγ receptor-dependent mechanism drives antibody-mediated target-receptor signaling in cancer cells," *Cancer Cell*, Jan. 18, 2011;19(1):101-13. doi: 10.1016/j.ccr.2010.11.012.
Xu et al., "Fc gamma Rs modulate cytotoxicity of anti-Fas antibodies: implications for agonistic antibody-based therapeutics," *J Immunol.*, Jul. 15, 2003;171(2):562-8.
Yuasa et al., "Deletion of fcgamma receptor IIB renders H-2(b) mice susceptible to collagen-induced arthritis," *J Exp Med.*, Jan. 4, 1999;189(1):187-94.
Zhang et al., "Effective therapy for a murine model of human anaplastic large-cell lymphoma with the anti-CD30 monoclonal antibody, HeFi-1,does not require activating Fc receptors," *Blood*, Jul. 15, 2006;108(2):705-10. Epub Mar. 21, 2006.
Armour et al., "Differential binding to human FcgammaRIIa and FcgammaRIIb receptors by human IgG wildtype and mutant antibodies," *Mol Immunol.*, Dec. 2003;40(9):585-93.
Bogdanovich et al., "Functional improvement of dystrophic muscle by myostatin blockade," *Nature*, Nov. 28, 2002;420(6914):418-21.
Boruchov et al., "Activating and inhibitory IgG Fc receptors on human DCs mediate opposing functions," *J Clin Invest.*, Oct. 2005;115(10):2914-23.
Desai et al., "Fc gamma receptor IIB on dendritic cells enforces peripheral tolerance by inhibiting effector T cell responses," *J Immunol.*, May 15, 2007;178(10):6217-26.
Dhodapkar et al., "Selective blockade of inhibitory Fcgamma receptor enables human dendritic cell maturation with IL-12p70 production and immunity to antibody-coated tumor cells," *Proc Natl Acad Sci USA*, Feb. 22, 2005;102:2910-5.
Hoodless et al., "Mechanism and function of signaling by the TGF beta superfamily," *Curr Top Microbiol Immunol.*, 1998;228:235-72.
Kingsley et al., "The TGF-beta superfamily: new members, new receptors, and new genetic tests of function in different organisms," *Genes Dev.*, Jan. 1994;8(2):133-46.
Lee et al., "Genetic analysis of the role of proteolysis in the activation of latent myostatin," *PLoS One*, Feb. 20, 2008;3(2):e1628.
Lee et al., "Regulation of myostatin activity and muscle growth," *Proc Natl Acad Sci U S A.*, Jul. 31, 2001;98(16):9306-11.
Li et al., "Apoptotic and antitumor activity of death receptor antibodies require inhibitory Fcγ receptor engagement," *Proc Natl Acad Sci U S A.*, Jul. 3, 2012;109(27):10966-71.

(56) References Cited

OTHER PUBLICATIONS

Li et al., "Inhibitory Fcγ receptor engagement drives adjuvant and anti-tumor activities of agonistic CD40 antibodies," *Science*, Aug. 19, 2011;333(6045):1030-4.

Malbec et al., "Antibodies against growth factor receptors can inhibit the proliferation of transformed cells via a cis-interaction with inhibitory FcR," *Immunol Lett.*, Mar. 30, 2012;143(1):28-33.

Manger et al., "Fcgamma receptor IIa polymorphism in Caucasian patients with systemic lupus erythematosus: association with clinical symptoms," *Arthritis Rheum.*, Jul. 1998;41(7):1181-9.

McCroskery et al., "Improved muscle healing through enhanced regeneration and reduced fibrosis in myostatin-null mice," *J Cell Sci.*, Aug. 1, 2005;118(Pt 15):3531-41.

McPherron et al., "Regulation of skeletal muscle mass in mice by a new TGF-beta superfamily member," *Nature*, May 1, 1997;387(6628):83-90.

McPherron et al., "Double muscling in cattle due to mutations in the myostatin gene," *Proc Natl Acad Sci U S A.*, Nov. 11, 1997;94(23):12457-61.

Richards et al., "Optimization of antibody binding to FcgammaRIIa enhances macrophage phagocytosis of tumor cells," *Mol Cancer Ther.*, Aug. 2008;7(8):2517-27.

Salmon et al., "Fc gamma RIIA alleles are heritable risk factors for lupus nephritis in African Americans," *J Clin Invest.*, Mar. 1, 1996;97(5):1348-54.

Szlama et al., "Latent myostatin has significant activity and this activity is controlled more efficiently by WFIKKN1 than by WFIKKN2," *FEBS J.*, Aug. 2013;280(16):3822-39. doi: 10.1111/febs.12377. Epub Jul. 5, 2013.

Wagner et al., "Loss of myostatin attenuates severity of muscular dystrophy in mdx mice," *Ann Neurol.*, Dec. 2002;52(6):832-6.

Warmerdam et al., Molecular basis for a polymorphism of human Fc gamma receptor II (CD32), *J Exp Med.*, Jul. 1, 1990;172(1):19-25.

Wenink et al., "The inhibitory Fc gamma IIb receptor dampens TLR4-mediated immune responses and is selectively up-regulated on dendritic cells from rheumatoid arthritis patients with quiescent disease," *J Immunol.*, Oct. 1, 2009;183(7):4509-20.

Whittemore et al., "Inhibition of myostatin in adult mice increases skeletal muscle mass and strength," *Biochem Biophys Res Commun.*, Jan. 24, 2003;300(4):965-71.

Zhang et al., "Immune complex/Ig negatively regulate TLR4-triggered inflammatory response in macrophages through Fc gamma RIIb-dependent PGE2 production," *J Immunol.*, Jan. 1, 2009;182(1):554-62.

Zimmers et al., "Induction of cachexia in mice by systemically administered myostatin," *Science*, May 24, 2002;296(5572):1486-8.

Mimoto et al., "Engineered antibody Fc variant with selectively enhanced FcγRIIb binding over both FcγRIIa(R131) and FcγRIIa(H131)," *Protein Eng Des Sel.*, Oct. 2013;26(10):589-98. doi: 10.1093/protein/gzt022. Epub Jun. 5, 2013.

U.S. Appl. No. 14/974,488, Ruike et al.

U.S. Appl. No. 15/015,287, Igawa et al.

Guilliams et al., "The function of Fcγ receptors in dendritic cells and macrophages," *Nat Rev Immunol.*, Feb. 2014; 14(2):94-108. doi: 10.1038/nri3582. Epub Jan. 21, 2014.

Hinton et al., "An engineered human IgG1 antibody with longer serum half-life," *J Immunol.* Jan. 1, 2006;176(1):346-56.

Holash et al., "VEGF-Trap: a VEGF blocker with potent antitumor effects," *Proc Natl Acad Sci U S A.* Aug. 20, 2002;99(17):11393-8. Epub Aug. 12, 2002.

Igawa et al., "Antibody recycling by engineered pH-dependent antigen binding improves the duration of antigen neutralization," *Nat Biotechnol.* Nov. 2010;28(11):1203-7. Epub Oct. 17, 2010.

Ito et al., "The His-probe method: effects of histidine residues introduced into the complementarity-determining regions of antibodies on antigen-antibody interactions at different pH values," *FEBS Lett.* Aug. 31, 1992;309(1):85-8.

Iwabe et al., "Pathogenetic significance of increased levels of interleukin-a in the peritoneal fluid of patients with endometriosis," *Fertil Steril.* May 1998;69(5):924-30.

Kim et al., "Antibody engineering for the development of therapeutic antibodies," *Mol Cells.* Aug. 31, 2005;20(1):17-29.

Marino et al., "Prevention of systemic lupus erythematosus in MRL/lpr mice by admmistration of an immunoglobulin-binding peptide," *Nat Biotechnol.* Jul. 2000;18(7):735-9.

Mazda et al., "Regulation of Muscle Homeostasis and Metabolism by the TGF-β Superfamily Cytokine, Myostatin/growth Differentiation Factor 8 (GDF8)," *Journal of Kyoto prefectural university of medicine.* 2013;122(3):133-41.

Natsume et al., "Engineered Antibodies of IgG1/IgG3 Mixed Isotype with Enhanced Cytotoxic Activities," *Cancer Res.* May 15, 2008;68(10):3863-72. doi: 10.1158/0008-5472.CAN-07-6297.

Patton et al., "An acid dissociation bridging ELISA for detection of antibodies directed against therapeutic proteins in the presence of antigen," *J Immunol Methods.* Sep. 2005;304(1-2):189-95.

Rajpal et al., "A general method for greatly improving the affinity of antibodies by using combinatorial libraries," *Proc Natl Acad Sci U S A.* Jun. 14, 2005;102(24):8466-71. Epub Jun. 6, 2005.

Russo et al., "The CXCL8/IL-8 chemokine family and its receptors in inflammatory diseases," *Expert Rev Clin Immunol.* May 2014;10(5):593-619. doi: 10.1586/1744666X.2014.894886. Epub Mar. 29, 2014.

Shinkawa et al., "The absence of fucose but not the presence of galactose or bisecting N-acetylglucosamine of human IgG1 complex-type oligosaccharides shows the critical role of enhancing antibody-dependent cellular cytotoxicity," *J Biol Chem.* Jan. 31, 2003;278(5):3466-73. Epub Nov. 8, 2002.

Werwitzke et al., "Treatment of lupus-prone NZB/NZW F1 mice with recombinant soluble Fcγ receptor II (CD32)," *Ann Rheum Dis.* Feb. 2008;67(2):154-61 . Epub Jun. 8, 2007.

Wu et al., "Development of motavizumab, an ultra-potent antibody for the prevention of respiratory syncytial vims infection in the upper and lower respiratory tract," *J Mol Biol.* May 4, 2007;368(3):652-65. Epub Feb. 20, 2007.

Wu et al., "Humanization of a Murine Monoclonal Antibody by Simultaneous Optimization of Framework and CDR Residues," *J Mol Biol.* Nov. 19, 1999;294(1):151-62.

Wu et al., "Structure-based engineering of a monoclonal antibody for improved solubility," *Protein Eng Des Sel.* Aug. 2010;23(8):643-51. doi: 10.1093/protein/gzq037. Epub Jun. 11, 2010.

Xi et al., "Increased survival and reduced renal injury in MRL/Ipr mice treated with a human Fcγ receptor 11 (CD32) peptide," *Immunology.* May 2012;136(1):46-53. doi:10.1111/j.1365-2567.2012.03553.x.

Xie et al., "A new format of bispecific antibody: highly efficient heterodimerization, expression and tumor cell lysis," *J Immunol Methods.* Jan. 2005;296(1-2):95-101. Epub Nov. 19, 2004.

Yeung et al., "Engineering Human IgG1 Affinity to Human Neonatal Fc Receptor: Impact of Affinity Improvement on Pharmacokinetics in Primates" *J Immunol.* Jun. 15, 2009;182(12):7663-71. doi:10.4049/ j inmunol. 0804182.

Zalevsky et al., "Enhanced antibody half-life improves in vivo activity," *Nat Biotechnol.* Feb. 2010;28(2):157-9, Epub Jan. 17, 2010.

Zheng et al., "Translational Pharmacokinetics and Pharmacodynamics of an FcRn-Variant Anti-CD4 Monoclonal Antibody From Preclinical Model to Phase I Study," *Clin Pharmacol Ther.* Feb. 2011;89(2):283-90, doi: 10.1038/clpt.2010.311. Epub Dec. 29, 2010.

Fish & Richardson P.C., Reply to Restriction Requirement dated Jun. 1, 2016 in U.S. Appl. No. 14/127,576, filed Aug. 24, 2016, 2 pages.

Devanaboyina et al., "The effect of pH dependence of antibody-antigen interactions on subcellular trafficking dynamics," *mAbs*, Nov. 1, 2013, 5(6):851-9.

Harvey et al., Lippincott's Illustrated Reviews: Immunology, Second Edition, 2013. Chapter 2 "Antigens and Receptors", pp. 11-23, and Chapter 11 "Lymphocyte Effector Functions", pp. 141-157.

Igawa et al., "Engineering the variable region of therapeutic IgG antibodies," mAbs, May-Jun. 2011, 3(3):243-52, Epub May 1, 2011.

Igawa et al., "Reduced elimination of IgG antibodies by engineering the variable region." Protein Eng Des Sel, May 2010, 23(5):385-92. Epub Feb. 15, 2010.

(56) References Cited

OTHER PUBLICATIONS

Schroter et al., "A generic approach to engineer antibody pH-switches using combinatorial histidine scanning libraries and yeast display," mAbs, Jan./Feb. 2015, 7(1):138-51. doi: 10.4161/19420862.2014.985993.
U.S. Pat. No. 10,000,560, Ruike et al., issued May 30, 2018.
Yada et al., Lippincott's Illustrated Reviews: Immunology, Second Edition, Nov. 30, 2013, Chapter 2, pp. 11-23 and Chapter 11, pp. 149-165 (in Japanese, with English equivalent).
[Anonymous] "Rabbit Antibody to Human pro-Myostatin (amino acids 79-92)," Meridian Life Science Inc., Nov. 13, 2015 (Nov. 13, 2015), XP055478289, Retrieved from the Internet: URL:https://meridianlifescience.com/biospecs/K24340R.pdf [retrieved on May 4, 2018].
[Anonymous] "Blog entry," Jun. 1, 2014 (Jun. 1, 2014), Retrieved from the Internet: URL:https://www.thundersplace.org/male-supplements/the-chemical-pe thread-7.html92 [retrieved on May 23, 2018].
[Anonymous] "polyclonal human pro-Myostatin (aa 79-92) antibody," Immun Diagnostik Antibodies Catalogue, Jun. 30, 2016 (Jun. 30, 2016), Retrieved from the Internet: URL:https://www.immundiagnostik.com/fileadmin/pdf/AK3004.pdf [retrieved on May 24, 2018].
[Anonymous] "Mouse GDF-8/Myostatin Propeptide Antibody," R&D Catalogue AF 1539, Feb. 6, 2018 (Feb. 6, 2018), XP055478493, Retrieved from the Internet: URL:https://resources.rndsystems.com/pdfs/datasheets/af1539.pdf [retrieved on May 25, 2018].
Becker et al., "Prevention of postoperative abdominal adhesions by a sodium hyaluronate-based bioresorbable membrane: a prospective, randomized, double-blind multicenter study," J Am Coll Surg, Oct. 1996, 183(4):297-306.
Breitbart et al., "Highly Specific Detection of Myostatin Prodomain by an Immunoradiometric Sandwich Assay in Serum of Healthy Individuals and Patients," PLoS One, Nov. 15, 2013, 8(11):e80454, doi:10.1371/journal.pone.0080454.eCollection 2013.
Brown et al., "Tolerance to Single, but Not Multiple, Amino Acid Replacements in Antibody V H CDR2," J Immunol, May 1996, 156(9):3285-91.
Bulun, "Endometriosis," New Eng J Med, Jan. 2009, 360(3):268-279.
Chaparro-Riggers et al., "Increasing Serum Half-life and Extending Cholesterol Lowering in Vivo by Engineering Antibody with pH-sensitive Binding to PCSK9," J Biol Chem, Mar. 30, 2012, 287(14):11090-7, doi: 10.1074/jbc.M111.319764. Epub Jan. 31, 2012.
Cooper et al., "Variable domain-identical antibodies exhibit IgG subclass-related differences in affinity and kinetic constants as determined by surface plasmon resonance," Mol Immunol, Jun. 1994, 31(8):577-84.
Donnez et al., "Current thinking on the pathogenesis of endometriosis," Gynecol Obstet Invest, 2002, 54(Suppl 1):52-62.
Giudice et al., "Endometriosis," Lancet, Nov. 2004, 364(9447):1789-1799.
Guo, "Recurrence of endometriosis and its control," Hum Reprod Update, Jul.-Aug. 2009 (Epub Mar. 2009), 15(4):441-461.
Han et al., "Targeting the Myostatin Signaling Pathway to Treat Muscle Wasting Diseases," Curr Opin Support Palliat Care, Dec. 2011, 5(4):334-41. doi: 10.1097/SPC.0b013e32834bddf9.
Hill et al., "The Myostatin Propeptide and the Follistatin-related Gene Are Inhibitory Binding Proteins of Myostatin in Normal Serum," J Biol Chem, Oct. 25, 2002, 277(43):40735-41. Epub Aug. 22, 2002.
Kim et al., "Production of a Polyclonal Anti-Myostatin Antibody and the Effects of In Ovo Administration of the Antibody on Posthatch Broiler Growth and Muscle Mass," Poult Sci, Jun. 2007, 86(6):1196-205.
Kim et al., "Production of a Monoclonal Anti-Myostatin Antibody and the Effects of In Ovo Administration of the Antibody on Posthatch Broiler Growth and Muscle Mass," Poult Sci, Jun. 2006, 85(6):1062-71.
OriGene Technologies, Inc., AP02123SU-N, Polyclonal Antibody to Myostatin (79-92)—Serum, Mar. 19, 2013,htps://ml.acris-antibodies.com/pdf/AP02123SU-N.pdf.
Vajdos et al., "Comprehensive Functional Maps of the Antigen-binding Site of an Anti-ErbB2 Antibody Obtained with Shotgun Scanning Mutagenesis," J Mol Biol, Jul. 5, 2002, 320(2):415-28.
Vercellini et al., "Postoperative oral contraceptive exposure and risk of endometrioma recurrence," Am J Obstet Gynecol, May 2008 (Epub Feb. 2008), 198(5):504.
Ying et al., "Large Yellow Croaker MSTN-1 Prodomain Prokaryotic Expression, Polyclonal Antibody Preparation and Antibody Function Identification," Chinese Journal of Cell Biology, Oct. 2014, 36(10):1344-1349 (with English abstract).
U.S. Appl. No. 16/697,310, filed Nov. 27, 2019, Igawa et al.
Arici, "Local Cytokines in Endometrial Tissue: The Role of Interleukin-8 in the Pathogenesis of Endometriosis," Ann NY Acad Sci, Mar. 2002, 955:101-9; discussion 118, 396-406.
Gonzalez et al., "BMP-1/Tolloid-like Metalloproteases Process Endorepellin, the Angiostatic C-terminal Fragment of Perlecan," J Biol Chem, Feb. 25, 2005, 280(8):7080-7, Epub Dec. 9, 2004.
Igawa et al., Engineered Monoclonal Antibody with Novel Antigen-Sweeping Activity In Vivo, PLoS One, May 7, 2013. 8(5):e63236. doi: 10.1371/journal.pone.0063236. Print 2013.
Igawa et al., "pH-dependent antigen-binding antibodies as a novel therapeutic modality." Biochim Biophys Acta, Nov. 2014, 1844(11):1943-1950. doi: 10.1016/j.bbapap.2014.08.003. Epub Aug. 12, 2014.
Pirruccello-Straub, "Blocking extracellular activation of myostatin as a strategy for treating muscle wasting," Scientific Reports, 2018, 8:2292.
U.S. Appl. No. 16/763,134, filed May 11, 2020, Feng et al.
U.S. Appl. No. 16/889,066, filed Jun. 1, 2020, Ruike et al.
U.S. Appl. No. 17/046,395, filed Oct. 9, 2020, Fukuzawa et al.
Sikkink et al., "Biochemical and aggregation analysis of Bence Jones proteins from different light chain diseases," Amyloid, Mar. 2008, 15(1):29-39.
Stavenhagen et al., "Enhancing the potency of therapeutic monoclonal antibodies via Fc optimization," Adv Enzyme Regul, 2008, 48:152-164.
Tarantul, "Antibodies," Explanatory Biotechnological Dictionary (Russian-English), Languages of Slavic Cultures, 2009, p. 72.
Wang et al., "Molecular Basis of Assembly and Activation of Complement Component C1 in Complex with Immunoglobulin G1 and Antigen," Mol Cell, Jul. 7, 2016, 63(1):135-145. doi: 10.1016/j.molcel.2016.05.016. Epub Jun. 16, 2016.
Wolfman et al., "Activation of latent myostatin by the BMP-1 / tolloid family of metalloproteinases," Proc Natl Acad Sci USA, Dec. 23, 2003, 100(26):15842-15846. Epub Dec. 11, 2003.
Yarilin, Fundamentals of Immunology, Moscow, Medicina, 1999, pp. 172-174 (with English translation).
USPTO Notice of Allowance in U.S. Appl. No. 14/007,947, dated Feb. 20, 2020, 8 pages.
USPTO Non-Final Office Action in U.S. Appl. No. 14/406,232, dated Aug. 11, 2020, 18 pages.
USPTO Notice of Allowance in U.S. Appl. No. 14/406,232, dated Mar. 25, 2021, 10 pages.
USPTO Notice of Allowance in U.S. Appl. No. 14/654,895, dated Dec. 26, 2019, 7 pages.
USPTO Notice of Allowance in U.S. Appl. No. 14/654,895, dated May 26, 2020, 7 pages.
USPTO Notice of Allowance and Examiner-Initiated Interview Summary in U.S. Appl. No. 14/423,269, dated Jun. 5, 2020, 10 pages.
USPTO Non-Final Office Action in U.S. Appl. No. 14/781,069, dated Mar. 13, 2020, 12 pages.
USPTO Final Office Action in U.S. Appl. No. 14/781,069, dated Nov. 9, 2020, 12 pages.
U.S. Pat. No. 10,000,560, Ruike et al., issued Jun. 19, 2018.
U.S. Pat. No. 10,738,111, Ruike et al., issued Aug. 11, 2020.
U.S. Pat. No. 9,969,800, Igawa et al., issued May 15, 2018.
U.S. Pat. No. 10,519,229, Igawa et al., issued Dec. 31, 2019.
U.S. Appl. No. 17/046,395, Fukuzawa et al., filed Oct. 9, 2020.
U.S. Appl. No. 17/333,256 filed May 28, 2021, Kakiuchi et al.

(56) References Cited

OTHER PUBLICATIONS

Abdiche et al., "Antibodies Targeting Closely Adjacent or Minimally Overlapping Epitopes Can Displace One Another," PLoS One, Jan. 6, 2017, 12(1):e0169535, doi: 10.1371/journal.pone. 0169535.

Alignment sequences 1047 and 30, Jan. 26, 2021, 1 page (document cited in the office action dated Feb. 2, 2021 for EP 15869566.8).

Alignment sequences 472 and 24, Jan. 26, 2021, 1 page (document cited in the office action dated Feb. 2, 2021 for EP 15869566.8).

Almitairi et al., "Structure of the C1r-C1s interaction of the C1 complex of complement activation," Proc Natl Acad Sci USA, Jan. 23, 2018, 115(4):768-773, doi:10.1073/pnas.1718709115.

Arduin et al., "Highly reduced binding to high and low affinity mouse Fc gamma receptors by L234A/L235A and N297A Fc mutations engineered into mouse IgG2a," Mol Immunol, Feb. 2015, 63(2):456-463.

Arlaud et al., "A Study on the Structure and Interactions of the C1 Sub-Components C1r and C1s in the Fluid Phase," Biochim Biophys Acta, Nov. 6, 1980, 616(1):105-115.

Bally et al., "Identification of the C1q-binding Sites of Human C1r and C1s—A Refined Three-Dimensional Model of the C1 Complex of Complement," J Biol Chem, Jul. 17, 2009, 284(29):19340-19348, doi: 10.1074/jbc.M109.004473.

Bork, "Powers and Pitfalls in Sequence Analysis: The 70% Hurdle," Genome Res, Apr. 2000, 10(4):398-400.

Bowie et al., "Deciphering the Message in Protein Sequences: Tolerance to Amino Acid Substitutions," Science, Mar. 16, 1990, 247(4948):1306-1310.

Buckler, Section 2.4 "Library Selection," vol. 4 Molecular Medicine and Medicinal Chemistry, Antibody Drug Discovery, edited by Wood, CR, London: Imperial College Press, 2012, pp. 49-57.

Burgess et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue," J Cell Biol, Nov. 1990, 111(5 Pt 1):2129-2138.

Chen et al., "Enhancement and destruction of antibody function by somatic mutation: unequal occurrence is controlled by V gene combinatorial associations," EMBO J, Jun. 15, 1995, 14(12):2784-2794.

Colman, "Effects of amino acid sequence changes on antibody-antigen interactions," Res Immunol, Jan. 1994, 145(1):33-36.

Dagbay et al., "Structural basis of specific inhibition of extracellular activation of pro- or latent myostatin by the monoclonal antibody SRK-015," J Biol Chem, Apr. 17, 2020, 295(16):5404-5418.

Datta-Mannan et al., "FcRn Affinity-Pharmacokinetic Relationship of Five Human IgG4 Antibodies Engineered for Improved In Vitro FcRn Binding Properties in Cynomolgus Monkeys," Drug Metab Dispos. Aug. 2012, 40(8)4545-1555.

Di Stefano et al., "Role of Interleukin-8 in the Pathogenesis and Treatment of COPD," Chest, Sep. 2004, 126(3):676-678, doi: 10.1378/chest.126.3.676.

Diamond et al., "Somatic mutation of the T15 heavy chain gives rise to an antibody with autoantibody specificity," Proc Natl Acad Sci USA, Sep. 1984, 81(18):5841-5844.

Gal et al., "Early complement proteases: C1r, C1s and MASPs. A structural insight into activation and functions," Mol Immunol, Sep. 2009, 46(14):2745-2752, doi:10.1016/j.molimm.2009.04.026.

Gershoni et al., "Epitope Mapping—The First Step in Developing Epitope-Based Vaccines," BioDrugs, 2007, 21(3):145-156.

Igawa et al., "Sweeping antibody as a novel therapeutic antibody modality capable of eliminating soluble antigens from circulations," Immunol Rev, Mar. 2016, 270(1):132-151.

Kim et al., "Affinity Maturation of Monoclonal Antibodies by Multi-Site- Directed Mutagenesis," Methods Mol Biol, 2014, 1131:407-420. doi: 10.1007/978-1-62703-992-5_24.

Lacroix et al., "Assembly and Enzymatic Properties of the Catalytic Domain of Human Complement Protease C1r," J Biol Chem, Sep. 28, 2001, 276(39):36233-36240. doi: 10.1074/jbc.M105688200.

Lazar et al., "Transforming Growth Factor α: Mutation of Aspartic Acid 47 and Leucine 48 Results in Different Biological Activities," Mol Cell Biol, Mar. 1988, 8(3)4247-1252.

Mariuzza et al., "The Structural Basis of Antigen-Antibody Recognition," Annu Rev Biophys Chem, Jun. 1987, 16:139-159.

Matsumoto et al., "Functional analysis of activated C1s, a subcomponent of the first component of human complement, by monoclonal antibodies," J Immunol, Nov. 1, 1986, 137(9):2907-2912.

Moore et al., "Engineered Fc variant antibodies with enhanced ability to recruit complement and mediate effector functions," mAbs, Mar.-Apr. 2010, 2(2):181-189.

Mortensen et al., "Structure and activation of C1, the complex initiating the classical pathway of the complement cascade," Proc Natl Acad Sci USA, Jan. 31, 2017, 114(5):986-991. doi: 10.1073/pnas.1616998114. Epub Jan. 19, 2017.

Muramatsu, "Latent myostatin specific elimination by sweeping antibody® is a novel therapeutic approach to improve muscle strength," Neuromuscular Disorders, Oct. 1, 2019, 29(Supplement 1):S86.

Ohno et al., "Antigen-binding specificities of antibodies are primarily determined by seven residues of $V_H$," Proc Natl Acad Sci USA, May 1985, 82(9)2945-2949.

Pakula et al., "Genetic Analysis of Protein Stability and Function," Annu Rev Genet, Dec. 1989, 23:289-310.

Petillot et al., "Analysis of the N-linked oligosaccharides of human C1s using electrospray ionisation mass spectrometiy," FEBS Lett, Jan. 30, 1995, 358(3):323-328.

Raghavan et al., "Analysis of the pH Dependence of the Neonatal Fc Receptor/Immunoglobulin G Interaction Using Antibody and Receptor Variants," Biochemistiy, Nov. 14, 1995, 34(45):14649-14657.

Rivas et al., "Calcium-Linked Self-Association of Human Complement C1s," Biochemistry, Dec. 1, 1992, 31(47):11707-11712.

Rossi et al., "Classical Complement Pathway Components C1r and C1s: Purification from Human Serum and in Recombinant Form and Functional Characterization," Methods Mol Biol, 2014, 1100:43-60. doi: 10.1007/978-1-62703-724-2_4.

Rossi et al., "Baculovirus-mediated Expression of Truncated Modular Fragments from the Catalytic Region of Human Complement Serine Protease C1s," J Biol Chem, Jan. 9, 1998, 273(2):1232-1239. doi:10.1074/jbc.273.2.1232.

Rudikoff et al., Single amino acid substitution altering antigen-binding specificity, Proc Natl Acad Sci USA, Mar. 1982, 79(6):1979-1983.

Shi et al., "TNT003, an inhibitor of the serine protease C1s, prevents complement activation induced by cold agglutinins," Blood, Jun. 26, 2014, 123(26):4015-4022. doi: 10.1182/blood-2014-02-556027. Epub Apr. 2, 2014.

Tseng et al., "Probing the Structure of C1 with an Anti-C1s Monoclonal Antibody: The Possible Existence of Two Forms of C1 in Solution," Mol Immunol, Jun. 1997, 34(8-9):671-679. doi:10.1016/s0161-5890(97)00039-4.

Vaccaro et al., "Engineering the Fc region of immunoglobulin G to modulate in vivo antibody levels," Nat Biotechnol, Oct. 2005, 23(10):1283-1288, Epub Sep. 25, 2005.

Wang et al., "Monoclonal Antibodies with Identical Fc Sequences Can Bind to FcRn Differentially with Pharmacokinetic Consequences," DrugMetab Dispos, Sep. 2011, 39(9):1469-1477. doi: 10.1124/dmd.111.039453. Epub May 24, 2011.

* cited by examiner

```
mFcgRII(NP_034317.1)    1    MGILPFLLIPMESNWTVHVFSRTCHMLLWTAVLNLAAGTHQLPKAVVKLPPWIQVLKE    60
mFcgRIII(NP_034318.2)   1    ------------MFQNAHSGSQWLLPLTILLLFAFADRQSAALPKAVVKLPPWIQVLKE    49 mFcgRII(NP_034317.1)    61   PTLWCEGTHNPGNSSTQWFHNGRSIRSQVQASYTFKATVNDSGEYRCQMEQTRLSDPV    120
mFcgRIII(NP_034318.2)   50   DMVTIMCEGTHNPGNSSTQWFHNGRSMRSQVQASYTFKATVNDSGEYRCQMEQTRLSDPV   109 mFcgRII(NP_034317.1)    121  DLGVISDWLLLQTPQRVFLEGETITLRCHSFFHNEKSVRYHHYSNFSIP             180
mFcgRIII(NP_034318.2)   110  DLGVISDWLLLQTPQRVFLEGETITLRCHSFFHNEKSVRYHHYKSNFSIP             169
                                                                        * mFcgRII(NP_034317.1)    181  KANHSHSGDYYCKGSLGSTHQSKPVTITVQRKSSRLPVLTIVAAVTGIAVAAIVIIL   240
mFcgRIII(NP_034318.2)   170  KANHSHSGDYYCKGSLGSTHQSKPVTITVQGRATTSISLVWYHTFSLVMCLLFAVDT   229
                                                * mFcgRII(NP_034317.1)    241  VSLVYLKKKQVPDNPPDLEEAAKTEAENTITYSLLKHPEALDEETEHDYQNHI       293
mFcgRIII(NP_034318.2)   230  GLYFVRRNLQTPREYWRKSLSIRKRQAPQDK--------------------       261
```

Figure 1

| CH1 | | | | | | | | | | | | | | | | | | | | | | | | |
|---|---|---|---|---|---|---|---|---|---|---|---|---|---|---|---|---|---|---|---|---|---|---|---|---|
| Kabat | 114 | 115 | 116 | 117 | 118 | 119 | 120 | 121 | 122 | 123 | 124 | 125 | 126 | 127 | 128 | 129 | 130 | 133 | 134 | 135 | 136 | 137 | | |
| EU | 118 | 119 | 120 | 121 | 122 | 123 | 124 | 125 | 126 | 127 | 128 | 129 | 130 | 131 | 132 | 133 | 134 | 135 | 136 | 137 | 138 | 139 | | |
| mIgG1 | A | K | T | T | P | P | S | V | Y | P | L | A | P | G | S | A | A | Q | T | N | S | M | | |
| mIgG2a | A | K | T | T | P | P | S | V | Y | P | L | A | P | G | S | G | D | T | T | G | S | S | | |
| mIgG2b | A | K | T | T | P | P | S | V | Y | P | L | A | P | G | S | G | D | T | T | G | S | S | | |
| mIgG3 | A | T | T | T | A | P | S | V | Y | P | L | V | P | G | C | S | D | T | S | G | Y | S | | |
| Kabat | 138 | 139 | 140 | 141 | 142 | 143 | 144 | 145 | 146 | 147 | 148 | 149 | 150 | 151 | 152 | 153 | 154 | 156 | 157 | 158 | 163 | 164 | | |
| EU | 140 | 141 | 142 | 143 | 144 | 145 | 146 | 147 | 148 | 149 | 150 | 151 | 152 | 153 | 154 | 155 | 156 | 157 | 158 | 159 | 160 | 161 | | |
| mIgG1 | V | T | L | G | C | L | V | K | G | Y | F | P | E | P | V | T | V | T | W | N | S | G | | |
| mIgG2a | V | T | L | G | C | L | V | K | G | Y | F | P | E | P | V | T | L | T | W | N | S | G | | |
| mIgG2b | V | T | S | G | C | L | V | K | G | Y | F | P | E | P | V | T | L | T | W | N | S | G | | |
| mIgG3 | V | T | L | G | C | L | V | K | G | Y | F | P | E | P | V | T | V | K | W | N | Y | G | | |
| Kabat | 165 | 166 | 167 | 168 | 169 | 171 | 172 | 173 | 174 | 175 | 176 | 177 | 178 | 179 | 180 | 182 | 183 | 184 | 185 | 186 | 187 | 188 | | |
| EU | 162 | 163 | 164 | 165 | 166 | 167 | 168 | 169 | 170 | 171 | 172 | 173 | 174 | 175 | 176 | 177 | 178 | 179 | 180 | 181 | 182 | 183 | | |
| mIgG1 | S | L | S | S | G | V | H | T | F | P | A | V | L | Q | S | - | D | L | Y | T | L | S | | |
| mIgG2a | S | L | S | S | G | V | H | T | F | P | A | V | L | Q | S | - | D | L | Y | T | L | S | | |
| mIgG2b | S | L | S | S | G | V | H | T | F | P | A | V | L | Q | S | - | G | L | Y | T | M | S | | |
| mIgG3 | A | L | S | S | G | V | R | T | V | S | S | V | L | F | Q | - | G | F | Y | S | L | S | | |
| Kabat | 189 | 190 | 191 | 192 | 193 | 194 | 195 | 196 | 197 | 198 | 199 | 200 | 202 | 203 | 204 | 205 | 206 | 207 | 208 | 209 | 210 | 211 | | |
| EU | 184 | 185 | 186 | 187 | 188 | 189 | 190 | 191 | 192 | 193 | 194 | 195 | | 196 | | 197 | 198 | 199 | 200 | 201 | 202 | 203 | | |
| mIgG1 | S | S | V | T | V | P | S | S | - | - | T | W | P | S | E | T | V | T | C | N | V | A | | |
| mIgG2a | S | S | V | T | V | T | S | S | T | T | W | P | S | Q | - | - | T | - | C | N | V | A | | |
| mIgG2b | S | S | V | T | V | P | T | S | T | T | W | P | S | Q | - | V | T | - | C | S | V | A | | |
| mIgG3 | S | L | S | T | V | P | R | - | - | - | W | P | S | Q | - | - | - | - | C | N | L | A | | |
| Kabat | 212 | 213 | 214 | 215 | 216 | 217 | 218 | 219 | 220 | 221 | 222 | 223 | | | | | | | | | | | | |
| EU | 204 | 205 | 206 | 207 | 208 | 209 | 210 | 211 | 212 | 213 | 214 | 215 | | | | | | | | | | | | |
| mIgG1 | H | P | A | S | S | T | K | V | D | K | K | I | | | | | | | | | | | | |
| mIgG2a | H | P | A | S | S | T | K | V | D | K | K | I | | | | | | | | | | | | |
| mIgG2b | H | P | A | S | S | T | T | V | D | K | K | L | | | | | | | | | | | | |
| mIgG3 | H | P | A | S | K | T | E | L | I | R | - | - | | | | | | | | | | | | |

Figure 11-1

| Hinge Kabat | 226 | 227 | 228 | 229 | 230 | 231 | 232 | 233 | 234 | 235 | 236 | 237 | 238 | 239 | 240 | 241 | 241A | 241B | 241C | 241D | 242 | 243 |
|---|---|---|---|---|---|---|---|---|---|---|---|---|---|---|---|---|---|---|---|---|---|---|
| EU | 216 | 217 | 218 | 219 | 220 | - | 221 | - | - | 222 | 223 | 224 | 225 | 226 | 227 | 228 | - | - | - | - | 229 | 230 |
| mIgG1 | V | P | R | D | - | - | - | - | - | C | G | C | K | P | C | - | - | - | - | - | C | T |
| mIgG2a | E | P | R | G | P | T | I | T | - | K | P | C | P | P | C | K | E | C | H | K | C | P |
| mIgG2b | E | - | S | G | P | - | S | P | - | N | P | C | P | P | G | K | S | C | - | - | C | P |
| mIgG3 | - | - | - | E | P | R | I | P | K | P | S | T | P | P | G | S | S | P | - | - | - | - |

MOUSE FCγAMMARII-SPECIFIC FC ANTIBODY

CROSS-REFERENCE TO RELATED APPLICATIONS

This application is the National Stage of International Application Serial No. PCT/JP2013/072598, filed on Aug. 23, 2013, which claims the benefit of Japanese Application Serial No. 2012-185865, filed on Aug. 24, 2012.

SEQUENCE LISTING

This application contains a Sequence Listing that has been submitted electronically as an ASCII text file named SequenceListing.txt. The ASCII text file, created on Dec. 31, 2014, is 115 kilobytes in size. The material in the ASCII text file is hereby incorporated by reference in its entirety.

TECHNICAL FIELD

The present invention relates to a polypeptide comprising an Fc variant selectively binding to mouse FcγRII relative to mouse FcγRIII. The present invention also relates to a method for using the Fc variant to predict the effects, on a human, of a polypeptide comprising an Fc variant selectively binding to human FcγRIIb relative to human FcγRIIa. The present invention further relates to a polypeptide prepared on the basis of information obtained using the method, and a therapeutic or preventive agent for a human disease, comprising the polypeptide as an active ingredient.

BACKGROUND ART

Antibodies have received attention as drugs because of their high stability in blood and few adverse reactions (Non Patent Literatures 1 and 2). Most of currently launched antibody drugs are antibodies of human IgG1 subclass. Antibody-dependent cell-mediated cytotoxicity (hereinafter, referred to as ADCC activity) is known as one of the functions of IgG class antibodies (Non Patent Literature 3). For exerting the ADCC activity of the antibodies, their Fc regions must bind to Fcγ receptors (hereinafter, referred to as FcγR), antibody-binding receptors, present on the surface of effector cells such as killer cells, natural killer cells, or activated macrophages.

In humans, FcγRIa (CD64A), FcγRIIa (CD32A), FcγRIIb (CD32B), FcγRIIIa (CD16A), and FcγRIIIb (CD16B) isoforms have been reported as the protein family of FcγR, and their respective allotypes have also been reported (Non Patent Literature 7). FcγRIa, FcγRIIa, and FcγRIIIa are each called activating FcγR because of having an immunologically activating function, while FcγRIIb is called inhibitory FcγR because of having an immunosuppressive function (Non Patent Literature 8).

For the binding between the Fc region and FcγR, some amino acid residues in the hinge regions and the CH2 domains of the antibody and sugar chains added to Asn 297 (EU numbering) of the CH2 domains have been found important (Non Patent Literatures 4, 5, 6, and 47). Mutants having various FcγR-binding properties have previously been studied by focusing on antibodies mutated at these sites, to yield Fc mutants having higher binding activity against activating FcγR (Patent Literatures 1, 2, 3, 4, 6, 7, and 8).

The activating FcγR, when cross-linked by an immune complex, causes the phosphorylation of immunoreceptor tyrosine-based activating motifs (ITAMs) contained in its intracellular domain or its interaction partner FcR common γ-chain, which results in the activation of a signal transducer SYK to initiate an activation signal cascade, thereby causing inflammatory immune response (Non Patent Literature 9).

FcγRIIb is the only FcγR that is expressed in B cells (Non Patent Literature 10). Reportedly, the priming of B cells is suppressed by the interaction of the Fc region of an antibody with FcγRIIb (Non Patent Literature 11). The cross-linking of FcγRIIb on B cells to a B cell receptor (BCR) via an immune complex in blood has been reported to suppress the activation of the B cells and thereby inhibit the antibody production of the B cells (Non Patent Literature 12). This immunosuppressive signal transduction mediated by BCR and FcγRIIb requires an immunoreceptor tyrosine-based inhibitory motif (ITIM) contained in the intracellular domain of FcγRIIb (Non Patent Literatures 13 and 14). In response to the signal, ITIM is phosphorylated to recruit SH2-containing inositol polyphosphate 5-phosphatase (SHIP), which in turn inhibits the transduction of other signal cascades involving activating FcγR, thereby suppressing inflammatory immune response (Non Patent Literature 15). In addition, the unique aggregation of FcγRIIb in a BCR-independent manner has been reported to transiently inhibit B cell proliferation and calcium influx triggered by BCR cross-linking without causing the apoptosis of IgM-producing B cells (Non Patent Literature 16).

FcγRIIb is also expressed in dendritic cells, macrophages, activated neutrophils, mast cells, and basophils. In these cells, FcγRIIb also inhibits the functions of activating FcγR, such as phagocytosis or the release of inflammatory cytokines, and suppresses inflammatory immune response (Non Patent Literature 8).

The importance of the immunosuppressive functions of FcγRIIb has been revealed by previous studies using FcγRIIb-knockout mice. For the FcγRIIb-knockout mice, it has been reported that: humoral immunity is not adequately regulated (Non Patent Literature 17); sensitivity to collagen-induced arthritis (CIA) is increased (Non Patent Literature 18); and lupus-like symptoms or Goodpasture's syndrome-like symptoms appear (Non Patent Literature 19).

Reportedly, the poor regulation of FcγRIIb is also associated with autoimmune disease in humans. For example, the association of a gene polymorphism in the promoter region or transmembrane region of FcγRIIb with the frequency of occurrence of systemic lupus erythematosus (SLE) (Non Patent Literatures 20, 21, 22, 23, and 24), and the decreased expression of FcγRIIb on the B cell surface of SLE patients (Non Patent Literatures 25 and 26) have been reported.

These findings from mouse models and clinical studies suggest that FcγRIIb is responsible for controlling autoimmune disease and inflammatory disease mainly by its involvement with B cells. Thus, FcγRIIb is a promising target molecule for controlling autoimmune disease and inflammatory disease.

IgG1, which is predominantly used as a commercially available antibody drug, is known to strongly bind not only to FcγRIIb but to activating FcγR (Non Patent Literature 27). It is considered that an antibody drug having immunosuppressive properties compared with the properties of IgG1 may be developed by use of an Fc mutant with enhanced binding to FcγRIIb or improved binding selectivity for FcγRIIb relative to activating FcγR. For example, the possibility is suggested that B cell activation is inhibited by use of an antibody having a variable region binding to BCR, and an Fc mutant with enhanced binding to FcγRIIb (Non Patent Literature 28). The cross-linking of FcγRIIb on B cells to IgE bound with a B cell receptor has been reported to inhibit the differentiation of the B cells into plasma cells and the resultant IgE production, thereby decreasing human IgE concentrations in human PBMC-transplanted mice while maintaining human IgG or IgM concentrations (Non Patent Literature 29). IgE-mediated as well as antibody-mediated cross-linking of CD79b and FcγRIIB that form a B cell receptor complex has been reported to inhibit B cell proliferation in vitro and to alleviate symptoms in collagen-induced arthritis models (Non Patent Literature 30).

As for cells other than B cells, FcεRI-FcγRIIb cross-linking on mast cells using a molecule in which the Fc domain of IgE binding to an IgE receptor FcεRI is fused with the Fc domain of IgG with enhanced binding to FcγRIIb has been reported to cause the phosphorylation of FcγRIIb, thereby suppressing FcεRI-dependent calcium influx. This suggests that the enhanced binding to FcγRIIb may inhibit degranulation through the stimulation of FcγRIIb (Non Patent Literature 31).

These findings imply that an antibody having an Fc mutant with improved binding activity against FcγRIIb is promising as a therapeutic drug for inflammatory diseases such as autoimmune disease.

It is also suggested that a mutant with enhanced binding to FcγRIIb is promising as a therapeutic drug for inflammatory diseases such as autoimmune disease as well as a therapeutic drug for cancer. FcγRIIb has previously been shown to also play an important role in the agonistic activity of agonist antibodies against the TNF receptor family. Specifically, it is suggested that the agonistic activity of antibodies against CD40, DR4, DR5, CD30, and CD137 included in the TNF receptor family requires interaction with FcγRIIb (Non Patent Literatures 32, 33, 34, 35, 36, and 37). Non Patent Literature 32 indicates that use of an antibody with enhanced binding to FcγRIIb enhances the antitumor effect of an anti-CD40 antibody. Thus, such an antibody with enhanced binding to FcγRIIb is expected to be effective for enhancing the agonistic effects of agonist antibodies including antibodies against the TNF receptor family.

There has been a report on an antibody having an Fc mutant with improved binding activity against FcγRIIb (Non Patent Literature 28). In this literature, alterations such as S267E/L328F, G236D/S267E, or S239D/S267E were added to the Fc regions of antibodies to thereby improve their binding activity against FcγRIIb. Among them, the S267E/L328F mutant antibody bound most strongly to FcγRIIb and maintained the same level of binding to FcγRIa and FcγRIIa H type as that of naturally occurring IgG1. According to another report, however, this alteration enhanced binding to FcγRIIa R type by several hundred times which are the same level as in binding to FcγRIIb. This means that binding selectivity for FcγRIIb relative to FcγRIIa R type is not improved (Patent Literature 5). In this literature, the binding activity of this S267E/L328F mutant antibody against mouse FcγRII (mouse homolog of FcγRIIb) was evaluated, but was not enhanced, suggesting the low species cross-reactivity of enhancement in FcγRIIb binding.

Some antibody drugs have been reported to produce adverse reactions derived from the interaction between IgG and FcγR. For example, a patient group that has received bevacizumab, an antibody against VEGF, is known to exhibit a rise in the incidence of thromboembolism (Non Patent Literature 38). Also, thromboembolism was observed in the clinical development trial of antibodies against CD40 ligand, and this clinical trial was discontinued (Non Patent Literature 39). The activating Fcγ receptor FcγRIIa is expressed on platelet cells (Non Patent Literature 40). Subsequent studies using animal models or the like suggest that all administered antibodies aggregate platelets via binding to FcγRIIa on the platelets, resulting in the formation of thrombus (Non Patent Literatures 41 and 42). It has been reported as to patients with systemic lupus erythematosus, which is an autoimmune disease, that an FcγRIIa-dependent mechanism causes platelet activation, which in turn correlates with the severity of the disease (Non Patent Literature 43).

Previous studies using animal models have also reported that immune complexes of antibodies and multivalent antigens induce anaphylaxis via activating FcγR (Non Patent Literature 44).

In addition, the activating FcγR-mediated uptake of immune complexes of multivalent antigens and antibodies has been reported to produce higher levels of antibodies against the antigens (Non Patent Literatures 45 and 46). This result suggests that, in the case of antibody drugs recognizing multivalent antigens, antibodies against the antibody drugs themselves may be more likely to be produced. Such produced antibodies against the antibody drugs are thought to deteriorate the kinetics of the drugs in blood or to cause neutralizing antibodies to reduce the effects of the drugs.

Thus, immune complexes are formed through the binding of antibodies to multivalent antigens and seem to induce various adverse reactions by their interaction with activating FcγR. This reduces the values of the antibodies as drugs. For circumventing this problem while maintaining the effects mediated by FcγRIIb, it is desirable to maintain binding to FcγRIIb and, at the same time, to selectively reduce binding to activating FcγR. Nonetheless, there has been no report on an Fc mutant that has such features in relation to mouse FcγR.

As mentioned above, there has been a report on an Fc mutant with partially improved binding selectivity for FcγRIIb in relation to human FcγR, whereas there has been no report on an Fc mutant with improved binding selectivity for its corresponding homolog FcγRII in relation to mouse FcγR. Owing to the absence of such an Fc mutant, the effects of the Fc mutant selectively binding to FcγRIIb have not been thoroughly tested yet in various disease models established using mice. The effects of the Fc mutant selectively binding to FcγRIIb have heretofore been evaluated by testing methods using, for example, human FcγRIIb transgenic mice (Non Patent Literatures 30, 31, and 32) or human PBMC-transplanted SCID mice (Non Patent Literatures 29 and 31). The former method, however, fails to test the effects of the Fc mutant selectively binding to FcγRIIb on disease models without mating with the disease models. Unfortunately, the transgenes in the transgenic mice thus do not always exert their original functions. The latter method fails to evaluate only the effects mediated by human FcγRIIb, because blood cells express human FcγRIIb but the other tissues express mouse-derived FcγR. For these reasons, the effects of the Fc mutant selectively binding to FcγRIIb have not been thoroughly evaluated yet in various disease models established using mice. If an Fc mutant selectively binding to mouse FcγRII can be developed, its effects on various mouse models of diseases can be tested without constraints as mentioned above. In addition, such an Fc mutant is very useful in determining the effects of an Fc mutant selectively binding to FcγRIIb on humans. From such viewpoints, there has been a demand for the development of an Fc mutant selectively binding to mouse FcγRII.

PRIOR ART LITERATURES

Patent Literatures

Patent Literature 1: WO 2000/42072
Patent Literature 2: WO 2006/019447
Patent Literature 3: WO 2004/99249
Patent Literature 4: WO 2004/29207
Patent Literature 5: US2009/0136485
Patent Literature 6: US2004/0132101
Patent Literature 7: WO2007/041635
Patent Literature 8: WO2008/150494

Non Patent Literatures

Non Patent Literature 1: Nat Biotechnol, 23 (9), 1073-1078, 2005
Non Patent Literature 2: Eur J Pharm Biopharm, 59 (3), 389-96, 2005
Non Patent Literature 3: Chem Immunol, 65, 88-110, 1997
Non Patent Literature 4: J Biol Chem, 276 (19), 16478-16483, 2001
Non Patent Literature 5: Eur J Immunol, 23 (5), 1098-1104, 1993
Non Patent Literature 6: Immunology, 86 (2), 319-324, 1995
Non Patent Literature 7: Immunol Lett, 82 (1-2), 57-65, 2002
Non Patent Literature 8: Nat Rev Immunol, 10 (5), 328-343, 2010
Non Patent Literature 9: Nat Rev Immunol, 8 (1), 34-47, 2008
Non Patent Literature 10: Eur J Immunol, 19 (8), 1379-1385, 1989
Non Patent Literature 11: J Exp Med, 129 (6), 1183-1201, 1969
Non Patent Literature 12: Immunol Lett, 88 (2), 157-161, 2003
Non Patent Literature 13: Science, 256 (5065), 1808-1812, 1992
Non Patent Literature 14: Nature, 368 (6466), 70-73, 1994
Non Patent Literature 15: Science, 290 (5489), 84-89, 2000
Non Patent Literature 16: J Immunol, 181 (8), 5350-5359, 2008
Non Patent Literature 17: J Immunol, 163 (2), 618-622, 1999
Non Patent Literature 18: J Exp Med, 189 (1), 187-194, 1999
Non Patent Literature 19: J Exp Med, 191 (5), 899-906, 2000
Non Patent Literature 20: Hum Genet, 117 (2-3), 220-227, 2005
Non Patent Literature 21: J Biol Chem, 282 (3), 1738-1746, 2007
Non Patent Literature 22: Arthritis Rheum, 54 (12), 3908-3917, 2006
Non Patent Literature 23: Nat Med, 11 (10), 1056-1058, 2005
Non Patent Literature 24: J Immunol, 176 (9), 5321-5328, 2006
Non Patent Literature 25: J Exp Med, 203 (9), 2157-2164, 2006
Non Patent Literature 26: J Immunol, 178 (5), 3272-3280, 2007
Non Patent Literature 27: Blood, 113 (16), 3716-3725, 2009
Non Patent Literature 28: Mol Immunol, 45 (15), 3926-3933, 2008
Non Patent Literature 29: J Allergy Clin Immunol, 129 (4), 1102-1115, 2012
Non Patent Literature 30: Arthritis Rheum, 62 (7), 1933-1943, 2010
Non Patent Literature 31: Immunol Lett, 143 (1), 34-43, 2012
Non Patent Literature 32: Science, 333 (6045), 1030-1034, 2011
Non Patent Literature 33: Cancer Cell, 19 (1), 101-113, 2011
Non Patent Literature 34: J Clin Invest, 122 (3), 1066-1075, 2012
Non Patent Literature 35: J Immunol, 171 (2), 562-568, 2003
Non Patent Literature 36: Blood, 108 (2), 705-710, 2006
Non Patent Literature 37: J Immunol, 166(8), 4891-4898, 2001
Non Patent Literature 38: J Natl Cancer Inst, 99 (16), 1232-1239, 2007
Non Patent Literature 39: Arthritis Rheum, 48 (3), 719-727, 2003
Non Patent Literature 40: J Exp Med, 203 (9), 2157-2164, 2006
Non Patent Literature 41: J Thromb Haemost, 7 (1), 171-181, 2009
Non Patent Literature 42: J Immunol, 185 (3), 1577-1583, 2010
Non Patent Literature 43: Sci Transl Med, 2 (47), 47-63, 2010
Non Patent Literature 44: Blood, 119 (24), 5640-5649, 2012
Non Patent Literature 45: Scand J Immunol, 64 (3), 177-184, 2006
Non Patent Literature 46: J Immunol, 163 (2), 618-622, 1999
Non Patent Literature 47: Mol Immunol, 29 (1), 53-59, 1992

SUMMARY OF INVENTION

Problems to be Solved by the Invention

The present invention has been made in light of these circumstances, and an object of the present invention is to provide a polypeptide comprising an Fc variant selectively binding to mouse FcγRII relative to mouse FcγRIII. Another object of the present invention is to provide a method for using the Fc variant to predict the effects, on a human, of a polypeptide comprising an Fc variant selectively binding to human FcγRIIb relative to human FcγRIIa. A further object of the present invention is to provide a polypeptide prepared on the basis of information obtained using the method, and a therapeutic or preventive agent for a human disease, comprising the polypeptide as an active ingredient.

Means for Solving the Problems

The present inventors have conducted diligent studies on a polypeptide comprising an Fc variant selectively binding to mouse FcγRII relative to mouse FcγRIII. As a result, the present inventors have successfully found a large number of Fc variants with remarkably increased binding activity against and/or binding selectivity for mouse FcγRII by introducing amino acid alteration(s) to the Fc region.

The present invention is based on these findings and specifically relates to the following aspects:

[1] A polypeptide which is a variant of a parent polypeptide comprising an Fc region, wherein the polypeptide comprises at least one amino acid alteration in the Fc region and has a ratio of [KD value for mouse FcγRIII]/[KD value for mouse FcγRII] of 6 or more.

[2] A polypeptide which is a variant of a parent polypeptide comprising an Fc region, wherein the polypeptide comprises at least one amino acid alteration in the Fc region and the binding selectivity of the polypeptide for mouse FcγRII relative to mouse FcγRIII is improved by 5 times or more compared with that of the parent polypeptide.

[3] The polypeptide according to [1] or [2], wherein the KD value for mouse FcγRII is 20 nM or smaller.

[4] The polypeptide according to [1] or [2], wherein the binding activity of the polypeptide against mouse FcγRII is enhanced by 10 times or more compared with that of the parent polypeptide.

[5] The polypeptide according to any of [1] to [4], wherein the KD value for mouse FcγRIII is 1 μM or larger.

[6] The polypeptide according to any of [1] to [4], wherein the binding activity of the polypeptide against mouse FcγRIII is reduced to 0.25 times or less compared with that of the parent polypeptide.

[7] The polypeptide according to any of [1] to [6], wherein the amino acid alteration is the alteration of at least one amino acid selected from the group consisting of amino acids at EU numbering positions 230, 231, 232, 237, 238, 239, 240, 241, 266, 267, 268, 271, 295, 296, 298, 324, 326, 327, 330, 331, 333, 334, 335, and 337.

[8] The polypeptide according to [7], wherein the amino acid alteration is at least one alteration selected from the group consisting of:
the substitution of an amino acid at position 230 by Asp, Glu, Ile, Pro, Gln, or Val,
the substitution of an amino acid at position 231 by Ala, Asp, Glu, Ile, Leu, Met, Asn, Pro, Gln, Thr, or Trp,
the substitution of an amino acid at position 232 by Ala, Asp, Glu, Phe, Lys, Leu, Asn, Val, Trp, or Tyr,
the substitution of an amino acid at position 237 by Glu,
the substitution of an amino acid at position 238 by Asp, Glu, Pro, or Gln,
the substitution of an amino acid at position 239 by Ala, Asp, Glu, Phe, Gly, His, Ile, Lys, Leu, Met, Asn, Pro, Gln, Arg, Thr, Val, Trp, or Tyr,
the substitution of an amino acid at position 240 by Glu, His, Gln, or Trp,
the substitution of an amino acid at position 241 by Asp, Glu, Thr, Trp, or Tyr,
the substitution of an amino acid at position 266 by Leu,
the substitution of an amino acid at position 267 by Ala, Glu, or Met,
the substitution of an amino acid at position 268 by Asp,
the substitution of an amino acid at position 271 by Leu,
the substitution of an amino acid at position 295 by Leu,
the substitution of an amino acid at position 296 by Glu, Asn, Thr, or Trp,
the substitution of an amino acid at position 298 by His, Leu, or Met,
the substitution of an amino acid at position 324 by Asp, Leu, or Met,
the substitution of an amino acid at position 326 by Asp,
the substitution of an amino acid at position 327 by Gly,
the substitution of an amino acid at position 330 by Gly, Lys, or Gln,
the substitution of an amino acid at position 331 by Asp, Phe, or Tyr,
the substitution of an amino acid at position 333 by Asn, Val, or Tyr,
the substitution of an amino acid at position 334 by Arg,
the substitution of an amino acid at position 335 by Asn or Tyr, and
the substitution of an amino acid at position 337 by Ile, Lys, or Trp
(wherein all positions are indicated by EU numbering).

[9] The polypeptide according to any of [1] to [8], wherein the Fc region is the Fc region of mouse IgG1.

[10] The polypeptide according to any of [1] to [9], wherein the polypeptide is an antibody.

[11] A method for altering a parent polypeptide comprising an Fc region to adjust a ratio of [KD value for mouse FcγRIII]/[KD value for mouse FcγRII] to 6 or more, the method comprising altering at least one amino acid selected from the group consisting of amino acids at EU numbering positions 230, 231, 232, 237, 238, 239, 240, 241, 266, 267, 268, 271, 295, 296, 298, 324, 326, 327, 330, 331, 333, 334, 335, and 337 of the Fc region.

[12] A method for altering a parent polypeptide comprising an Fc region to improve the binding selectivity of the variant for mouse FcγRII relative to mouse FcγRIII by 5 times or more compared with that of the parent polypeptide, the method comprising altering at least one amino acid selected from the group consisting of amino acids at EU numbering positions 230, 231, 232, 237, 238, 239, 240, 241, 266, 267, 268, 271, 295, 296, 298, 324, 326, 327, 330, 331, 333, 334, 335, and 337 of the Fc region.

[13] The method according to [11] or [12], wherein the amino acid alteration is at least one alteration selected from the group consisting of:
the substitution of an amino acid at position 230 by Asp, Glu, Ile, Pro, Gln, or Val,
the substitution of an amino acid at position 231 by Ala, Asp, Glu, Ile, Leu, Met, Asn, Pro, Gln, Thr, or Trp,
the substitution of an amino acid at position 232 by Ala, Asp, Glu, Phe, Lys, Leu, Asn, Val, Trp, or Tyr,
the substitution of an amino acid at position 237 by Glu,
the substitution of an amino acid at position 238 by Asp, Glu, Pro, or Gln,
the substitution of an amino acid at position 239 by Ala, Asp, Glu, Phe, Gly, His, Ile, Lys, Leu, Met, Asn, Pro, Gln, Arg, Thr, Val, Trp, or Tyr,
the substitution of an amino acid at position 240 by Glu, His, Gln, or Trp,
the substitution of an amino acid at position 241 by Asp, Glu, Thr, Trp, or Tyr,
the substitution of an amino acid at position 266 by Leu,
the substitution of an amino acid at position 267 by Ala, Glu, or Met,
the substitution of an amino acid at position 268 by Asp,
the substitution of an amino acid at position 271 by Leu,
the substitution of an amino acid at position 295 by Leu,
the substitution of an amino acid at position 296 by Glu, Asn, Thr, or Trp,
the substitution of an amino acid at position 298 by His, Leu, or Met,
the substitution of an amino acid at position 324 by Asp, Leu, or Met,
the substitution of an amino acid at position 326 by Asp,
the substitution of an amino acid at position 327 by Gly,
the substitution of an amino acid at position 330 by Gly, Lys, or Gln,
the substitution of an amino acid at position 331 by Asp, Phe, or Tyr,
the substitution of an amino acid at position 333 by Asn, Val, or Tyr,
the substitution of an amino acid at position 334 by Arg, the substitution of an amino acid at position 335 by Asn or Tyr, and the substitution of an amino acid at position 337 by Ile, Lys, or Trp (wherein all positions are indicated by EU numbering).

[14] The method according to any of [11] to [13], wherein the Fc region is the Fc region of mouse IgG1.

[15] The method according to any of [11] to [14], wherein the polypeptide is an antibody.

[16] A method for producing a polypeptide which is a variant of a parent polypeptide comprising an Fc region, wherein the polypeptide has a ratio of [KD value for mouse FcγRIII]/[KD value for mouse FcγRII] of 6 or more, the method comprising altering at least one amino acid selected from the group consisting of amino acids at EU numbering positions 230, 231, 232, 237, 238, 239, 240, 241, 266, 267, 268, 271, 295, 296, 298, 324, 326, 327, 330, 331, 333, 334, 335, and 337 of the Fc region.

[17] A method for producing a polypeptide which is a variant of a parent polypeptide comprising an Fc region, wherein the binding selectivity of the polypeptide for mouse FcγRII relative to mouse FcγRIII is improved by 5 times or more compared with that of the parent polypeptide, the method comprising altering at least one amino acid selected from the group consisting of amino acids at EU numbering positions 230, 231, 232, 237, 238, 239, 240, 241, 266, 267, 268, 271, 295, 296, 298, 324, 326, 327, 330, 331, 333, 334, 335, and 337 of the Fc region.

[18] The method according to [16] or [17], wherein the amino acid alteration is at least one alteration selected from the group consisting of:

the substitution of an amino acid at position 230 by Asp, Glu, Ile, Pro, Gln, or Val, the substitution of an amino acid at position 231 by Ala, Asp, Glu, Ile, Leu, Met, Asn, Pro, Gln, Thr, or Trp, the substitution of an amino acid at position 232 by Ala, Asp, Glu, Phe, Lys, Leu, Asn, Val, Trp, or Tyr, the substitution of an amino acid at position 237 by Glu, the substitution of an amino acid at position 238 by Asp, Glu, Pro, or Gln, the substitution of an amino acid at position 239 by Ala, Asp, Glu, Phe, Gly, His, Ile, Lys, Leu, Met, Asn, Pro, Gln, Arg, Thr, Val, Trp, or Tyr, the substitution of an amino acid at position 240 by Glu, His, Gln, or Trp, the substitution of an amino acid at position 241 by Asp, Glu, Thr, Trp, or Tyr, the substitution of an amino acid at position 266 by Leu, the substitution of an amino acid at position 267 by Ala, Glu, or Met, the substitution of an amino acid at position 268 by Asp, the substitution of an amino acid at position 271 by Leu, the substitution of an amino acid at position 295 by Leu, the substitution of an amino acid at position 296 by Glu, Asn, Thr, or Trp, the substitution of an amino acid at position 298 by His, Leu, or Met, the substitution of an amino acid at position 324 by Asp, Leu, or Met, the substitution of an amino acid at position 326 by Asp, the substitution of an amino acid at position 327 by Gly, the substitution of an amino acid at position 330 by Gly, Lys, or Gln, the substitution of an amino acid at position 331 by Asp, Phe, or Tyr, the substitution of an amino acid at position 333 by Asn, Val, or Tyr, the substitution of an amino acid at position 334 by Arg, the substitution of an amino acid at position 335 by Asn or Tyr, and the substitution of an amino acid at position 337 by Ile, Lys, or Trp (wherein all positions are indicated by EU numbering).

[19] The method according to any of [16] to [18], wherein the Fc region is the Fc region of mouse IgG1.

[20] The method according to any of [16] to [19], wherein the polypeptide is an antibody.

[21] A polypeptide produced by a method according to any of [16] to [20].

[22] A polypeptide which is a variant of a parent polypeptide comprising a mouse Fc region, wherein the polypeptide comprises, in the Fc region, at least one amino acid alteration selected from the group consisting of:

the substitution of an amino acid at position 230 by Asp, Glu, Ile, Pro, Gln, or Val, the substitution of an amino acid at position 231 by Ala, Asp, Glu, Ile, Leu, Met, Asn, Pro, Gln, Thr, or Trp, the substitution of an amino acid at position 232 by Ala, Asp, Glu, Phe, Lys, Leu, Asn, Val, Trp, or Tyr, the substitution of an amino acid at position 237 by Glu, the substitution of an amino acid at position 238 by Asp, Glu, Pro, or Gln, the substitution of an amino acid at position 239 by Ala, Phe, Gly, His, Ile, Lys, Leu, Met, Asn, Pro, Gln, Arg, Thr, Val, Trp, or Tyr, the substitution of an amino acid at position 240 by Glu, His, Gln, or Trp, the substitution of an amino acid at position 241 by Asp, Glu, Thr, Trp, or Tyr, the substitution of an amino acid at position 266 by Leu, the substitution of an amino acid at position 267 by Glu or Met, the substitution of an amino acid at position 268 by Asp, the substitution of an amino acid at position 271 by Leu, the substitution of an amino acid at position 295 by Leu, the substitution of an amino acid at position 296 by Glu, Asn, Thr, or Trp, the substitution of an amino acid at position 298 by His, Leu, or Met, the substitution of an amino acid at position 324 by Asp, Leu, or Met, the substitution of an amino acid at position 326 by Asp, the substitution of an amino acid at position 327 by Gly, the substitution of an amino acid at position 330 by Gly, Lys, or Gln, the substitution of an amino acid at position 331 by Asp, Phe, or Tyr, the substitution of an amino acid at position 333 by Asn, Val, or Tyr, the substitution of an amino acid at position 334 by Arg, the substitution of an amino acid at position 335 by Asn or Tyr, and the substitution of an amino acid at position 337 by Ile, Lys, or Trp (wherein all positions are indicated by EU numbering).

[23] The polypeptide according to [22], wherein the polypeptide further comprises amino acid alteration(s) selected from the group consisting of:

the substitution of an amino acid at position 239 by Asp or Glu, and the substitution of an amino acid at position 267 by Ala (wherein all positions are indicated by EU numbering).

[24] The polypeptide according to [22] or [23], wherein the Fc region is the Fc region of mouse IgG1.

[25] The polypeptide according to any of [22] to [24], wherein the polypeptide is an antibody.

[26] A method for predicting a therapeutic or preventive effect on a disease when a polypeptide comprising an Fc variant selectively binding to human FcγRIIb relative to human FcγRIIa is administered to a human, the method comprising the following steps:
(a) obtaining a polypeptide comprising an antigen-binding region binding to a mouse antigen;
(b) preparing a polypeptide comprising the antigen-binding region of the polypeptide obtained in step (a), and an Fc variant according to any of [1] to [10] and [21] to [25];
(c) administering the polypeptide prepared in step (b) to a mouse model of a human disease; and
(d) when a therapeutic or preventive effect on the disease is observed in the mouse as a result of step (c), determining that a polypeptide comprising an antigen-binding region binding to a human counterpart of the mouse antigen, and the Fc variant selectively binding to human FcγRIIb relative to human FcγRIIa is effective for the treatment or prevention of the human disease.

[27] The method according to [26], wherein the method further comprises, in addition to steps (b) and (c):
(b') preparing a polypeptide comprising the antigen-binding region of the polypeptide obtained in step (a), and the Fc region of naturally occurring IgG; and
(c') administering the polypeptide prepared in step (b') to a mouse model of a human disease, and step (d) is the step of
(d) when a stronger therapeutic or preventive effect on the disease is observed in the mouse that has received the polypeptide of step (b) than in the mouse that has received the polypeptide of step (b') as a result of steps (c) and (c'), determining that a polypeptide comprising an antigen-binding region binding to a human counterpart of the mouse antigen, and the Fc variant selectively binding to human FcγRIIb relative to human FcγRIIa is effective for the treatment or prevention of the human disease.

[28] A method for selecting a disease suitable for treatment or prevention using a polypeptide comprising an Fc variant selectively binding to human FcγRIIb relative to human FcγRIIa, the method comprising the following:
(a) obtaining a polypeptide comprising an antigen-binding region binding to a mouse antigen;
(b) preparing a polypeptide comprising the antigen-binding region of the polypeptide obtained in step (a), and an Fc variant according to any of [1] to [10] and [21] to [25];
(c) administering the polypeptide prepared in step (b) to a mouse model of a human disease; and
(d) when a therapeutic or preventive effect on the disease is observed in the mouse as a result of step (c), selecting the human disease as the disease suitable for treatment or prevention using a polypeptide comprising an antigen-binding region binding to a human counterpart of the mouse antigen, and the Fc variant selectively binding to human FcγRIIb relative to human FcγRIIa.

[29] The method according to [28], wherein the method further comprises, in addition to steps (b) and (c):
(b') preparing a polypeptide comprising the antigen-binding region of the polypeptide obtained in step (a), and the Fc region of naturally occurring IgG; and
(c') administering the polypeptide prepared in step (b') to a mouse model of a human disease, and step (d) is the step of
(d) when a stronger therapeutic or preventive effect on the disease is observed in the mouse that has received the polypeptide of step (b) than in the mouse that has received the polypeptide of step (b') as a result of steps (c) and (c'), selecting the human disease as the disease suitable for treatment or prevention using a polypeptide comprising an antigen-binding region binding to a human counterpart of the mouse antigen, and the Fc variant selectively binding to human FcγRIIb relative to human FcγRIIa.

[30] A method for selecting a target antigen suitable for treatment or prevention using a polypeptide comprising an Fc variant selectively binding to human FcγRIIb relative to human FcγRIIa, the method comprising the following:
(a) obtaining a polypeptide comprising an antigen-binding region binding to a mouse antigen;
(b) preparing a polypeptide comprising the antigen-binding region of the polypeptide obtained in step (a), and an Fc variant according to any of [1] to [10] and [21] to [25];
(c) administering the polypeptide prepared in step (b) to a mouse model of a human disease; and
(d) when a therapeutic or preventive effect on the disease is observed in the mouse as a result of step (c), selecting a human counterpart of the mouse antigen as the target antigen suitable for treatment or prevention using a polypeptide comprising the Fc variant selectively binding to human FcγRIIb relative to human FcγRIIa.

[31] The method according to [30], wherein the method further comprises, in addition to steps (b) and (c):
(b') preparing a polypeptide comprising the antigen-binding region of the polypeptide obtained in step (a), and the Fc region of naturally occurring IgG; and
(c') administering the polypeptide prepared in step (b') to a mouse model of a human disease, and step (d) is the step of
(d) when a stronger therapeutic or preventive effect on the disease is observed in the mouse that has received the polypeptide of step (b) than in the mouse that has received the polypeptide of step (b') as a result of steps (c) and (c'), selecting a human counterpart of the mouse antigen as the target antigen suitable for treatment or prevention using a polypeptide comprising the Fc variant selectively binding to human FcγRIIb relative to human FcγRIIa.

[32] A method for selecting an antigen-binding region suitable for treatment or prevention using a polypeptide comprising an Fc variant selectively binding to human FcγRIIb relative to human FcγRIIa, the method comprising the following:
(a) obtaining a plurality of polypeptides comprising antigen-binding regions binding to the same mouse antigen;
(b) preparing a polypeptide comprising each of the antigen-binding regions of the polypeptides obtained in step (a), and an Fc variant according to any of [1] to [10] and [21] to [25];
(c) administering the polypeptide prepared in step (b) to a mouse model of a human disease; and
(d) as a result of step (c), selecting the antigen-binding region of a polypeptide that exhibits a stronger therapeutic or preventive effect as the antigen-binding region suitable for treatment or prevention of the human disease using a polypeptide comprising the Fc variant selectively binding to human FcγRIIb relative to human FcγRIIa.

[33] A method for predicting safety or toxicity when a polypeptide comprising an Fc variant selectively binding to human FcγRIIb relative to human FcγRIIa is administered to a human, the method comprising the following:
(a) obtaining a polypeptide comprising an antigen-binding region binding to a mouse antigen;
(b) preparing a polypeptide comprising the antigen-binding region of the polypeptide obtained in step (a), and an Fc variant according to any of [1] to [10] and [21] to [25];
(c) administering the polypeptide prepared in step (b) to a mouse; and
(d) analogically inferring the safety or toxicity, in a human, of a polypeptide comprising an antigen-binding region binding to a human counterpart of the mouse antigen, and the Fc variant selectively binding to human FcγRIIb relative to human FcγRIIa from the result(s) obtained in step (c) about the safety or toxicity of the polypeptide of step (b) in the mouse.

[34] A method for predicting pharmacokinetics when a polypeptide comprising an Fc variant selectively binding to human FcγRIIb relative to human FcγRIIa is administered to a human, the method comprising the following:

(a) obtaining a polypeptide comprising an antigen-binding region binding to a mouse antigen;

(b) preparing a polypeptide comprising the antigen-binding region of the polypeptide obtained in step (a), and an Fc variant according to any of [1] to [10] and [21] to [25];

(c) administering the polypeptide prepared in step (b) to a mouse; and (d) analogically inferring the pharmacokinetics, in a human, of a polypeptide comprising an antigen-binding region binding to a human counterpart of the mouse antigen, and the Fc variant selectively binding to human FcγRIIb relative to human FcγRIIa from the result(s) obtained in step (c) about the pharmacokinetics of the polypeptide of step (b) in the mouse.

[35] The method according to any of [26] to [32], wherein the disease is an immune inflammatory disease.

[36] The method according to [35], wherein the immune inflammatory disease is autoimmune disease.

[37] The method according to any of [26] to [36], wherein the mouse is a genetically modified mouse expressing the human antigen.

[38] The method according to any of [26] to [37], wherein the Fc region is the Fc region of IgG.

[39] The method according to any of [26] to [38], wherein the polypeptide is an antibody.

[40] A polypeptide comprising an antigen-binding region binding to a target antigen selected by a method according to [30] or [31], and an Fc variant selectively binding to human FcγRIIb relative to human FcγRIIa.

[41] A polypeptide comprising an antigen-binding region selected by a method according to [32], and an Fc variant selectively binding to human FcγRIIb relative to human FcγRIIa.

[42] The polypeptide according to [40] or [41], wherein the Fc region is the Fc region of IgG.

[43] The polypeptide according to any of [40] to [42], wherein the polypeptide is an antibody.

[44] A therapeutic or preventive agent for a human disease, comprising a polypeptide according to any of [40] to [43] as an active ingredient.

BRIEF DESCRIPTION OF THE DRAWINGS

FIG. 1 is a diagram showing results of comparing the sequences from amino acid positions 7 to 267 of mouse FcγRII (in the present specification, also referred to as mFcγRII or mFcgRII) (SEQ ID NO: 21) and mouse FcγRIII (in the present specification, also referred to as mFcγRIII or mFcgRIII) (SEQ ID NO: 22). In mFcγRII and mFcγRIII, sites corresponding to sites of human FcγR that interact with the Fc region of human IgG as shown in J Mol Biol (2001) 309, 737-749 are enclosed by heavy line. In each of these sites, portions differing in residue between mFcγRII and mFcγRIII are indicated by * below the sequences.

FIG. 2 is a diagram showing the results of comparing binding to mFcγRII and mFcγRIII. Each variant in which an alteration used in Example 3 was introduced was labeled. At the straight line, the degree of enhancement in binding activity against mFcγRII coincides with the degree of enhancement in binding activity against mFcγRIII.

FIG. 3 is a diagram showing the results of comparing binding to mFcγRII and mFcγRIII. An variant with Ser 239 (EU numbering) substituted by Asp and each variant with another alteration further introduced in addition to this alteration were labeled.

FIG. 4 is a diagram showing the results of comparing binding to mFcγRII and mFcγRIII. Each variant whose relative binding activity against mFcγRII was enhanced by 200 times or more compared with that of H237-mIgG1/MRAL-k0 was labeled.

FIG. 5 is a diagram showing change in binding to mFcγRII and mFcγRIII by amino acid substitutions at EU numbering positions 231 and 232.

FIG. 6 is a diagram showing the results of comparing binding to mFcγRII and selectivity between mFcγRII and mFcγRIII. Each variant having 200-fold or more relative mFcγRII-binding activity or 25-fold or more relative I/A compared with that of H237-mIgG1/MRAL-k0 was labeled.

FIG. 7 is a diagram showing the results of comparing the effects of the type of an amino acid at EU numbering position 239 on each template in relation to binding to mFcγRII and selectivity between mFcγRII and mFcγRIII.

FIG. 8 is a diagram showing the results of comparing binding to mFcγRII and mFcγRIII. Each variant having 1.1-fold or more relative mFcγRII-binding activity compared with that of H237-MB397/MRAL-k0 was labeled.

FIG. 9 is a diagram showing the results of comparing binding to mFcγRII and mFcγRIII. Each variant having 1.1-fold or more relative mFcγRII-binding activity compared with that of H237-MB390/MRAL-k0 was labeled.

FIG. 10 is a diagram showing time-dependent change in the concentration of each administered antibody in mouse plasma when H237-MB367/L104-mk1 or H237-mF46/L104-mk1 was administered to a normal mouse.

FIGS. 11-1 to 11-4 show the relationship of amino acid residues constituting mouse IgG heavy chain constant regions (SEQ ID NOs: 24 to 27) or Fc regions to the Kabat numbering and the EU numbering (in the present specification, also referred to as EU INDEX). FIG. 11-1 shows the CH1 domain. The Kabat and EU numbering positions were numbered on the basis of the contents of the description of Non Patent Literature (SEQUENCES OF PROTEINS OF IMMUNOLOGICAL INTEREST VOL. 1). For mIgG1, sequence (81) cited from [CELL, 18, 559-568 (1979); NATURE, 277, 627-633 (1979); and GENE, 9, 87-97 (1980)] in this literature was referred to. For mIgG2a, sequence (92) cited from [NUC. ACIDS RES., 8, 3143-3155 (1980); PROC. NAT. ACAD. SCI. USA, 78, 2442-2446 (1981); NUC. ACIDS RES., 9, 1365-1381 (1981); and CELL, 32, 515-523 (1983)] in this literature was referred to. For mIgG2b, sequence (86) cited from [SCIENCE, 206, 1303-1306 (1979)] in this literature was referred to. For mIgG3, sequence (79) cited from [EMBO J., 3, 2041-2046 (1984)] in this literature was referred to.

FIG. 11-2 is a sequel to FIG. 11-1 and shows the hinge.

FIG. 11-3 is a sequel to FIG. 11-2 and shows the CH2 domain.

FIG. 11-4 is a sequel to FIG. 11-3 and shows the CH3 domain.

FIG. 12 shows the relationship of amino acid residues constituting human IgG1, IgG2, IgG3, and IgG4 heavy chain constant regions (SEQ ID NOs: 28 to 31) or Fc regions to the EU numbering (in the present specification, also referred to as EU INDEX).

FIG. 13 is a diagram showing results of comparing binding to mFcγRII and selectivity between mFcγRII and mFcγRIII. Each variant having 0.75-fold or more relative I/A compared with that of each template was labeled.

Figure 16:
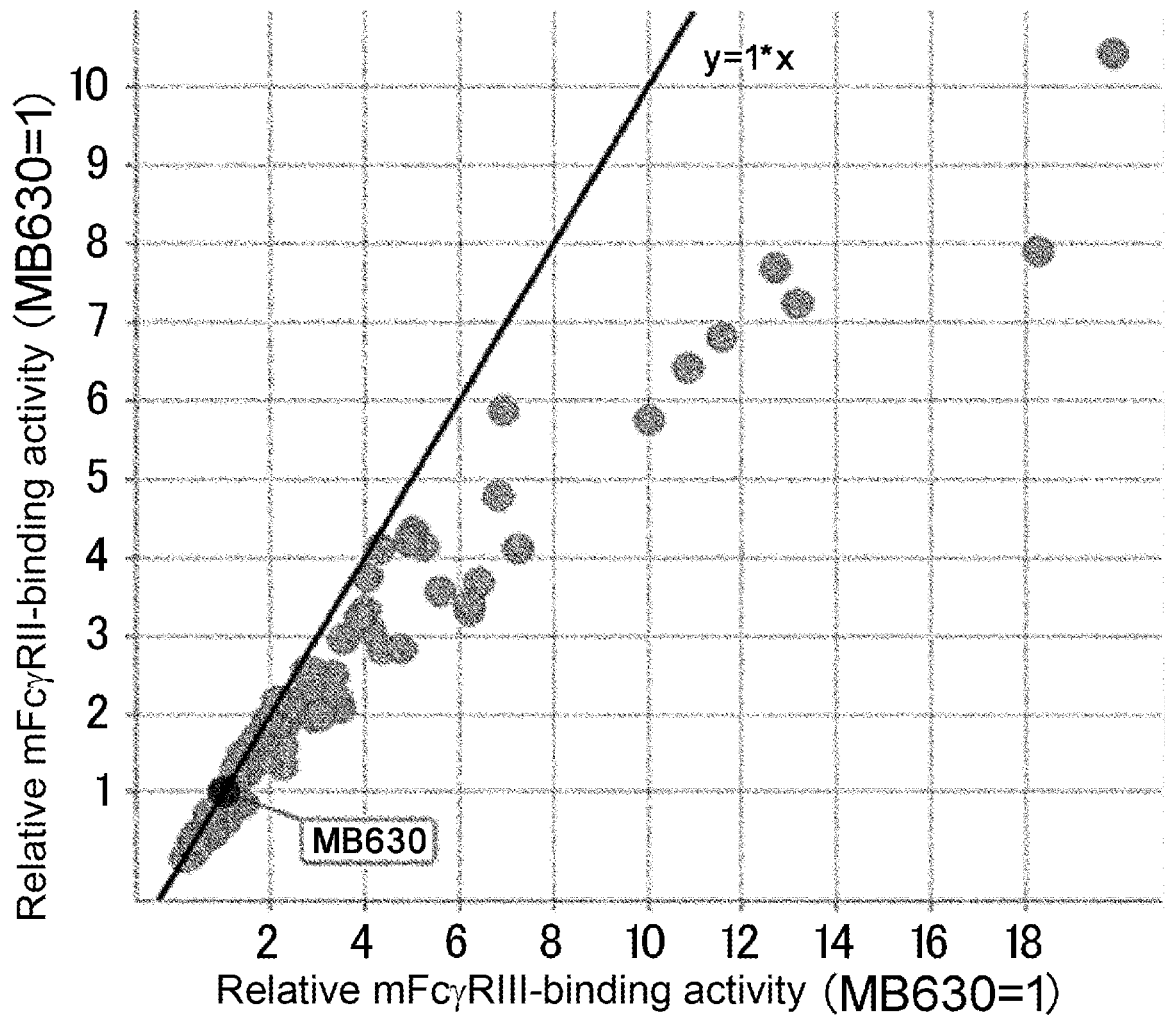

FIG. 16 is a diagram showing the results of comparing binding to mFcγRII and mFcγRIII. Templated H237-MB630/MRAL-k0 was labeled. At the straight line, the degree of enhancement in binding activity against mFcγRII coincides with the degree of enhancement in binding activity against mFcγRIII.

Figure 17:
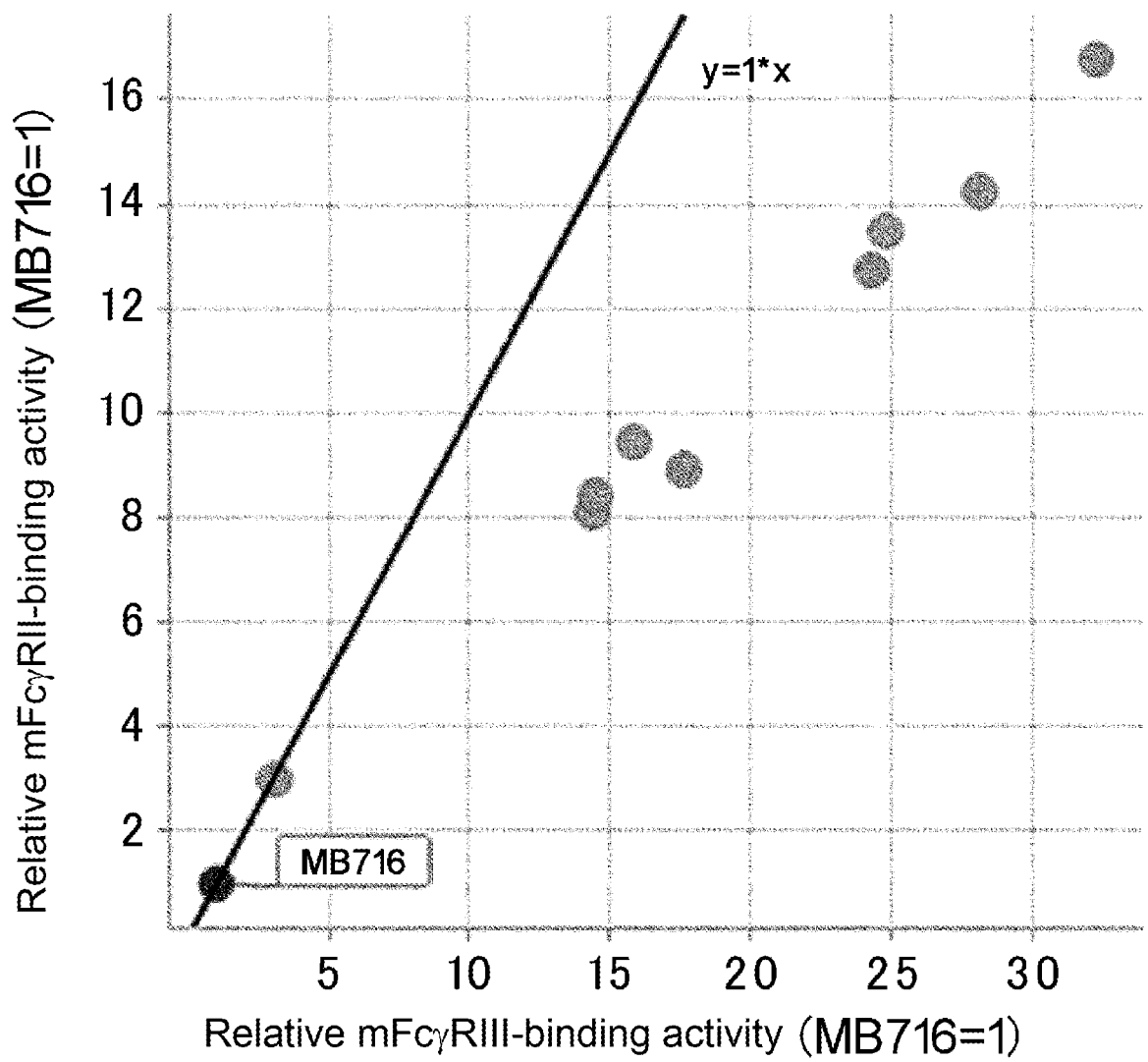

FIG. 17 is a diagram showing the results of comparing binding to mFcγRII and mFcγRIII. Templated H237-MB716/MRAL-k0 was labeled. At the straight line, the degree of enhancement in binding activity against mFcγRII coincides with the degree of enhancement in binding activity against mFcγRIII.

Figure 18:
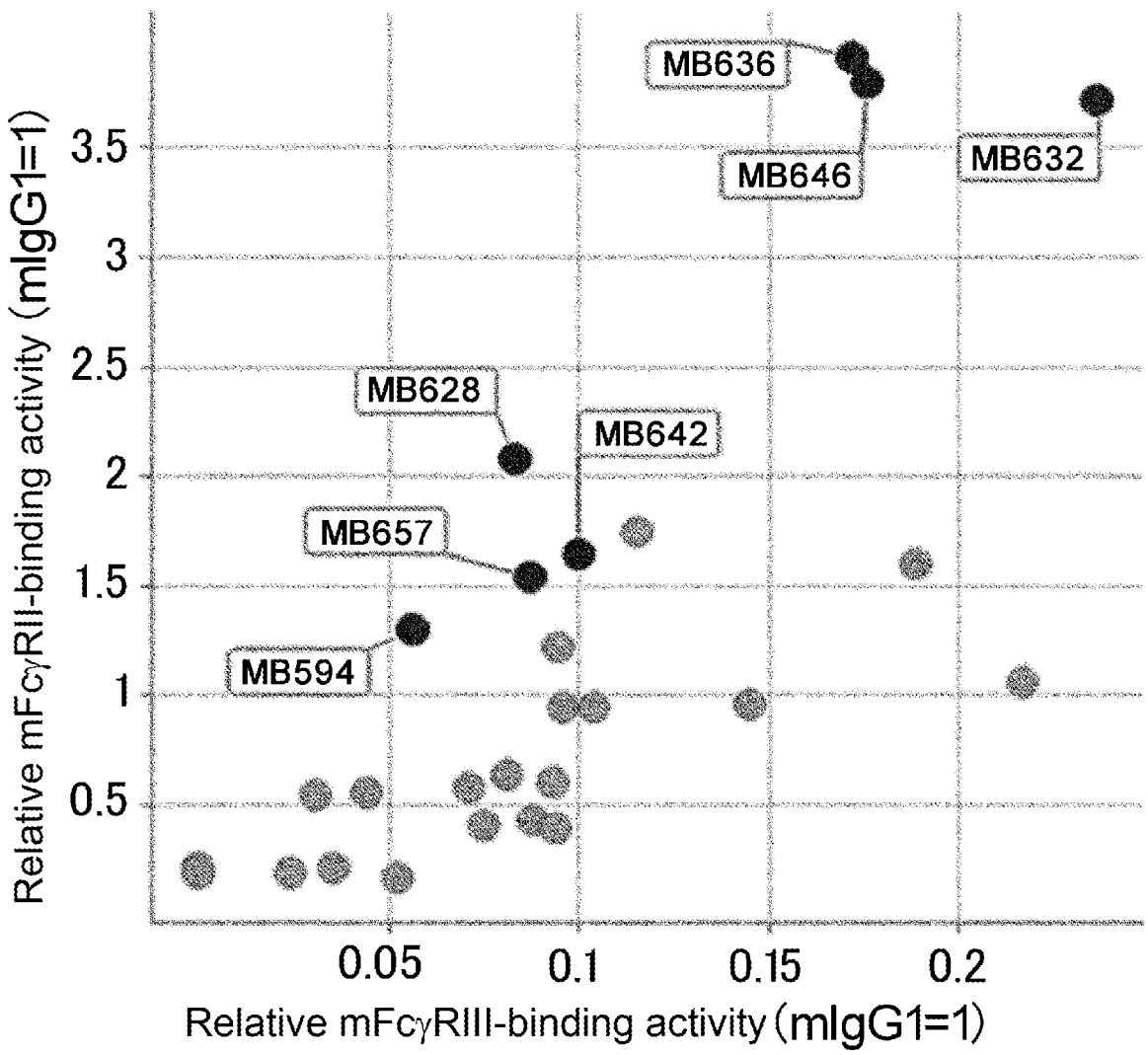

FIG. 18 is a diagram showing the results of comparing binding to mFcγRII and mFcγRIII. Seven templated variants were labeled.

Figure 19:
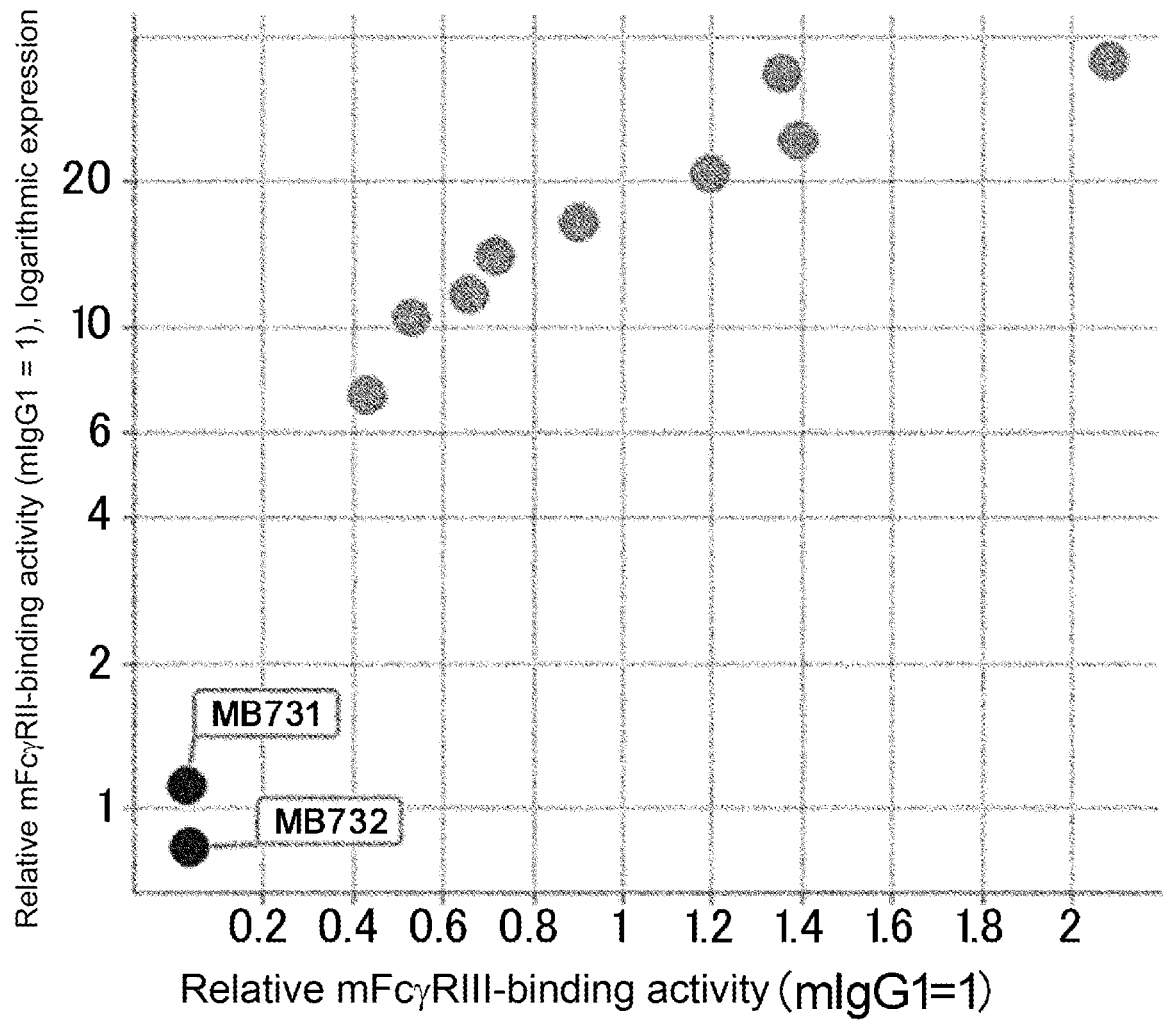

FIG. 19 is a diagram showing the results of comparing binding to mFcγRII and mFcγRIII. Each variant having 0.5-fold or more and 2.0-fold or less relative mFcγRII-binding activity and 5-fold or more relative I/A compared with that of H237-mIgG1/MRAL-k0 was labeled.

Figure 20:
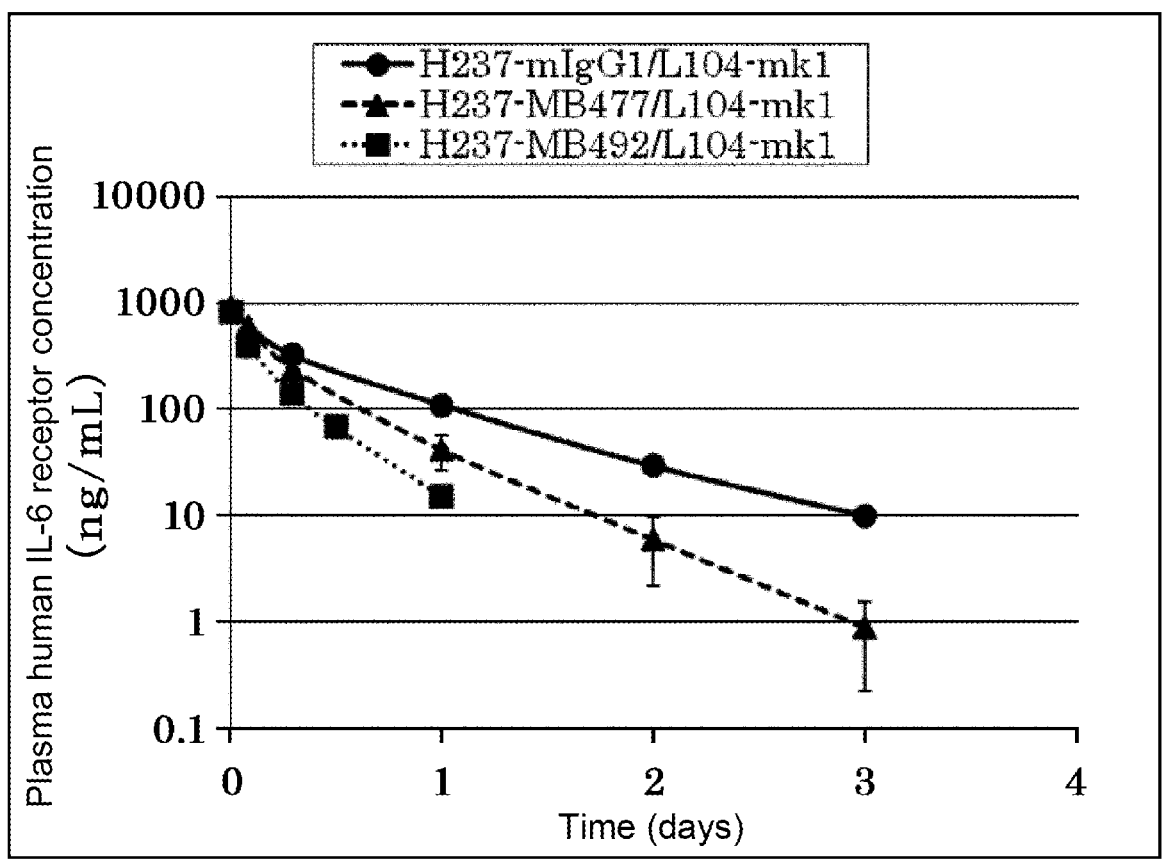

FIG. 20 is a diagram showing time-dependent change in the concentration of an antigen administered simultaneously with each antibody in mouse plasma when H237-mIgG1/L104-mk1, H237-MB477/L104-mk1, or H237-MB492/L104-mk1 was administered to normal mice.

Figure 21:
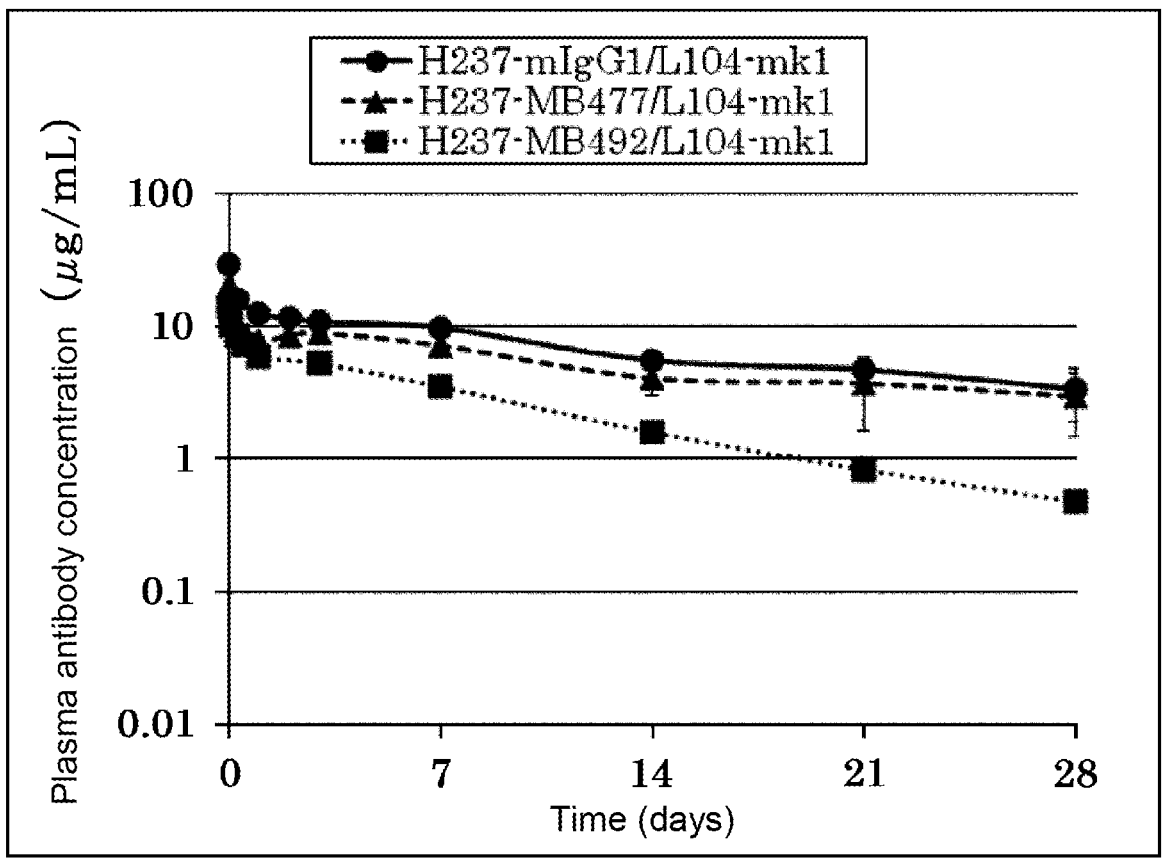

FIG. 21 is a diagram showing time-dependent change in the concentration of each administered antibody in mouse plasma when H237-mIgG1/L104-mk1, H237-MB477/L104-mk1, or H237-MB492/L104-mk1 was administered to normal mice.

MODE FOR CARRYING OUT THE INVENTION

The present invention relates to an Fc variant selectively binding to mouse FcγRII relative to mouse FcγRIII.

The present invention provides a polypeptide which is a variant of a parent polypeptide comprising an Fc region, wherein the polypeptide comprises at least one amino acid alteration in the Fc region and has a ratio of [KD value for mouse FcγRIII]/[KD value for mouse FcγRII] of 6 or more. The present invention also provides a polypeptide which is a variant of a parent polypeptide comprising an Fc region, wherein the polypeptide comprises at least one amino acid alteration in the Fc region and the binding selectivity of the polypeptide for mouse FcγRII relative to mouse FcγRIII is improved by 5 times or more compared with that of the parent polypeptide.

Each polypeptide of the present invention can be prepared by the alteration of appropriate amino acid(s) in the Fc region of the parent polypeptide comprising an Fc region. The position, number, type, etc. of the amino acid alteration are not particularly limited. Any alteration may be acceptable as long as the polypeptide comprising the Fc variant produced by this alteration has the following property: the ratio of [KD value for mouse FcγRIII]/[KD value for mouse FcγRII] is 6 or more; or the binding selectivity of the polypeptide for mouse FcγRII relative to mouse FcγRIII is improved by 5 times or more compared with that of the parent polypeptide.

The selectivity for mouse FcγRII and mouse FcγRIII can be indicated by the ratio between the binding activity against mouse FcγRII and the binding activity against mouse FcγRIII. The binding selectivity for mouse FcγRII relative to mouse FcγRIII is defined as a value determined by dividing [KD value for mouse FcγRIII] by [KD value for mouse FcγRII] (in the present specification, also referred to as I/A). In this case, a larger value thereof means higher selectivity for mouse FcγRII, whereas a smaller value thereof means lower selectivity for mouse FcγRII. I/A of the parent polypeptide and I/A of the altered polypeptide are each calculated. When I/A of the parent polypeptide is defined as 1, I/A of the altered polypeptide (in the present specification, also referred to as relative I/A) is determined. Relative I/A exceeding 1 means that the alteration has improved the selectivity for mouse FcγRII. Relative I/A below 1 means that the alteration has reduced the selectivity for mouse FcγRII.

In the polypeptide of the present invention, the ratio of [KD value for mouse FcγRIII]/[KD value for mouse FcγRII] is 6 or more, preferably 10 or more, 15 or more, 20 or more, 25 or more, or 30 or more, more preferably 35 or more, 40 or more, 50 or more, 60 or more, 70 or more, 80 or more, or 90 or more. The binding selectivity of the polypeptide of the present invention for mouse FcγRII relative to mouse FcγRIII is improved by 5 times or more, preferably 10 times or more, 15 times or more, 20 times or more, 25 times or more, or 30 times or more, more preferably 35 times or more, 40 times or more, 50 times or more, 60 times or more, 70 times or more, 80 times or more, or 90 times or more, compared with that of the parent polypeptide.

One example of the preferred properties possessed by the polypeptide of the present invention can include the property of strongly binding to mouse FcγRII. Specifically, the polypeptide of the present invention preferably has the following property:
the KD value for mouse FcγRII is 20 nM or smaller; or
the binding activity of the polypeptide against mouse FcγRII is enhanced by 10 times or more compared with that of the parent polypeptide.

The KD value of the polypeptide of the present invention for mouse FcγRII is 20 nM or smaller, preferably 10 nM or smaller, 4 nM or smaller, or 2 nM or smaller, more preferably 1.5 nM or smaller, 1 nM or smaller, 0.7 nM or smaller, or 0.5 nM or smaller. Also, the binding activity of the polypeptide of the present invention against mouse FcγRII is enhanced by 10 times or more, preferably 20 times or more, 50 times or more, or 100 times or more, more preferably 150 times or more, 200 times or more, 300 times or more, or 400 times or more, compared with that of the parent polypeptide.

As mentioned later, an amount bound can also be used as an index instead of the KD value. Specifically, in the present specification, the binding activity against mouse FcγRII may be interchanged with an amount bound to mouse FcγRII, and the binding activity against mouse FcγRIII may be interchanged with an amount bound to mouse FcγRIII.

Examples of the amino acid alteration that can confer the property as mentioned above include the alteration of an amino acid at EU numbering position 230, the alteration of an amino acid at EU numbering position 231, the alteration of an amino acid at EU numbering position 232, the alteration of an amino acid at EU numbering position 238, the alteration of an amino acid at EU numbering position 239, the alteration of an amino acid at EU numbering position 240, the alteration of an amino acid at EU numbering position 241, the alteration of an amino acid at EU numbering position 266, the alteration of an amino acid at EU numbering position 267, the alteration of an amino acid at EU numbering position 268, the alteration of an amino acid at EU numbering position 271, the alteration of an amino acid at EU numbering position 295, the alteration of an amino acid at EU numbering position 296, the alteration of an amino acid at EU numbering position 298, the alteration of an amino acid at EU numbering position 324, the alteration of an amino acid at EU numbering position 326, the alteration of an amino acid at EU numbering position 327, the alteration of an amino acid at EU numbering position 330, the alteration of an amino acid at EU numbering position 331, the alteration of an amino acid at EU numbering position 333, the alteration of an amino acid at EU numbering position 334, the alteration of an amino acid at EU numbering position 335, and the alteration of an amino acid at EU numbering position 337. One of these amino acid alterations may be carried out, or two or more thereof may be combined.

Examples of a further preferred amino acid alteration include an alteration that substitutes an amino acid at EU numbering position 230 by Asp, Glu, Ile, Pro, Gln, or Val, an alteration that substitutes an amino acid at EU numbering position 231 by Ala, Asp, Glu, Ile, Leu, Met, Asn, Pro, Gln, Thr, or Trp, an alteration that substitutes an amino acid at EU numbering position 232 by Ala, Asp, Glu, Phe, Leu, Asn, Val, Trp, or Tyr, an alteration that substitutes an amino acid at EU numbering position 238 by Glu, Pro, or Gln, an alteration that substitutes an amino acid at EU numbering position 239 by Ala, Asp, Glu, Phe, Gly, His, Ile, Leu, Met, Asn, Pro, Gln, Arg, Thr, Val, Trp, or Tyr, an alteration that substitutes an amino acid at EU numbering position 240 by Glu, His, Gln, or Trp, an alteration that substitutes an amino acid at EU numbering position 241 by Trp or Tyr, an alteration that substitutes an amino acid at EU numbering position 266 by Leu, an alteration that substitutes an amino acid at EU numbering position 267 by Ala or Glu, an alteration that substitutes an amino acid at EU numbering position 268 by Asp, an alteration that substitutes an amino acid at EU numbering position 271 by Leu, an alteration that substitutes an amino acid at EU numbering position 295 by Leu, an alteration that substitutes an amino acid at EU numbering position 296 by Glu, Asn, Thr, or Trp, an alteration that substitutes an amino acid at EU numbering position 298 by Leu or Met, an alteration that substitutes an amino acid at EU numbering position 324 by Asp, Leu, or Met, an alteration that substitutes an amino acid at EU numbering position 326 by Asp, an alteration that substitutes an amino acid at EU numbering position 327 by Gly, an alteration that substitutes an amino acid at EU numbering position 330 by Gly, Lys, or Gln, an alteration that substitutes an amino acid at EU numbering position 331 by Asp, Phe, or Tyr, an alteration that substitutes an amino acid at EU numbering position 333 by Asn, Val, or Tyr, an alteration that substitutes an amino acid at EU numbering position 334 by Arg, an alteration that substitutes an amino acid at EU numbering position 335 by Asn or Tyr, and an alteration that substitutes an amino acid at EU numbering position 337 by Ile, Lys, or Trp. One of these alterations may be carried out, or two or more thereof may be combined. Preferred examples of such alterations include alterations described in Tables 2 to 17, 24, and 25.

The present invention encompasses a polypeptide which is a variant of a parent polypeptide comprising a mouse Fc region, wherein the polypeptide comprises particular amino acid alteration(s) in the Fc region. Examples of such amino acid alterations include an alteration that substitutes an amino acid at position 230 by Asp, Glu, Ile, Pro, Gln, or Val, an alteration that substitutes an amino acid at position 231 by Ala, Asp, Glu, Ile, Leu, Met, Asn, Pro, Gln, Thr, or Trp, an alteration that substitutes an amino acid at position 232 by Ala, Asp, Glu, Phe, Leu, Asn, Val, Trp, or Tyr, an alteration that substitutes an amino acid at position 238 by Glu, Pro, or Gln, an alteration that substitutes an amino acid at position 239 by Ala, Phe, Gly, His, Ile, Leu, Met, Asn, Pro, Gln, Arg, Thr, Val, Trp, or Tyr, an alteration that substitutes an amino acid at position 240 by Glu, His, Gln, or Trp, an alteration that substitutes an amino acid at position 241 by Trp or Tyr, an alteration that substitutes an amino acid at position 266 by Leu, an alteration that substitutes an amino acid at position 267 by Glu, an alteration that substitutes an amino acid at position 268 by Asp, an alteration that substitutes an amino acid at position 271 by Leu, an alteration that substitutes an amino acid at position 295 by Leu, an alteration that substitutes an amino acid at position 296 by Glu, Asn, Thr, or Trp, an alteration that substitutes an amino acid at position 298 by Leu or Met, an alteration that substitutes an amino acid at position 324 by Asp, Leu, or Met, an alteration that substitutes an amino acid at position 326 by Asp, an alteration that substitutes an amino acid at position 327 by Gly, an alteration that substitutes an amino acid at position 330 by Gly, Lys, or Gln, an alteration that substitutes an amino acid at position 331 by Asp, Phe, or Tyr, an alteration that substitutes an amino acid at position 333 by Asn, Val, or Tyr, an alteration that substitutes an amino acid at position 334 by Arg, an alteration that substitutes an amino acid at position 335 by Asn or Tyr, and an alteration that substitutes an amino acid at position 337 by Ile, Lys, or Trp (wherein all positions are indicated by EU numbering). One of these alterations may be carried out, or two or more thereof may be combined.

The polypeptide may further comprise different amino acid alteration(s) in addition to these amino acid alterations. Such amino acid alteration(s) is preferably, for example, an alteration that substitutes an amino acid at EU numbering position 239 by Asp or Glu and/or an alteration that substitutes an amino acid at EU numbering position 267 by Ala. One of these alterations may be carried out, or two or more thereof may be combined. Preferred examples of such alterations include alterations described in Tables 2 to 17, 24, and 25. The resulting polypeptides are useful in terms of having the feature to selectively bind to mouse FcγRII relative to mouse FcγRIII.

Another example of the preferred properties of the polypeptide of the present invention can include the property of weakly binding to mouse FcγRIII. Specifically, the polypeptide of the present invention preferably has the following property:

the KD value for mouse FcγRIII is 1 μM or larger; or
the binding activity of the polypeptide against mouse FcγRIII is reduced to 0.25 times or less that of the parent polypeptide.

The KD value of the polypeptide of the present invention for mouse FcγRIII is 1 μM or larger, preferably 1.2 μM or larger, 1.5 μM or larger, or 2 μM or larger, more preferably 2.5 μM or larger, 3 μM or larger, 4 μM or larger, or 5 μM or larger. Also, the binding activity of the polypeptide of the present invention against mouse FcγRIII is reduced to 0.25 times or less, preferably 0.20 times or less, 0.18 times or less, 0.16 times or less, or 0.14 times or less, more preferably 0.12 times or less, 0.10 times or less, 0.08 times or less, or 0.06 times or less that of the parent polypeptide.

As mentioned later, an amount bound can also be used as an index instead of the KD value. Specifically, in the present specification, the binding activity against mouse FcγRII may be interchanged with an amount bound to mouse FcγRII, and the binding activity against mouse FcγRIII may be interchanged with an amount bound to mouse FcγRIII.

Examples of the amino acid alteration that can confer the property as mentioned above include the alteration of an amino acid at EU numbering position 230, the alteration of an amino acid at EU numbering position 231, the alteration of an amino acid at EU numbering position 232, the alteration of an amino acid at EU numbering position 237, the alteration of an amino acid at EU numbering position 238, the alteration of an amino acid at EU numbering position 239, the alteration of an amino acid at EU numbering position 241, the alteration of an amino acid at EU numbering position 267, and the alteration of an amino acid at EU numbering position 298. One of these amino acid alterations may be carried out, or two or more thereof may be combined.

Examples of a further preferred amino acid alteration include an alteration that substitutes an amino acid at EU numbering position 230 by Glu, Ile, or Gln, an alteration that substitutes an amino acid at EU numbering position 231 by Ala, Asp, Asn, Pro, or Thr, an alteration that substitutes an amino acid at EU numbering position 232 by Ala, Lys, Asn, or Tyr, an alteration that substitutes an amino acid at EU numbering position 237 by Glu, an alteration that substitutes an amino acid at EU numbering position 238 by Asp or Glu, an alteration that substitutes an amino acid at EU numbering position 239 by Asp, Glu, Phe, Lys, Leu, Asn, Trp, or Tyr, an alteration that substitutes an amino acid at EU numbering position 241 by Asp, Glu, or Thr, an alteration that substitutes an amino acid at EU numbering position 267 by Met, and an alteration that substitutes an amino acid at EU numbering position 298 by His. One of these alterations may be carried out, or two or more thereof may be combined. Preferred examples of such alterations include alterations described in Tables 18 to 23, 26, and 27.

The present invention encompasses a polypeptide which is a variant of a parent polypeptide comprising a mouse Fc region, wherein the polypeptide comprises particular amino acid alteration(s) in the Fc region. Examples of such amino acid alterations include an alteration that substitutes an amino acid at position 230 by Glu, Ile, or Gln, an alteration that substitutes an amino acid at position 231 by Ala, Asp, Asn, Pro, or Thr, an alteration that substitutes an amino acid at position 232 by Ala, Lys, Asn, or Tyr, an alteration that substitutes an amino acid at position 237 by Glu, an alteration that substitutes an amino acid at position 238 by Asp or Glu, an alteration that substitutes an amino acid at position 239 by Phe, Lys, Leu, Asn, Trp, or Tyr, an alteration that substitutes an amino acid at position 241 by Asp, Glu, or Thr, an alteration that substitutes an amino acid at position 266 by Leu, an alteration that substitutes an amino acid at position 267 by Met, and an alteration that substitutes an amino acid at position 298 by His (wherein all positions are indicated by EU numbering). One of these alterations may be carried out, or two or more thereof may be combined.

The polypeptide may further comprise different amino acid alteration(s) in addition to these amino acid alterations. Such amino acid alteration(s) is preferably, for example, an alteration that substitutes an amino acid at EU numbering position 239 by Asp or Glu. One of these alterations may be carried out, or two or more thereof may be combined. Preferred examples of such alterations include alterations described in Tables 18 to 23, 26, and 27. The resulting polypeptides are useful in terms of having the feature to selectively bind to mouse FcγRII relative to mouse FcγRIII.

A further example of the preferred properties of the polypeptide of the present invention can include the property of binding to mouse FcγRII with strength equivalent to or higher than that of the parent polypeptide and binding to mouse FcγRIII more weakly compared with the parent polypeptide. Specifically, the polypeptide of the present invention preferably has the following property:
the KD value for mouse FcγRII is 400 nM or smaller, and the KD value for mouse FcγRIII is 1 μM or larger; or
the binding activity of the polypeptide against mouse FcγRII is 0.5 times or more that of the parent polypeptide, and the binding activity of the polypeptide against mouse FcγRIII is 0.25 times or less that of the parent polypeptide.

The KD value of the polypeptide of the present invention for mouse FcγRII is 400 nM or smaller, preferably 360 nM or smaller, 320 nM or smaller, or 280 nM or smaller, more preferably 250 nM or smaller, 200 nM or smaller, 150 nM or smaller, or 100 nM or smaller, and the KD value of the polypeptide of the present invention for mouse FcγRIII is 1 μM or larger, preferably 1.2 μM or larger, 1.5 μM or larger, or 2 μM or larger, more preferably 2.5 μM or larger, 3 μM or larger, 4 μM or larger, or 5 μM or larger. Also, the binding activity of the polypeptide of the present invention against mouse FcγRII is 0.5 times or more, preferably 0.6 times or more, 0.75 times or more, or 1.0 times or more, more preferably 1.5 times or more, 2 times or more, 2.5 times or more, or 3 times or more that of the parent polypeptide, and the binding activity of the polypeptide of the present invention against mouse FcγRIII is 0.25 times or less, preferably 0.20 times or less, 0.18 times or less, 0.16 times or less, or 0.14 times or less, more preferably 0.12 times or less, 0.10 times or less, 0.08 times or less, or 0.06 times or less that of the parent polypeptide.

As mentioned later, an amount bound can also be used as an index instead of the KD value. Specifically, in the present specification, the binding activity against mouse FcγRII may be interchanged with an amount bound to mouse FcγRII, and the binding activity against mouse FcγRIII may be interchanged with an amount bound to mouse FcγRIII.

The polypeptide according to the present invention refers to a peptide having a plurality of amino acids, or a protein. The polypeptide may be a polypeptide consisting of an organism-derived sequence or may be a polypeptide consisting of an artificially designed sequence. Alternatively, a natural polypeptide, a synthetic polypeptide, a recombinant polypeptide, or the like may be used.

The Fcγ receptor (in the present specification, also referred to as an Fcγ receptor, FcγR, or FcgR) refers to a receptor capable of binding to the Fc region of an IgG subclass monoclonal antibody and means any member of the protein family substantially encoded by Fcγ receptor genes. The human Fcγ receptor refers to a receptor capable of binding to the Fc region of a human IgG1, IgG2, IgG3, or IgG4 monoclonal antibody. This family includes, but not limited to: FcγRI (CD64) including isoforms FcγRIa, FcγRIb, and FcγRIc; FcγRII (CD32) including isoforms FcγRIIa (including allotypes H131 (H type) and R131 (R type)), FcγRIIb (including FcγRIIb-1 and FcγRIIb-2), and FcγRIIc; and FcγRIII (CD16) including isoforms FcγRIIIa (including allotypes V158 and F158) and FcγRIIIb (including allotypes FcγRIIIb-NA1 and FcγRIIIb-NA2); and any yet-to-be-discovered human FcγR member or FcγR isoform or allotype. Preferred examples of the human Fcγ receptor include human FcγRI (CD64), FcγRIIA (CD32), FcγRIIB (CD32), FcγRIIIA (CD16), and FcγRIIIB (CD16). The mouse FcγR refers to a receptor capable of binding to the Fc region of a mouse IgG1, IgG2a, IgG2b, or IgG3 monoclonal antibody and means any member of the protein family substantially encoded by Fcγ receptor genes. The mouse FcγR family includes, but not limited to, FcγRI (CD64), FcγRII (CD32), FcγRIII (CD16), and FcγRIII-2 (CD16-2 or FcγRIV), and any yet-to-be-discovered mouse FcγR member or FcγR isoform or allotype. Preferred examples of the mouse Fcγ receptor include mouse FcγRI (CD64), FcγRII (CD32), FcγRIII (CD16), and FcγRIII-2 (CD16-2 or FcγRIV). The FcγR includes those derived from humans, mice, rats, rabbits, and monkeys. The FcγR is not limited to them and may be derived from any organism.

The polynucleotide sequence and amino acid sequence of human FcγRI are described in SEQ ID NOs: 10 (NM_000566.3) and 11 (NP_000557.1), respectively;
the polynucleotide sequence and amino acid sequence of human FcγRIIA are described in SEQ ID NOs: 12 (BC020823.1) and 13 (AAH20823.1), respectively;
the polynucleotide sequence and amino acid sequence of human FcγRIIB are described in SEQ ID NOs: 14 (BC146678.1) and 15 (AAI46679.1), respectively;
the polynucleotide sequence and amino acid sequence of human FcγRIIIA are described in SEQ ID NOs: 16 (BC033678.1) and 17 (AAH33678.1), respectively; and
the polynucleotide sequence and amino acid sequence of human FcγRIIIB are described in SEQ ID NOs: 18 (BC128562.1) and 19 (AAI28563.1), respectively (RefSeq registration numbers are shown in parentheses).

Human FcγRIIa has two types of gene polymorphisms that substitute the 131st amino acid of FcγRIIa by histidine (H type) or arginine (R type) (J Exp Med, 172, 19-25, 1990).

FcγRIIb1 and FcγRIIb2 have been reported as splicing variants of human FcγRIIb. In addition, a splicing variant called FcγRIIb3 has also been reported (J. Exp. Med, 1989, 170: 1369). The human FcγRIIb includes, in addition to these splicing variants, all of splicing variants registered in NCBI under NP_001002273.1, NP_001002274.1, NP_001002275.1, NP_001177757.1, and NP_003992.3. Also, the human FcγRIIb includes every previously reported gene polymorphism and also includes FcγRIIb (Arthritis Rheum, 2003, 48: 3242-52; Hum Mol Genet, 2005, 14: 2881-92; and Arthritis Rheum. 2002 May; 46 (5): 1242-54) and every gene polymorphism that may be reported in the future.

The polynucleotide sequence and amino acid sequence of mouse FcγRI are described in SEQ ID NOs: 33 (NM_010186.5) and 20 (NP_034316.1), respectively;
the polynucleotide sequence and amino acid sequence of mouse FcγRII are described in SEQ ID NOs: 34 (NM_010187.2) and 21 (NP_034317.1), respectively;
the polynucleotide sequence and amino acid sequence of mouse FcγRIII are described in SEQ ID NOs: 35 (NM_010188.5) and 22 (NP_034318.2), respectively; and
the polynucleotide sequence and amino acid sequence of mouse FcγRIV are described in SEQ ID NOs: 36 (NM_144559.2) and 23 (NP_653142.2), respectively (NCBI Reference Sequence registration numbers are shown in parentheses).

FcγRIIb1 and FcγRIIb2 have been reported as splicing variants of mouse FcγRII and registered under GenBank accession Nos. M16367 and X04648, respectively. Other splicing variants have been reported in J. Immunol, 1996, 157: 189 and J. Immunol, 1996, 157: 4707. These splicing variants are also included in the mouse FcγRII. The mouse FcγRII includes every previously reported gene polymorphism and also includes every gene polymorphism that may be reported in the future.

As also shown later in Examples, mouse FcγR having the highest sequence identity to mouse FcγRII is mouse FcγRIII (sequence identity of their extracellular regions: 93%). Mouse IgG1 exhibits binding only to mouse FcγRII and FcγRIII among 4 types of mouse Fcγ receptors, without binding to mouse FcγRI and FcγRIV (Science, 310, 1510-1512, 2005). From such viewpoints, desirably, the Fc variant selectively binding to mouse FcγRII has higher binding activity against FcγRII and lower binding activity against FcγRIII than those of the Fc region of naturally occurring IgG. In the present specification, the Fc variant selectively binding to mouse FcγRII relative to mouse FcγRIII means an Fc region in which a value of the Fc region determined by dividing [KD value for mouse FcγRIII] by [KD value for mouse FcγRII] is larger than a value of the Fc region of naturally occurring mouse IgG determined by dividing [KD value for mouse FcγRIII] by [KD value for mouse FcγRII].

The naturally occurring IgG means a polypeptide that contains an amino acid sequence identical to that of IgG found in nature and belongs to a class of an antibody substantially encoded by an immunoglobulin gamma gene. For example, the naturally occurring mouse IgG means naturally occurring mouse IgG1, naturally occurring mouse IgG2a, naturally occurring mouse IgG2b, naturally occurring mouse IgG3, or the like. The naturally occurring human IgG means naturally occurring human IgG1, naturally occurring human IgG2, naturally occurring human IgG3, naturally occurring human IgG4, or the like. The naturally occurring IgG also includes variants or the like spontaneously derived therefrom.

Figure 4:
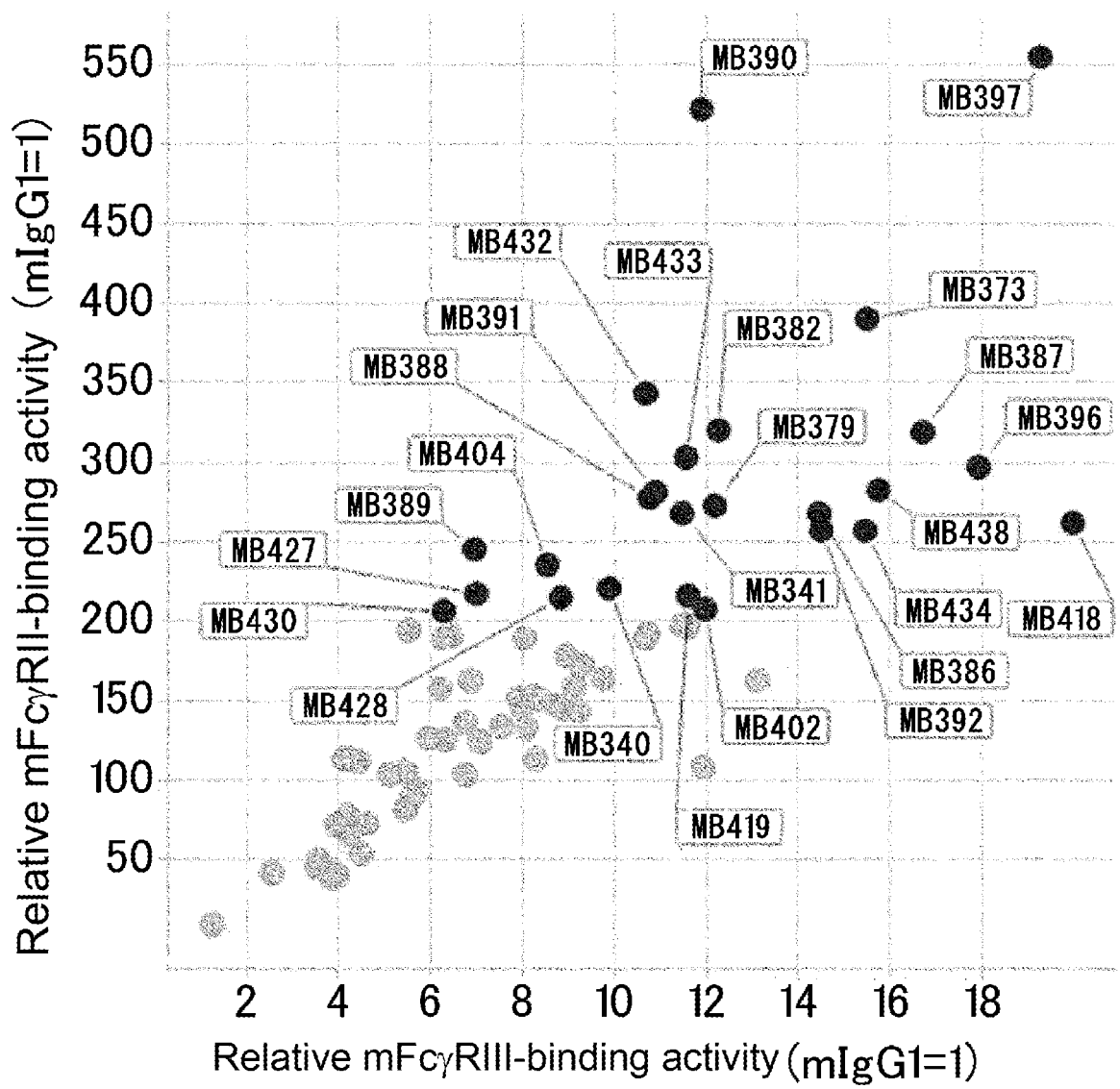
Figure 12:
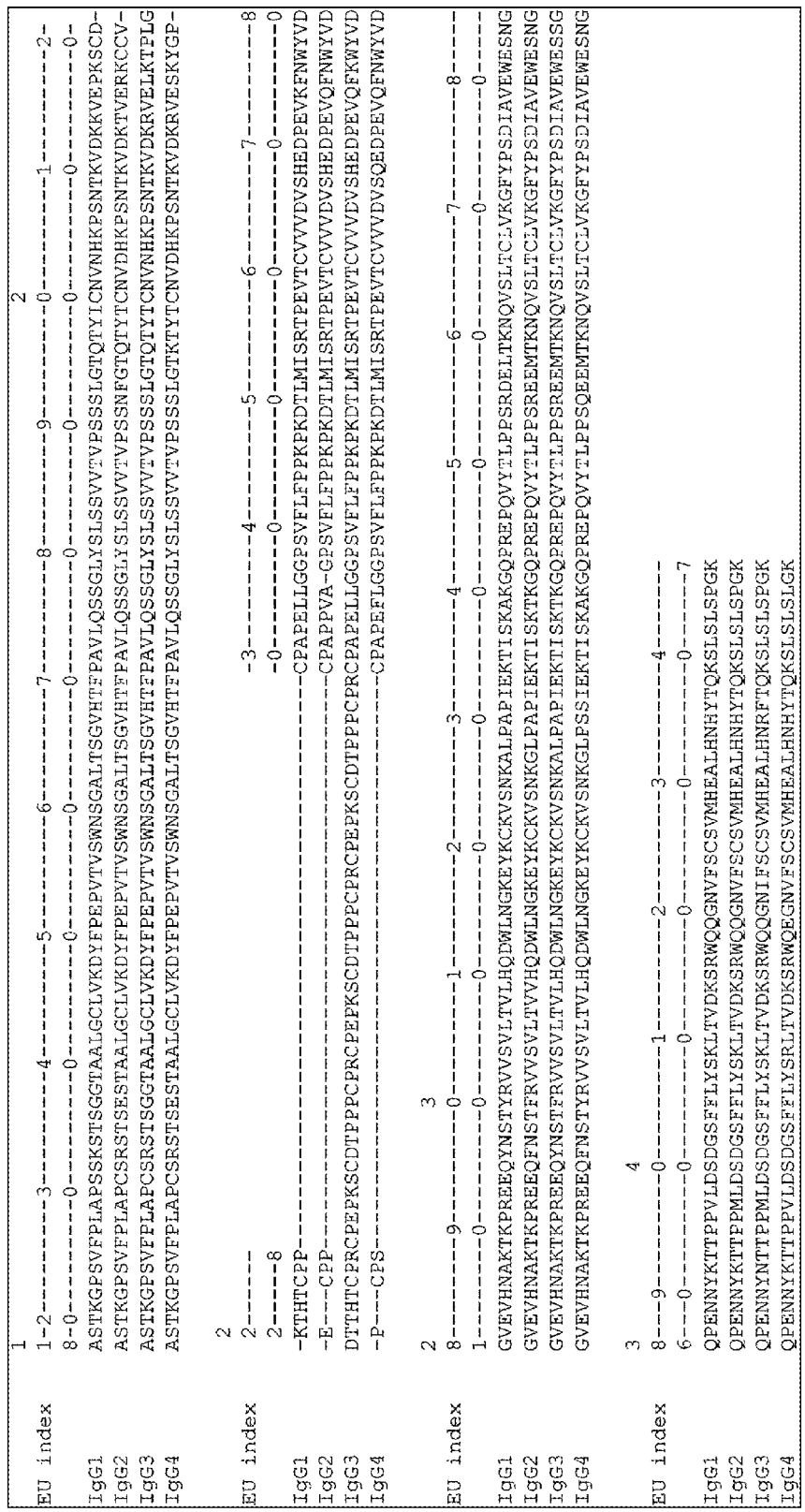

The heavy chain constant region of naturally occurring IgG means a heavy chain constant region containing an amino acid sequence identical to that of a heavy chain constant region originated from IgG found in nature. For example, the heavy chain constant region originated from naturally occurring mouse IgG means a heavy chain constant region originated from naturally occurring mouse IgG1, a heavy chain constant region originated from naturally occurring mouse IgG2a, a heavy chain constant region originated from naturally occurring mouse IgG2b, or a heavy chain constant region originated from naturally occurring mouse IgG3. The heavy chain constant region originated from naturally occurring human IgG means a heavy chain constant region originated from naturally occurring human IgG1, a heavy chain constant region originated from naturally occurring human IgG2, a heavy chain constant region originated from naturally occurring human IgG3, or a heavy chain constant region originated from naturally occurring human IgG4. The heavy chain constant region of naturally occurring IgG also includes variants or the like spontaneously derived therefrom. The heavy chain constant region of naturally occurring mouse IgG is shown in FIGS. 11-1 to 11-4 (SEQ ID NOs: 24 to 27), and the heavy chain constant region of naturally occurring human IgG is shown in FIG. 12 (SEQ ID NOs: 28 to 31). The heavy chain constant region of naturally occurring IgG also includes every previously reported gene polymorphism and every gene polymorphism that may be reported in the future. For example, a heavy chain constant region consisting of the amino acid sequence represented by SEQ ID NO: 24 is known as the heavy chain constant region of naturally occurring mouse IgG1. The naturally occurring mouse IgG1 also includes all of gene polymorphisms registered under, for example, GenBank accession Nos. J00453 and J35252. In the present invention, amino acid residues at main positions to be altered are common among all of these gene polymorphisms. The present invention is therefore effective even for these gene polymorphisms.

The Fc region refers to a region comprising hinges or a portion thereof and CH2 and CH3 domains in an antibody molecule. The Fc region of IgG class means, but not limited to, a region from, for example, cysteine 226 (EU numbering (in the present specification, also referred to as EU INDEX)) (see FIGS. 11-1 to 11-4 and FIG. 12) to the C terminus or from proline 230 (EU numbering) to the C terminus.

The Fc region of naturally occurring IgG means an Fc region containing an amino acid sequence identical to that of an Fc region originated from IgG found in nature. For example, the Fc region originated from naturally occurring mouse IgG means an Fc region originated from naturally occurring mouse IgG1, an Fc region originated from naturally occurring mouse IgG2a, an Fc region originated from naturally occurring mouse IgG2b, or an Fc region originated from naturally occurring mouse IgG3. The Fc region originated from naturally occurring human IgG means an Fc region originated from naturally occurring human IgG1, an Fc region originated from naturally occurring human IgG2, an Fc region originated from naturally occurring human IgG3, or an Fc region originated from naturally occurring human IgG4. The Fc region of naturally occurring IgG also includes variants or the like spontaneously derived therefrom. The Fc region of naturally occurring mouse IgG is shown as a partial sequence of FIGS. 11-1 to 11-4 (SEQ ID NOs: 24 to 27), and the Fc region of naturally occurring human IgG is shown as a partial sequence of FIG. 12 (SEQ ID NOs: 28 to 31).

The Fc region can be preferably obtained by the partial digestion of, for example, an IgG monoclonal antibody with a proteolytic enzyme such as pepsin followed by re-elution of a fraction adsorbed on a protein A or protein G column. Such a proteolytic enzyme is not particularly limited as long as the enzyme is capable of digesting a whole antibody to restrictively form Fab or F(ab')2 under appropriately set reaction conditions (e.g., pH) of the enzyme. Examples thereof can include pepsin and papain.

In the present specification, the "parent polypeptide" means a polypeptide that forms the basis for the preparation of the polypeptide of the present invention. Specifically, the parent polypeptide means a polypeptide comprising an Fc region before addition of amino acid alteration(s) to the Fc region. An exemplary parent polypeptide according to the present invention is preferably a polypeptide comprising the Fc region of an antibody (IgA, IgD, IgE, IgG, or IgM), particularly, IgG, more preferably a polypeptide comprising the Fc region of mouse or human IgG, particularly preferably a polypeptide comprising the Fc region of mouse IgG1. The parent polypeptide may be a polypeptide comprising the Fc region of naturally occurring IgG or may be a polypeptide comprising an Fc variant derived from the Fc region of naturally occurring IgG by the addition of alteration(s) other than the amino acid alteration of the present invention.

The Fc region of the present invention is not limited as long as the Fc region is of an antibody (IgA, IgD, IgE, IgG, or IgM), particularly, IgG. The Fc region of the present invention is preferably the Fc region of mouse IgG (IgG1, IgG2a, IgG2b, or IgG3) or human IgG (IgG1, IgG2, IgG3, or IgG4), more preferably the Fc region of mouse IgG1. The amino acid sequences of the mouse and human IgG Fc regions are known in the art as shown in FIGS. 11-1 to 11-4 (SEQ ID NOs: 24 to 27) and FIG. 12 (SEQ ID NOs: 28 to 31).

The polypeptide of the present invention is not particularly limited as long as the polypeptide comprises the Fc region. Preferably, the polypeptide of the present invention comprises an antigen-binding region (variable regions, Fab, F(ab')2, Fv, CDRs, etc.) and the Fc region. The polypeptide of the present invention is particularly preferably an antibody (IgA, IgD, IgE, IgG, or IgM). Preferred examples of the antibody can include IgG, particularly, mouse IgG (IgG1, IgG2a, IgG2b, or IgG3) and human IgG (IgG1, IgG2, IgG3, or IgG4). The antibody is more preferably mouse IgG1. The amino acid sequences of the mouse and human IgG heavy chain constant regions are known in the art as shown in FIGS. 11-1 to 11-4 (SEQ ID NOs: 24 to 27) and FIG. 12 (SEQ ID NOs: 28 to 31).

Alternatively, the polypeptide of the present invention is preferably an Fc fusion protein. Examples of the protein to be fused include, but not limited to, biologically active peptides, adhesion molecules, ligands/receptors, and enzymes. Specific examples thereof include: receptor extracellular regions such as TNFR, IL1R, VEGFR, and CTLA4 (Nat Med 2003, 9 (1), 47-52; and BioDrugs 2006, 20 (3), 151-60); antibody-like molecules such as scFv (WO2005/037989), single-domain antibodies (WO2004/058821 and WO2003/002609), DARPins (WO2002/020565), Affibody (WO1995/001937), Avimer (WO2004/044011 and WO2005/040229), and Adnectin (WO2002/032925) (Current Opinion in Biotechnology 2006, 17, 653-658; Current Opinion in Biotechnology 2007, 18, 1-10; Current Opinion in Structural Biology 1997, 7, 463-469; and Protein Science 2006, 15, 14-27); and self-antigens recognized by autoantibodies, such as acetylcholine receptor, desmoglein 1, desmoglein 3, double-stranded DNA, histidine-tRNA ligase, ribonucleoprotein, snRNP core protein, Ro/SS-A, La/SS-B, centromere, Ri, topoisomerase-1, histone, nucleoporin 62, Sp100 nuclear antigen, nucleoporin 210 kDa, ganglioside GQ1B, ganglioside GD3, ganglioside GM1, actin, thrombin, phospholipid, neutrophil cytoplasmic antigen, neutrophil perinuclear antigen, intracellular enzyme, smooth muscle cell membrane antigen, mitochondria, muscle-specific kinase (MUSK), voltage-gated calcium channel (P/Q-type), iodide peroxidase (microsomal), TSH receptor, Hu, cerebellar Purkinje cells, aminophylline, voltage-gated potassium channel (VGKC), basal ganglion, N-methyl-D-aspartate receptor (NMDA), glutamate decarboxylase (GAD65), amphiphysin, and aquaporin-4. The polypeptide of the present invention may bind to one type of target molecule or epitope as with general antibodies or may bind to plural types of target molecules or epitopes as with multispecific antibodies.

Amino acid substitution for improving binding activity against FcRn (J Immunol 2006 January 1; 176 (1), 346-356; J Biol Chem 2006 Aug. 18; 281(33), 23514-23524; Int Immunol 2006 December; 18 (12), 1759-1769; Nat Biotechnol 2010 February; 28 (2), 157-159; WO2006/019447, WO2006/053301, and WO2009/086320) or amino acid substitution for improving antibody heterogeneity or stability (WO2009/041613) may be added to the polypeptide of the present invention. Alternatively, amino acid substitution for promoting the disappearance of an antigen (WO2011/122011 and PCT/JP2011/072550) or amino acid substitution for allowing the polypeptide of the present invention to repetitively bind to a plurality of antigen molecules (WO2009/125825 and PCT/JP2011/077619) may be added to the polypeptide of the present invention.

The type of the amino acid alteration according to the present invention can be, for example, any of amino acid substitution, deletion, addition, insertion, and modification or a combination thereof and is preferably amino acid substitution.

In the present invention, the term "antibody" is used in the broadest sense and includes any antibody such as monoclonal antibodies (including whole monoclonal antibodies), polyclonal antibodies, antibody variants, antibody fragments, multispecific antibodies (e.g., bispecific antibodies), chimeric antibodies, and humanized antibodies as long as the antibody exhibits the desired biological activity.

The antibody of the present invention is not limited by the type of its antigen, an animal of its origin, etc. and can be any antibody. Examples of the origin of the antibody can include, but not particularly limited to, human antibodies, mouse antibodies, rat antibodies, rabbit antibodies, and monkey antibodies. The antibody of the present invention is preferably a mouse or human antibody, more preferably a mouse antibody.

The antibody can be prepared by a method well known to those skilled in the art. For example, the monoclonal antibodies may be produced by a hybridoma method (Kohler and Milstein, Nature 256, 495 (1975)) or a recombination method (U.S. Pat. No. 4,816,567). Alternatively, the monoclonal antibodies may be isolated from phage-displayed antibody libraries (Clackson et al, Nature 352, 624-628 (1991); and Marks et al, J Mol Biol 222, 581-597 (1991)).

The humanized antibodies are also called reshaped human antibodies. Specifically, for example, a humanized antibody consisting of a nonhuman animal (e.g., mouse) antibody CDR-grafted human antibody is known in the art. General gene recombination approaches are also known for obtaining the humanized antibodies. Specifically, for example, overlap extension PCR is known in the art as a method for grafting mouse antibody CDRs to human FRs.

A DNA encoding an antibody variable region comprising three CDRs and four FRs linked and a human antibody constant region-encoding DNA can be inserted into expression vectors such that these DNAs are fused in frame to prepare vectors for humanized antibody expression. These vectors having the inserts are transferred to hosts to establish recombinant cells. Then, the recombinant cells are cultured for the expression of the humanized antibody-encoding DNA to produce the humanized antibodies into the cultures of the cultured cells (see European Patent Publication No. EP 239400 and International Publication No. WO1996/002576).

If necessary, FR amino acid residue(s) may be substituted such that the CDRs of the reshaped human antibody form an appropriate antigen-binding site. For example, the amino acid sequence of FR can be mutated by the application of the PCR method used in the mouse CDR grafting to the human FRs.

The desired human antibody can be obtained by DNA immunization using transgenic animals having all repertoires of human antibody genes (see International Publication Nos. WO1993/012227, WO1992/003918, WO1994/002602, WO1994/025585, WO1996/034096, and WO1996/033735) as immunized animals.

In addition, a technology of obtaining human antibodies by panning using human antibody libraries is also known. For example, human antibody variable regions are expressed as a single-chain antibody (scFv) on the surface of phages by a phage display method. A phage expressing antigen-binding scFv can be selected. The gene of the selected phage can be analyzed to determine DNA sequences encoding the variable regions of the antigen-binding human antibody. After the determination of the DNA sequence of the antigen-binding scFv, the variable region sequences can be fused in frame with the sequences of the desired human antibody constant regions and then inserted to appropriate expression vectors to prepare expression vectors. The expression vectors are transferred to the preferred expression cells as exemplified above. The human antibody-encoding genes are expressed by the cells to obtain the human antibodies. These methods are already known in the art (see International Publication Nos. WO1992/001047, WO1992/020791, WO1993/006213, WO1993/011236, WO1993/019172, WO1995/001438, and WO1995/015388).

The variable regions constituting the antibody of the present invention can be variable regions that recognize an arbitrary antigen.

In the present specification, the antigen is not particularly limited and can be any antigen. Examples of the antigen preferably include ligands (cytokines, chemokines, etc.), receptors, cancer antigens, MHC antigens, differentiation antigens, immunoglobulins, and immune complexes partially comprising immunoglobulins.

Examples of the cytokines can include interleukins 1 to 18, colony-stimulating factors (G-CSF, M-CSF, GM-CSF, etc.), interferons (IFN-$\alpha$, IFN-$\beta$, IFN-$\gamma$, etc.), growth factors (EGF, FGF, IGF, NGF, PDGF, TGF, HGF, etc.), tumor necrosis factors (TNF-$\alpha$ and TNF-$\beta$), lymphotoxin, erythropoietin, leptin, SCF, TPO, MCAF, and BMP.

Examples of the chemokines can include: CC chemokines such as CCL1 to CCL28; CXC chemokines such as CXCL1 to CXCL17; C chemokines such as XCL1 to XCL2; and CX3C chemokines such as CX3CL1.

Examples of the receptors can include receptors belonging to receptor families such as hematopoietic growth factor receptor family, cytokine receptor family, tyrosine kinase receptor family, serine/threonine kinase receptor family, TNF receptor family, G protein-coupled receptor family, GPI-anchored receptor family, tyrosine phosphatase receptor family, adhesion factor family, and hormone receptor family. These receptors belonging to the receptor families and their features are described in many literatures, for example, Cooke B A, King R J B, van der Molen H J ed. New Comprehensive Biochemistry Vol 18B "Hormones and their Actions Part II" pp. 1-46 (1988) Elsevier Science Publishers BV, Patthy (Cell (1990) 61 (1), 13-14), Ullrich et al. (Cell (1990) 61 (2), 203-212), Massague (e with acute accent) (Cell (1992) 69 (6), 1067-1070), Miyajima et al. (Annu Rev Immunol (1992) 10, 295-331), Taga et al. (FASEB J (1992) 6, 3387-3396), Fantl et al. (Annu Rev Biochem (1993), 62, 453-481), Smith et al. (Cell (1994) 76 (6), 959-962), and Flower DR (Biochim Biophys Acta (1999) 1422 (3), 207-234).

Specific examples of the receptors belonging to the receptor families mentioned above preferably include human or mouse erythropoietin (EPO) receptors (Blood (1990) 76 (1), 31-35; and Cell (1989) 57 (2), 277-285), human or mouse granulocyte colony-stimulating factor (G-CSF) receptors (Proc Natl Acad Sci USA (1990) 87 (22), 8702-8706; and mG-CSFR, Cell (1990) 61 (2), 341-350), human or mouse thrombopoietin (TPO) receptors (Proc Natl Acad Sci USA (1992) 89 (12), 5640-5644; and EMBO J (1993) 12 (7), 2645-53), human or mouse insulin receptors (Nature (1985) 313 (6005), 756-761), human or mouse Flt-3 ligand receptors (Proc Natl Acad Sci USA (1994) 91 (2), 459-463), human or mouse platelet-derived growth factor (PDGF) receptors (Proc Natl Acad Sci USA (1988) 85 (10), 3435-3439), human or mouse interferon (IFN)-$\alpha$ and -$\beta$ receptors (Cell (1990) 60 (2), 225-234; and Cell (1994) 77 (3), 391-400), human or mouse leptin receptors, human or mouse growth hormone (GH) receptors, human or mouse interleukin (IL)-10 receptors, human or mouse insulin-like growth factor (IGF)-I receptors, human or mouse leukemic inhibitory factor (LIF) receptors, and human or mouse ciliary neurotrophic factor (CNTF) receptors.

The cancer antigens refer to antigens that are expressed in conjunction with the malignant transformation of cells and are also called tumor-specific antigens. Abnormal sugar chains that appear on cell surface or protein molecules during the malignant transformation of cells are also cancer antigens and are also called cancer carbohydrate antigens. Examples of the cancer antigens preferably include GPC3 (Int J Cancer (2003) 103 (4), 455-65) which belongs to the GPI-anchored receptor family as one of the receptors mentioned above and is expressed in some cancers including liver cancer, EpCAM (Proc Natl Acad Sci USA (1989) 86 (1), 27-31) which is expressed in a plurality of cancers including lung cancer, CA19-9, CA15-3, and sialyl SSEA-1 (SLX).

The MHC antigens are classified mainly into MHC class I antigens and MHC class II antigens. The MHC class I antigens include HLA-A, -B, -C, -E, -F, -G, and -H. The MHC class II antigens include HLA-DR, -DQ, and -DP.

The differentiation antigens can include CD1, CD2, CD4, CD5, CD6, CD7, CD8, CD10, CD11a, CD11b, CD11c, CD13, CD14, CD15s, CD16, CD18, CD19, CD20, CD21, CD23, CD25, CD28, CD29, CD30, CD32, CD33, CD34, CD35, CD38, CD40, CD41a, CD41b, CD42a, CD42b, CD43, CD44, CD45, CD45RO, CD48, CD49a, CD49b, CD49c, CD49d, CD49e, CD49f, CD51, CD54, CD55, CD56, CD57, CD58, CD61, CD62E, CD62L, CD62P, CD64, CD69, CD71, CD73, CD95, CD102, CD106, CD122, CD126, and CDw130.

The immunoglobulins include IgA, IgM, IgD, IgG, and IgE. The immune complexes comprise at least any component of the immunoglobulins.

Other examples of the antigen can include the following molecules: 17-IA, 4-1BB, 4Dc, 6-keto-PGF1a, 8-iso-PGF2a, 8-oxo-dG, A1 adenosine receptor, A33, ACE, ACE-2, activin, activin A, activin AB, activin B, activin C, activin RIA, activin RIA ALK-2, activin RIB ALK-4, activin RIIA, activin RIIB, ADAM, ADAM10, ADAM12, ADAM15, ADAM17/TACE, ADAM8, ADAM9, ADAMTS, ADAMTS4, ADAMTS5, addressin, aFGF, ALCAM, ALK, ALK-1, ALK-7, alpha-1-antitrypsin, alpha-V/beta-1 antagonist, ANG, Ang, APAF-1, APE, APJ, APP, APRIL, AR, ARC, ART, artemin, anti-Id, ASPARTIC, atrial natriuretic factor, av/b3 integrin, Axl, b2M, B7-1, B7-2, B7-H, B-lymphocyte stimulator (BlyS), BACE, BACE-1, Bad, BAFF, BAFF-R, Bag-1, BAK, Bax, BCA-1, BCAM, Bcl, BCMA, BDNF, b-ECGF, bFGF, BID, Bik, BIM, BLC, BL-CAM, BLK, BMP, BMP-2 BMP-2a, BMP-3 osteogenin, BMP-4, BMP-2b, BMP-5, BMP-6 Vgr-1, BMP-7 (OP-1), BMP-8 (BMP-8a, OP-2), BMPR, BMPR-IA (ALK-3), BMPR-IB (ALK-6), BRK-2, RPK-1, BMPR-II (BRK-3), BMP, b-NGF, BOK, bombesin, bone-derived neurotrophic factor, BPDE, BPDE-DNA, BTC, complement factor 3 (C3), C3a, C4, C5, C5a, C10, CA125, CAD-8, calcitonin, cAMP, carcinoembryonic antigen (CEA), carcinoma-associated antigen, cathepsin A, cathepsin B, cathepsin C/DPPI, cathepsin D, cathepsin E, cathepsin H, cathepsin L, cathepsin 0, cathepsin S, cathepsin V, cathepsin X/Z/P, CBL, CCI, CCK2, CCL, CCL1, CCL11, CCL12, CCL13, CCL14, CCL15, CCL16, CCL17, CCL18, CCL19, CCL2, CCL20, CCL21, CCL22, CCL23, CCL24, CCL25, CCL26, CCL27, CCL28, CCL3, CCL4, CCL5, CCL6, CCL7, CCL8, CCL9/10, CCR, CCR1, CCR10, CCR10, CCR2, CCR3, CCR4, CCR5, CCR6, CCR7, CCR8, CCR9, CD1, CD2, CD3, CD3E, CD4, CD5, CD6, CD7, CD8, CD10, CD11a, CD11b, CD11c, CD13, CD14, CD15, CD16, CD18, CD19, CD20, CD21, CD22, CD23, CD25, CD27L, CD28, CD29, CD30, CD30L, CD32, CD33 (p67 protein), CD34, CD38, CD40, CD40L, CD44, CD45, CD46, CD49a, CD52, CD54, CD55, CD56, CD61, CD64, CD66e, CD74, CD80 (B7-1), CD89, CD95, CD123, CD137, CD138, CD140a, CD146, CD147, CD148, CD152, CD164, CEACAM5, CFTR, cGMP, CINC, *Clostridium botulinum* toxin, *Clostridium perfringens* toxin, CKb8-1, CLC, CMV, CMV UL, CNTF, CNTN-1, COX, C-Ret, CRG-2, CT-1, CTACK, CTGF, CTLA-4, CX3CL1, CX3CR1, CXCL, CXCL1, CXCL2, CXCL3, CXCL4, CXCL5, CXCL6, CXCL7, CXCL8, CXCL9, CXCL10, CXCL11, CXCL12, CXCL13, CXCL14, CXCL15, CXCL16, CXCR, CXCR1, CXCR2, CXCR3, CXCR4, CXCR5, CXCR6, cytokeratin tumor-associated antigen, DAN, DCC, DcR3, DC-SIGN, decay accelerating factor, des(1-3)-IGF-I (brain IGF-1), Dhh, digoxin, DNAM-1, Dnase, Dpp, DPPIV/CD26, Dtk, ECAD, EDA, EDA-A1, EDA-A2, EDAR, EGF, EGFR (ErbB-1), EMA, EMMPRIN, ENA, endothelin receptor, enkephalinase, eNOS, Eot, eotaxin 1, EpCAM, ephrin B2/EphB4, EPO, ERCC, E-selectin, ET-1, factor IIa, factor VII, factor VIIIc, factor IX, fibroblast activation protein (FAP), Fas, FcR1, FEN-1, ferritin, FGF, FGF-19, FGF-2, FGF3, FGF-8, FGFR, FGFR-3, fibrin, FL, FLIP, Flt-3, Flt-4, follicle-stimulating hormone, fractalkine, FZD1, FZD2, FZD3, FZD4, FZD5, FZD6, FZD7, FZD8, FZD9, FZD10, G250, Gas6, GCP-2, GCSF, GD2, GD3, GDF, GDF-1, GDF-3 (Vgr-2), GDF-5 (BMP-14, CDMP-1), GDF-6 (BMP-13, CDMP-2), GDF-7 (BMP-12, CDMP-3), GDF-8 (myostatin), GDF-9, GDF-15 (MIC-1), GDNF, GDNF, GFAP, GFRa-1, GFR-alpha 1, GFR-alpha 2, GFR-alpha 3, GITR, glucagon, Glut4, glycoprotein IIb/IIIa (GPIIb/IIIa), GM-CSF, gp130, gp72, GRO, growth hormone-releasing factor, hapten (NP-cap or NIP-cap), HB-EGF, HCC, HCMV gB envelope glycoprotein, HCMV gH envelope glycoprotein, HCMV UL, hematopoietic growth factor (HGF), Hep B gp120, heparanase, Her2, Her2/neu (ErbB-2), Her3 (ErbB-3), Her4 (ErbB-4), herpes simplex virus (HSV) gB glycoprotein, HSV gD glycoprotein, HGFA, high-molecular-weight melanoma-associated antigen (HMW-MAA), HIV gp120, HIV IIIB gp 120 V3 loop, HLA, HLA-DR, HM1.24, HMFG PEM, HRG, Hrk, human heart myosin, human cytomegalovirus (HCMV), human growth hormone (HGH), HVEM, 1-309, IAP, ICAM, ICAM-1, ICAM-3, ICE, ICOS, IFNg, Ig, IgA receptor, IgE, IGF, IGF-binding protein, IGF-1R, IGFBP, IGF-I, IGF-II, IL, IL-1, IL-1R, IL-2, IL-2R, IL-4, IL-4R, IL-5, IL-5R, IL-6, IL-6R, IL-8, IL-9, IL-10, IL-12, IL-13, IL-15, IL-18, IL-18R, IL-23, interferon (INF)-alpha, INF-beta, INF-gamma, inhibin, iNOS, insulin A chain, insulin B chain, insulin-like growth factor 1, integrin alpha 2, integrin alpha 3, integrin alpha 4, integrin alpha 4/beta 1, integrin alpha 4/beta 7, integrin alpha 5 (alpha V), integrin alpha 5/beta 1, integrin alpha 5/beta 3, integrin alpha 6, integrin beta 1, integrin beta 2, interferon gamma, IP-10, I-TAC, JE, kallikrein 2, kallikrein 5, kallikrein 6, kallikrein 11, kallikrein 12, kallikrein 14, kallikrein 15, kallikrein L1, kallikrein L2, kallikrein L3, kallikrein L4, KC, KDR, keratinocyte growth factor (KGF), laminin 5, LAMP, LAP, LAP (TGF-1), latent TGF-1, latent TGF-1 bp1, LBP, LDGF, LECT2, lefty, Lewis-Y antigen, Lewis-Y-related antigen, LFA-1, LFA-3, Lfo, LIF, LIGHT, lipoprotein, LIX, LKN, Lptn, L-selectin, LT-a, LT-b, LTB4, LTBP-1, lung surfactant, luteinizing hormone, lymphotoxin beta receptor, Mac-1, MAdCAM, MAG, MAP2, MARC, MCAM, MCAM, MCK-2, MCP, M-CSF, MDC, Mer, METALLOPROTEASES, MGDF receptor, MGMT, MHC (HLA-DR), MIF, MIG, MIP, MIP-1-alpha, MK, MMAC1, MMP, MMP-1, MMP-10, MMP-11, MMP-12, MMP-13, MMP-14, MMP-15, MMP-2, MMP-24, MMP-3, MMP-7, MMP-8, MMP-9, MPIF, Mpo, MSK, MSP, mucin (Muc1), MUC18, mullerian-inhibiting factor, Mug, MuSK, NAIP, NAP, NCAD, N-cadherin, NCA 90, NCAM, NCAM, neprilysin, neurotrophin-3, -4, or -6, neurturin, nerve growth factor (NGF), NGFR, NGF-beta, nNOS, NO, NOS, Npn, NRG-3, NT, NTN, OB, OGG1, OPG, OPN, OSM, OX40L, OX40R, p150, p95, PADPr, parathyroid hormone, PARC, PARP, PBR, PBSF, PCAD, P-cadherin, PCNA, PDGF, PDGF, PDK-1, PECAM, PEM, PF4, PGE, PGF, PGI2, PGJ2, PIN, PLA2, placental alkaline phosphatase (PLAP), P1GF, PLP, PP14, proinsulin, prorelaxin, protein C, PS, PSA, PSCA, prostate-specific membrane antigen (PSMA), PTEN, PTHrp, Ptk, PTN, R51, RANK, RANKL, RANTES, RANTES, relaxin A chain, relaxin B chain, renin, respiratory syncytial virus (RSV) F, RSV Fgp, Ret, rheumatoid factor, RLIP76, RPA2, RSK, 5100, SCF/ KL, SDF-1, SERINE, serum albumin, sFRP-3, Shh, SIGIRR, SK-1, SLAM, SLPI, SMAC, SMDF, SMOH, SOD, SPARC, Stat, STEAP, STEAP-II, TACE, TACI, TAG-72 (tumor-associated glycoprotein-72), TARC, TCA-3, T cell receptor (e.g., T cell receptor alpha/beta), TdT, TECK, TEM1, TEMS, TEM7, TEM8, TERT, testicular PLAP-like alkaline phosphatase, TfR, TGF, TGF-alpha, TGF-beta, TGF-beta Pan Specific, TGF-beta RI (ALK-5), TGF-beta RII, TGF-beta RIIb, TGF-beta RIII, TGF-beta 1, TGF-beta 2, TGF-beta 3, TGF-beta 4, TGF-beta 5, thrombin, thymus Ck-1, thyroid stimulating hormone, Tie, TIMP, TIQ, tissue factor, TMEFF2, Tmpo, TMPRSS2, TNF, TNF-alpha, TNF-alpha beta, TNF-beta 2, TNFc, TNF-RI, TNF-RII, TNFRSF10A (TRAIL R1 Apo-2, DR4), TNFRSF10B (TRAIL R2 DR5, KILLER, TRICK-2A, TRICK-B), TNFRSF10C (TRAIL R3 DcR1, LIT, TRID), TNFRSF10D (TRAIL R4 DcR2, TRUNDD), TNFRSF11A (RANK ODF R, TRANCE R), TNFRSF11B (OPG OCIF, TR1), TNFRSF12 (TWEAK R FN14), TNFRSF13B (TACI), TNFRSF13C (BAFF R), TNFRSF14 (HVEM ATAR, HveA, LIGHT R, TR2), TNFRSF16 (NGFR p75NTR), TNFRSF17 (BCMA), TNFRSF18 (GITR AITR), TNFRSF19 (TROY TAJ, TRADE), TNFRSF19L (RELT), TNFRSF1A (TNF RI CD120a, p55-60), TNFRSF1B (TNF RII CD120b, p75-80), TNFRSF26 (TNFRH3), TNFRSF3 (LTbR TNF RIII, TNFC R), TNFRSF4 (OX40 ACT35, TXGP1 R), TNFRSF5 (CD40 p50), TNFRSF6 (Fas Apo-1, APT1, CD95), TNFRSF6B (DcR3 M68, TR6), TNFRSF7 (CD27), TNFRSF8 (CD30), TNFRSF9 (4-1BB CD137, ILA), TNFRSF21 (DR6), TNFRSF22 (DcTRAIL R2 TNFRH2), TNFRST23 (Dc-TRAIL R1 TNFRH1), TNFRSF25 (DR3 Apo-3, LARD, TR-3, TRAMP, WSL-1), TNFSF10 (TRAIL Apo-2 ligand, TL2), TNFSF11 (TRANCE/RANK ligand ODF, OPG ligand), TNFSF12 (TWEAK Apo-3 ligand, DR3 ligand), TNFSF13 (APRIL TALL2), TNFSF13B (BAFF BLYS, TALL1, THANK, TNFSF20), TNFSF14 (LIGHT HVEM ligand, LTg), TNFSF15 (TL1A/VEGI), TNFSF18 (GITR ligand AITR ligand, TL6), TNFSF1A (TNF-a Conectin, DIF, TNFSF2), TNFSF1B (TNF-b LTa, TNFSF1), TNFSF3 (LTb TNFC, p33), TNFSF4 (OX40 ligand gp34, TXGP1), TNFSF5 (CD40 ligand CD154, gp39, HIGM1, IMD3, TRAP), TNFSF6 (Fas ligand Apo-1 ligand, APT1 ligand), TNFSF7 (CD27 ligand CD70), TNFSF8 (CD30 ligand CD153), TNFSF9 (4-1BB ligand CD137 ligand), TP-1, t-PA, Tpo, TRAIL, TRAIL R, TRAIL-R1, TRAIL-R2, TRANCE, transferrin receptor, TRF, Trk, TROP-2, TSG, TSLP, tumor-associated antigen CA125, tumor-associated antigen exhibiting Lewis Y-related carbohydrate, TWEAK, TXB2, Ung, uPAR, uPAR-1, urokinase, VCAM, VCAM-1, VECAD, VE-Cadherin, VE-cadherin-2, VEFGR-1 (flt-1), VEGF, VEGFR, VEGFR-3 (flt-4), VEGI, VIM, viral antigen, VLA, VLA-1, VLA-4, VNR integrin, von Willebrand factor, WIF-1, WNT1, WNT2, WNT2B/13, WNT3, WNT3A, WNT4, WNTSA, WNTSB, WNT6, WNT7A, WNT7B, WNT8A, WNT8B, WNT9A, WNT9A, WNT9B, WNT10A, WNT10B, WNT11, WNT16, XCL1, XCL2, XCR1, XCR1, XEDAR, XIAP, XPD, HMGB1, IgA, Aβ, CD81, CD97, CD98, DDR1, DKK1, EREG, Hsp90, IL-17/ IL-17R, IL-20/IL-20R, oxidized LDL, PCSK9, prekallikrein, RON, TMEM16F, SOD1, Chromogranin A, Chromogranin B, tau, VAP1, high-molecular-weight kininogen, IL-31, IL-31R, Nav1.1, Nav1.2, Nav1.3, Nav1.4, Nav1.5, Nav1.6, Nav1.7, Nav1.8, Nav1.9, EPCR, C1, C1q, C1r, C1s, C2, C2a, C2b, C3, C3a, C3b, C4, C4a, C4b, C5, C5a, C5b, C6, C7, C8, C9, factor B, factor D, factor H, properdin, sclerostin, fibrinogen, fibrin, prothrombin, thrombin, tissue factor, factor V, factor Va, factor VII, factor VIIa, factor VIII, factor VIIIa, factor IX, factor IXa, factor X, factor Xa, factor XI, factor XIa, factor XII, factor XIIa, factor XIII, factor XIIIa, TFPI, antithrombin III, EPCR, thrombomodulin, TAPI, tPA, plasminogen, plasmin, PAI-1, PAI-2, GPC3, Syndecan-1, Syndecan-2, Syndecan-3, Syndecan-4, LPA, S1P, and receptors for hormone and growth factors.

The alteration of one or more amino acid residue(s) is acceptable for the amino acid sequence constituting each variable region as long as its antigen-binding activity is maintained. In the case of altering the amino acid sequence of the variable region, the alteration site, the type of the alteration, or the number of the amino acid to be altered is not particularly limited. For example, amino acid(s) present in CDRs and/or FRs can be appropriately altered. The variable region with the altered amino acid(s) preferably maintains its binding activity and preferably has, but not particularly limited to, for example, 50% or higher, more preferably 80% or higher, further preferably 100% or higher binding activity, compared with that before the alteration. Alternatively, the binding activity of the variable region may be increased by amino acid alteration and may be, for example, 2 times, 5 times, or 10 times the binding activity before the alteration. In the antibody of the present invention, the alteration of an amino acid sequence can be at least one of the substitution, deletion, addition, insertion, and modification of amino acid residue(s).

For example, the modification of N-terminal glutamine of the variable region to pyroglutamic acid by pyroglutamylation is a modification well known to those skilled in the art. Thus, the antibody of the present invention having glutamine at the N terminus of its heavy chain may contain a variable region with this N-terminal glutamine modified to pyroglutamic acid.

The variable regions of the antibody of the present invention may have arbitrary sequences and may be variable regions of an antibody of any origin, including mouse antibodies, rat antibodies, rabbit antibodies, goat antibodies, camel antibodies, humanized antibodies obtained by the humanization of these nonhuman antibodies, and human antibodies. The "humanized antibodies", also called reshaped human antibodies, are obtained by grafting CDRs (complementarity determining regions) of a nonhuman mammal-derived antibody, for example, a mouse antibody to human antibody CDRs. Methods for identifying CDRs are known in the art (Kabat et al, Sequence of Proteins of Immunological Interest (1987), National Institute of Health, Bethesda, Md.; and Chothia et al, Nature (1989) 342, 877). General gene recombination approaches therefor are also known in the art (see European Patent Application Publication No. EP125023 and WO96/02576). Alternatively, various amino acid substitutions may be introduced to the variable regions of these antibodies in order to improve their antigen binding, pharmacokinetics, stability, or immunogenicity. The variable regions of the antibody of the present invention may bind to an antigen in a pH-dependent manner and be thereby capable of repetitively binding to the antigen (WO2009/125825).

The light chain constant region of the antibody includes x and λ chain constant regions and can be any of these light chain constant regions. Alternatively, the light chain constant region according to the present invention may be a light chain constant region prepared by the alteration such as substitution, deletion, addition, insertion, and/or modification of amino acid(s).

The heavy chain constant region of the antibody includes, for example, IgA, IgD, IgE, IgG, and IgM constant regions. In the present invention, for example, an IgG heavy chain constant region, particularly, a mouse or human IgG heavy chain constant region, can be used. A mouse IgG1 heavy chain constant region is preferred.

The antibody of the present invention also includes modified forms of the antibody. Examples of the modified forms of the antibody can include antibodies conjugated with various molecules such as polyethylene glycol (PEG) or cytotoxic substances. Such modified forms of the antibody can be obtained by the chemical modification of the antibody of the present invention. The antibody modification method has already been established in the art.

In addition, the antibody of the present invention may be a multispecific antibody, particularly, a bispecific antibody. The multispecific antibody refers to an antibody having, in one antibody molecule, variable regions that recognize a plurality of different epitopes. The epitopes may be present in different molecules or may be present in the same molecule.

The polypeptide of the present invention can be produced by a method generally known to those skilled in the art. For example, the antibody can be prepared by the following method, though the method for preparing the antibody of the present invention is not limited thereto.

A DNA encoding the heavy chain of the antibody, which is a DNA encoding a heavy chain with one or more amino acid(s) in its Fc region altered to different amino acid(s), and a DNA encoding the light chain of the antibody are expressed. The DNA encoding a heavy chain with one or more amino acid(s) in its Fc region altered to different amino acid(s) can be obtained, for example, by obtaining the Fc region of a DNA encoding a naturally occurring heavy chain and appropriately altering a codon encoding the particular amino acid in the Fc region to a codon encoding the different amino acid.

Alternatively, a DNA encoding a heavy chain derived from a naturally occurring heavy chain by the alteration of one or more amino acid(s) in its Fc region to different amino acid(s) may be designed in advance and chemically synthesized to obtain a DNA encoding the heavy chain with one or more amino acid(s) in its Fc region altered to different amino acid(s). The amino acid alteration site, the type of the alteration, or the number of the amino acid to be altered is not particularly limited. The type of the alteration may be any of substitution, deletion, addition, insertion, and modification, or a combination thereof.

The DNA encoding the heavy chain with one or more amino acid(s) in its Fc region altered to different amino acid(s) can be produced as separate partial DNAs. Examples of the combination of the partial DNAs include, but not limited to: the combination of a variable region-encoding DNA and a constant region-encoding DNA; and the combination of a Fab region-encoding DNA and an Fc region-encoding DNA. Likewise, the light chain-encoding DNA can also be produced as separate partial DNAs.

These DNAs can be expressed by the following exemplary method: a heavy chain variable region-encoding DNA, together with a heavy chain constant region-encoding DNA, is incorporated into an expression vector to construct a heavy chain expression vector. Likewise, a light chain variable region-encoding DNA, together with a light chain constant region-encoding DNA, is incorporated into an expression vector to construct a light chain expression vector. These heavy chain- and light chain-encoding DNAs may be incorporated into a single expression vector.

The DNAs encoding the antibody heavy and light chains are incorporated into expression vectors so as to be expressed under the control of expression control regions, for example, an enhancer and a promoter. Next, host cells are transformed with the resulting expression vectors and allowed to express antibodies. In this case, appropriate hosts and expression vectors can be used in combination.

Examples of the vectors include M13 series vectors, pUC series vectors, pBR322, pBluescript, and pCR-Script. In addition to these vectors, for example, pGEM-T, pDIRECT, or pT7 can also be used for the purpose of cDNA subcloning and excision.

Particularly, expression vectors are useful for using the vectors for the purpose of producing the polypeptide of the present invention. For example, when the host is *E. coli* such as JM109, DH5α, HB101, or XL1-Blue, the expression vectors indispensably have a promoter that permits efficient expression in *E. coli*, for example, lacZ promoter (Ward et al., Nature (1989) 341, 544-546; and FASEB J (1992) 6, 2422-2427, which are incorporated herein by reference in their entirety), araB promoter (Better et al., Science (1988) 240, 1041-1043, which is incorporated herein by reference in its entirety), or T7 promoter. Examples of such vectors include the vectors mentioned above as well as pGEX-5X-1 (manufactured by Pharmacia), "QIAexpress system" (manufactured by Qiagen N. V.), pEGFP, and pET (in this case, the host is preferably BL21 expressing T7 RNA polymerase).

The vectors may contain a signal sequence for polypeptide secretion. In the case of production in the periplasm of *E. coli*, pelB signal sequence (Lei, S P et al, J Bacteriol (1987) 169, 4397, which is incorporated herein by reference in its entirety) can be used as the signal sequence for polypeptide secretion. The vectors can be transferred to the host cells using an approach generally known to those skilled in the art, for example, a calcium phosphate method, a DEAE-dextran method, a method using cationic ribosome DOTAP (manufactured by Boehringer Mannheim), electroporation, lipofection, or microinjection.

In addition to the *E. coli*-derived expression vectors, examples of the vectors for producing the polypeptide of the present invention include mammal-derived expression vectors (e.g., pcDNA3 (manufactured by Invitrogen Corp.), pEGF-BOS (Nucleic Acids Res 1990, 18 (17), 5322, which is incorporated herein by reference in its entirety), pEF, and pCDM8), insect cell-derived expression vectors (e.g., "Bac-to-BAC baculovirus expression system" (manufactured by GIBCO BRL), and pBacPAK8), plant-derived expression vectors (e.g., pMH1 and pMH2), animal virus-derived expression vectors (e.g., pHSV, pMV, and pAdexLcw), retrovirus-derived expression vectors (e.g., pZIPneo), yeast-derived expression vectors (e.g., "Pichia Expression Kit" (manufactured by Invitrogen Corp.), pNV11, and SP-Q01), and *Bacillus subtilis*-derived expression vectors (e.g., pPL608 and pKTH50).

For the purpose of expression in animal cells such as CHO cells, COS cells, or NIH3T3 cells, the vectors indispensably have a promoter necessary for intracellular expression, for example, SV40 promoter (Mulligan et al., Nature (1979) 277, 108, which is incorporated herein by reference in its entirety), MMTV-LTR promoter, EF1α promoter (Mizushima et al., Nucleic Acids Res (1990) 18, 5322, which is incorporated herein by reference in its entirety), CAG promoter (Gene (1991) 108, 193, which is incorporated herein by reference in its entirety), or CMV promoter and, more preferably, have a gene for screening for transformed cells (e.g., a drug resistance gene that can work as a marker by a drug (neomycin, G418, etc.)). Examples of the vectors having such properties include pMAM, pDR2, pBK-RSV, pBK-CMV, pOPRSV, and pOP13.

An exemplary method intended to stably express the gene and increase the number of intracellular gene copies involves transfecting CHO cells deficient in nucleic acid synthesis pathway with vectors having a DHFR gene serving as a complement thereto (e.g., pCHOI) and using methotrexate (MTX) in the gene amplification. An exemplary method intended to transiently express the gene involves using COS cells having an SV40 T antigen gene on their chromosomes to transform the cells with vectors having a replication origin of SV40 (pcD, etc.). Also, a replication origin derived from polyomavirus, adenovirus, bovine papillomavirus (BPV), or the like may be used. The expression vectors for increasing the number of gene copies can additionally contain a selection marker such as an aminoglycoside transferase (APH) gene, a thymidine kinase (TK) gene, an *E. coli* xanthine guanine phosphoribosyltransferase (Ecogpt) gene, or a dihydrofolate reductase (dhfr) gene. Also, cells given below can be used as host cells. In the case of using eukaryotic cells as the host cells, animal, plant, or fungus cells can be appropriately used. Specifically, examples of the animal cells can include the following cells:
(1) mammalian cells such as CHO (Chinese hamster ovary cell line), COS (monkey kidney cell line), myeloma cells (Sp2/0, NS0, etc.), BHK (baby hamster kidney cell line), Hela, Vero, HEK293 (human embryonic kidney cell line with sheared adenovirus (Ad)5 DNA), Freestyle 293, and PER. C6 cell (human embryonic retinal cell line transformed with the Adenovirus Type 5 (Ad5) E1A and E1B genes) (Current Protocols in Protein Science (May, 2001, Unit 5.9, Table 5.9.1));
(2) amphibian cells such as *Xenopus* oocytes; and
(3) insect cells such as sf9, sf21, and Tn5.

Alternatively, antibody gene expression systems using cells derived from plants of the genus *Nicotiana* such as *Nicotiana tabacum* as the plant cells are known in the art. Cultured callus cells can be appropriately used for the plant cell transformation. The following cells can be used as the fungus cells:
cells derived from yeasts of the genus *Saccharomyces* (e.g., *Saccharomyces cerevisiae*) and the genus *Pichia* (e.g., *Pichia pastoris*), and cells derived from filamentous fungi of the genus *Aspergillus* (e.g., *Aspergillus niger*).

The antibody thus expressed can be recovered, for example, by culturing the transformed cells, then recovering the extracellular culture solution or intracellular extracts, and separating and purifying the antibody therefrom. The antibody can be separated and purified by appropriately using in combination methods such as centrifugation, ammonium sulfate fractionation, salting out, ultrafiltration, affinity chromatography, ion-exchanged chromatography, and gel filtration chromatography.

The amino acid alteration can be performed by various methods known in the art. Preferred examples of these methods can include, but not limited to, site-directed mutagenesis (Hashimoto-Gotoh T, Mizuno T, Ogasahara Y and Nakagawa M (1995) An oligodeoxyribonucleotide-directed dual amber method for site-directed mutagenesis. Gene 152, 271-275, Zoller M J, and Smith M (1983) Oligonucleotide-directed mutagenesis of DNA fragments cloned into M13 vectors. Methods Enzymol 100, 468-500, Kramer W, Drutsa V, Jansen H W, Kramer B, Pflugfelder M and Fritz H J (1984) The gapped duplex DNA approach to oligonucleotide-directed mutation construction. Nucleic Acids Res 12, 9441-9456, Kramer W, and Fritz H J (1987) Oligonucleotide-directed construction of mutations via gapped duplex DNA. Methods Enzymol 154, 350-367, Kunkel T A (1985) Rapid and efficient site-specific mutagenesis without phenotypic selection. Proc Natl Acad Sci USA 82, 488-492), PCR mutagenesis, and cassette mutagenesis.

The substitution of an amino acid residue is carried out by replacement with another amino acid residue for the purpose of altering, for example, any of the following (a) to (c):
(a) the polypeptide backbone structure of a region having a sheet structure or helix structure;
(b) the electric charge or hydrophobicity of a target site; and
(c) the size of a side chain.

Amino acid residues are classified into the following groups on the basis of general side chain properties:
(1) hydrophobic residues: norleucine, Met, Ala, Val, Leu, and Ile;
(2) neutral hydrophilic residues: Cys, Ser, Thr, Asn, and Gln;
(3) acidic residues: Asp and Glu;
(4) basic residues: His, Lys, and Arg;
(5) residues that influence chain orientation: Gly and Pro; and
(6) aromatic residues: Trp, Tyr, and Phe.

The substitution of amino acid residues within each of these groups is called conservative substitution, while the substitution of an amino acid residue in one of these groups by an amino acid residue in another group is called non-conservative substitution. The substitution according to the present invention may be conservative substitution, non-conservative substitution, or a combination of conservative substitution and non-conservative substitution.

The amino acid modification of the present invention includes posttranslational modification. Specifically, the posttranslational modification can refer to the addition or deletion of a sugar chain. For example, an amino acid residue at EU numbering position 297 in an IgG1 heavy chain constant region can be modified with a sugar chain. Alternatively, sialic acid may be added to the sugar chain of the Fc region (MAbs 2010 September-October; 2 (5), 519-27). The sugar chain structure used in the modification is not limited. In general, antibodies expressed by eukaryotic cells involve sugar chain modification in their constant regions.

In this context, the eukaryotic cells include yeast and animal cells. For example, CHO cells or HEK293 cells are typical animal cells for use in transformation with expression vectors comprising antibody-encoding DNAs. On the other hand, the constant region of the present invention also includes regions lacking sugar chain modification at the position. The antibodies having sugar chain-unmodified constant regions can be obtained by the expression of their antibody-encoding genes in prokaryotic cells such as *E. coli*.

In the present invention, the binding activity of the polypeptide of the present invention against each FcγR can be measured by use of ELISA, FACS (fluorescence activated cell sorting), ALPHAScreen (amplified luminescent proximity homogeneous assay screen), the BIACORE method based on a surface plasmon resonance (SPR) phenomenon, or the like.

The ALPHAScreen method is carried out by the ALPHA technology using two types of beads (donor and acceptor) on the basis of the following principle: luminescence signals are detected only when these two beads are located in proximity through the biological interaction between a molecule bound with the donor bead and a molecule bound with the acceptor bead. A laser-excited photosensitizer in the donor bead converts ambient oxygen to singlet oxygen in an excited state. The singlet oxygen diffuses around the donor bead and reaches the acceptor bead located in proximity thereto to thereby cause chemiluminescent reaction in the bead, which finally emits light. In the absence of the interaction between the molecule bound with the donor bead and the molecule bound with the acceptor bead, singlet oxygen produced by the donor bead does not reach the acceptor bead. Thus, no chemiluminescent reaction occurs.

For example, a polypeptide comprising the Fc region of naturally occurring IgG is bound to the donor bead, and the Fcγ receptor is bound to the acceptor bead. In the absence of the polypeptide of the present invention comprising a mutated Fc region, the polypeptide comprising the Fc region of naturally occurring IgG interacts with the Fcγ receptor to generate luminescence signals of 520 to 620 nm. In the presence of the polypeptide of the present invention comprising a mutated Fc region, the polypeptide of the present invention competes with the polypeptide comprising the Fc region of naturally occurring IgG to inhibit its interaction with the Fcγ receptor. Decrease in luminescence signals generated as a result of the competition can be quantified to thereby determine relative binding activity. The polypeptide (e.g., antibody) of the present invention can be biotinylated by a method known in the art using sulfo-NHS-biotin or the like. The Fcγ receptor can be tagged with GST by an appropriately adopted method which involves, for example: fusing a polynucleotide encoding the Fcγ receptor in flame with a polynucleotide encoding GST; and allowing the resulting fusion gene to be expressed by cells or the like carrying vectors capable of expression thereof to express the GST-tagged Fcγ receptor, which is then purified using a glutathione column. The obtained luminescence signals are preferably analyzed using, for example, software GRAPH-PAD PRISM (GraphPad Software, Inc., San Diego) adapted to a one-site competition model based on nonlinear regression analysis.

The BIACORE method based on a surface plasmon resonance (SPR) phenomenon is described as follows: one (ligand) of the substances between which the interaction is to be observed is immobilized on a thin gold film of a sensor chip. The sensor chip is irradiated with light from the back such that total reflection occurs at the interface between the thin gold film and glass. As a result, a site having a drop in reflection intensity (SPR signal) is formed in a portion of reflected light. The other (analyte) of the substances between which the interaction is to be observed is flowed on the surface of the sensor chip and thereby bound to the ligand so that the mass of the immobilized ligand molecule is increased to change the refractive index of the solvent on the sensor chip surface. This change in the refractive index shifts the position of the SPR signal (on the contrary, the dissociation of the bound molecules gets the signal back to the original position). The Biacore system plots on the vertical axis the amount of the shift, i.e., change in mass on the sensor chip surface, against time on the horizontal axis and thereby displays time-dependent change in mass as assay data (sensorgram). The amount of the analyte bound to the ligand captured on the sensor chip surface can be determined from the sensorgram. An association rate constant (ka) and a dissociation rate constant (kd) can be determined from the curve of the sensorgram, while a dissociation constant (KD) can be determined from the ratio between these constants. Inhibition assay is also preferably used in the BIACORE method (Proc Natl Acad Sci USA, 103 (11), 4005-4010, 2006).

The binding activity of the polypeptide of the present invention against each FcγR can be preferably measured using, for example, the BIACORE method based on a surface plasmon resonance (SPR) phenomenon, as shown later in Examples. Specifically, the polypeptide (e.g., antibody) of the present invention is immobilized directly or via protein A, protein L, protein A/G, protein G, an anti-lambda chain antibody, an anti-kappa chain antibody, an antigen peptide, an antigen protein, or the like onto a sensor chip, which is then allowed to interact with each FcγR as an analyte. The dissociation constant (KD) is calculated from results of analyzing the sensorgram. When the KD value is small, the binding activity can be confirmed to be high. When the KD value is large, the binding activity can be confirmed to be low. Alternatively, FcγR is immobilized directly or via an anti-tag antibody or the like onto a sensor chip, which is then allowed to interact with the polypeptide (e.g., antibody) of the present invention to be evaluated as an analyte. The dissociation constant (KD) is calculated from results of analyzing the sensorgram. When the KD value is small, the binding activity can be confirmed to be high. When the KD value is large, the binding activity can be confirmed to be low.

Alternatively, the binding activity of the polypeptide of the present invention may be measured on the basis of an amount bound instead of the KD value. In this context, the amount bound means an amount of the analyte bound under substantially the same amounts of the polypeptide to be evaluated, such as a value determined by dividing the difference in RU value in the sensorgram between before and after the interaction of the analyte with the polypeptide by the difference in RU value in the sensorgram between before and after the capturing of the polypeptide onto the sensor chip.

Specifically, the polypeptide (e.g., antibody) of the present invention is immobilized directly or via protein A, protein L, protein A/G, protein G, an anti-lambda chain antibody, an anti-kappa chain antibody, an antigen peptide, an antigen protein, or the like onto a sensor chip, which is then allowed to interact with each FcγR as an analyte. Then, the amount of change in resonance unit (RU) value on the sensorgram is divided by the amount of change in resonance unit (RU) derived from the polypeptide (e.g., antibody) of the present invention immobilized on the sensor chip to calculate a value. When the value is large, the binding activity can be confirmed to be high. When the value is small, the binding activity can be confirmed to be low. Alternatively, FcγR is immobilized directly or via an anti-tag antibody or the like onto a sensor chip, which is then allowed to interact with the polypeptide (e.g., antibody) of the present invention to be evaluated as an analyte. Then, the amount of change in resonance unit (RU) value on the sensorgram is divided by the amount of change in resonance unit (RU) derived from FcγR immobilized on the sensor chip to calculate a value. When the value is large, the binding activity can be confirmed to be high. When the value is small, the binding activity can be confirmed to be low.

The present invention also relates to a method for altering an Fc region such that the Fc region selectively binds to mouse FcγRII relative to mouse FcγRIII.

The present invention provides a method for altering a parent polypeptide comprising an Fc region to adjust a ratio of [KD value for mouse FcγRIII]/[KD value for mouse FcγRII] to 6 or more, the method comprising altering at least one amino acid in the Fc region. The present invention also provides a method for altering a parent polypeptide comprising an Fc region to improve the binding selectivity of the variant for mouse FcγRII relative to mouse FcγRIII by 5 times or more compared with that of the parent polypeptide, the method comprising altering at least one amino acid in the Fc region.

According to a preferred aspect, each method mentioned above may comprise, for example, the following steps:
obtaining a nucleic acid encoding the parent polypeptide comprising an Fc region;
altering the nucleic acid such that at least one amino acid in the Fc region is altered;
transferring the altered nucleic acid to a host cell, and culturing the host cell to express the polypeptide encoded by the nucleic acid; and
recovering the variant of the parent polypeptide from the cultures of the host cell.

In the method, the ratio of [KD value for mouse FcγRIII]/[KD value for mouse FcγRII] is adjusted to 6 or more, preferably 10 or more, 15 or more, 20 or more, 25 or more, or 30 or more, more preferably 35 or more, 40 or more, 50 or more, 60 or more, 70 or more, 80 or more, or 90 or more. The binding selectivity of the variant for mouse FcγRII relative to mouse FcγRIII is improved by 5 times or more, preferably 10 times or more, 15 times or more, 20 times or more, 25 times or more, or 30 times or more, more preferably 35 times or more, 40 times or more, 50 times or more, 60 times or more, 70 times or more, 80 times or more, or 90 times or more, compared with that of the parent polypeptide.

One example of the preferred properties conferred by the method can include the property of strongly binding to mouse FcγRII. Specifically, the method preferably confers the following property:
the KD value for mouse FcγRII is 20 nM or smaller; or
the binding activity of the variant against mouse FcγRII is enhanced by 10 times or more compared with that of the parent polypeptide.

In the method, the KD value for mouse FcγRII is adjusted to 20 nM or smaller, preferably 10 nM or smaller, 4 nM or smaller, or 2 nM or smaller, more preferably 1.5 nM or smaller, 1 nM or smaller, 0.7 nM or smaller, or 0.5 nM or smaller. Also, the binding activity of the variant against mouse FcγRII is enhanced by 10 times or more, preferably 20 times or more, 50 times or more, or 100 times or more, more preferably 150 times or more, 200 times or more, 300 times or more, or 400 times or more, compared with that of the parent polypeptide.

Examples of the amino acid alteration that can confer the property as mentioned above include the alteration of an amino acid at EU numbering position 230, the alteration of an amino acid at EU numbering position 231, the alteration of an amino acid at EU numbering position 232, the alteration of an amino acid at EU numbering position 238, the alteration of an amino acid at EU numbering position 239, the alteration of an amino acid at EU numbering position 240, the alteration of an amino acid at EU numbering position 241, the alteration of an amino acid at EU numbering position 266, the alteration of an amino acid at EU numbering position 267, the alteration of an amino acid at EU numbering position 268, the alteration of an amino acid at EU numbering position 271, the alteration of an amino acid at EU numbering position 295, the alteration of an amino acid at EU numbering position 296, the alteration of an amino acid at EU numbering position 298, the alteration of an amino acid at EU numbering position 324, the alteration of an amino acid at EU numbering position 326, the alteration of an amino acid at EU numbering position 327, the alteration of an amino acid at EU numbering position 330, the alteration of an amino acid at EU numbering position 331, the alteration of an amino acid at EU numbering position 333, the alteration of an amino acid at EU numbering position 334, the alteration of an amino acid at EU numbering position 335, and the alteration of an amino acid at EU numbering position 337. One of these amino acid alterations may be carried out, or two or more thereof may be combined Examples of a further preferred amino acid alteration include an alteration that substitutes an amino acid at EU numbering position 230 by Asp, Glu, Ile, Pro, Gln, or Val, an alteration that substitutes an amino acid at EU numbering position 231 by Ala, Asp, Glu, Ile, Leu, Met, Asn, Pro, Gln, Thr, or Trp, an alteration that substitutes an amino acid at EU numbering position 232 by Ala, Asp, Glu, Phe, Leu, Asn, Val, Trp, or Tyr, an alteration that substitutes an amino acid at EU numbering position 238 by Glu, Pro, or Gln, an alteration that substitutes an amino acid at EU numbering position 239 by Ala, Asp, Glu, Phe, Gly, His, Ile, Leu, Met, Asn, Pro, Gln, Arg, Thr, Val, Trp, or Tyr, an alteration that substitutes an amino acid at EU numbering position 240 by Glu, His, Gln, or Trp, an alteration that substitutes an amino acid at EU numbering position 241 by Trp or Tyr, an alteration that substitutes an amino acid at EU numbering position 266 by Leu, an alteration that substitutes an amino acid at EU numbering position 267 by Ala or Glu, an alteration that substitutes an amino acid at EU numbering position 268 by Asp, an alteration that substitutes an amino acid at EU numbering position 271 by Leu, an alteration that substitutes an amino acid at EU numbering position 295 by Leu, an alteration that substitutes an amino acid at EU numbering position 296 by Glu, Asn, Thr, or Trp, an alteration that substitutes an amino acid at EU numbering position 298 by Leu or Met, an alteration that substitutes an amino acid at EU numbering position 324 by Asp, Leu, or Met, an alteration that substitutes an amino acid at EU numbering position 326 by Asp, an alteration that substitutes an amino acid at EU numbering position 327 by Gly, an alteration that substitutes an amino acid at EU numbering position 330 by Gly, Lys, or Gln, an alteration that substitutes an amino acid at EU numbering position 331 by Asp, Phe, or Tyr, an alteration that substitutes an amino acid at EU numbering position 333 by Asn, Val, or Tyr, an alteration that substitutes an amino acid at EU numbering position 334 by Arg, an alteration that substitutes an amino acid at EU numbering position 335 by Asn or Tyr, and an alteration that substitutes an amino acid at EU numbering position 337 by Ile, Lys, or Trp. One of these alterations may be carried out, or two or more thereof may be combined. Preferred examples of such alterations include alterations described in Tables 2 to 17, 24, and 25.

Another example of the preferred properties conferred by the method can include the property of weakly binding to mouse FcγRIII. Specifically, the method preferably confers the following property:
the KD value for mouse FcγRIII is 1 µM or larger; or
the binding activity of the variant against mouse FcγRIII is reduced to 0.25 times or less that of the parent polypeptide.

In the method, the KD value for mouse FcγRIII is adjusted to 1 µM or larger, preferably 1.2 µM or larger, 1.5 µM or larger, or 2 µM or larger, more preferably 2.5 µM or larger, 3 µM or larger, 4 µM or smaller, or 5 µM or larger. Also, the binding activity of the variant against mouse FcγRIII is reduced to 0.25 times or less, preferably 0.20 times or less, 0.18 times or less, 0.16 times or less, or 0.14 times or less, more preferably 0.12 times or less, 0.10 times or less, 0.08 times or less, or 0.06 times or less that of the parent polypeptide.

Examples of the amino acid alteration that can confer the property as mentioned above include the alteration of an amino acid at EU numbering position 230, the alteration of an amino acid at EU numbering position 231, the alteration of an amino acid at EU numbering position 232, the alteration of an amino acid at EU numbering position 237, the alteration of an amino acid at EU numbering position 238, the alteration of an amino acid at EU numbering position 239, the alteration of an amino acid at EU numbering position 241, the alteration of an amino acid at EU numbering position 267, and the alteration of an amino acid at EU numbering position 298. One of these amino acid alterations may be carried out, or two or more thereof may be combined Examples of a further preferred amino acid alteration include an alteration that substitutes an amino acid at EU numbering position 230 by Glu, Ile, or Gln, an alteration that substitutes an amino acid at EU numbering position 231 by Ala, Asp, Asn, Pro, or Thr, an alteration that substitutes an amino acid at EU numbering position 232 by Ala, Lys, Asn, or Tyr, an alteration that substitutes an amino acid at EU numbering position 237 by Glu, an alteration that substitutes an amino acid at EU numbering position 238 by Asp or Glu, an alteration that substitutes an amino acid at EU numbering position 239 by Asp, Glu, Phe, Lys, Leu, Asn, Trp, or Tyr, an alteration that substitutes an amino acid at EU numbering position 241 by Asp, Glu, or Thr, an alteration that substitutes an amino acid at EU numbering position 267 by Met, and an alteration that substitutes an amino acid at EU numbering position 298 by His. One of these alterations may be carried out, or two or more thereof may be combined. Preferred examples of such alterations include alterations described in Tables 18 to 23, 26, and 27.

A further example of the preferred properties conferred by the method can include the property of binding to mouse FcγRII with strength equivalent to or higher than that of the parent polypeptide and binding to mouse FcγRIII more weakly compared with the parent polypeptide.
Specifically, the method preferably confers the following property:
the KD value for mouse FcγRII is 400 nM or smaller, and the KD value for mouse FcγRIII is 1 µM or larger; or
the binding activity of the variant against mouse FcγRII is 0.5 times or more that of the parent polypeptide, and the binding activity of the variant against mouse FcγRIII is 0.25 times or less that of the parent polypeptide.

In the method, the KD value for mouse FcγRII is adjusted to 400 nM or smaller, preferably 360 nM or smaller, 320 nM or smaller, or 280 nM or smaller, more preferably 250 nM or smaller, 200 nM or smaller, 150 nM or smaller, or 100 nM or smaller, and the KD value for mouse FcγRIII is adjusted to 1 µM or larger, preferably 1.2 µM or larger, 1.5 µM or larger, or 2 µM or larger, more preferably 2.5 µM or larger, 3 µM or larger, 4 µM or larger, or 5 µM or larger. Also, the binding activity of the variant against mouse FcγRII is adjusted to 0.5 times or more, preferably 0.6 times or more, 0.75 times or more, or 1.0 times or more, more preferably 1.5 times or more, 2 times or more, 2.5 times or more, or 3 times or more that of the parent polypeptide, and the binding activity of the variant against mouse FcγRIII is adjusted to 0.25 times or less, preferably 0.20 times or less, 0.18 times or less, 0.16 times or less, or 0.14 times or less, more preferably 0.12 times or less, 0.10 times or less, 0.08 times or less, or 0.06 times or less that of the parent polypeptide.

Polypeptides produced by alteration according to the method are also included in the scope of the present invention.

The present invention also relates to a method for producing an Fc variant selectively binding to mouse FcγRII relative to mouse FcγRIII.

The present invention provides a method for producing a polypeptide which is a variant of a parent polypeptide comprising an Fc region, wherein the polypeptide has a ratio of [KD value for mouse FcγRIII]/[KD value for mouse FcγRII] of 6 or more, the method comprising altering at least one amino acid in the Fc region. The present invention also provides a method for producing a polypeptide which is a variant of a parent polypeptide comprising an Fc region, wherein the binding selectivity of the polypeptide for mouse FcγRII relative to mouse FcγRIII is improved by 5 times or more compared with that of the parent polypeptide, the method comprising altering at least one amino acid in the Fc region.

According to a preferred aspect, each method mentioned above may comprise, for example, the following steps:
obtaining a nucleic acid encoding the parent polypeptide comprising an Fc region;
altering the nucleic acid such that at least one amino acid in the Fc region is altered;
transferring the altered nucleic acid to a host cell, and culturing the host cell to express the polypeptide encoded by the nucleic acid; and
recovering the variant of the parent polypeptide from the cultures of the host cell.

In the method, the ratio of [KD value for mouse FcγRIII]/[KD value for mouse FcγRII] is 6 or more, preferably 10 or more, 15 or more, 20 or more, 25 or more, or 30 or more, more preferably 35 or more, 40 or more, 50 or more, 60 or more, 70 or more, 80 or more, or 90 or more. The binding selectivity of the polypeptide for mouse FcγRII relative to mouse FcγRIII is improved by 5 times or more, preferably 10 times or more, 15 times or more, 20 times or more, 25 times or more, or 30 times or more, more preferably 35 times or more, 40 times or more, 50 times or more, 60 times or more, 70 times or more, 80 times or more, or 90 times or more, compared with that of the parent polypeptide.

One example of the preferred properties possessed by the polypeptide produced by the method can include the property of strongly binding to mouse FcγRII. Specifically, the polypeptide preferably has the following property:
the KD value for mouse FcγRII is 20 nM or smaller; or
the binding activity of the polypeptide against mouse FcγRII is enhanced by 10 times or more compared with that of the parent polypeptide.

In the method, the KD value for mouse FcγRII is 20 nM or smaller, preferably 10 nM or smaller, 4 nM or smaller, or 2 nM or smaller, more preferably 1.5 nM or smaller, 1 nM or smaller, 0.7 nM or smaller, or 0.5 nM or smaller. Also, the binding activity of the polypeptide against mouse FcγRII is enhanced by 10 times or more, preferably 20 times or more, 50 times or more, or 100 times or more, more preferably 150 times or more, 200 times or more, 300 times or more, or 400 times or more, compared with that of the parent polypeptide.

Examples of the amino acid alteration that can confer the property as mentioned above include the alteration of an amino acid at EU numbering position 230, the alteration of an amino acid at EU numbering position 231, the alteration of an amino acid at EU numbering position 232, the alteration of an amino acid at EU numbering position 238, the alteration of an amino acid at EU numbering position 239, the alteration of an amino acid at EU numbering position 240, the alteration of an amino acid at EU numbering position 241, the alteration of an amino acid at EU numbering position 266, the alteration of an amino acid at EU numbering position 267, the alteration of an amino acid at EU numbering position 268, the alteration of an amino acid at EU numbering position 271, the alteration of an amino acid at EU numbering position 295, the alteration of an amino acid at EU numbering position 296, the alteration of an amino acid at EU numbering position 298, the alteration of an amino acid at EU numbering position 324, the alteration of an amino acid at EU numbering position 326, the alteration of an amino acid at EU numbering position 327, the alteration of an amino acid at EU numbering position 330, the alteration of an amino acid at EU numbering position 331, the alteration of an amino acid at EU numbering position 333, the alteration of an amino acid at EU numbering position 334, the alteration of an amino acid at EU numbering position 335, and the alteration of an amino acid at EU numbering position 337. One of these amino acid alterations may be carried out, or two or more thereof may be combined.

Examples of a further preferred amino acid alteration include an alteration that substitutes an amino acid at EU numbering position 230 by Asp, Glu, Ile, Pro, Gln, or Val, an alteration that substitutes an amino acid at EU numbering position 231 by Ala, Asp, Glu, Ile, Leu, Met, Asn, Pro, Gln, Thr, or Trp, an alteration that substitutes an amino acid at EU numbering position 232 by Ala, Asp, Glu, Phe, Leu, Asn, Val, Trp, or Tyr, an alteration that substitutes an amino acid at EU numbering position 238 by Glu, Pro, or Gln, an alteration that substitutes an amino acid at EU numbering position 239 by Ala, Asp, Glu, Phe, Gly, His, Ile, Leu, Met, Asn, Pro, Gln, Arg, Thr, Val, Trp, or Tyr, an alteration that substitutes an amino acid at EU numbering position 240 by Glu, His, Gln, or Trp, an alteration that substitutes an amino acid at EU numbering position 241 by Trp or Tyr, an alteration that substitutes an amino acid at EU numbering position 266 by Leu, an alteration that substitutes an amino acid at EU numbering position 267 by Ala or Glu, an alteration that substitutes an amino acid at EU numbering position 268 by Asp, an alteration that substitutes an amino acid at EU numbering position 271 by Leu, an alteration that substitutes an amino acid at EU numbering position 295 by Leu, an alteration that substitutes an amino acid at EU numbering position 296 by Glu, Asn, Thr, or Trp, an alteration that substitutes an amino acid at EU numbering position 298 by Leu or Met, an alteration that substitutes an amino acid at EU numbering position 324 by Asp, Leu, or Met, an alteration that substitutes an amino acid at EU numbering position 326 by Asp, an alteration that substitutes an amino acid at EU numbering position 327 by Gly, an alteration that substitutes an amino acid at EU numbering position 330 by Gly, Lys, or Gln, an alteration that substitutes an amino acid at EU numbering position 331 by Asp, Phe, or Tyr, an alteration that substitutes an amino acid at EU numbering position 333 by Asn, Val, or Tyr, an alteration that substitutes an amino acid at EU numbering position 334 by Arg, an alteration that substitutes an amino acid at EU numbering position 335 by Asn or Tyr, and an alteration that substitutes an amino acid at EU numbering position 337 by Ile, Lys, or Trp. One of these alterations may be carried out, or two or more thereof may be combined. Preferred examples of such alterations include alterations described in Tables 2 to 17, 24, and 25.

Another example of the preferred properties possessed by the polypeptide produced by the method can include the property of weakly binding to mouse FcγRIII. Specifically, the polypeptide preferably has the following property:
the KD value for mouse FcγRIII is 1 µM or larger; or
the binding activity of the polypeptide against mouse FcγRIII is reduced to 0.25 times or less that of the parent polypeptide.

In the method, the KD value for mouse FcγRIII is 1 µM or larger, preferably 1.2 µM or larger, 1.5 µM or larger, or 2 µM or larger, more preferably 2.5 µM or larger, 3 µM or larger, 4 µM or larger, or 5 µM or larger. Also, the binding activity of the polypeptide against mouse FcγRIII is reduced to 0.25 times or less, preferably 0.20 times or less, 0.18 times or less, 0.16 times or less, or 0.14 times or less, more preferably 0.12 times or less, 0.10 times or less, 0.08 times or less, or 0.06 times or less that of the parent polypeptide.

Examples of the amino acid alteration that can confer the property as mentioned above include the alteration of an amino acid at EU numbering position 230, the alteration of an amino acid at EU numbering position 231, the alteration of an amino acid at EU numbering position 232, the alteration of an amino acid at EU numbering position 237, the alteration of an amino acid at EU numbering position 238, the alteration of an amino acid at EU numbering position 239, the alteration of an amino acid at EU numbering position 241, the alteration of an amino acid at EU numbering position 267, and the alteration of an amino acid at EU numbering position 298. One of these amino acid alterations may be carried out, or two or more thereof may be combined.

Examples of a further preferred amino acid alteration include an alteration that substitutes an amino acid at EU numbering position 230 by Glu, Ile, or Gln, an alteration that substitutes an amino acid at EU numbering position 231 by Ala, Asp, Asn, Pro, or Thr, an alteration that substitutes an amino acid at EU numbering position 232 by Ala, Lys, Asn, or Tyr, an alteration that substitutes an amino acid at EU numbering position 237 by Glu, an alteration that substitutes an amino acid at EU numbering position 238 by Asp or Glu, an alteration that substitutes an amino acid at EU numbering position 239 by Asp, Glu, Phe, Lys, Leu, Asn, Trp, or Tyr, an alteration that substitutes an amino acid at EU numbering position 241 by Asp, Glu, or Thr, an alteration that substitutes an amino acid at EU numbering position 267 by Met, and an alteration that substitutes an amino acid at EU numbering position 298 by His. One of these alterations may be carried out, or two or more thereof may be combined. Preferred examples of such alterations include alterations described in Tables 18 to 23, 26, and 27.

A further example of the preferred properties possessed by the polypeptide produced by the method can include the property of binding to mouse FcγRII with strength equivalent to or higher than that of the parent polypeptide and binding to mouse FcγRIII more weakly compared with the parent polypeptide. Specifically, the polypeptide preferably has the following property:

the KD value for mouse FcγRII is 400 nM or smaller, and the KD value for mouse FcγRIII is 1 µM or larger; or the binding activity of the polypeptide against mouse FcγRII is 0.5 times or more that of the parent polypeptide, and the binding activity of the polypeptide against mouse FcγRIII is 0.25 times or less that of the parent polypeptide.

In the method, the KD value for mouse FcγRII is 400 nM or smaller, preferably 360 nM or smaller, 320 nM or smaller, or 280 nM or smaller, more preferably 250 nM or smaller, 200 nM or smaller, 150 nM or smaller, or 100 nM or smaller, and the KD value for mouse FcγRIII is 1 µM or larger, preferably 1.2 µM or larger, 1.5 µM or larger, or 2 µM or larger, more preferably 2.5 µM or larger, 3 µM or larger, 4 µM or larger, or 5 µM or larger. Also, the binding activity of the polypeptide against mouse FcγRII is 0.5 times or more, preferably 0.6 times or more, 0.75 times or more, or 1.0 times or more, more preferably 1.5 times or more, 2 times or more, 2.5 times or more, or 3 times or more that of the parent polypeptide, and the binding activity of the polypeptide against mouse FcγRIII is 0.25 times or less, preferably 0.20 times or less, 0.18 times or less, 0.16 times or less, or 0.14 times or less, more preferably 0.12 times or less, 0.10 times or less, 0.08 times or less, or 0.06 times or less that of the parent polypeptide.

Polypeptides produced by the method are also included in the scope of the present invention.

The present invention also encompasses a nucleic acid encoding the polypeptide of the present invention. The nucleic acid of the present invention may be in any form such as DNA or RNA.

The present invention further encompasses a vector comprising the nucleic acid of the present invention. The type of the vector can be appropriately selected by those skilled in the art according to host cells to which the vector is transferred. For example, any of the vectors mentioned above can be used.

The present invention further encompasses a host cell transformed with the vector of the present invention. The host cell can be appropriately selected by those skilled in the art. For example, any of the host cells mentioned above can be used.

The present invention provides a pharmaceutical composition comprising the polypeptide of the present invention as an active ingredient. The pharmaceutical composition of the present invention can be formulated according to a method known in the art by using the polypeptide of the present invention in combination with a pharmaceutically acceptable carrier. For example, the pharmaceutical composition may be formulated with the polypeptide of the present invention mixed in a unit dosage form required for generally accepted pharmaceutical practice, in appropriate combination with pharmacologically acceptable carriers or media, specifically, sterilized water, physiological saline, plant oil, an emulsifier, a suspending agent, a surfactant, a stabilizer, a flavoring agent, an excipient, a vehicle, a preservative, a binder, etc. Examples of the carrier can include light anhydrous silicic acid, lactose, crystalline cellulose, mannitol, starch, carmellose calcium, carmellose sodium, hydroxypropylcellulose, hydroxypropylmethylcellulose, polyvinyl acetal diethylaminoacetate, polyvinylpyrrolidone, gelatin, medium-chain fatty acid triglyceride, polyoxyethylene hydrogenated castor oil 60, saccharide, carboxymethylcellulose, cornstarch, and inorganic salts. The amount of the active ingredient in such a preparation can be appropriately determined within the prescribed range of doses.

Examples of aqueous solutions for injection include isotonic solutions or physiological saline containing glucose, D-sorbitol, D-mannose, D-mannitol, sodium chloride, and the like. These solutions may be used in combination with an appropriate solubilizer, for example, an alcohol (ethanol, propylene glycol, polyethylene glycol, etc.) or a nonionic surfactant (polysorbate 80(TM), HCO-50, etc.).

Examples of oily solutions include sesame oil and soybean oil. These solutions may be used in combination with benzyl benzoate or benzyl alcohol as a solubilizer. The solutions may be further mixed with a buffer (a phosphate buffer solution, a sodium acetate buffer solution, etc.), a soothing agent (procaine hydrochloride, etc.), a stabilizer (benzyl alcohol, phenol, etc.), an antioxidant, and the like. The injection solutions thus prepared are usually charged into appropriate ampules.

The dose or administration method of the pharmaceutical composition of the present invention varies depending on the body weight, age, symptoms, etc. of a patient and can be appropriately selected by those skilled in the art. The single dose thereof can be selected, for example, within a range of 0.0001 mg to 1000 mg per kg of body weight or within a range of 0.001 to 100000 mg/body per patient, though the dose is not necessarily limited to these numeric values. Oral administration or parenteral administration may be selected as an administration method. Parenteral administration is preferred. Examples of the parenteral administration include injection, intranasal administration, transpulmonary administrations, and percutaneous administration. Examples of the injection include intravenous injection, intramuscular injection, intraperitoneal injection, and subcutaneous injection. The pharmaceutical composition can be administered systemically or locally through these administration methods.

The present invention also relates to a method for using the polypeptide comprising an Fc variant selectively binding to mouse FcγRII relative to mouse FcγRIII to predict the effects, on a human, of a polypeptide comprising an Fc variant selectively binding to human FcγRIIb relative to human FcγRIIa.

Even an Fc variant that exhibits binding selectivity for human FcγRIIb is likely to exhibit no binding selectivity for mouse FcγRII due to difference of species cross-reactivity. For this reason, it has been difficult to evaluate drug effects, safety, etc. in animal (e.g., mouse) models in an attempt to develop a drug having the feature to selectively bind to human FcγRIIb using the Fc variant. The Fc variant found in the present invention which selectively binds to mouse FcγRII is very useful in terms of improving this situation and enabling effects, safety, etc. to be evaluated in mice. As shown later in Examples, members of the FcγR family other than mouse FcγRII (or human FcγRIIb) seem to also participate in time-dependent change in the concentration of a polypeptide comprising an Fc region, such as an antibody, in blood. In this respect, the polypeptide of the present invention selectively binding to mouse FcγRII is indispensable for accurately evaluating, in mice, the effects or safety of a drug having the feature to selectively bind to human FcγRIIb.

The present invention provides a method for predicting a therapeutic or preventive effect on a disease when a polypeptide comprising an Fc variant selectively binding to human FcγRIIb relative to human FcγRIIa is administered to a human, the method comprising the steps of administering a polypeptide comprising an Fc variant selectively binding to mouse FcγRII relative to mouse FcγRIII, to a mouse model of the human disease and evaluating the therapeutic or preventive effect thereof.

Specifically, according to a preferred aspect, the method may comprise, for example, the following steps:
(a) obtaining a polypeptide comprising an antigen-binding region binding to a mouse antigen;
(b) preparing a polypeptide comprising the antigen-binding region of the polypeptide obtained in step (a), and the Fc variant of the present invention;
(c) administering the polypeptide prepared in step (b) to a mouse model of a human disease; and
(d) when a therapeutic or preventive effect on the disease is observed in the mouse as a result of step (c), determining that a polypeptide comprising an antigen-binding region binding to a human counterpart of the mouse antigen, and the Fc variant selectively binding to human FcγRIIb relative to human FcγRIIa is effective for the treatment or prevention of the human disease.

According to a more preferred aspect, the method may further comprise steps (b') and (c') in addition to the steps (b) and (c) and the step (d) may be a step given below:
(b') preparing a polypeptide comprising the antigen-binding region of the polypeptide obtained in step (a), and the Fc region of naturally occurring IgG; and
(c') administering the polypeptide prepared in step (b') to a mouse model of a human disease, and
(d) when a stronger therapeutic or preventive effect on the disease is observed in the mouse that has received the polypeptide of step (b) than in the mouse that has received the polypeptide of step (b') as a result of steps (c) and (c'), determining that a polypeptide comprising an antigen-binding region binding to a human counterpart of the mouse antigen, and the Fc variant selectively binding to human FcγRIIb relative to human FcγRIIa is effective for the treatment or prevention of the human disease.

The present invention provides a method for selecting a disease suitable for treatment or prevention using a polypeptide comprising an Fc variant selectively binding to human FcγRIIb relative to human FcγRIIa, the method comprising the steps of administering a polypeptide comprising an Fc variant selectively binding to mouse FcγRII relative to mouse FcγRIII, to a mouse model of a human disease and evaluating the therapeutic or preventive effect thereof.

Specifically, according to a preferred aspect, the method may comprise, for example, the following steps:
(a) obtaining a polypeptide comprising an antigen-binding region binding to a mouse antigen;
(b) preparing a polypeptide comprising the antigen-binding region of the polypeptide obtained in step (a), and the Fc variant of the present invention;
(c) administering the polypeptide prepared in step (b) to a mouse model of a human disease; and
(d) when a therapeutic or preventive effect on the disease is observed in the mouse as a result of step (c), selecting the human disease as the disease suitable for treatment or prevention using a polypeptide comprising an antigen-binding region binding to a human counterpart of the mouse antigen, and the Fc variant selectively binding to human FcγRIIb relative to human FcγRIIa.

According to a more preferred aspect, the method may further comprise steps (b') and (c') in addition to the steps (b) and (c) and the step (d) may be a step given below:
(b') preparing a polypeptide comprising the antigen-binding region of the polypeptide obtained in step (a), and the Fc region of naturally occurring IgG; and
(c') administering the polypeptide prepared in step (b') to a mouse model of a human disease, and
(d) when a stronger therapeutic or preventive effect on the disease is observed in the mouse that has received the polypeptide of step (b) than in the mouse that has received the polypeptide of step (b') as a result of steps (c) and (c'), selecting the human disease as the disease suitable for treatment or prevention using a polypeptide comprising an antigen-binding region binding to a human counterpart of the mouse antigen, and the Fc variant selectively binding to human FcγRIIb relative to human FcγRIIa.

The present invention provides a method for selecting a target antigen suitable for treatment or prevention using a polypeptide comprising an Fc variant selectively binding to human FcγRIIb relative to human FcγRIIa, the method comprising the steps of administering a polypeptide comprising an Fc variant selectively binding to mouse FcγRII relative to mouse FcγRIII, to a mouse model of a human disease and evaluating the therapeutic or preventive effect thereof.

Specifically, according to a preferred aspect, the method may comprise, for example, the following steps:
(a) obtaining a polypeptide comprising an antigen-binding region binding to a mouse antigen;
(b) preparing a polypeptide comprising the antigen-binding region of the polypeptide obtained in step (a), and the Fc variant of the present invention;
(c) administering the polypeptide prepared in step (b) to a mouse model of a human disease; and
(d) when a therapeutic or preventive effect on the disease is observed in the mouse as a result of step (c), selecting a human counterpart of the mouse antigen as the target antigen suitable for treatment or prevention using a polypeptide comprising the Fc variant selectively binding to human FcγRIIb relative to human FcγRIIa.

According to a more preferred aspect, the method may further comprise steps (b') and (c') in addition to the steps (b) and (c) and the step (d) may be a step given below:
(b') preparing a polypeptide comprising the antigen-binding region of the polypeptide obtained in step (a), and the Fc region of naturally occurring IgG; and
(c') administering the polypeptide prepared in step (b') to a mouse model of a human disease, and
(d) when a stronger therapeutic or preventive effect on the disease is observed in the mouse that has received the polypeptide of step (b) than in the mouse that has received the polypeptide of step (b') as a result of steps (c) and (c'), selecting a human counterpart of the mouse antigen as the target antigen suitable for treatment or prevention using a polypeptide comprising the Fc variant selectively binding to human FcγRIIb relative to human FcγRIIa.

The present invention provides a method for selecting an antigen-binding region suitable for treatment or prevention using a polypeptide comprising an Fc variant selectively binding to human FcγRIIb relative to human FcγRIIa, the method comprising the steps of administering a polypeptide comprising an Fc variant selectively binding to mouse FcγRII relative to mouse FcγRIII, to a mouse model of a human disease and evaluating the therapeutic or preventive effect thereof.

Specifically, according to a preferred aspect, the method may comprise, for example, the following steps:
(a) obtaining a plurality of polypeptides comprising antigen-binding regions binding to the same mouse antigen;
(b) preparing a polypeptide comprising each of the antigen-binding regions of the polypeptides obtained in step (a), and the Fc variant of the present invention;

(c) administering the polypeptide prepared in step (b) to a mouse model of a human disease; and (d) as a result of step (c), selecting the antigen-binding region of a polypeptide that exhibits a stronger therapeutic or preventive effect as the antigen-binding region suitable for treatment or prevention of the human disease using a polypeptide comprising the Fc variant selectively binding to human FcγRIIb relative to human FcγRIIa.

The present invention provides a method for predicting safety or toxicity when a polypeptide comprising an Fc variant selectively binding to human FcγRIIb relative to human FcγRIIa is administered to a human, the method comprising the steps of administering a polypeptide comprising an Fc variant selectively binding to mouse FcγRII relative to mouse FcγRIII, to a mouse and evaluating the safety or toxicity thereof.

In the aforementioned method for selecting an antigen-binding region, the mouse antigen is preferably identical to the human antigen as mentioned later. Specifically, a genetically modified mouse prepared by the transfer of a human gene is selected as the mouse model of a human disease, and a gene product expressed from the human gene is used as the mouse antigen in this method. As a result, the optimum antigen-binding region is preferably selected from among a plurality of antigen-binding regions binding to the human gene product.

In drug development, safety tests are carried out at the preclinical stage using monkeys or rodents such as mice. Depending on animal species, however, the target antigen is low homologous to its human counterpart. A development candidate drug therefore may not cross-react with the monkey or mouse antigen. Particularly, the mouse antigen is low analogous to its human counterpart and often does not have sufficient cross-reactivity. In such a case, the development candidate may be evaluated for its safety by use of a surrogate binding to the mouse target antigen with strength or properties similar to those of the human target antigen (reference: MAbs, 2009, 1 (1), 2-11). Likewise, the Fc variant of the present invention can be used as a mouse surrogate for an Fc variant selectively binding to human FcγRIIb. The polypeptide (preferably, antibody, etc.) comprising the Fc variant of the present invention can be administered to a mouse to thereby evaluate the safety of the polypeptide comprising an Fc variant selectively binding to human FcγRIIb.

Specifically, according to a preferred aspect, the method may comprise, for example, the following step:
(a) obtaining a polypeptide comprising an antigen-binding region binding to a mouse antigen;
(b) preparing a polypeptide comprising the antigen-binding region of the polypeptide obtained in step (a), and the Fc variant of the present invention;
(c) administering the polypeptide prepared in step (b) to a mouse; and
(d) analogically inferring the safety or toxicity, in a human, of a polypeptide comprising an antigen-binding region binding to a human counterpart of the mouse antigen, and the Fc variant selectively binding to human FcγRIIb relative to human FcγRIIa from the results obtained in step (c) about the safety or toxicity of the polypeptide of step (b) in the mouse.

The present invention provides a method for predicting pharmacokinetics when a polypeptide comprising an Fc variant selectively binding to human FcγRIIb relative to human FcγRIIa is administered to a human, the method comprising the steps of administering a polypeptide comprising an Fc variant selectively binding to mouse FcγRII relative to mouse FcγRIII, to a mouse and measuring the pharmacokinetics thereof.

Specifically, according to a preferred aspect, the method may comprise, for example, the following steps:
(a) obtaining a polypeptide comprising an antigen-binding region binding to a mouse antigen;
(b) preparing a polypeptide comprising the antigen-binding region of the polypeptide obtained in step (a), and the Fc variant of the present invention;
(c) administering the polypeptide prepared in step (b) to a mouse; and
(d) analogically inferring the pharmacokinetics, in a human, of a polypeptide comprising an antigen-binding region binding to a human counterpart of the mouse antigen, and the Fc variant selectively binding to human FcγRIIb relative to human FcγRIIa from the results obtained in step (c) about the pharmacokinetics of the polypeptide of step (b) in the mouse.

Preferably, the polypeptide comprising an Fc variant selectively binding to human FcγRIIb further comprises an antigen-binding region binding to a human antigen. The human antigen is preferably an antigen capable of serving as a target for the treatment or prevention of the human disease. The antigen-binding region preferably has functions that lead to the treatment or prevention of the human disease through binding to the antigen. In this case, the polypeptide comprising an Fc variant selectively binding to mouse FcγRII has an antigen-binding region binding to a mouse counterpart of the human antigen. In addition, the antigen-binding region preferably has, in mice, functions corresponding to the functions of treating or preventing the human disease by the human antigen-binding region.

Human FcγRIIb and human FcγRIIa have 93% sequence identity at their extracellular regions. Desirably, the Fc variant selectively binding to human FcγRIIb has higher binding activity against FcγRIIb and lower binding activity against FcγRIIa than those of the Fc region of naturally occurring IgG. In the present specification, the Fc variant selectively binding to human FcγRIIb relative to human FcγRIIa means an Fc region in which a value of the Fc region determined by dividing [KD value for human FcγRIIa] by [KD value for human FcγRIIb] is larger than a value of the Fc region of naturally occurring human IgG determined by dividing [KD value for human FcγRIIa] by [KD value for human FcγRIIb]. Examples of such Fc variants are described in, for example, WO2012/115241 and WO2008/150494. Thus, any of these Fc variants can be used.

The disease suitable for treatment or prevention using the polypeptide comprising the Fc variant selectively binding to human FcγRIIb is not particularly limited. Preferred examples of the disease include immune inflammatory disease (particularly, autoimmune disease), renal disease, hepatic disease, pulmonary disease, diabetes mellitus, bone disease, blood disease, and cancer disease.

The polypeptide comprising an antigen-binding region binding to a mouse antigen can be obtained by a method generally known to those skilled in the art, for example, a hybridoma method (Kohler and Milstein, Nature 256, 495 (1975)) or a phage-displayed antibody library method (Clackson et al, Nature 352, 624-628 (1991); and Marks et al, J Mol Biol 222, 581-597 (1991)).

Also, the polypeptide comprising an antigen-binding region and an Fc region (the Fc region of naturally occurring IgG, the Fc variant of the present invention, etc.) can be prepared by fusing a DNA encoding the antigen-binding region in frame with a DNA encoding the Fc region, and then inserting the fusion product to appropriate expression vectors, which are then transferred to preferred expression cells so that the polypeptide is expressed.

In the present specification, the "treatment or prevention" means that some pharmacological and/or physiological effect is obtained for a subject having the disease. The "treatment" means the suppression of progression of pathological conditions in a subject already diagnosed with the disease, or the mitigation of these pathological conditions. The "prevention" means the suppression of onset of a disease in a subject yet to be diagnosed with the disease. The strength of such effects may be determined qualitatively from some finding related to the disease or may be determined quantitatively from some index. The index can be selected from, for example, the concentration of a disease marker such as a peptide or a metabolite, disease scores for the numerical rating of symptoms, latency period/incidence, or progression-free survival/survival rate according to the disease, though the index is not particularly limited thereto. When the disease is, for example, asthma, the therapeutic effect can be evaluated on the basis of reduction in plasma IgE concentration or decrease in the number of B cells, mast cells, plasma cells, IgE-producing B cells, or IgE-producing plasma cells.

In the present specification, the "safety" of the polypeptide means that any adverse event (toxicity or adverse reaction) is not observed in a recipient of the polypeptide, particularly, a mouse or human recipient of the polypeptide. The recipient may be healthy or may have some disease.

In the present specification, the "toxicity" of the polypeptide means that some adverse event (toxicity or adverse reaction) is observed in a recipient of the polypeptide, particularly, a mouse or human recipient of the polypeptide. The recipient may be healthy or may have some disease.

In the present specification, the phrase "evaluating the safety" of the polypeptide or "predicting the safety" of the polypeptide means evaluating whether or not some adverse event (toxicity or adverse reaction) is observed in a recipient of the polypeptide, particularly, a mouse or human recipient of the polypeptide. The recipient may be healthy or may have some disease.

In the present specification, the pharmacokinetics means the behavior of a drug in the body (e.g., the concentration of the drug in blood) after administration of the drug to a subject. Examples thereof include absorption, distribution, metabolism, and excretion. Examples of parameters that exhibit the pharmacokinetics include, but not particularly limited to, half-life, distribution volume, clearance, the rate of absorption/disappearance, and bioavailability.

The mouse that receives the polypeptide comprising an Fc variant selectively binding to mouse FcγRII may be a wild-type mouse or may be a genetically modified mouse.

In the present specification, the "mouse antigen" means a molecule that exists as a possible antigen in the living body of a mouse and is capable of serving as a target for the treatment or prevention of the disease. In this context, the mouse antigen is not limited to a mouse-derived molecule as long as the antigen exists in the living body of a mouse. The mouse antigen also includes, for example, molecules derived from bacteria or viruses in mice infected with the bacteria or the viruses. Alternatively, the mouse antigen also includes molecules derived from organisms other than mice, such as proteins expressed from genetically modified mice prepared by the transfer of genes of the organisms (e.g., humans) other than mice.

In the present specification, the "human counterpart of the mouse antigen" means an antigen having, in humans, functions equivalent to the functions of the mouse antigen in mice. When the mouse antigen is a mouse-derived molecule, its human counterpart means a homolog molecule thereof in humans. When the mouse antigen is a molecule derived from an organism other than the mouse, its human counterpart means a molecule that exhibits, on a human disease, effects equivalent to the effects of the molecule on a mouse disease. When the mouse antigen is a molecule derived from a bacterium or a virus capable of infecting both mice and humans, the mouse antigen is identical to the human antigen. Also, when the mouse antigen is a gene product in a mouse transfected with a human gene, the mouse antigen is identical to the human antigen.

Examples of the mouse model of a human disease can specifically include, but not limited to: Mrl/lpr mice, NZB/W F1 mice, DNA-induced SLE mouse models, pristane-induced SLE mouse models, and BXSB mice as mouse models of lupus nephritis; IgE-induced mouse models and NC/Nga mice as mouse models of atopic dermatitis; EAE mouse models as mouse models of multiple sclerosis; LPS-induced mouse models as mouse models of sepsis; collagen-induced mouse models, adjuvant-induced mouse models, bacterium-derived cell wall-induced mouse models, NZB/KN mice, Biozzi mice, HTLV-1 transgenic mice, human TNFα transgenic mice, and K/BxN transgenic mice as mouse models of rheumatoid arthritis; NOD mice and STZ mice as mouse models of type 1 diabetes mellitus; db/db mice and KKAy mice as mouse models of type 2 diabetes mellitus; Bleomycin-induced mouse models as mouse models of systemic scleroderma; chronic Thy-1 mouse models as mouse models of chronic kidney disease (CKD); UUO mouse models, I/R mouse models, and NEP25 mice as mouse models of renal fibrosis; β-1,4-galactose transferase-deficient mice as mouse models of IgA nephropathy; CDAHFD mice and high-carbohydrate, high-fat mouse models as mouse models of non-alcoholic steatohepatitis (NASH); and TAA mice and BDL mice as mouse models of hepatic fibrosis.

Alternatively, a wild-type mouse may be used as the mouse model of a human disease. The wild-type mouse may be subjected to exogenous treatment for developing some disease, and the resulting mouse can serve as the mouse model of a human disease. Examples of the wild-type mouse include, but not limited to, BALB/C and C57BL/6.

The mouse model used in the present invention is preferably selected from among mouse models having the same disease as that in which the aforementioned mouse antigen can be targeted by the treatment or prevention.

A polypeptide comprising an antigen-binding region binding to the target antigen selected by the method mentioned above, and an Fc variant selectively binding to human FcγRIIb relative to human FcγRIIa is also included in the scope of the present invention.

A polypeptide comprising the antigen-binding region selected by the method mentioned above, and an Fc variant selectively binding to human FcγRIIb relative to human FcγRIIa is also included in the scope of the present invention.

In addition, a therapeutic or preventive agent for a human disease, comprising such a polypeptide as an active ingredient is also included in the scope of the present invention. A method for treating or preventing a human disease, comprising administering such a polypeptide to a patient is also included in the scope of the present invention. Use of such a polypeptide in the production of a therapeutic or preventive agent for a human disease is also included in the scope of the present invention. Such a polypeptide for use in the treatment or prevention of a human disease is also included in the scope of the present invention. The human disease is preferably a disease evaluated by the method mentioned above as being suitable for treatment or prevention using the polypeptide.

The present invention also provides a kit for use in the treatment or prevention of a human disease, comprising such a polypeptide. The human disease is preferably a disease evaluated by the method mentioned above as being suitable for treatment or prevention using the polypeptide. The kit may additionally comprise pharmaceutically acceptable carriers and media, an instruction that provides usage, etc., in a package.

The polypeptide comprising an Fc variant selectively binding to human FcγRIIb is useful as an active ingredient in an inhibitor of the activation of B cells, mast cells, dendritic cells, and/or basophils. This polypeptide can inhibit the activation of B cells, mast cells, dendritic cells, and/or basophils by the selective action on FcγRIIb without the activation of activating FcγR. The activation of B cells includes proliferation, IgE production, IgM production, IgA production, and the like. According to one aspect, the polypeptide can inhibit the IgE production of B cells through the cross-link of FcγRIIb to IgE, the IgM production of B cells through the cross-link of FcγRIIb to IgM, and the IgA production of B cells through the cross-link of FcγRIIb to IgA. In addition, the polypeptide can exert an inhibitory effect similar to that described above through the direct or indirect cross-link of FcγRIIb to a molecule, such as BCR, CD19, or CD79b, which is expressed on B cells and intracellularly contains an ITAM domain or interacts with an ITAM domain. The activation of mast cells includes proliferation, activation by IgE or the like, degranulation, and the like. According to one aspect, the polypeptide can inhibit the proliferation, activation by IgE or the like, or degranulation of mast cells through the direct or indirect cross-link of FcγRIIb to an IgE receptor molecule, such as FcεRI, DAP12, or CD200R3, which is expressed on mast cells and contains an ITAM domain or interacts with an ITAM domain. The activation of basophils includes proliferation, degranulation, and the like. According to one aspect, the polypeptide can also inhibit the activation, degranulation, or proliferation of basophils through the direct or indirect cross-link of FcγRIIb to a molecule that resides on the cell membrane and intracellularly contains an ITAM domain or interacts with an ITAM domain. The activation of dendritic cells includes proliferation, degranulation, and the like. The polypeptide can also inhibit the activation, degranulation, or proliferation of dendritic cells through the direct or indirect cross-link of FcγRIIb to a molecule that resides on the cell membrane and intracellularly contains an ITAM domain or interacts with an ITAM domain.

The polypeptide comprising an Fc variant selectively binding to human FcγRIIb is also useful as an active ingredient in a therapeutic or preventive agent for immune inflammatory disease. As mentioned above, the polypeptide can inhibit the activation of B cells, mast cells, dendritic cells, and/or basophils and as such, can treat or prevent immune inflammatory disease through its administration. The "immune inflammatory disease" encompasses, but not limited to: rheumatoid arthritis, autoimmune hepatitis, autoimmune thyroiditis, autoimmune bullous disease, autoimmune adrenocortical inflammation, autoimmune hemolytic anemia, autoimmune thrombocytopenic purpura, megalocytic anemia, autoimmune atrophic gastritis, autoimmune neutropenia, autoimmune orchitis, autoimmune encephalomyelitis, autoimmune receptor disease, autoimmune infertility, chronic active hepatitis, glomerulonephritis, interstitial lung fibrosis, multiple sclerosis, Paget's disease, osteoporosis, multiple myeloma, uveitis, acute and chronic spondylitis, gouty arthritis, inflammatory bowel disease, adult respiratory distress syndrome (ARDS), psoriasis, Crohn's disease, Basedow disease, juvenile diabetes mellitus, Addison's disease, myasthenia gravis, lens-induced uveitis, systemic lupus erythematosus, allergic rhinitis, allergic dermatitis, ulcerative colitis, hypersensitivity, muscle degeneration, cachexia, systemic scleroderma, morphea, Sjogren's syndrome, Behcet's disease, Reiter's syndrome, type I and type II diabetes mellitus, bone resorption, graft-versus-host reaction, ischemia-reperfusion injury, atherosclerosis, brain trauma, cerebral malaria, sepsis, septic shock, toxic shock syndrome, fever, stain-induced myalgias, aplastic anemia, hemolytic anemia, idiopathic thrombocytopenia, Goodpasture's syndrome, Guillain-Barre syndrome, Hashimoto's disease, pemphigus, IgA nephropathy, pollinosis, anti-phospholipid antibody syndrome, polymyositis, Wegener's granulomatosis, arteritis nodosa, mixed connective-tissue disease, fibromyalgia syndrome, asthma, atopic dermatitis, chronic atrophic gastritis, primary biliary cirrhosis, primary sclerosing cholangitis, autoimmune pancreatitis, aortitis syndrome, rapidly progressive glomerulonephritis, megaloblastic anemia, idiopathic thrombocytopenic purpura, primary hypothyroidism, idiopathic Addison's disease, insulin-dependent diabetes mellitus, chronic discoid lupus erythematodes, pemphigoid, herpes gestationis, linear IgA bullous dermatosis, epidermolysis bullosa acquisita, alopecia areata, vitiligo vulgaris, leukoderma acquisitum centrifugum Sutton, Harada's disease, autoimmune optic neuropathy, idiopathic azoospermia, recurrent fetal loss, hypoglycemia, chronic urticaria, ankylosing spondylitis, psoriatic arthritis, enteropathic arthritis, reactive arthritis, spondyloarthropathy, enthesitis, irritable bowel syndrome, chronic fatigue symptom, dermatomyositis, inclusion body myositis, Schmidt's syndrome, Graves' disease, pernicious anemia, lupoid hepatitis, pre-senile dementia, Alzheimer's disease, demyelinating disease, amyotrophic lateral sclerosis, hypoparathyroidism, Dressler's syndrome, Eaton-Lambert syndrome, herpetiform dermatitis, alopecia, progressive systemic sclerosis, CREST syndrome (calcinosis, Raynaud's phenomenon, esophageal motor disturbance, sclerodactylia, and telangiectasis), sarcoidosis, rheumatic fever, erythema multiforme, Cushing's syndrome, transfusion reaction, Hansen's disease, Takayasu arteritis, polymyalgia rheumatica syndrome, temporal arteritis, giant cell arthritis, eczema, lymphomatoid granulomatosis, Kawasaki disease, endocarditis, endomyocardial fibrosis, endophthalmitis, erythroblastosis fetalis, eosinophilic fasciitis, Felty syndrome, Henoch-Shonlein purpura, transplantation rejection, mumps, cardiomyopathy, purulent arthritis, familial Mediterranean fever, Muckle-Wells syndrome, and hyper-IgD syndrome.

The polypeptide comprising an Fc variant selectively binding to human FcγRIIb is also useful as an active ingredient in a drug treating or preventing autoimmune disease presumably caused by the production of an antibody (autoantibody) against a self-antigen, by inhibiting the production of the autoantibody. Reportedly, use of a molecule comprising a myasthenia gravis self-antigen AchR fused with an antibody Fc domain inhibits the proliferation of B cells expressing AchR-recognizing BCR and enhances the apoptosis thereof (J Neuroimmunol, 227, 35-43, 2010). Use of a fusion protein of an antigen that is recognized by an autoantibody, and the Fc region can inhibit the proliferation of B cells expressing BCR against the self-antigen and induce the apoptosis thereof by cross-linking FcγRIIb to BCR in the B cells expressing BCR against the self-antigen. Such autoimmune disease includes, but not limited to, Guillain-Barre syndrome, myasthenia gravis, chronic atrophic gastritis, autoimmune hepatitis, primary biliary cirrhosis, primary sclerosing cholangitis, autoimmune pancreatitis, aortitis syndrome, Goodpasture's syndrome, rapidly progressive glomerulonephritis, megaloblastic anemia, autoimmune hemolytic anemia, autoimmune neutropenia, idiopathic thrombocytopenic purpura, Basedow disease, Hashimoto's disease, primary hypothyroidism, idiopathic Addison's disease, insulin-dependent diabetes mellitus, chronic discoid lupus erythematodes, morphea, pemphigus, pemphigoid, herpes gestationis, linear IgA bullous dermatosis, epidermolysis bullosa acquisita, alopecia areata, vitiligo vulgaris, leukoderma acquisitum centrifugum Sutton, Harada's disease, autoimmune optic neuropathy, idiopathic azoospermia, recurrent fetal loss, type II diabetes mellitus, hypoglycemia, and chronic urticaria.

The polypeptide comprising an Fc variant selectively binding to human FcγRIIb is also useful as an active ingredient in a therapeutic agent for a disease with deficiency in a protein necessary for organisms. For the disease with deficiency in a protein necessary for organisms, replacement therapy involving administering the protein as a drug to a patient is used. Since the patient, however, is originally deficient in this protein, the protein supplied from the outside is recognized as a foreign substance, resulting in the production of an antibody against the protein. Consequently, the protein is easily removed to reduce its drug effect. Use of a fusion protein of such a protein and the Fc region can inhibit the production of an antibody against the protein by cross-linking FcγRIIb to BCR on B cells that recognize the protein. The protein to be supplied includes Factor VIII, Factor IX, TPO, EPO, α-iduronidase, iduronate sulfatase, type A heparan N-sulfatase, type B α-N-acetylglucosaminidase, type C acetyl CoA:α-glucosaminidase acetyltransferase, type D N-acetylglucosamine 6-sulfatase, galactose 6-sulfatase, N-acetylgalactosamine 4-sulfatase, β-glucuronidase, α-galactosidase, acidic α-galactosidase, and glucocerebrosidase. The disease to be treated by the replacement therapy of such a protein includes, but not limited to, hemophilia, idiopathic thrombocytopenic purpura, renal anemia, lysosomal disease (mucopolysaccharidosis, Fabry's disease, Pompe's disease, and Gaucher's disease), and the like.

The polypeptide comprising an Fc variant selectively binding to human FcγRIIb is also useful as an active ingredient in an antiviral agent. An antibody that is directed to a virus and comprises the Fc region can inhibit antibody-dependent enhancement found in an antibody against the virus. The antibody-dependent enhancement refers to the phenomenon in which a virus is englobed via activating FcγR by use of a neutralizing antibody against the virus to infect FcγR-expressing cells, thereby spread the infection. The FcγRIIb binding of a neutralizing antibody against dengue virus has been reported to play an important role in inhibiting the antibody-dependent enhancement (Proc Natl Acad Sci USA, 108, 12479-12484, 2011). An immune complex of dengue virus formed by a neutralizing antibody against the dengue virus cross-links FcγRIIb and thereby inhibits englobement mediated by FcγR, resulting in the inhibition of the antibody-dependent enhancement. The virus includes, but not limited to, dengue virus (DENV1, DENV2, and DENV4) and HIV.

The polypeptide comprising an Fc variant selectively binding to human FcγRIIb is also useful as an active ingredient in a preventive or therapeutic agent for arteriosclerosis. An antibody that is directed to oxidized LDL, which is responsible for arteriosclerosis, and comprises the Fc region can prevent FcγRIIa-dependent inflammatory cell adhesion. The anti-oxidized LDL antibody inhibits the interaction between oxidized LDL and CD36. The anti-oxidized LDL antibody has been reported to bind to endothelial cells so that its Fc domain is recognized by monocytes in an FcγRIIa- or FcγRI-dependent manner for adhesion (Immunol Lett, 108, 52-61, 2007). The antibody comprising the Fc region can be used as such an antibody to thereby probably inhibit FcγRIIa-dependent binding and inhibit monocyte adhesion through inhibitory signals mediated by FcγRIIb.

The polypeptide comprising an Fc variant selectively binding to human FcγRIIb is also useful as an active ingredient in a therapeutic or preventive agent for cancer. Enhanced binding to FcγRIIb is known to enhance the agonistic activity of an agonist antibody and also enhance an antitumor effect based on the agonistic activity. Thus, an agonist antibody comprising the Fc region is useful in the treatment or prevention of cancer. The Fc region enhances the agonistic activity of agonist antibodies against the TNF receptor family including Aliases, CD120a, CD120b, Lymphotoxin β receptor, CD134, CD40, FAS, TNFRSF6B, CD27, CD30, CD137, TNFRSF10A, TNFRSF10B, TNFRSF10C, TNFRSF10D, RANK, Osteoprotegerin, TNFRSF12A, TNFRSF13B, TNFRSF13C, TNFRSF14, Nerve growth factor receptor, TNFRSF17, TNFRSF18, TNFRSF19, TNFRSF21, TNFRSF25, and Ectodysplasin A2 receptor. The Fc region also enhances the agonistic activity of other agonist antibodies. The cancer encompasses, but not limited to: lung cancer (including small-cell lung cancer, non-small-cell lung cancer, lung adenocarcinoma, and lung squamous cell carcinoma), large bowel cancer, rectal cancer, colon cancer, breast cancer, liver cancer, stomach cancer, pancreatic cancer, kidney cancer, prostate cancer, ovary cancer, thyroid gland cancer, bile duct cancer, peritoneal cancer, mesothelioma, squamous cell cancer, uterine cervix cancer, uterine body cancer, bladder cancer, esophagus cancer, head and neck cancer, nasopharyngeal cancer, salivary gland tumor, thymoma, skin cancer, basal cell tumor, malignant melanoma, anus cancer, penis cancer, testis cancer, Wilms's tumor, acute myeloid leukemia (including acute myeloleukemia, acute myeloblastic leukemia, acute promyelocytic leukemia, acute myelomonocytic leukemia, and acute monocytic leukemia), chronic myeloid leukemia, acute lymphoid leukemia, chronic lymphoid leukemia, Hodgkin's lymphoma, non-Hodgkin's lymphoma (Burkitt's lymphoma, chronic lymphocytic leukemia, mycosis fungoides, mantle cell lymphoma, follicular lymphoma, diffuse large-cell lymphoma, marginal zone lymphoma, hairy cell leukemia, plasmacytoma, peripheral T-cell lymphoma, and adult T-cell leukemia/lymphoma), Langerhans' cell histiocytosis, multiple myeloma, myelodysplastic syndrome, brain tumor (including glioma, astroglioma, glioblastoma, meningioma, and ependymoma), neuroblastoma, retinoblastoma, osteosarcoma, Kaposi's sarcoma, Ewing's sarcoma, angiosarcoma, and hemangiopericytoma.

The three-letter codes and one-letter codes of the amino acids used herein are defined as follows:
Alanine: Ala: A
Arginine: Arg: R
Asparagine: Asn: N
Aspartic acid: Asp: D
Cysteine: Cys: C Glutamine: Gln: Q
Glutamic acid: Glu: E
Glycine: Gly: G
Histidine: His: H
Isoleucine: Ile: I
Leucine: Leu: L
Lysine: Lys: K
Methionine: Met: M
Phenylalanine: Phe: F
Proline: Pro: P
Serine: Ser: S
Threonine: Thr: T
Tryptophan: Trp: W
Tyrosine: Tyr: Y
Valine: Val: V All literatures cited herein are incorporated herein by reference.

EXAMPLES

The present invention will be further illustrated with reference to Examples below. However, the present invention is not intended to be limited by Examples below.

[Example 1] Regarding Existing Fc Variants with Enhanced Binding to Mouse FcγR (Comparison with Conventional Technologies)

There has been no report on an Fc variant having selectively enhanced binding activity against mouse FcγRII (in the present specification, also referred to as mFcγRII or mFcgRII). Meanwhile, in Patent Literature 5 (US2009/0136485), Fc variants having enhanced binding activity against human FcγRIIb (in the present specification, also referred to as hFcγRIIb or hFcgRIIb) were evaluated for their binding activities against mFcγRII. These Fc variants were prepared on the basis of human IgG1. As seen from the results of this evaluation, an Fc variant whose binding activity against mFcγRII was most strongly enhanced was Fc with introduced alterations that substituted Ser 239 (EU numbering) by Asp, Lys 326 (EU numbering) by Asp, and Leu 328 (EU numbering) by Tyr, and the mFcγRII-binding activity was enhanced by approximately 130 times compared with that of human IgG1. Nonetheless, the mFcγRII selectivity of the Fc variant was still unknown, because the literature makes no mention about data on binding activity against mouse FcγRIII (in the present specification, also referred to as mFcγRIII or mFcgRIII).

Thus, in order to evaluate the selectivity, 8 Fc variants were selected mainly on the basis of strongly enhanced binding to mFcγRII from among the human IgG1-templated Fc variants described in Patent Literature 5 (US2009/0136485). Variants having these Fc variants were expressed and purified by the method of Reference Example 1 and evaluated for their binding to mFcγRII and mFcγRIII by the method of Reference Example 2 using Biacore T200. The antibody H chain variable region used was the variable region H237 (SEQ ID NO: 1) of the H chain VH3-IgG1 of the anti-IL-6 receptor antibody Fv4-IgG1 described in WO2009/125825. The antibody L chain commonly used was the L chain MRAL-k0 (SEQ ID NO: 2) of the anti-IL-6 receptor antibody tocilizumab. The antibody H chain constant region used was each of the aforementioned 8 Fc variants prepared by altering human IgG1 hIgG1 (SEQ ID NO: 3) as a template. In this context, the introduced alterations involved 10 types of alterations (alteration that substituted Leu 234 (EU numbering) by Trp: L234W, alteration that substituted Ser 239 (EU numbering) by Asp: S239D, alteration that substituted Ser 267 (EU numbering) by Ala: S267A, alteration that substituted Ser 267 (EU numbering) by Glu: S267E, alteration that substituted His 268 (EU numbering) by Asp: H268D, alteration that substituted Lys 326 (EU numbering) by Asp: K326D, alteration that substituted Ala 327 (EU numbering) by Asp: A327D, alteration that substituted Leu 328 (EU numbering) by Phe: L328F, alteration that substituted Leu 328 (EU numbering) by Trp: L328W, and alteration that substituted Leu 328 (EU numbering) by Tyr: L328Y). A variant H237-mIgG1/MRAL-k0 comprised of H237-mIgG1 (SEQ ID NO: 7) having a mouse IgG1 H chain constant region (mIgG1, SEQ ID NO: 4) and MRAL-k0 was used as a control.

Table 1 shows the relative binding activity against each mFcγR and relative I/A (mFcγRII selectivity) of all of the evaluated variants with the values of H237-mIgG1/MRAL-k0 as 1. "Name" in the table represents the name of the H chain constant region (CH) of each evaluated variant. As for alterations, "X000Z" represents the substitution of amino acid X at EU numbering position 000 by amino acid Z. In this context, X and Z represent the one-letter codes of the amino acid residues. All of the alterations described in Table 1 were alterations introduced to the H chain constant region (SEQ ID NO: 3) of human IgG1 (hIgG1).

A value I/A determined by dividing a KD value for mFcγRIII by a KD value for mFcγRII was used as an index for evaluating selectivity for mFcγRII. This index exhibits a larger value when the KD value for mFcγRII is smaller or when the KD value for mFcγRIII is larger. This means that an variant exhibiting a larger I/A value has higher selectivity for mFcγRII relative to mFcγRIII.

TABLE 1

| Name (CH) | Introduced alteration | Relative mFcγRII-binding activity (mIgG1 = 1) | Relative mFcγRIII-binding activity (mIgG1 = 1) | I/A (mFcγRII selectivity) | Relative I/A (mFcγRII selectivity) (mIgG1 = 1) |
|---|---|---|---|---|---|
| mIgG1 | none | 1.0 | 1.0 | 1.34 | 1.00 |
| FS130 | S267E | 0.3 | 0.3 | 1.36 | 1.01 |
| P253 | S267E/L328F | 1.0 | 4.6 | 0.29 | 0.21 |
| FS131 | L234W/S239D/L328Y | 144.3 | 33.2 | 5.83 | 4.34 |
| FS132 | S239D/A327D/L328Y | 96.7 | 41.8 | 3.10 | 2.31 |
| FS133 | S239D/H268D/L328W | 161.7 | 86.5 | 2.51 | 1.87 |
| FS134 | S239D/H268D/L328Y | 58.2 | 20.8 | 3.75 | 2.80 |
| F616 | S239D/K326D/L328Y | 186.5 | 50.1 | 5.00 | 3.72 |
| FS135 | S239D/S267A/L328Y | 137.9 | 34.4 | 5.38 | 4.01 |

(Relative binding activity: value determined by dividing the KD value of H237-mIgG1/MRAL-k0 for each mFcγR by the KD value of each variant for each mFcγR, Relative I/A (mFcγRII selectivity): value determined by dividing I/A (value determined by dividing the KD value for mFcγRIII by the KD value for mFcγRII) of each variant by I/A of H237-mIgG1/MRAL-k0)

As seen from the results of Table 1, some of the hIgG1-templated Fc variants described in Patent Literature 5 (US2009/0136485) had relative mFcγRII-binding activity enhanced by approximately 190 times compared with that of mIgG1, but exhibited approximately 4-fold relative I/A which indicated weak mFcγRII selectivity.

In short, there has been no report on an Fc variant having enhanced binding to mFcγRII with sufficient selectivity relative to mFcγRIII. The results described above demonstrated that an Fc variant having enhanced mFcγRII-selective binding with higher selectivity is necessary for more accurately testing the effects of an Fc variant with selectively enhanced FcγRII binding in mouse models of various diseases including autoimmune disease.

[Example 2] Comprehensive Analysis of Mouse IgG1-Derived Fc Variant for its Binding to Mouse FcγR Naturally occurring mouse IgG1 (in the present specification, also referred to as mIgG1) exhibits binding only to mFcγRII and mFcγRIII among 4 types of mouse FcγR (in the present specification, also referred to as mFcγR or mFcgR) without binding to mouse FcγRI (in the present specification, also referred to as mFcγRI or mFcgRI) and mouse FcγRIV (in the present specification, also referred to as mFcγRIV or mFcgRIV) (Science 2005, 310, 1510-1512). For this reason, the present inventors believed that an Fc variant with selectively enhanced binding to mFcγRII could be prepared by conferring selectivity for mFcγRII relative to mFcγRIII with mIgG1 as a template.

In order to find an alteration to selectively enhance binding activity against inhibitory mFcγR (i.e., mFcγRII) relative to activating mFcγR, particularly, mFcγRIII, compared with that of mIgG1, the mIgG1 antibody was mutated and then comprehensively analyzed for its binding to each mFcγR.

In the evaluation below, the antibody H chain variable region used was the variable region H237 (SEQ ID NO: 1) of the H chain VH3-IgG1 of the anti-IL-6 receptor antibody Fv4-IgG1 described in WO2009/125825. The antibody H chain constant region used was mIgG1 (SEQ ID NO: 4). The resulting H chain was designated as H237-mIgG1 (SEQ ID NO: 7). Likewise, the antibody L chain commonly used was the L chain MRAL-k0 (SEQ ID NO: 2) of the anti-IL-6 receptor antibody tocilizumab.

FIG. 1 shows results of comparing the sequences of mFcγRII (NCBI Reference Sequence: NP_034317.1) and mFcγRIII (NCBI Reference Sequence: NP_034318.2). FIG. 1 demonstrated that mFcγRII and mFcγRIII differ only by two residues at their sites predicted to interact with IgG Fc.

For preparing an Fc variant with selectively enhanced binding activity against mFcγRII relative to mFcγRIII, it is necessary to distinguish these two residues differing therebetween. In addition, three-dimensional structural information about mFcγRII and mFcγRIII remained to be gained. Thus, the rational design of the Fc variant of interest seemed to be difficult. Accordingly, H237-mIgG1/MRAL-k0 having the H chain constant region mIgG1 was used as a template to substitute each of the amino acids considered to participate in binding to mFcγR and their neighboring amino acids (EU numbering positions 230 to 232, 236 to 241, 265 to 268, 296, 298, and 300) by 18 types of amino acids except for the original amino acid and Cys. The resulting Fc variants were designated as mIgG1 variants. The mIgG1 variants were expressed and purified by the method of Reference Example 1 and comprehensively evaluated for their binding to mFcγRII and mFcγRIII by the method of Reference Example 2 using Biacore 4000.

The results of analyzing interaction with each mFcγR were plotted according to the following method: the KD value of unmutated H237-mIgG1/MRAL-k0 for mFcγR was divided by the KD value of each mIgG1 variant for mFcγR, and the obtained value was used as an index for the relative binding activity of the mIgG1 variant for each mFcγR. The horizontal axis indicates the value of the relative binding activity of each mIgG1 variant for mFcγRIII, and the vertical axis indicates the value of the relative binding activity of each mIgG1 variant for mFcγRII (FIG. 2).

Figure 2:
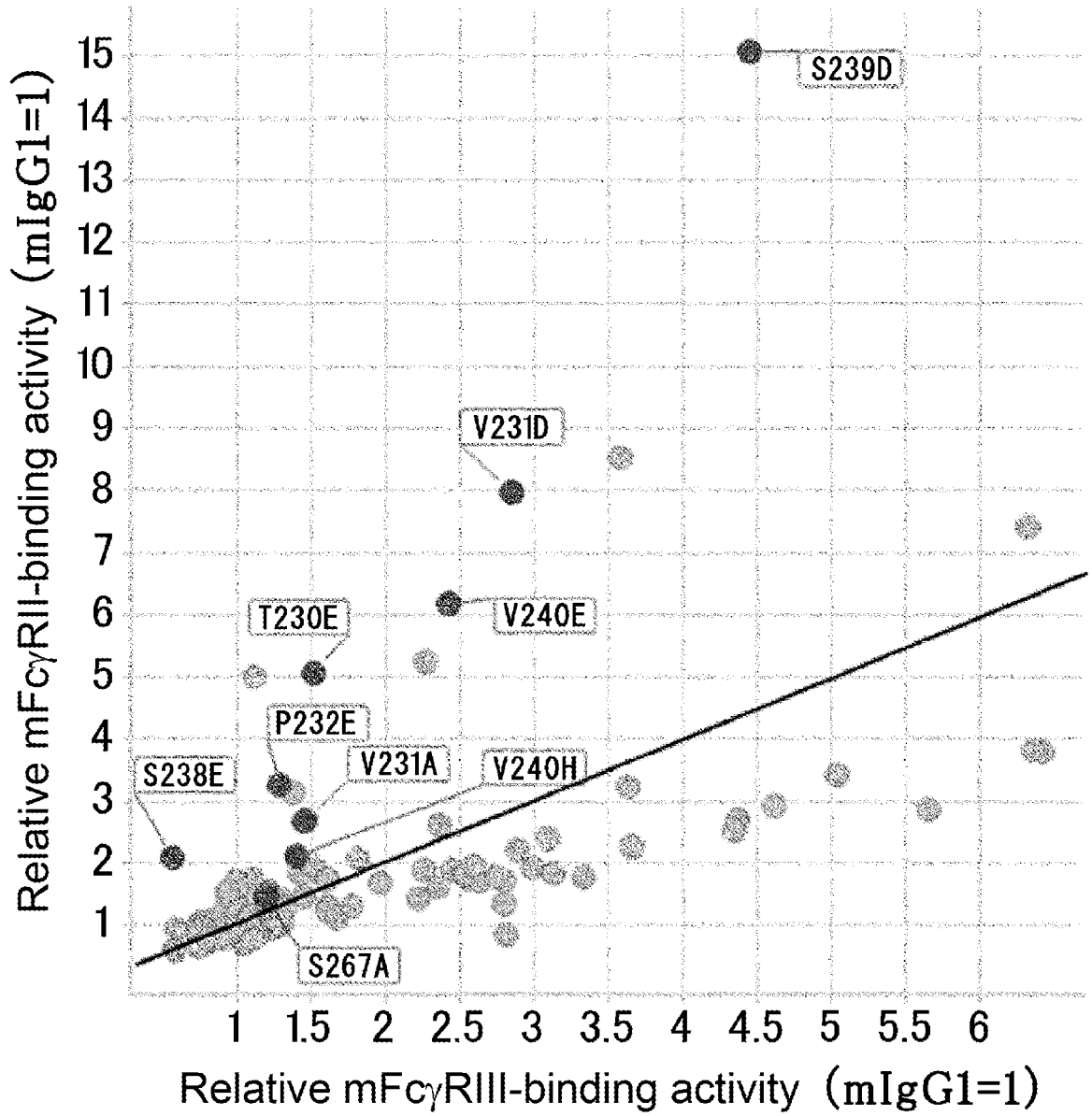

From the results shown in FIG. 2, some alterations were found to enhance relative mFcγRII-binding activity over relative mFcγRIII-binding activity, i.e., to improve selectivity for mFcγRII. In the comprehensive analysis of the mIgG1 variants for their binding to mFcγR, the effects of alterations that enhanced relative mFcγRII-binding activity by 1.1 times or more and improved relative I/A (mFcγRII selectivity) by 1.1 times or more were summarized in Table 2. "Name" in the table represents the name of the H chain constant region (CH) of each evaluated variant. As for alterations, "X000Z" represents the substitution of amino acid X at EU numbering position 000 by amino acid Z. In this context, X and Z represent the one-letter codes of the amino acid residues. All of the alterations described in Table 2 were alterations introduced to the H chain constant region (SEQ ID NO: 4) of mouse IgG1 (mIgG1).

Among a total of 288 variants evaluated, only 39 variants satisfied the criteria. The highest relative I/A (mFcγRII selectivity) was 4.51 times. Among them, only 26 alterations (9 alterable sites) enhanced relative mFcγRII-binding activity by 1.4 times or more and improved relative I/A (mFcγRII selectivity) by 1.2 times or more, and these alterations were considered more advantageous. This implied that it is very difficult to enhance mFcγRII-binding activity while conferring selectivity for mFcγRII relative to mFcγRIII.

TABLE 2

| Name (CH) | Introduced alteration | Relative mFcγRII-binding activity (mIgG1 = 1) | Relative mFcγRIII-binding activity (mIgG1 = 1) | Relative I/A (mFcγRII selectivity) (mIgG1 = 1) |
|---|---|---|---|---|
| MB002 | T230D | 2.72 | 1.47 | 1.85 |
| MB003 | T230E | 5.06 | 1.51 | 3.35 |
| MB013 | T230Q | 1.20 | 1.07 | 1.12 |
| MB016 | T230V | 1.15 | 1.00 | 1.15 |
| MB019 | V231A | 2.70 | 1.44 | 1.87 |
| MB020 | V231D | 7.97 | 2.84 | 2.80 |
| MB021 | V231E | 8.52 | 3.58 | 2.38 |
| MB025 | V231I | 1.19 | 1.06 | 1.13 |
| MB027 | V231L | 1.88 | 1.55 | 1.21 |
| MB028 | V231M | 1.83 | 1.42 | 1.29 |
| MB030 | V231P | 5.26 | 2.27 | 2.31 |
| MB031 | V231Q | 1.99 | 1.48 | 1.34 |
| MB034 | V231T | 1.25 | 1.12 | 1.11 |
| MB037 | P232A | 1.54 | 1.22 | 1.26 |
| MB038 | P232D | 3.15 | 1.37 | 2.30 |
| MB039 | P232E | 3.27 | 1.29 | 2.54 |
| MB040 | P232F | 1.47 | 1.17 | 1.26 |
| MB045 | P232L | 1.20 | 0.90 | 1.34 |
| MB052 | P232V | 1.36 | 1.20 | 1.14 |
| MB053 | P232W | 1.36 | 1.02 | 1.33 |
| MB054 | P232Y | 1.75 | 1.11 | 1.58 |
| MB093 | S238E | 2.09 | 0.56 | 3.71 |
| MB102 | S238P | 2.62 | 2.37 | 1.11 |
| MB103 | S238Q | 1.27 | 1.05 | 1.21 |
| MB110 | S239D | 15.07 | 4.45 | 3.39 |
| MB111 | S239E | 5.01 | 1.11 | 4.51 |
| MB118 | S239M | 1.74 | 0.99 | 1.76 |
| MB121 | S239Q | 1.48 | 0.94 | 1.58 |
| MB126 | S239Y | 1.58 | 0.94 | 1.69 |
| MB129 | V240E | 6.19 | 2.42 | 2.55 |
| MB132 | V240H | 2.12 | 1.39 | 1.52 |
| MB139 | V240Q | 1.54 | 1.20 | 1.28 |
| MB143 | V240W | 7.42 | 6.32 | 1.17 |
| MB161 | F241W | 1.47 | 1.13 | 1.30 |
| MB162 | F241Y | 1.40 | 1.20 | 1.17 |
| MB188 | I266L | 1.16 | 1.00 | 1.15 |
| MB199 | S267A | 1.48 | 1.19 | 1.24 |

TABLE 2-continued

| Name (CH) | Introduced alteration | Relative mFcγRII-binding activity (mIgG1 = 1) | Relative mFcγRIII-binding activity (mIgG1 = 1) | Relative I/A (mFcγRII selectivity) (mIgG1 = 1) |
|---|---|---|---|---|
| MB251 | F296W | 1.49 | 1.23 | 1.22 |
| MB261 | S298L | 2.11 | 1.81 | 1.17 |

(Relative binding activity: value determined by dividing the KD value of H237-mIgG1/MRAL-k0 for each mFcγR by the KD value of each variant for each mFcγR,
Relative I/A (mFcγRII selectivity): value determined by dividing I/A (value determined by dividing the KD value for mFcγRIII by the KD value for mFcγRII) of each variant by I/A of H237-mIgG1/MRAL-k0)

[Example 3] Evaluation of Effects of Combined Alterations to Selectively Enhance Binding Activity Against Mouse FcγRII Of the alterations found in Example 2 to selectively enhance binding to mFcγRII, the variant H237-MB110/MRAL-k0 with the introduced alteration that substituted Ser 239 (EU numbering) by Asp had the highest enhancement in relative mFcγRII-binding activity (15.1 times the mFcγRII-binding activity of H237-mIgG1/MRAL-k0) and also exhibited 3.4-fold relative I/A (mFcγRII selectivity) compared with that of H237-mIgG1/MRAL-k0. Thus, on the basis of this variant, one or more alteration(s) to selectively enhance mFcγRII-binding activity was further introduced thereto to evaluate the effects of combined alterations. For the study on the effects of combinations, 8 types of alterations (alteration that substituted Tyr 230 (EU numbering) by Glu: T230E, alteration that substituted Val 231 (EU numbering) by Ala: V231A, alteration that substituted Val 231 (EU numbering) by Asp: V231D, alteration that substituted Pro 232 (EU numbering) by Glu: P232E, alteration that substituted Ser 238 (EU numbering) by Glu: S238E, alteration that substituted Val 240 (EU numbering) by Glu: V240E, alteration that substituted Val 240 (EU numbering) by His: V240H, and alteration that substituted Ser 267 (EU numbering) by Ala: S267A) were selected from Table 1 and introduced as the alterations.

The antibody H chain variable region used was the variable region H237 (SEQ ID NO: 1) of the H chain VH3-IgG1 of the anti-IL-6 receptor antibody Fv4-IgG1 described in WO2009/125825. The antibody L chain commonly used was the L chain MRAL-k0 (SEQ ID NO: 2) of the anti-IL-6 receptor antibody tocilizumab. H237-MB110/MRAL-k0 with the S239D alteration introduced in H237-mIgG1/MRAL-k0 was used as a template to introduce combinations of the alterations. The resulting variant group was designated as MB110 variants. These variants were expressed and purified by the method of Reference Example 1 and evaluated for their binding to mFcγRII and mFcγRIII by the method of Reference Example 2 using Biacore T200.

Figure 3:
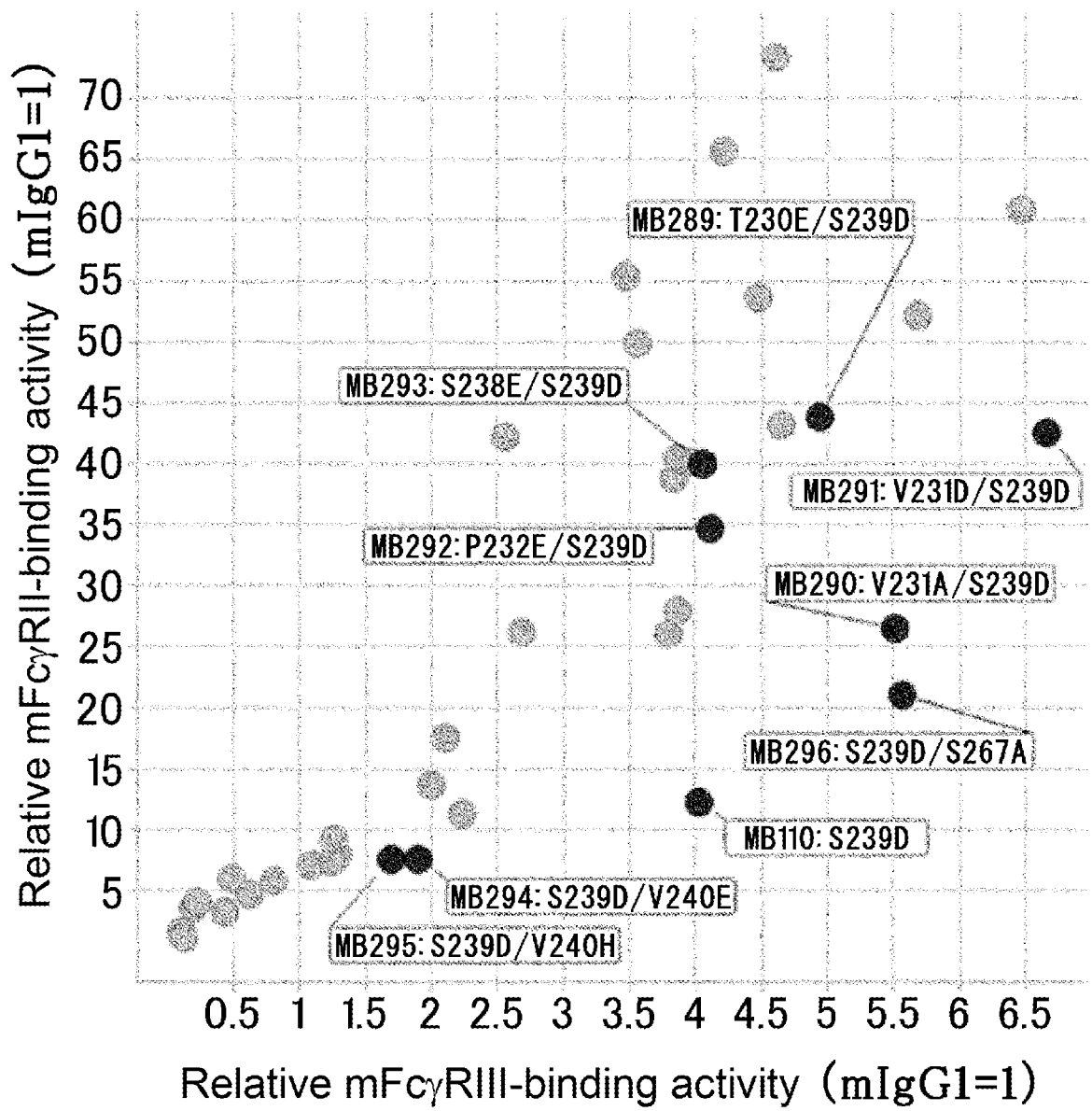

The results of analyzing interaction with each mFcγR were plotted according to the following method: the KD value of unmutated H237-mIgG1/MRAL-k0 for mFcγR was divided by the KD value of H237-MB110/MRAL-k0 or each MB110 variant for mFcγR, and the obtained value was used as an index for the relative binding activity for each mFcγR. The horizontal axis indicates the value of the relative binding activity of H237-MB110/MRAL-k0 or each MB110 variant for mFcγRIII, and the vertical axis indicates the value of the relative binding activity of H237-MB110/MRAL-k0 or each MB110 variant for mFcγRII (FIG. 3).

Table 3 shows the relative binding activity against each mFcγR and relative I/A (mFcγRII selectivity) of all of the evaluated MB110 variants with the values of H237-mIgG1/MRAL-k0 as 1. Table 4 shows results with the binding activity and I/A (mFcγRII selectivity) of H237-MB110/MRAL-k0 having no additional alteration as 1. "Name" in each table represents the name of the H chain constant region (CH) of each evaluated variant. As for alterations, "X000Z" represents the substitution of amino acid X at EU numbering position 000 by amino acid Z. In this context, X and Z represent the one-letter codes of the amino acid residues. All of the alterations described in Tables 3 and 4 were alterations introduced to the H chain constant region (SEQ ID NO: 4) of mouse IgG1 (mIgG1).

TABLE 3

| Name (CH) | Introduced alteration | Relative mFcγRII-binding activity (mIgG1 = 1) | Relative mFcγRIII-binding activity (mIgG1 = 1) | Relative I/A (mFcγRII selectivity) (mIgG1 = 1) |
|---|---|---|---|---|
| MB110 | S239D | 12.3 | 4.0 | 3.1 |
| MB289 | T230E/S239D | 43.8 | 4.9 | 8.9 |
| MB290 | V231A/S239D | 26.5 | 5.5 | 4.8 |
| MB291 | V231D/S239D | 42.6 | 6.7 | 6.4 |
| MB292 | P232E/S239D | 34.6 | 4.1 | 8.4 |
| MB293 | S238E/S239D | 39.9 | 4.1 | 9.9 |
| MB294 | S239D/V240E | 7.6 | 1.9 | 4.0 |
| MB295 | S239D/V240H | 7.6 | 1.7 | 4.5 |
| MB296 | S239D/S267A | 21.0 | 5.6 | 3.8 |
| MB299 | T230E/V231A/S239D | 60.8 | 6.5 | 9.4 |
| MB300 | T230E/V231D/S239D | 52.3 | 5.7 | 9.2 |
| MB301 | T230E/P232E/S239D | 43.2 | 4.6 | 9.3 |
| MB302 | T230E/S238E/S239D | 53.7 | 4.5 | 12.0 |
| MB303 | T230E/S239D/V240E | 7.8 | 1.3 | 6.1 |
| MB304 | T230E/S239D/V240H | 13.7 | 2.0 | 6.8 |
| MB305 | V231A/P232E/S239D | 26.0 | 3.8 | 6.9 |
| MB306 | V231A/S238E/S239D | 65.8 | 4.2 | 15.7 |
| MB307 | V231A/S239D/V240E | 11.3 | 2.2 | 5.1 |
| MB308 | V231A/S239D/V240H | 26.3 | 2.7 | 9.8 |
| MB309 | V231D/P232E/S239D | 27.9 | 3.9 | 7.2 |
| MB310 | V231D/S238E/S239D | 38.8 | 3.8 | 10.1 |
| MB311 | V231D/S239D/V240E | 17.6 | 2.1 | 8.3 |
| MB312 | V231D/S239D/V240H | 55.4 | 3.5 | 16.0 |
| MB313 | P232E/S238E/S239D | 40.1 | 4.0 | 10.1 |

TABLE 3-continued

| Name (CH) | Introduced alteration | Relative mFcγRII-binding activity (mIgG1 = 1) | Relative mFcγRIII-binding activity (mIgG1 = 1) | Relative I/A (mFcγRII selectivity) (mIgG1 = 1) |
|---|---|---|---|---|
| MB314 | P232E/S239D/V240E | 7.1 | 1.1 | 6.5 |
| MB315 | P232E/S239D/V240H | 5.9 | 0.8 | 7.3 |
| MB316 | S238E/S239D/V240E | 7.4 | 1.2 | 6.0 |
| MB317 | S238E/S239D/V240H | 6.0 | 0.5 | 12.2 |
| MB318 | T230E/P232E/S238E/S239D | 40.5 | 3.9 | 10.5 |
| MB319 | T230E/V231A/P232E/S238E/S239D | 50.0 | 3.6 | 14.1 |
| MB320 | T230E/V231A/P232E/S238E/S239D/V240E | 3.2 | 0.4 | 7.5 |
| MB321 | T230E/V231A/P232E/S238E/S239D/V240H | 3.5 | 0.2 | 17.9 |
| MB322 | T230E/V231D/P232E/S238E/S239D | 9.2 | 1.3 | 7.3 |
| MB323 | T230E/V231D/P232E/S238E/S239D/V240E | 1.7 | 0.1 | 15.0 |
| MB324 | T230E/V231D/P232E/S238E/S239D/V240H | 1.1 | 0.1 | 9.2 |
| MB325 | T230E/P232E/S238E/S239D/V240E | 4.7 | 0.6 | 7.7 |
| MB326 | T230E/P232E/S238E/S239D/V240H | 4.0 | 0.2 | 17.7 |
| MB337 | T230E/V231A/S238E/S239D | 73.4 | 4.6 | 16.0 |
| MB338 | T230E/V231D/S238E/S239D | 42.2 | 2.6 | 16.5 |

(Relative binding activity: value determined by dividing the KD value of H237-mIgG1/MRAL-k0 for each mFcγR by the KD value of each variant for each mFcγR, Relative I/A (mFcγRII selectivity): value determined by dividing I/A (value determined by dividing the KD value for mFcγRIII by the KD value for mFcγRII) of each variant by I/A of H237-mIgG1/MRAL-k0)

TABLE 4

| Name (CH) | Introduced alteration | Relative mFcγRII-binding activity (MB110 = 1) | Relative mFcγRIII-binding activity (MB110 = 1) | Relative I/A (mFcγRII selectivity) (MB110 = 1) |
|---|---|---|---|---|
| MB110 | S239D | 1.00 | 1.00 | 1.00 |
| MB289 | T230E/S239D | 3.57 | 1.23 | 2.87 |
| MB290 | V231A/S239D | 2.16 | 1.37 | 1.55 |
| MB291 | V231D/S239D | 3.47 | 1.66 | 2.06 |
| MB292 | P232E/S239D | 2.82 | 1.02 | 2.71 |
| MB293 | S238E/S239D | 3.25 | 1.01 | 3.19 |
| MB294 | S239D/V240E | 0.62 | 0.47 | 1.29 |
| MB295 | S239D/V240H | 0.62 | 0.42 | 1.45 |
| MB296 | S239D/S267A | 1.71 | 1.39 | 1.23 |
| MB299 | T230E/V231A/S239D | 4.96 | 1.61 | 3.03 |
| MB300 | T230E/V231D/S239D | 4.25 | 1.41 | 2.97 |
| MB301 | T230E/P232E/S239D | 3.52 | 1.16 | 3.00 |
| MB302 | T230E/S238E/S239D | 4.37 | 1.11 | 3.87 |
| MB303 | T230E/S239D/V240E | 0.64 | 0.32 | 1.97 |
| MB304 | T230E/S239D/V240H | 1.11 | 0.50 | 2.19 |
| MB305 | V231A/P232E/S239D | 2.12 | 0.94 | 2.23 |
| MB306 | V231A/S238E/S239D | 5.36 | 1.05 | 5.06 |
| MB307 | V231A/S239D/V240E | 0.92 | 0.55 | 1.65 |
| MB308 | V231A/S239D/V240H | 2.14 | 0.67 | 3.16 |
| MB309 | V231D/P232E/S239D | 2.27 | 0.96 | 2.32 |
| MB310 | V231D/S238E/S239D | 3.16 | 0.96 | 3.26 |
| MB311 | V231D/S239D/V240E | 1.43 | 0.52 | 2.68 |
| MB312 | V231D/S239D/V240H | 4.51 | 0.87 | 5.16 |
| MB313 | P232E/S238E/S239D | 3.27 | 0.99 | 3.26 |
| MB314 | P232E/S239D/V240E | 0.58 | 0.27 | 2.10 |
| MB315 | P232E/S239D/V240H | 0.48 | 0.20 | 2.35 |
| MB316 | S238E/S239D/V240E | 0.61 | 0.31 | 1.94 |
| MB317 | 8238E/S239D/V240H | 0.49 | 0.12 | 3.94 |
| MB318 | T230E/P232E/S238E/S239D | 3.29 | 0.96 | 3.39 |
| MB319 | T230E/V231A/P232E/S238E/S239D | 4.07 | 0.89 | 4.55 |
| MB320 | T230E/V231A/P232E/S238E/S239D/V240E | 0.26 | 0.11 | 2.42 |
| MB321 | T230E/V231A/P232E/S238E/S239D/V240H | 0.28 | 0.05 | 5.77 |
| MB322 | T230E/V231D/P232E/S238E/S239D | 0.75 | 0.31 | 2.35 |
| MB323 | T230E/V231D/P232E/S238E/S239D/V240E | 0.13 | 0.03 | 4.84 |
| MB324 | T230E/V231D/P232E/S238E/S239D/V240H | 0.09 | 0.03 | 2.97 |
| MB325 | T230E/P232E/S238E/S239D/V240E | 0.38 | 0.15 | 2.48 |
| MB326 | T230E/P232E/S238E/S239D/V240H | 0.33 | 0.06 | 5.71 |
| MB337 | T230E/V231A/S238E/S239D | 5.98 | 1.15 | 5.16 |
| MB338 | T230E/V231D/S238E/S239D | 3.44 | 0.64 | 5.32 |

(Relative binding activity: value determined by dividing the KD value of H237-MB110/MRAL-k0 for each mFcγR by the KD value of each MB110 variant for each mFcγR, Relative I/A (mFcγRII selectivity): value determined by dividing I/A (value determined by dividing the KD value for mFcγRIII by the KD value for mFcγRII) of each MB110 variant by I/A of H237-MB110/MRAL-k0)

First, as a result of introducing any one of the aforementioned 8 alterations to H237-MB110/MRAL-k0, 6 (T230E, V231A, V231D, P232E, S238E, and S267A) of the introduced alterations were found to enhance binding activity against mFcγRII while maintaining or improving I/A (mFcγRII selectivity) (Tables 3 and 4). Next, of these 6 alterations, 5 alterations (T230E, V231A, V231D, P232E, and S238E) effective for enhancing relative mFcγRII-binding activity by 2 times or more with the value of H237-MB110/MRAL-k0 as 1 were introduced in various combinations. As a result, further improvement in I/A (mFcγRII selectivity) and further enhancement in binding activity against mFcγRII were observed. All of the variants with 3 or more alterations introduced in H237-mIgG1/MRAL-k0, evaluated in this study produced results superior to the relative I/A (mFcγRII selectivity) of the antibodies having the conventional Fc variants shown in Table 1 of Example 1. Among them, the variant (H237-MB337/MRAL-k0) with 4 alterations, i.e., T230E, V231A, S238E, and S239D, introduced in H237-mIgG/MRAL-k0 had relative mFcγRII-binding activity enhanced by 73.4 times and relative I/A (mFcγRII selectivity) improved by 16 times compared with those of mIgG1 (Tables 3 and 4).

On the other hand, the results of Tables 3 and 4 revealed that the combination of two or more alterations produced many changes in mFcγRII-binding activity and I/A (mFcγRII selectivity) that were unexpectable from the comprehensive analysis results of the H237-mIgG1/MRAL-k0-templated point-mutation variants. For example, the introduction of P232E alteration to H237-MB110/MRAL-k0 enhanced mFcγRII-binding activity by 2.8 times compared with that before its introduction, whereas the variant H237-MB305/MRAL-k0 with P232E alteration further introduced in the variant H237-MB290/MRAL-k0 with V231A alteration introduced in H237-MB110/MRAL-k0 exhibited no enhancement in mFcγRII-binding activity compared with that before the introduction of P232E alteration. Likewise, the introduction of V231D alteration to H237-MB110/MRAL-k0 enhanced mFcγRII-binding activity by 3.5 times compared with that before its introduction, whereas the variant H237-MB338/MRAL-k0 with V231D alteration further introduced in the variant H237-MB302/MRAL-k0 with T230E and S238E alterations introduced in H237-MB110/MRAL-k0 was shown to reduce mFcγRII-binding activity to approximately 0.8 times compared with that before the introduction of V231D alteration.

As mentioned above, the further combinations of the alterations did not produce the expected effects, presumably because the alterations are introduced at adjacent positions and therefore influence each other on the same H chain and also because the alterations are introduced at positions in the lower hinge region of an antibody, which correspond to the interacting interface between the antibody and mFcγR as well as the interacting interface between the Fc chains of this antibody, and therefore influence each other even on different H chains. For these reasons, it was considered difficult to predict the effects of combined alterations from the comprehensive analysis results of the H237-mIgG1/MRAL-k0-templated point-mutation variants.

[Example 4] Search for Optimum Combination of Alterations at EU Numbering Positions 230, 231, and 232 for Enhancement in Mouse FcγRII-Binding Activity As shown in Example 3, the further combinations of the alterations did not produce the effects expected from the comprehensive analysis results of the H237-mIgG1/MRAL-k0-templated point-mutation variants, in some cases. Thus, it was difficult to predict combinations of alterations aimed at further enhancement in mFcγRII-binding activity, from the results obtained in Examples 2 and 3. Accordingly, as mentioned above, the adjacent amino acids at EU numbering positions 230, 231, and 232 to be altered in the lower hinge region were each substituted by an amino acid having a characteristic property, such as a negatively charged amino acid, a positively charged amino acid, a highly hydrophilic amino acid, an amino acid having a characteristic side chain length, or an amino acid having an aromatic ring, and variously combined to thereby search for a combination of alterations more suitable for enhancement in mFcγRII-binding activity and improvement in I/A (mFcγRII selectivity).

As in Examples 2 and 3, the antibody H chain variable region used was the variable region H237 (SEQ ID NO: 1) of the H chain VH3-IgG1 of the anti-IL-6 receptor antibody Fv4-IgG1 described in WO2009/125825. The antibody L chain commonly used was the L chain MRAL-k0 (SEQ ID NO: 2) of the anti-IL-6 receptor antibody tocilizumab. S238E and S239D alterations were introduced to H237-mIgG1/MRAL-k0, and combinations of the amino acids at EU numbering positions 230, 231, and 232 were then studied. These variants were expressed and purified by the method of Reference Example 1 and evaluated for their binding to mFcγRII and mFcγRIII by the method of Reference Example 2 using Biacore T200.

The results of analyzing interaction with each mFcγR were plotted according to the following method: the KD value of unmutated H237-mIgG1/MRAL-k0 for mFcγR was divided by the KD value of each variant for mFcγR, and the obtained value was used as an index for the relative binding activity for each mFcγR. The horizontal axis indicates the value of the relative binding activity of each variant for mFcγRIII, and the vertical axis indicates the value of the relative binding activity of each variant for mFcγRII (FIG. 4).

Figure 5:
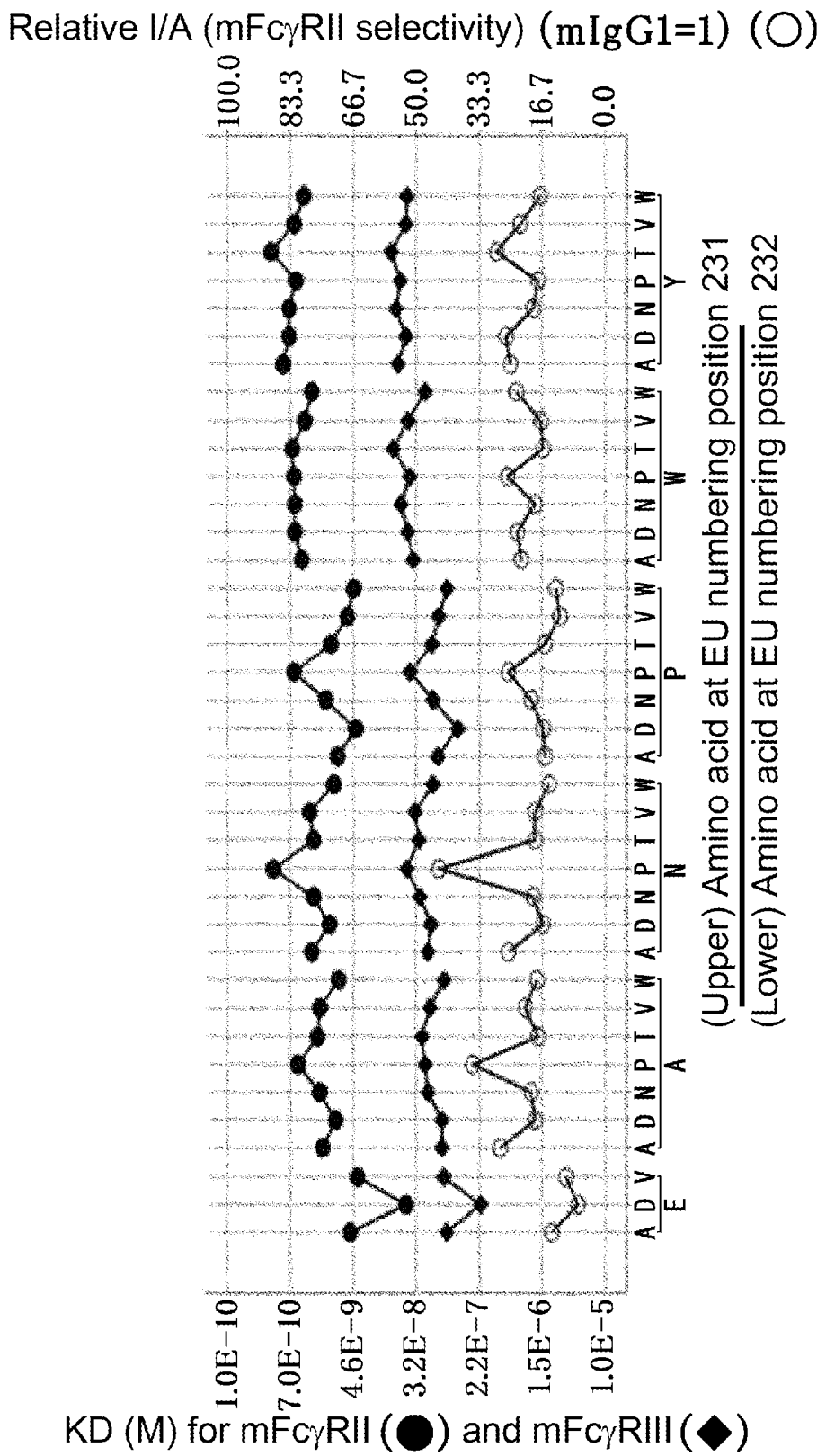

Among the variants evaluated in this study, only the variant having T230E alteration was plotted according to the method given below in order to evaluate effects brought about by the substitution of amino acids at EU numbering positions 231 and 232. These variants had 3 alterations (T230E/S238E/S239D) in common and differed only in the amino acids at EU numbering positions 231 and 232. In the drawing, the lower row of the horizontal axis represents the type of the amino acid at EU numbering position 232 in each variant, and the upper row of the horizontal axis represents the type of the amino acid at EU numbering position 231 in each variant. The left vertical axis indicates the KD value of each variant for mFcγRII (p circle) and mFcγRIII (filled rhombus), and the right vertical axis indicates relative I/A (mFcγRII selectivity) (open circle) in comparison with mIgG1 (FIG. 5). Since the left vertical axis is indicated by inverted log scale, more enhanced binding activity is shown at an upper position.

In the foregoing, the P232E alteration that exhibited the highest enhancement in mFcγRII-binding activity and improvement in I/A (mFcγRII selectivity) in the results of Table 2 of Example 2 was used for the amino acid at EU numbering position 232. The results of FIG. 5, however, showed that variants with the amino acid substituted by each of 5 amino acids (Ala, Asn, Pro, Trp, and Tyr) newly studied in this Example produced more favorable results about mFcγRII-binding activity and I/A (mFcγRII selectivity) than those of the P232E variant used above. Particularly, the substitution of the amino acid at EU numbering position 232 by an aromatic amino acid such as Trp or Tyr generally exhibited strong mFcγRII-binding activity, regardless of the type of the amino acid at EU numbering position 231. In this respect, enhancement in binding to mFcγRIII was also observed, but remained at a low level, resulting in relative I/A (mFcγRII selectivity) as high as 15 times or more. When the amino acid at EU numbering position 232 was substituted by an amino acid other than the aromatic amino acid such as Trp or Tyr, the substitution of Val 231 (EU numbering) by Pro was shown to remarkably enhance binding to mFcγRII, but weakly enhance binding to mFcγRIII, and to greatly improve mFcγRII selectivity. These results implied that the alteration that substitutes the amino acid at EU numbering position 232 by an aromatic amino acid such as Trp or Tyr and the alteration that substitutes Val 231 (EU numbering) by Pro are preferred from the viewpoint of enhancing binding activity against mFcγRII and improving I/A (mFcγRII selectivity).

Table 5 shows the relative binding activity against each mFcγR and relative I/A (mFcγRII selectivity) of all of the variants evaluated in this study with the values of H237-mIgG1/MRAL-k0 as 1. "Name" in the table represents the name of the H chain constant region (CH) of each evaluated variant. As for alterations, "X000Z" represents the substitution of amino acid X at EU numbering position 000 by amino acid Z. In this context, X and Z represent the one-letter codes of the amino acid residues. All of the alterations described in Table 5 were alterations introduced to the H chain constant region (SEQ ID NO: 4) of mouse IgG1 (mIgG1).

TABLE 5

| Name (CH) | Introduced alteration | Relative mFcγRII-binding activity (mIgG1 = 1) | Relative mFcγRIII-binding activity (mIgG1 = 1) | Relative I/A (mFcγRII selectivity) (mIgG1 = 1) |
|---|---|---|---|---|
| MB302 | T230E/S238E/S239D | 53.7 | 4.5 | 12.0 |
| MB306 | V231A/S238E/S239D | 65.8 | 4.2 | 15.7 |
| MB310 | V231D/S238E/S239D | 38.8 | 3.8 | 10.1 |
| MB313 | P232E/S238E/S239D | 40.1 | 4.0 | 10.1 |
| MB318 | T230E/P232E/S238E/S239D | 40.5 | 3.9 | 10.5 |
| MB319 | T230E/V231A/P232E/S238E/S239D | 50.0 | 3.6 | 14.1 |
| MB322 | T230E/V231D/P232E/S238E/S239D | 9.2 | 1.3 | 7.3 |
| MB337 | T230E/V231A/S238E/S239D | 73.4 | 4.6 | 16.0 |
| MB338 | T230E/V231D/S238E/S239D | 42.2 | 2.6 | 16.5 |
| MB339 | T230E/P232W/S238E/S239D | 196.8 | 11.6 | 17.0 |
| MB340 | T230E/V231A/P232W/S238E/S239D | 220.7 | 9.9 | 22.4 |
| MB341 | T230E/V231D/P232W/S238E/S239D | 268.5 | 11.5 | 23.4 |
| MB358 | T230E/V231A/P232A/S238E/S239D | 113.8 | 4.1 | 27.7 |
| MB367 | T230E/V231A/P232N/S238E/S239D | 158.6 | 6.2 | 25.6 |
| MB373 | T230E/V231A/P232Y/S238E/S239D | 390.4 | 15.5 | 25.2 |
| MB377 | T230E/P232A/S238E/S239D | 127.0 | 6.0 | 21.3 |
| MB378 | T230E/P232N/S238E/S239D | 172.4 | 9.3 | 18.6 |
| MB379 | T230E/P232Y/S238E/S239D | 273.4 | 12.2 | 22.5 |
| MB380 | T230E/V231D/P232A/S238E/S239D | 78.1 | 4.2 | 18.7 |
| MB381 | T230E/V231D/P232N/S238E/S239D | 93.5 | 5.7 | 16.5 |
| MB382 | T230E/V231D/P232Y/S238E/S239D | 320.7 | 12.3 | 26.2 |
| MB383 | T230E/V231N/S238E/S239D | 106.4 | 5.4 | 19.6 |
| MB384 | T230E/V231N/P232A/S238E/S239D | 125.1 | 6.3 | 19.8 |
| MB385 | T230E/V231N/P232N/S238E/S239D | 151.7 | 7.9 | 19.2 |
| MB386 | T230E/V231N/P232W/S238E/S239D | 268.0 | 14.5 | 18.6 |
| MB387 | T230E/V231N/P232Y/S238E/S239D | 318.7 | 16.7 | 19.1 |
| MB388 | T230E/V231P/S238E/S239D | 277.3 | 10.8 | 25.9 |
| MB389 | T230E/V231P/P232A/S238E/S239D | 244.8 | 7.0 | 35.3 |
| MB390 | T230E/V231P/P232N/S238E/S239D | 521.7 | 11.9 | 44.0 |
| MB391 | T230E/V231P/P232W/S238E/S239D | 281.2 | 10.9 | 25.9 |
| MB392 | T230E/V231P/P232Y/S238E/S239D | 257.2 | 14.5 | 17.8 |
| MB393 | T230E/V231T/S238E/S239D | 89.9 | 5.6 | 16.0 |
| M8394 | T230E/V231T/P232A/S238E/S239D | 133.8 | 7.5 | 17.8 |
| MB395 | T230E/V231T/P232N/S238E/S239D | 153.7 | 8.2 | 18.7 |
| MB396 | T230E/V231T/P232W/S238E/S239D | 297.2 | 17.9 | 16.6 |
| MB397 | T230E/V231T/P232Y/S238E/S239D | 554.8 | 19.3 | 28.9 |
| MB398 | T230E/V231W/S238E/S239D | 45.8 | 3.5 | 13.0 |
| MB399 | T230E/V231W/P232A/S238E/S239D | 71.8 | 3.9 | 18.2 |
| MB400 | T230E/V231W/P232N/S238E/S239D | 81.7 | 5.5 | 15.0 |
| MB401 | T230E/V231W/P232W/S238E/S239D | 162.3 | 6.9 | 23.7 |
| MB402 | T230E/V231W/P232Y/S238E/S239D | 207.5 | 12.0 | 17.4 |
| M8404 | T230D/V231A/P232Y/S238E/S239D | 235.7 | 8.6 | 27.6 |
| MB405 | T230I/V231A/P232Y/S238E/S239D | 145.5 | 8.0 | 18.2 |
| MB406 | T230P/V231A/P232Y/S238E/S239D | 191.1 | 6.5 | 29.6 |
| MB407 | T230Q/V231A/P232Y/S238E/S239D | 164.4 | 9.8 | 16.9 |
| MB408 | V231A/P232Y/S238E/S239D | 163.2 | 13.1 | 12.5 |
| MB409 | T230D/P232Y/S238E/S239D | 192.5 | 10.7 | 18.0 |
| MB410 | T230I/P232Y/3238E/S239D | 104.0 | 6.7 | 15.5 |
| MB411 | T230P/P232Y/S238E/S239D | 132.2 | 8.1 | 16.4 |
| MB412 | T230Q/P232Y/S238E/S239D | 113.3 | 8.3 | 13.7 |
| MB413 | P232Y/S238E/S239D | 107.9 | 11.9 | 9.1 |
| MB414 | T230D/V231D/P232Y/S238E/S239D | 189.4 | 8.1 | 23.6 |
| MB415 | T230I/V231D/P232Y/S238E/S239D | 159.2 | 9.1 | 17.5 |
| MB416 | T230P/V231D/P232Y/S238E/S239D | 189.0 | 6.3 | 30.2 |

TABLE 5-continued

| Name (CH) | Introduced alteration | Relative mFcγRII-binding activity (mIgG1 = 1) | Relative mFcγRIII-binding activity (mIgG1 = 1) | Relative I/A (mFcγRII selectivity) (mIgG1 = 1) |
|---|---|---|---|---|
| MB417 | T230Q/V231D/P232Y/S238E/S239D | 189.5 | 10.7 | 17.8 |
| MB418 | V231D/P232Y/S238E/S239D | 261.9 | 20.0 | 13.1 |
| MB419 | T230D/V231N/P232Y/S238E/S239D | 215.6 | 11.6 | 18.6 |
| MB420 | T230I/V231N/P232Y/S238E/S239D | 123.8 | 7.1 | 17.5 |
| MB421 | T230P/V231N/P232Y/S238E/S239D | 178.3 | 9.0 | 19.9 |
| MB422 | T230Q/V231N/P232Y/S238E/S239D | 144.2 | 8.9 | 16.3 |
| MB423 | V231N/P232Y/S238E/S239D | 143.1 | 9.2 | 15.5 |
| MB424 | T230D/V231P/P232A/S238E/S239D | 104.2 | 5.1 | 20.4 |
| MB425 | T230I/V231P/P232A/S238E/S239D | 194.3 | 5.5 | 35.2 |
| MB426 | T230PA/231P/P232A/S238E/S239O | 111.8 | 4.4 | 25.2 |
| MB427 | T230Q/V231P/P232A/S238E/S239D | 217.4 | 7.0 | 31.1 |
| MB428 | V231P/P232A/S238E/S239D | 214.9 | 8.8 | 24.4 |
| MB429 | T230D/V231P/P232N/S238E/S239D | 136.8 | 6.8 | 20.3 |
| MB430 | T230I/V231P/P232N/S238E/S239D | 206.7 | 6.3 | 33.0 |
| MB431 | T230P/V231P/P232N/S238E/S239D | 112.8 | 4.2 | 26.8 |
| MB432 | T230Q/V231P/P232N/S238E/S239D | 342.8 | 10.7 | 32.2 |
| MB433 | V231P/P232N/S238E/S239D | 302.7 | 11.6 | 26.2 |
| MB434 | T230D/V231T/P232Y/S238E/S239D | 256.8 | 15.5 | 16.7 |
| MB435 | T230I/V231T/P232Y/S238E/S239D | 146.5 | 8.7 | 16.8 |
| MB436 | T230P/V231T/P232Y/S238E/S239D | 150.8 | 8.4 | 18.0 |
| MB437 | T230Q/V231T/P232Y/S238E/S239D | 197.6 | 11.5 | 17.3 |
| MB438 | V231T/P232Y/S238E/S239D | 282.9 | 15.7 | 18.0 |

(Relative binding activity: value determined by dividing the KD value of H237-mIgG1/MRAL-k0 for each mFcγR by the KD value of each variant for each mFcγR, Relative I/A (mFcγRII selectivity): value determined by dividing I/A (value determined by dividing the KD value for mFcγRIII by the KD value for mFcγRII) of each variant by I/A of H237-mIgG1/MRAL-k0)

From these results (FIGS. 4 and 5 and Table 5), many variants were found to enhance binding activity against mFcγRII while maintaining or improving I/A (mFcγRII selectivity), compared with those of H237-MB337/MRAL-k0, one of the best variants found in Example 3 before the combination study. The effects of such combined alterations of the amino acids at EU numbering positions 230, 231, and 232 were effects unpredictable from the comprehensive analysis results of the H237-mIgG1/MRAL-k0-templated point-mutation variants obtained in Example 2. In other words, the combinations of the alterations found this time were combinations of the alterations that were able to be found for the first time by this study. The results of Table 5 showed that all of the variants evaluated in this study were superior in relative I/A (mFcγRII selectivity) to the antibodies having the conventional Fc variants shown in Table 1 of Example 1 while some of the variants were also much superior in relative mFcγRII-binding activity to the antibodies having the conventional Fc variants. Among them, H237-MB390/MRAL-k0 with 5 alterations (T230E/V231P/P232N/S238E/S239D) introduced in H237-mIgG1/MRAL-k0, and H237-MB397/MRAL-k0 with 5 alterations (T230E/V231T/P232Y/S238E/S239D) introduced in H237-mIgG1/MRAL-k0 exhibited values as high as 44.0-fold and 28.9-fold relative I/A (mFcγRII selectivity), respectively, with the value of H237-mIgG1/MRAL-k0 as 1, while being both effective for strongly enhancing relative mFcγRII-binding activity by more than 500 times compared with that of H237-mIgG1/MRAL-k0, demonstrating that these Fc variants are much superior in both selectivity and binding activity to the conventional Fc variants. These results implied that use of these Fc variants with selectively enhanced mFcγRII binding enables Fc variants with selectively enhanced hFcγRIIb binding to be more accurately evaluated for their drug efficacy and safety in humans in in vivo and in vitro tests using mice.

For reference, Table 6 shows the KD values for each mFcγR and I/A (mFcγRII selectivity) of H237-mIgG1/MRAL-k0 and each variant that exhibited 200-fold or more relative mFcγRII-binding activity with the value of H237-mIgG1/MRAL-k0 as 1. “Name” in the table represents the name of the H chain constant region of each evaluated variant. As for alterations, “X000Z” represents the substitution of amino acid X at EU numbering position 000 by amino acid Z. In this context, X and Z represent the one-letter codes of the amino acid residues. All of the alterations described in Table 6 were alterations introduced to the H chain constant region (SEQ ID NO: 4) of mouse IgG1 (mIgG1).

TABLE 6

| Name (CH) | Introduced alteration | KD (mFcγRII) | KD (mFcγRIII) | I/A (mFcγRII selectivity) |
|---|---|---|---|---|
| mIgG1 | — | 2.10E−07 | 2.82E−07 | 1.3 |
| MB340 | T230E/V231A/P232W/S238E/S239D | 9.52E−10 | 2.86E−08 | 30.0 |
| MB341 | T230E/V231D/P232W/S238E/S239D | 7.82E−10 | 2.46E−08 | 31.4 |
| MB373 | T230E/V231A/P232Y/S238E/S239D | 5.38E−10 | 1.82E−08 | 33.8 |
| MB379 | T230E/P232Y/S238E/S239D | 7.68E−10 | 2.32E−08 | 30.2 |
| MB382 | T230E/V231D/P232Y/S238E/S239D | 6.55E−10 | 2.30E−08 | 35.1 |
| MB386 | T230E/V231N/P232W/S238E/S239D | 7.84E−10 | 1.95E−08 | 24.9 |
| MB387 | T230E/V231N/P232Y/S238E/S239D | 6.59E−10 | 1.69E−08 | 25.6 |

TABLE 6-continued

| Name (CH) | Introduced alteration | KD (mFcγRII) | KD (mFcγRIII) | I/A (mFcγRII selectivity) |
|---|---|---|---|---|
| MB388 | T230E/V231P/S238E/S239D | 7.57E−10 | 2.62E−08 | 34.6 |
| MB389 | T230E/V231P/P232A/S238E/S239D | 8.58E−10 | 4.06E−08 | 47.3 |
| MB390 | T230E/V231P/P232N/S238E/S239D | 4.03E−10 | 2.37E−08 | 59.0 |
| MB391 | T230E/V231P/P232W/S238E/S239D | 7.47E−10 | 2.59E−08 | 34.7 |
| MB392 | T230E/V231P/P232Y/S238E/S239D | 8.17E−10 | 1.95E−08 | 23.9 |
| MB396 | T230E/V231T/P232W/S238E/S239D | 7.07E−10 | 1.58E−08 | 22.3 |
| MB397 | T230E/V231T/P232Y/S238E/S239D | 3.79E−10 | 1.46E−08 | 38.7 |
| MB402 | T230E/V231W/P232Y/S238E/S239D | 1.01E−09 | 2.36E−08 | 23.3 |
| MB404 | T230D/V231A/P232Y/S238E/S239D | 8.91E−10 | 3.30E−08 | 37.0 |
| MB418 | V231D/P232Y1S238E/S239D | 8.02E−10 | 1.41E−08 | 17.6 |
| MB419 | T230D/V231N/P232Y/S238E/S239D | 9.74E−10 | 2.43E−08 | 25.0 |
| MB427 | T230Q/V231P/P232A/S238E/S239D | 9.66E−10 | 4.03E−08 | 41.7 |
| MB428 | V231P/P232A/S238E/S239D | 9.77E−10 | 3.20E−08 | 32.7 |
| MB430 | T230I/V231P/P232N/S238E/S239D | 1.02E−09 | 4.50E−08 | 44.3 |
| MB432 | T230Q/V231P/P232N/S238E/S239D | 6.13E−10 | 2.64E−08 | 43.1 |
| MB433 | V231P/P232N/S238E/S239D | 6.94E−10 | 2.44E−08 | 35.2 |
| MB434 | T230D/V231T/P232Y/S238E/S239D | 8.18E−10 | 1.83E−08 | 22.3 |
| MB438 | V231T/P232Y/S238E/S239D | 7.42E−10 | 1.79E−08 | 24.1 |

(I/A (mFcγRII selectivity): value determined by dividing the KD value for mFcγRIII by the KD value for mFcγRII)

[Example 5] Study on Amino Acid Substitution at EU Numbering Position 239

In Example 4, the optimum combination of alterations of the amino acids at EU numbering positions 230, 231, and 232 was studied to successfully prepare variants excellent in enhanced mFcγRII binding and I/A (mFcγRII selectivity). In this Example 5, amino acid substitution at EU numbering position 239 was studied for the purpose of further improving I/A (mFcγRII selectivity) and preventing enhancement in binding to mFcγRIII. In the foregoing, the amino acid Ser at EU numbering position 239 was substituted by Asp. In this study, the amino acid at EU numbering position 239 was newly substituted by Glu, Met, or Trp and substituted by the original amino acid Ser. The antibody H chain variable region used was the variable region H237 (SEQ ID NO: 1) of the H chain VH3-IgG1 of the anti-IL-6 receptor antibody Fv4-IgG1 described in WO2009/125825. The antibody L chain commonly used was the L chain MRAL-k0 (SEQ ID NO: 2) of the anti-IL-6 receptor antibody tocilizumab. For the study, 9 variants shown in Table 7 were selected from among the variants obtained in Example 4, and given template names. In this context, variants having the same sequences except for the amino acid at EU numbering position 239 were commonly given the same template name. These 9 variants were altered as templates to substitute the amino acid at EU numbering position 239 by Glu, Met, Trp, or Ser. The resulting variants were expressed and purified by the method of Reference Example 1 and evaluated for their binding to mFcγRII and mFcγRIII by the method of Reference Example 2 using Biacore T200. The group of these variants also including the templated variants was designated as S239X variants.

TABLE 7

| Variant name | Introduced alteration | Template name |
|---|---|---|
| H237-MB373/MRAL-k0 | T230E/N231A/P232Y/S238E/S239D | T1 |
| H237-MB382/MRAL-k0 | T230E/N231D/P232Y/S238E/S239D | T2 |
| H237-MB387/MRAL-k0 | T230E/N231N/P232Y/S238E/S239D | T3 |
| H237-MB397/MRAL-k0 | T230E/N231T/P232Y/S238E/S239D | T4 |
| H237-MB379/MRAL-k0 | T230E/P232Y/S238E/S239D | T5 |
| H237-MB389/MRAL-k0 | T230E/N231P/P232A/S238E/S239D | T6 |

TABLE 7-continued

| Variant name | Introduced alteration | Template name |
|---|---|---|
| H237-MB425/MRAL-k0 | T230I/V231P/P232A/S238E/S239D | T7 |
| H237-MB390/MRAL-k0 | T230E/N231P/P232N/S238E/S239D | T8 |
| H237-MB432/MRAL-k0 | T230Q/N231P/P232N/S238E/S239D | T9 |

Figure 6:
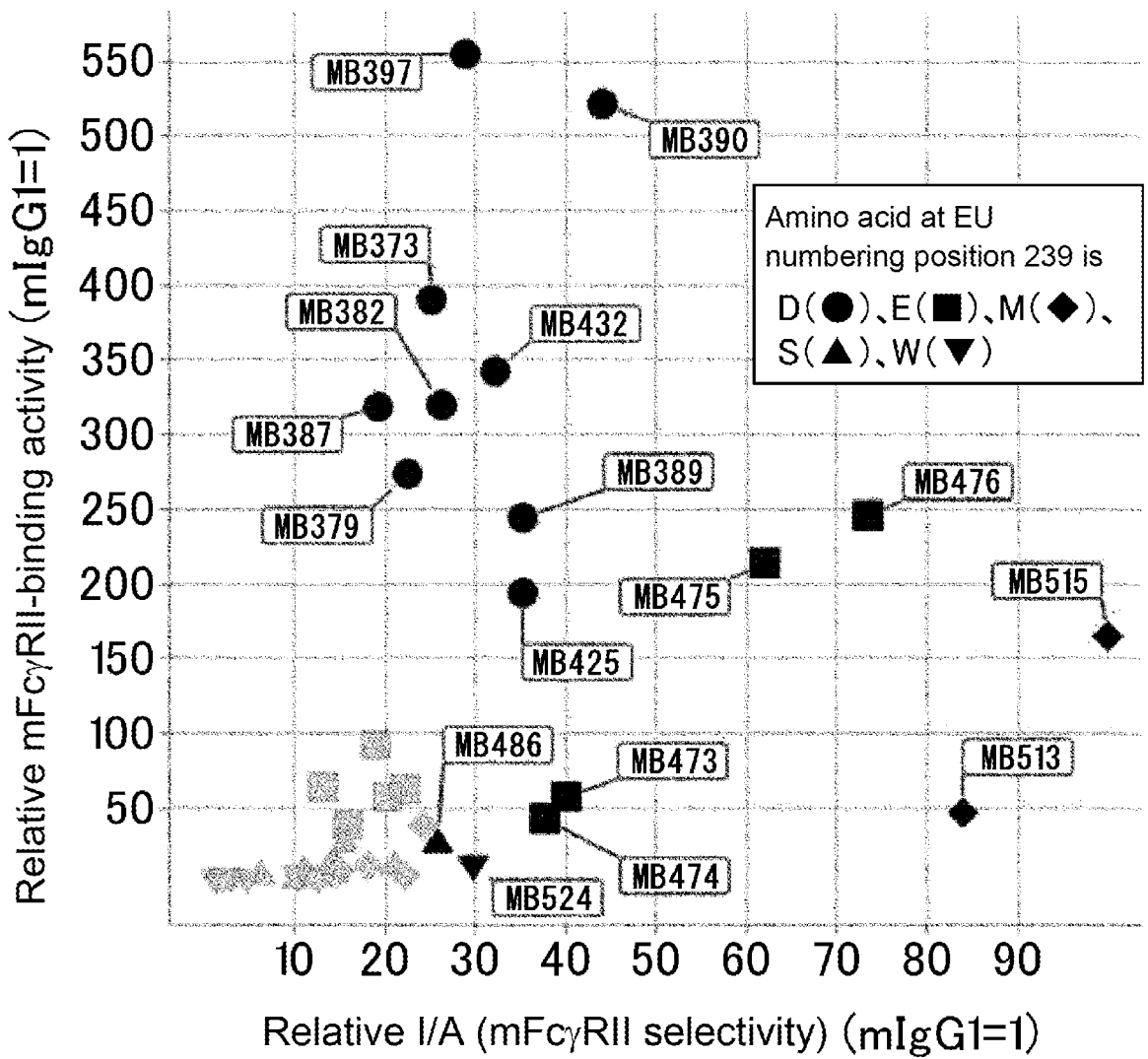

The results of analyzing interaction with each mFcγR were plotted according to the following method: the KD value of unmutated H237-mIgG1/MRAL-k0 for mFcγR was divided by the KD value of each S239X variant for mFcγR, and the obtained value was used as an index for the relative binding activity for each mFcγR. The horizontal axis indicates I/A (mFcγRII selectivity) which is a value determined by dividing the KD value of each S239X variant for mFcγRIII by its KD value for mFcγRII, and the vertical axis indicates the value of the relative binding activity of each S239X variant for mFcγRII (FIG. 6). In this drawing, the variant having Asp (D) as the amino acid at EU numbering position 239 was indicated by filled circle; the variant having Glu (E) as the amino acid at EU numbering position 239 was indicated by filled square; the variant having Met (M) as the amino acid at EU numbering position 239 was indicated by filled rhombus; the variant having Ser (S) as the amino acid at EU numbering position 239 was indicated by filled triangle; and the variant having Trp (W) as the amino acid at EU numbering position 239 was indicated by filled inverted triangle. In order to compare the effects of the types of the amino acid at EU numbering position 239 on each template, FIG. 7 was drawn by the method given below. The lower row of the horizontal axis represents the type of the amino acid at EU numbering position 239, and the upper row of the horizontal axis represents the template name. The vertical axis indicates the relative mFcγRII-binding activity (filled square) and relative I/A (mFcγRII selectivity) (open square) of each S239X variant with the values of H237-mIgG1/MRAL-k0 as 1.

Table 8 shows the relative binding activity against each mFcγR and relative I/A (mFcγRII selectivity) of all of the S239X variants evaluated in this study with the values of H237-mIgG1/MRAL-k0 as 1. "Name" in the table represents the name of the H chain constant region (CH) of each evaluated variant. As for alterations, "X000Z" represents the substitution of amino acid X at EU numbering position 000 by amino acid Z. In this context, X and Z represent the one-letter codes of the amino acid residues. All of the alterations described in Table 8 were alterations introduced to the H chain constant region (SEQ ID NO: 4) of mouse IgG1 (mIgG1).

position 239 are influenced by the types of the amino acids at EU numbering positions 230, 231, and 232.

Figure 7:
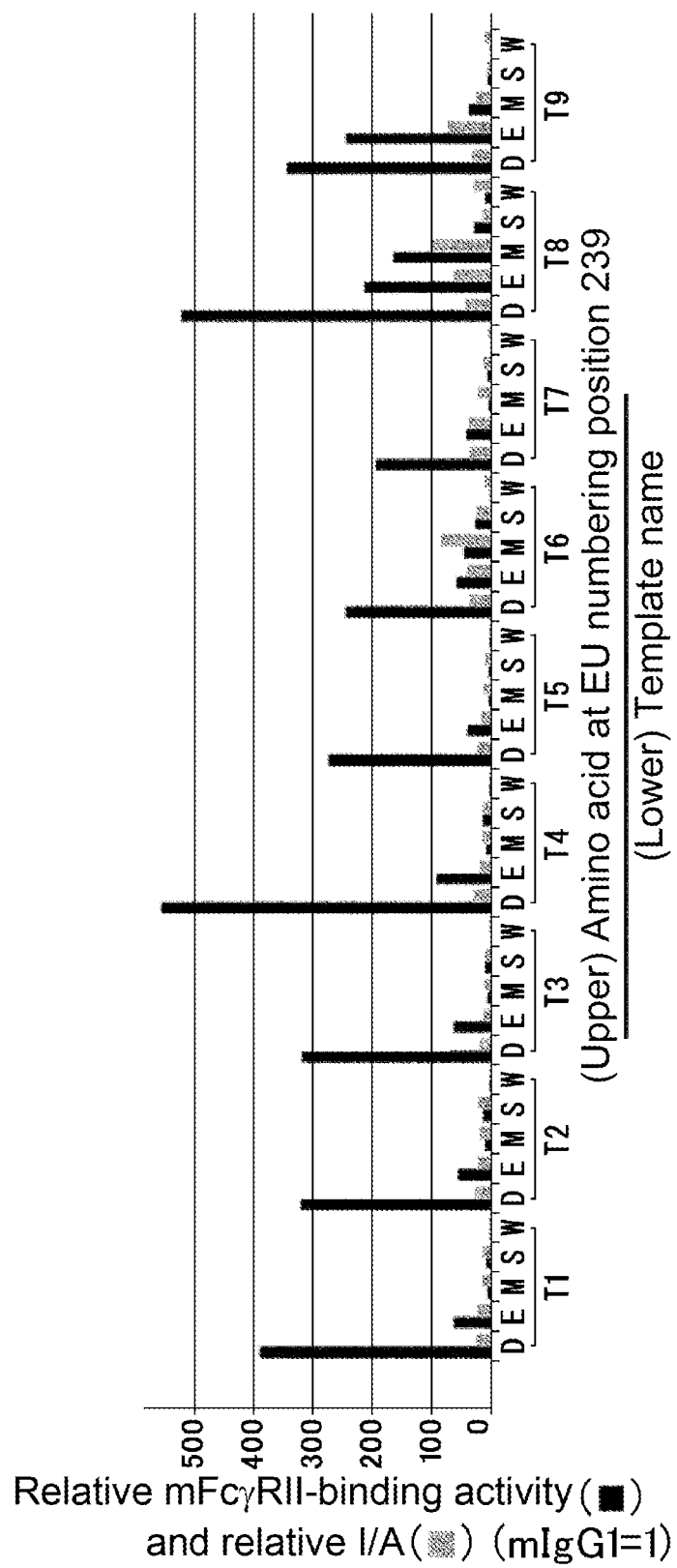

From the results of FIGS. 6 and 7 and Table 8, some variants with the amino acid at EU numbering position 239 substituted by Glu, Met, Ser, or Trp were newly found to reduce mFcγRII-binding activity compared with that of the variants containing the S239D alteration obtained in

TABLE 8

| Name (CH) | Introduced alteration | Amino acid at EU numbering position 239 | Template name | Relative mFcγRII-binding activity (mIgG1 = 1) | Relative mFcγRIII-binding activity (mIgG1 = 1) | Relative I/A (mFcγRII selectivity) (mIgG1 = 1) |
|---|---|---|---|---|---|---|
| mIgG1 | — | S | | 1.0 | 1.0 | 1.0 |
| MB373 | T230E/V231A/P232Y/S238E/S239D | D | T1 | 390.4 | 15.5 | 25.2 |
| MB382 | T230E/V231D/P232Y/S238E/S239D | | T2 | 320.7 | 12.3 | 26.2 |
| MB387 | T230E/V231N/P232Y/S238E/S239D | | T3 | 318.7 | 16.7 | 19.1 |
| MB397 | T230E/V231T/P232Y/S238E/S239D | | T4 | 554.8 | 19.3 | 28.9 |
| MB379 | T230E/P232Y/S238E/S239D | | T5 | 273.4 | 12.2 | 22.5 |
| MB389 | T230E/V231P/P232A/S238E/S239D | | T6 | 244.8 | 7.0 | 35.3 |
| MB425 | T230I/V231P/P232A/S238E/S239D | | T7 | 194.3 | 5.5 | 35.2 |
| MB390 | T230E/V231P/P232N/S238E/S239D | | T8 | 521.7 | 11.9 | 44.0 |
| MB432 | T230Q/V231P/P232N/S238E/S239D | | T9 | 342.8 | 10.7 | 32.2 |
| MB468 | T230E/V231A/P232Y/S238E/S239E | E | T1 | 63.1 | 2.8 | 22.2 |
| MB469 | T230E/V231D/P232Y/S238E/S239E | | T2 | 57.1 | 2.8 | 20.3 |
| MB470 | T230E/V231N/P232Y/S238E/S239E | | T3 | 63.8 | 4.9 | 13.1 |
| MB471 | T230E/V231T/P232Y/S238E/S239E | | T4 | 91.4 | 4.8 | 18.9 |
| MB472 | T230E/P232Y/S238E/S239E | | T5 | 39.4 | 2.5 | 15.9 |
| MB473 | T230E/V231P/P232A/S238E/S239E | | T6 | 57.6 | 1.4 | 40.1 |
| MB474 | T230I/V231P/P232A/S238E/S239E | | T7 | 42.9 | 1.1 | 37.6 |
| MB475 | T230E/V231P/P232N/S238E/S239E | | T8 | 214.4 | 3.5 | 62.0 |
| MB476 | T230Q/V231P/P232N/S238E/S239E | | T9 | 245.8 | 3.4 | 73.4 |
| MB508 | T230E/V231A/P232Y/S238E/S239M | M | T1 | 5.5 | 0.4 | 14.5 |
| MB509 | T230E/V231D/P232Y/S238E/S239M | | T2 | 10.7 | 0.6 | 18.0 |
| MB510 | T230E/V231N/P232Y/S238E/S239M | | T3 | 6.5 | 0.6 | 11.1 |
| MB511 | T230E/V231T/P232Y/S238E/S239M | | T4 | 8.3 | 0.6 | 15.0 |
| MB512 | T230E/P232Y/S238E/S239M | | T5 | 3.5 | 0.3 | 12.7 |
| MB513 | T230E/V231P/P232A/S238E/S239M | | T6 | 46.3 | 0.6 | 83.8 |
| MB514 | T230I/V231P/P232A/S238E/S239M | | T7 | 4.5 | 0.2 | 22.3 |
| MB515 | T230E/V231P/P232N/S238E/S239M | | T8 | 165.0 | 1.7 | 100.0 |
| MB516 | T230Q/V231P/P232N/S238E/S239M | | T9 | 38.6 | 1.6 | 24.3 |
| MB481 | T230E/V231A/P232Y/S238E | S | T1 | 8.5 | 0.6 | 14.1 |
| MB482 | T230E/V231D/P232Y/S238E | | T2 | 14.1 | 0.7 | 21.1 |
| MB483 | T230E/V231N/P232Y/S238E | | T3 | 9.4 | 0.9 | 10.8 |
| MB484 | T230E/V231T/P232Y/S238E | | T4 | 14.9 | 1.1 | 14.1 |
| MB485 | T230E/P232Y/S238E | | T5 | 5.0 | 0.5 | 10.2 |
| MB486 | T230E/V231P/P232A/S238E | | T6 | 28.1 | 1.1 | 25.8 |
| MB487 | T230I/V231P/P232A/S238E | | T7 | 6.8 | 0.5 | 13.5 |
| MB488 | T230E/V231P/P232N/S238E | | T8 | 28.7 | 1.8 | 15.6 |
| MB489 | T230Q/V231P/P232N/S238E | | T9 | 6.9 | 1.1 | 6.3 |
| MB517 | T230E/V231A/P232Y/S238E/S239W | W | T1 | 1.2 | 0.4 | 3.0 |
| MB518 | T230E/V231D/P232Y/S238E/S239W | | T2 | 1.2 | 0.4 | 2.8 |
| MB519 | T230E/V231N/P232Y/S238EIS239W | | T3 | 1.0 | 0.9 | 1.2 |
| MB520 | T230E/V231T/P232Y1S238E/S239W | | T4 | 1.8 | 1.3 | 1.4 |
| MB521 | T230E/P232Y/S238E/S239W | | T5 | 1.6 | 0.7 | 2.1 |
| MB522 | T230E/V231P/P232A/S238E/S239W | | T6 | 1.5 | 0.1 | 10.3 |
| MB523 | T230I/V231P/P232A/S238E/S239W | | T7 | 0.5 | 0.1 | 4.6 |
| MB524 | T230E/V231P/P232N/S238EIS239W | | T8 | 10.0 | 0.3 | 29.8 |
| MB525 | T230Q/V231P/P232N/S238E/S239W | | T9 | 2.8 | 0.3 | 10.3 |

(Relative binding activity: value determined by dividing the KD value of H237-mIgGl/MRAL-k0 for each mFcγR by the KD value of each variant for each mFcγR,
Relative I/A (mFcγRII selectivity): value determined by dividing I/A (value determined by dividing the KD value for mFcγRIII by the KD value for mFcγRII) of each variant by I/A of H237-mIgGl/MRAL-k0)

As seen from the results of FIG. 7, the substitution of the amino acid at EU numbering position 239 by the same amino acid produced the common rank of mFcγRII-binding activity among the templates, though the degree of this change largely differed among the templates. In addition, no common behavior was observed in change in selectivity. These S239X variants had S238E alteration in common and additionally had alterations at some of EU numbering positions 230, 231, 232, and 239. These results demonstrated that the effects of amino acid substitution at EU numbering Example 4, but to maintain or improve relative I/A (mFcγRII selectivity). These variants also include an variant with mFcγRIII-binding activity enhanced by less than 2 times, suggesting that use of these Fc variants enables the effects of enhanced mFcγRII-binding activity to be more accurately evaluated while substantially excluding the influence of enhanced binding activity against mFcγRIII. Four variants, i.e., H237-MB475/MRAL-k0 (T230E, V231P, P232N, S238E, and S239E alterations were introduced in H237-mIgG1/MRAL-k0), H237-MB476/MRAL-k0 (T230Q, V231P, P232N, S238E, and S239E alterations were introduced in H237-mIgG1/MRAL-k0), H237-MB513/MRAL-k0 (T230E, V231P, P232A, S238E, and S239M alterations were introduced in H237-mIgG1/MRAL-k0), and H237-MB515/MRAL-k0 (T230E, V231P, P232N, S238E, and S239M alterations were introduced in H237-mIgG1/MRAL-k0) exhibited 62.1-fold, 73.4-fold, 83.9-fold, and 100-fold relative I/A (mFcγRII selectivity), respectively, with the value of H237-mIgG1/MRAL-k0 as 1 and were much superior to H237-MB390/MRAL-k0 having the highest selectivity (44-fold) in the foregoing.

For reference, Table 9 shows the KD values for each mFcγR and I/A (mFcγRII selectivity) of H237-mIgG1/MRAL-k0 and each variant that exhibited 200-fold or more relative mFcγRII-binding activity or 25-fold or more relative I/A (mFcγRII selectivity) compared with that of H237-mIgG1/MRAL-k0. "Name" in the table represents the name of the H chain constant region of each evaluated variant. As for alterations, "X000Z" represents the substitution of amino acid X at EU numbering position 000 by amino acid Z. In this context, X and Z represent the one-letter codes of the amino acid residues. All of the alterations described in Table 9 were alterations introduced to the H chain constant region (SEQ ID NO: 4) of mouse IgG1 (mIgG1).

more compared with that of H237-mIgG1/MRAL-k0 in Example 4 were used as templates to introduce new alterations. The resulting variant groups were designated as MB397 variants and MB390 variants, respectively. These variants were expressed and purified by the method of Reference Example 1 and evaluated for their binding to mFcγRII and mFcγRIII by the method of Reference Example 2 using Biacore T200.

Figure 8:
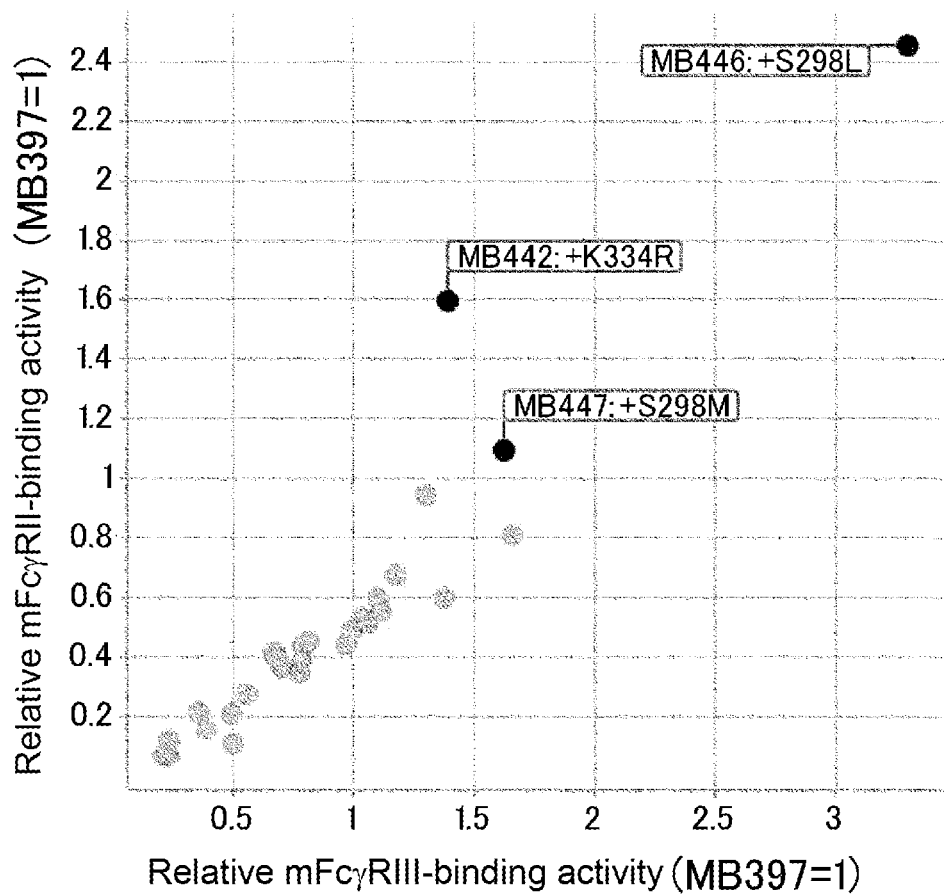
Figure 9:
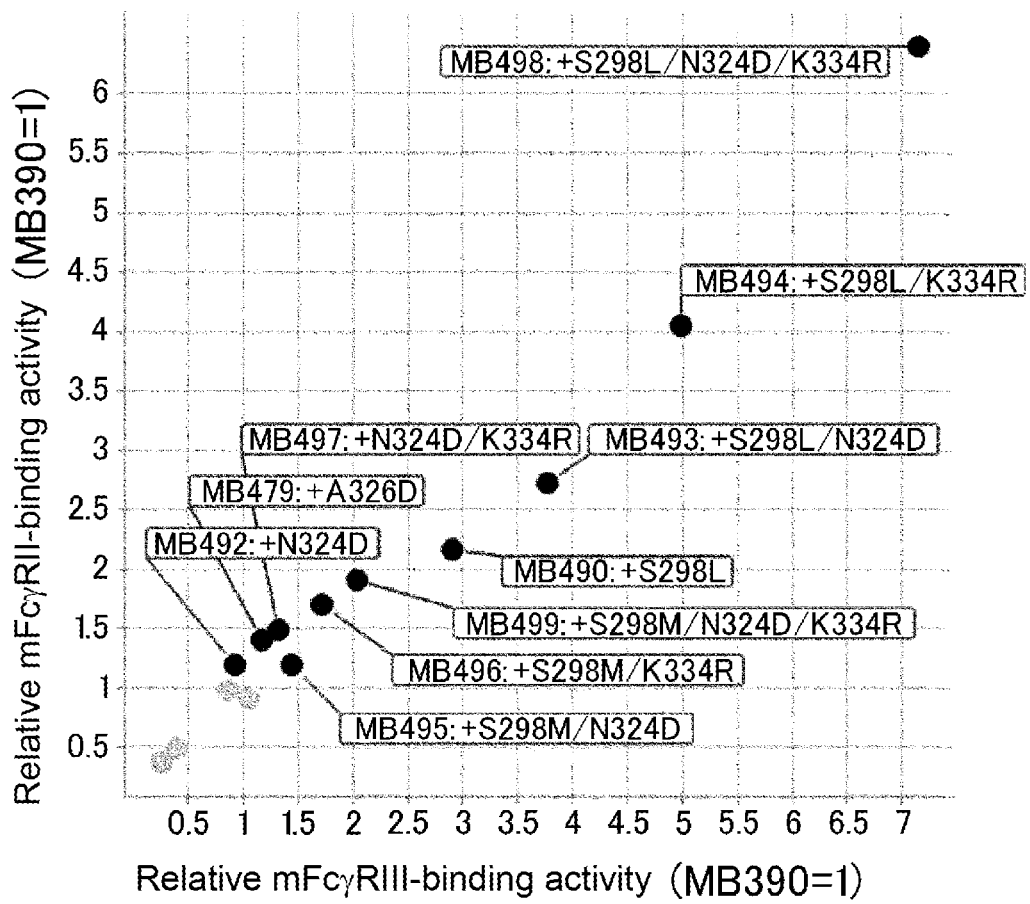

The results of analyzing interaction with each mFcγR were plotted according to the following method: the KD value of templated H237-MB397/MRAL-k0 or H237-MB390/MRAL-k0 for mFcγR was divided by the KD value of each corresponding variant for mFcγR, and the obtained value was used as an index for the relative binding activity for each mFcγR with the value of H237-MB397/MRAL-k0 or H237-MB390/MRAL-k0 as 1. The horizontal axis indicates the value of the relative binding activity of each variant for mFcγRIII, and the vertical axis indicates the value of the relative binding activity of each variant for mFcγRII (FIG. 8: MB397 variants, FIG. 9: MB390 variants).

TABLE 9

| Name (CH) | Introduced alteration | KD (mFcgR2) | KD (mFcgR3) | I/A (mFcγRII selectivity) |
|---|---|---|---|---|
| mIgG1 | — | 2.10E−07 | 2.82E−07 | 1.3 |
| MB373 | T230E/V231A/P232Y/S238E/S239D | 5.38E−10 | 1.82E−08 | 33.8 |
| MB379 | T230E/P232Y/S238E/S239D | 7.68E−10 | 2.32E−08 | 30.2 |
| MB382 | T230E/V231D/P232Y/S238E/S239D | 6.55E−10 | 2.30E−08 | 35.1 |
| MB387 | T230EN231N/P232Y/S238E/S239D | 6.59E−10 | 1.69E−08 | 25.6 |
| MB389 | T230E/V231P/P232A/S238E/S239D | 8.58E−10 | 4.06E−08 | 47.3 |
| MB390 | T230E/V231P/P232N/S238E/S239D | 4.03E−10 | 2.37E−08 | 59.0 |
| MB397 | T230E/V231T/P232Y/S238E/S239D | 3.79E−10 | 1.46E−08 | 38.7 |
| MB425 | T230I/V231P/P232A/S238E/S239D | 1.08E−09 | 5.10E−08 | 47.2 |
| MB432 | T230Q/V231P/P232N/S238E/S239D | 6.13E−10 | 2.64E−08 | 43.1 |
| MB473 | T230E/V231P/P232A/S238E/S239E | 3.65E−09 | 1.96E−07 | 53.8 |
| MB474 | T230I/V231P/P232A/S238E/S239E | 4.89E−09 | 2.47E−07 | 50.4 |
| MB475 | T230EN231P/P232N/S238E/S239E | 9.79E−10 | 8.14E−08 | 83.1 |
| MB476 | T230Q/V231P/P232N/S238E/S239E | 8.54E−10 | 8.40E−08 | 98.3 |
| MB486 | T230E/V231P/P232A/S238E | 7.47E−09 | 2.58E−07 | 34.5 |
| MB513 | T230E/V231P/P232A/S238E/S239M | 4.53E−09 | 5.09E−07 | 112.4 |
| MB515 | T230E/V231P/P232N/S238E/S239M | 1.27E−09 | 1.71E−07 | 133.9 |
| MB524 | T230E/V231P/P232N/S238E/S239W | 2.10E−08 | 8.37E−07 | 39.9 |

(I/A (mFcγRII selectivity): value determined by dividing the KD value for mFcγRII) by the KD value for mFcγRII)

[Example 6] Study on Amino Acid Substitution at Position Other than EU Numbering Positions 230, 231, 232, 238, and 239

In the foregoing, amino acid substitution at EU numbering positions 230, 231, 232, 238, and 239 was studied. Amino acid substitution at sites other than these positions was studied for the purpose of further enhancing mFcγRII-binding activity.

The antibody H chain variable region used was the variable region H237 (SEQ ID NO: 1) of the H chain VH3-IgG1 of the anti-IL-6 receptor antibody Fv4-IgG1 described in WO2009/125825. The antibody L chain commonly used was the L chain MRAL-k0 (SEQ ID NO: 2) of the anti-IL-6 receptor antibody tocilizumab. H237-MB397/MRAL-k0 and H237-MB390/MRAL-k0 that exhibited relative mFcγRII-binding activity enhanced by 500 times or Table 10 shows the relative binding activity against each mFcγR and relative I/A (mFcγRII selectivity) of all of the evaluated MB397 variants with the values of H237-mIgG1/MRAL-k0 or H237-MB397/MRAL-k0 as 1. Likewise, Table 11 shows the relative binding activity against each mFcγR and relative I/A (mFcγRII selectivity) of all of the evaluated MB390 variants with the values of H237-mIgG1/MRAL-k0 or H237-MB390/MRAL-k0 as 1. "Name" in each table represents the name of the H chain constant region (CH) of each evaluated variant. As for alterations, "X000Z" represents the substitution of amino acid X at EU numbering position 000 by amino acid Z. In this context, X and Z represent the one-letter codes of the amino acid residues. All of the alterations described in Table 10 were alterations introduced to the H chain constant region (SEQ ID NO: 5) of MB397. All of the alterations described in Table 11 were alterations introduced to the H chain constant region (SEQ ID NO: 6) of MB390.

TABLE 10

| Name (CH) | Alteration added to MB397 | Relative mFcγRII-binding activity (MB397 = 1) | Relative mFcγRIII-binding activity (MB397 = 1) | Relative I/A (mFcγRII selectivity) (MB397 = 1) | Relative mFcγRII binding activity (mIgG1 = 1) | Relative mFcγRIII-binding activity (mIgG1 = 1) | Relative I/A (mFcγRII selectivity) (mIgG1 = 1) |
|---|---|---|---|---|---|---|---|
| MB397 | — | 1.00 | 1.00 | 1.00 | 554.8 | 19.3 | 28.9 |
| MB439 | S267E | 0.07 | 0.23 | 0.30 | 39.5 | 4.5 | 8.8 |
| MB440 | P271L | 0.22 | 0.36 | 0.61 | 120.1 | 6.9 | 17.5 |
| MB441 | A330K | 0.07 | 0.21 | 0.34 | 39.7 | 4.1 | 9.7 |
| MB442 | K334R | 1.60 | 1.39 | 1.14 | 884.2 | 26.9 | 33.0 |
| MB443 | F296E | 0.44 | 0.79 | 0.55 | 243.3 | 15.3 | 15.9 |
| MB444 | F296N | 0.42 | 0.67 | 0.62 | 231.1 | 12.9 | 17.9 |
| MB445 | F296T | 0.40 | 0.68 | 0.58 | 220.3 | 13.2 | 16.7 |
| MB446 | S298L | 2.45 | 3.30 | 0.74 | 1360.1 | 63.7 | 21.4 |
| MB447 | S298M | 1.10 | 1.63 | 0.67 | 608.0 | 31.4 | 19.4 |
| MB448 | N324D | 0.95 | 1.30 | 0.73 | 525.1 | 25.1 | 20.9 |
| MB449 | N324L | 0.28 | 0.56 | 0.50 | 154.3 | 10.7 | 14.4 |
| MB450 | N324M | 0.68 | 1.18 | 0.58 | 376.6 | 22.7 | 16.6 |
| MB451 | A330G | 0.11 | 0.50 | 0.22 | 60.1 | 9.7 | 6.2 |
| MB452 | A330Q | 0.08 | 0.23 | 0.37 | 46.9 | 4.4 | 10.8 |
| MB453 | P331D | 0.21 | 0.49 | 0.43 | 117.8 | 9.5 | 12.4 |
| MB454 | P331F | 0.53 | 1.04 | 0.51 | 295.0 | 20.0 | 14.8 |
| MB455 | P331Y | 0.60 | 1.38 | 0.43 | 331.7 | 26.6 | 12.5 |
| MB456 | E333N | 0.12 | 0.23 | 0.53 | 67.9 | 4.5 | 15.2 |
| MB457 | E333Y | 0.36 | 0.70 | 0.52 | 202.1 | 13.6 | 14.9 |
| MB458 | E333V | 0.46 | 0.81 | 0.56 | 252.6 | 15.7 | 16.2 |
| MB459 | T335N | 0.51 | 1.06 | 0.48 | 285.0 | 20.5 | 13.9 |
| MB460 | T335Y | 0.60 | 1.10 | 0.54 | 331.6 | 21.2 | 15.7 |
| MB461 | S337I | 0.45 | 0.97 | 0.46 | 246.9 | 18.8 | 13.2 |
| MB462 | S337K | 0.39 | 0.78 | 0.49 | 213.9 | 15.1 | 14.2 |
| MB463 | S337W | 0.55 | 1.12 | 0.49 | 307.2 | 21.6 | 14.3 |
| MB464 | S267A | 0.16 | 0.39 | 0.40 | 88.5 | 7.6 | 11.7 |
| MB465 | Q295L | 0.35 | 0.77 | 0.45 | 192.3 | 15.0 | 12.9 |
| MB466 | A326D | 0.81 | 1.66 | 0.49 | 449.1 | 32.0 | 14.1 |
| MB467 | A327G | 0.49 | 0.99 | 0.49 | 270.8 | 19.2 | 14.2 |

(Relative binding activity: value determined by dividing the KD value of H237-mIgG1/MRAL-k0 or H237-MB397/MRAL-k0 for each mFcγR by the KD value of each variant for each mFcγR,
Relative I/A (mFcγRII selectivity): value determined by dividing I/A (value determined by dividing the KD value for mFcγRIII by the KD value for mFcγRII) of each variant by I/A of H237-mIgG1/MRAL-k0 or H237-MB397/MRAL-k0)

TABLE 11

| Name (CH) | Alteration added to MB390 | Relative mFcγRII-binding activity (MB390 = 1) | Relative mFcγRIII-binding activity (MB390 = 1) | Relative I/A (mFcγRII selectivity) (MB390 = 1) | Relative mFcγRII-binding activity (mIgG1 = 1) | Relative mFcγRIII-binding activity (mIgG1 = 1) | Relative I/A (mFcγRII selectivity) (mIgG1 = 1) |
|---|---|---|---|---|---|---|---|
| MB390 |  | 1.00 | 1.00 | 1.00 | 521.7 | 11.9 | 44.0 |
| MB477 | S267A | 0.38 | 0.25 | 1.49 | 195.7 | 3.0 | 65.3 |
| MB478 | Q295L | 0.49 | 0.39 | 1.23 | 254.2 | 4.7 | 54.3 |
| MB479 | A326D | 1.41 | 1.16 | 1.21 | 733.8 | 13.8 | 53.2 |
| MB480 | K334R | 0.98 | 0.85 | 1.15 | 511.3 | 10.2 | 50.4 |
| MB490 | S298L | 2.16 | 2.90 | 0.74 | 1127.8 | 34.6 | 32.7 |
| MB491 | S298M | 0.92 | 1.05 | 0.87 | 478.0 | 12.4 | 38.5 |
| MB492 | N324D | 1.19 | 0.92 | 1.29 | 621.5 | 10.9 | 57.0 |
| MB493 | S298L/N324D | 2.73 | 3.77 | 0.72 | 1423.7 | 44.9 | 31.8 |
| MB494 | S298L/K334R | 4.05 | 4.99 | 0.81 | 2111.4 | 59.4 | 35.6 |
| MB495 | S298M/N324D | 1.20 | 1.45 | 0.82 | 623.1 | 17.2 | 36.3 |
| MB496 | S298M/K334R | 1.70 | 1.71 | 0.99 | 883.5 | 20.3 | 43.6 |
| MB497 | N324D/K334R | 1.48 | 1.32 | 1.12 | 772.6 | 15.7 | 49.3 |
| MB498 | S298L/N324D/K334R | 6.40 | 7.15 | 0.89 | 3335.5 | 85.1 | 39.3 |
| MB499 | S298M/N324D/K334R | 1.90 | 2.03 | 0.93 | 992.0 | 24.2 | 41.1 |

(Relative binding activity: value determined by dividing the KD value of H237-mIgG1/MRAL-k0 or H237-MB390/MRAL-k0 for each mFcγR by the KD value of each variant for each mFcγR,
Relative I/A (mFcγRII selectivity): value determined by dividing I/A (value determined by dividing the KD value for mFcγRIII by the KD value for mFcγRII) of each variant by I/A of H237-mIgG1/MRAL-k0 or H237-MB390/MRAL-k0)

From these results (FIGS. 8 and 9 and Tables 10 and 11), it was newly found that: the introduction of one or two or more of the S298L, S298M, N324D, A326D, and K334R alterations enhances binding activity against mFcγRII without largely reducing I/A (mFcγRII selectivity); and these alterations are effective for enhancing binding activity against mFcγRII. The introduction of these alterations to the highly selective variants (H237-MB475/MRAL-k0, H237-MB476/MRAL-k0, H237-MB513/MRAL-k0, and H237-MB515/MRAL-k0) found in Example 5 is expected to further enhance binding activity against mFcγRII while maintaining their high selectivity.

[Example 7] Evaluation of Time-Dependent Change in In Vivo Plasma Concentration of Antibody Having Fc Variant with Selectively Enhanced Binding Activity Against mFcγRII (7-1) Evaluation of Time-Dependent Change in Plasma Concentration of Mouse Antibody with Selectively Enhanced Binding Activity Against mFcγRII In the foregoing Examples, the antibodies having the Fc variants with selectively enhanced binding activity against mFcγRII were obtained. These antibodies having the Fc variants with selectively enhanced binding activity against mFcγRII were tested for time-dependent change in their in vivo plasma concentrations by comparison with antibodies having Fc variants with both mFcγRII-binding activity and mFcγRIII-binding activity enhanced at the same levels. For this purpose, the following tests were conducted using normal mice.

(7-2) Preparation of Antibody with Enhanced Binding Activity Against FcγR

The antibody H chain variable region used was the variable region H237 (SEQ ID NO: 1) of the H chain VH3-IgG1 of the anti-IL-6 receptor antibody Fv4-IgG1 described in WO2009/125825. The antibody L chain commonly used was the L chain MRAL-k0 (SEQ ID NO: 2) of the anti-IL-6 receptor antibody tocilizumab. An anti-human IL-6 receptor antibody H237-mIgG1/MRAL-k0 comprised of H237-mIgG1 (SEQ ID NO: 7) having the H chain constant region mIgG1, and MRAL-k0, an anti-human IL-6 receptor antibody H237-MB367/MRAL-k0 comprised of H237-MB367 (SEQ ID NO: 8) having the Fc variant with selectively enhanced binding activity against mFcγRII, and MRAL-k0, and an anti-human IL-6 receptor antibody H237-mF46/MRAL-k0 comprised of H237-mF46 (SEQ ID NO: 9) having an Fc variant with mIgG1 Ser 239 (EU numbering) substituted by Asp and Ala 327 (EU numbering) substituted by Asp for the purpose of enhancing binding activity against mFcγRII and mFcγRIII, and MRAL-k0 were expressed and purified by the method of Reference Example 1 and evaluated for their binding to mFcγRII and mFcγRIII by the method of Reference Example 2 using Biacore T200. Table 12 shows the binding activity against each mFcγR and I/A (mFcγRII selectivity) of each evaluated antibody. Furthermore, Table 13 shows the relative binding activity against each mFcγR and relative I/A (mFcγRII selectivity) of each evaluated antibody with the values of H237-mIgG1/MRAL-k0 as 1. As for alterations, "X000Z" represents the substitution of amino acid X at EU numbering position 000 by amino acid Z. In this context, X and Z represent the one-letter codes of the amino acid residues. All of the alterations described in Tables 12 and 13 were alterations introduced to the H chain constant region of H237-mIgG1 (SEQ ID NO: 7).

TABLE 12

| Antibody name | Introduced alteration | KD (mFcγRII) | KD (mFcγRIII) | I/A (mFcγRII selectivity) |
|---|---|---|---|---|
| H237-mIgG1/MRAL-k0 | — | 2.10E−07 | 2.82E−07 | 1.3 |
| H237-MB367/MRAL-k0 | T230E/N231A/ P232N/S238E/ S239D | 1.32E−09 | 4.54E−08 | 34.3 |
| H237-mF46/MRAL-k0 | S239D/A327D | 1.33E−09 | 6.40E−09 | 4.8 |

(I/A (mFcγRII selectivity): value determined by dividing the KD value of each variant for mFcγRIII by its KD value for mFcγRII)

TABLE 13

| Antibody name | Introduced alteration | Relative mFcγRII-binding activity (mIgG1 = 1) | Relative mFcγRIII-binding activity (mIgG1 = 1) | Relative I/A (mFcγRII selectivity) (mIgG1 = 1) |
|---|---|---|---|---|
| H237-mIgG1/MRAL-k0 | — | 1.0 | 1.0 | 1.0 |
| H237-MB367/MRAL-k0 | T230E/V231A/P232N/S238E/S239D | 158.6 | 6.2 | 25.6 |
| H237-mF46/MRAL-k0 | S239D/A327D | 158.5 | 44.0 | 3.6 |

(Relative binding activity: value determined by dividing the KD value of H237-mIgG1/MRAL-k0 for each mFcγR by the KD value of each variant for each mFcγR, Relative I/A (mFcγRII selectivity): value determined by dividing I/A (value determined by dividing the KD value for mFcγRIII by the KD value for mFcγRII) of each variant by I/A of H237-mIgG1/MRAL-k0)

From these results, H237-MB367/MRAL-k0 was confirmed to have an Fc variant with more selectively enhanced mFcγRII binding which enhanced binding activity against mFcγRII at the same level as that of H237-mF46/MRAL-k0 and prevented enhancement in binding to mFcγRIII.

(7-3) In Vivo Test Using Normal Mice

A soluble human IL-6 receptor (prepared in Reference Example 3) was administered alone or simultaneously with an anti-human IL-6 receptor mouse antibody to each normal mouse (C57BL/6J mouse, Charles River Laboratories Japan, Inc.). Then, the anti-human IL-6 receptor mouse antibody was evaluated for its disposition. The soluble human IL-6 receptor solution (5 μg/mL) or the mixed solution of the soluble human IL-6 receptor and the anti-human IL-6 receptor mouse antibody was administered to the tail vein at a dose of 10 mL/kg. The doses of the antibody and the soluble human IL-6 receptor were set to 1 mg/kg and 50 μg/kg, respectively. The anti-human IL-6 receptor mouse antibody used was H237-MB367/L104-mk1 and H237-mF46/L104-mk1 derived from the aforementioned H237-MB367/MRAL-k0 and H237-mF46/MRAL-k0, respectively, by the replacement of its L chain with L104-mk1 (SEQ ID NO: 32) comprised of the variable region L104 of the L chain VL3-CK of the anti-IL-6 receptor antibody Fv4-IgG1 described in WO2009/125825 and the constant region mk1 of the mouse chain. After a lapse of 5 minutes, 7 hours, 1 day, 2 days, 3 days, 7 days, 14 days, and 21 days after the administration of the anti-human IL-6 receptor mouse antibody, blood was collected from the mouse. The collected blood was immediately centrifuged at 15,000 rpm at 4° C. for 15 minutes to obtain plasma. The separated plasma was stored in a refrigerator set to −20° C. or lower until measurement.

(7-4) Measurement of Anti-Human IL-6 Receptor Mouse Antibody Concentration in Plasma by ELISA The anti-human IL-6 receptor mouse antibody concentration in the mouse plasma was measured by ELISA. First, a soluble human IL-6 receptor was dispensed to wells of Nunc-Immuno Plate, MaxiSoup (Nalge Nunc International). The plate was left standing overnight at 4° C. to prepare a soluble human IL-6 receptor-immobilized plate. Calibration curve samples containing the anti-human IL-6 receptor mouse antibody at a plasma concentration of 2.50, 1.25, 0.625, 0.313, 0.156, 0.078, or 0.039 μg/mL, and mouse plasma assay samples diluted 100-fold or more were prepared. These calibration curve samples and plasma assay samples were dispensed at a volume of 100 μL/well to the soluble human IL-6 receptor-immobilized plate, followed by stirring at room temperature for 2 hours. Then, the plate was reacted with Anti-Mouse IgG-Peroxidase antibody (Sigma-Aldrich Corp.) at room temperature for 2 hours. The chromogenic reaction of the reaction solution in each well was performed using TMB One Component HRP Microwell Substrate (BioFX Laboratories, Inc.) as a substrate. The reaction was stopped by the addition of 1 N sulfuric acid (Showa Chemical Industry Co., Ltd.). The absorbance of the reaction solution in each well was measured at 450 nm using a microplate reader. The antibody concentration in the mouse plasma was calculated using analysis software SOFTmax PRO (Molecular Devices, LLC) from the absorbance of the calibration curve. The results are shown in FIG. 10.

Figure 10:
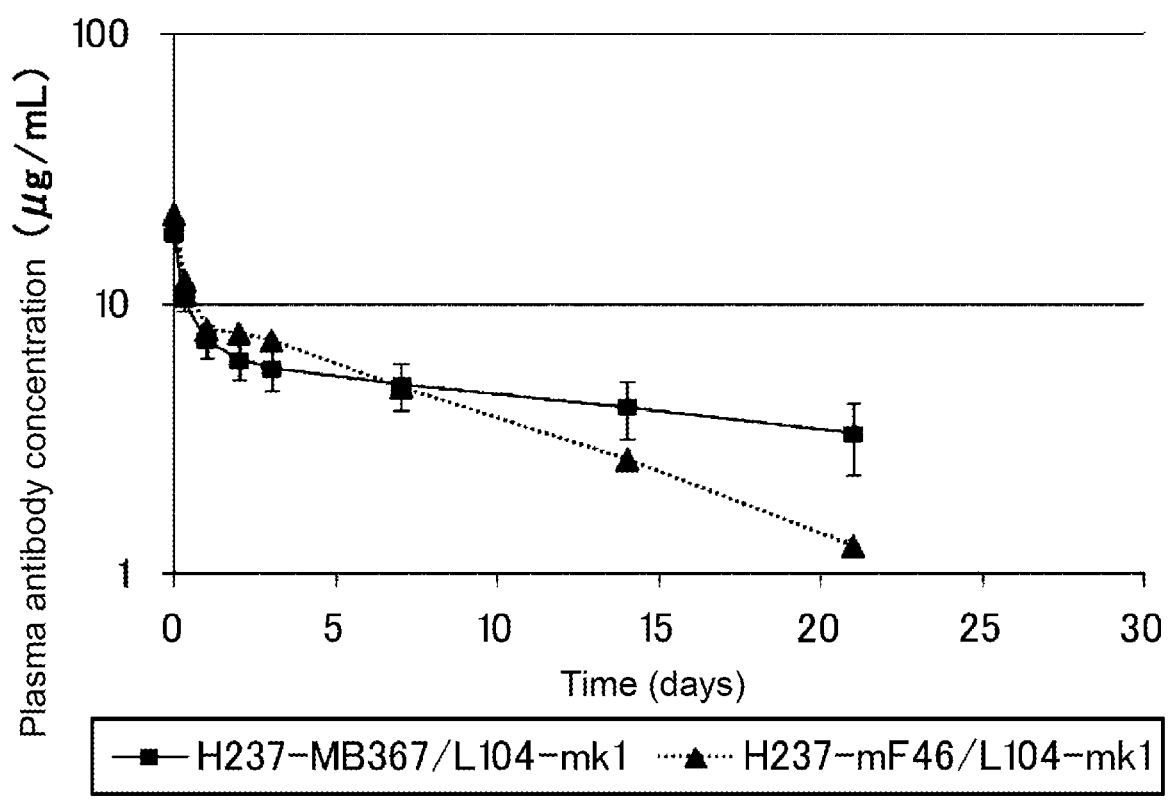

As seen from the results of FIG. 10, H237-MB367/L104-mk1 with selectively enhanced binding activity against mFcγRII exhibited time-dependent change that kept its plasma concentration high compared with that of H237-mF46/L104-mk1 with enhanced binding activity against both mFcγRII and mFcγRIII. This suggests that the antibody H237-mF46/L104-mk1 in comparison with H237-MB367/L104-mk1 disappears via mFcγRIII due to its enhanced binding not only to mFcγRII but to mFcγRIII. In other words, use of such a low selective molecule seems to fail to accurately test the effects of a molecule with selectively enhanced binding activity against mouse FcγRII (or human FcγRIIb). These results demonstrated that use of an Fc variant, such as MB367, which has selectively enhanced binding activity against mFcγRII enables the effects of selectively enhanced binding activity against mouse FcγRII (or human FcγRIIb) to be more accurately tested in vivo.

[Example 8] Preparation of Variant with Selectively Enhanced Binding Activity Against mFcγRII (8-1) Study on Additional Alteration to H237-MB476/MRAL-k0 and H237-MB515/MRAL-k0

For the purpose of obtaining Fc having enhanced binding activity against mFcγRII and also having high selectivity, two highly selective variants (H237-MB476/MRAL-k0 and H237-MB515/MRAL-k0) found in Example 5 were studied to introduce one or two or more of the S298L, N324D, A326D, and K334R alterations found in Example 6.

The antibody H chain variable region used was the variable region H237 (SEQ ID NO: 1) of the H chain VH3-IgG1 of the anti-IL-6 receptor antibody Fv4-IgG1 described in WO2009/125825. The antibody L chain commonly used was the L chain MRAL-k0 (SEQ ID NO: 2) of the anti-IL-6 receptor antibody tocilizumab. H237-MB476/MRAL-k0 and H237-MB515/MRAL-k0 were used as templates to introduce new alterations. These variants were expressed and purified by the method of Reference Example 1 and evaluated for their binding to mFcγRII and mFcγRIII by the method of Reference Example 2 using Biacore T200.

Figure 13:
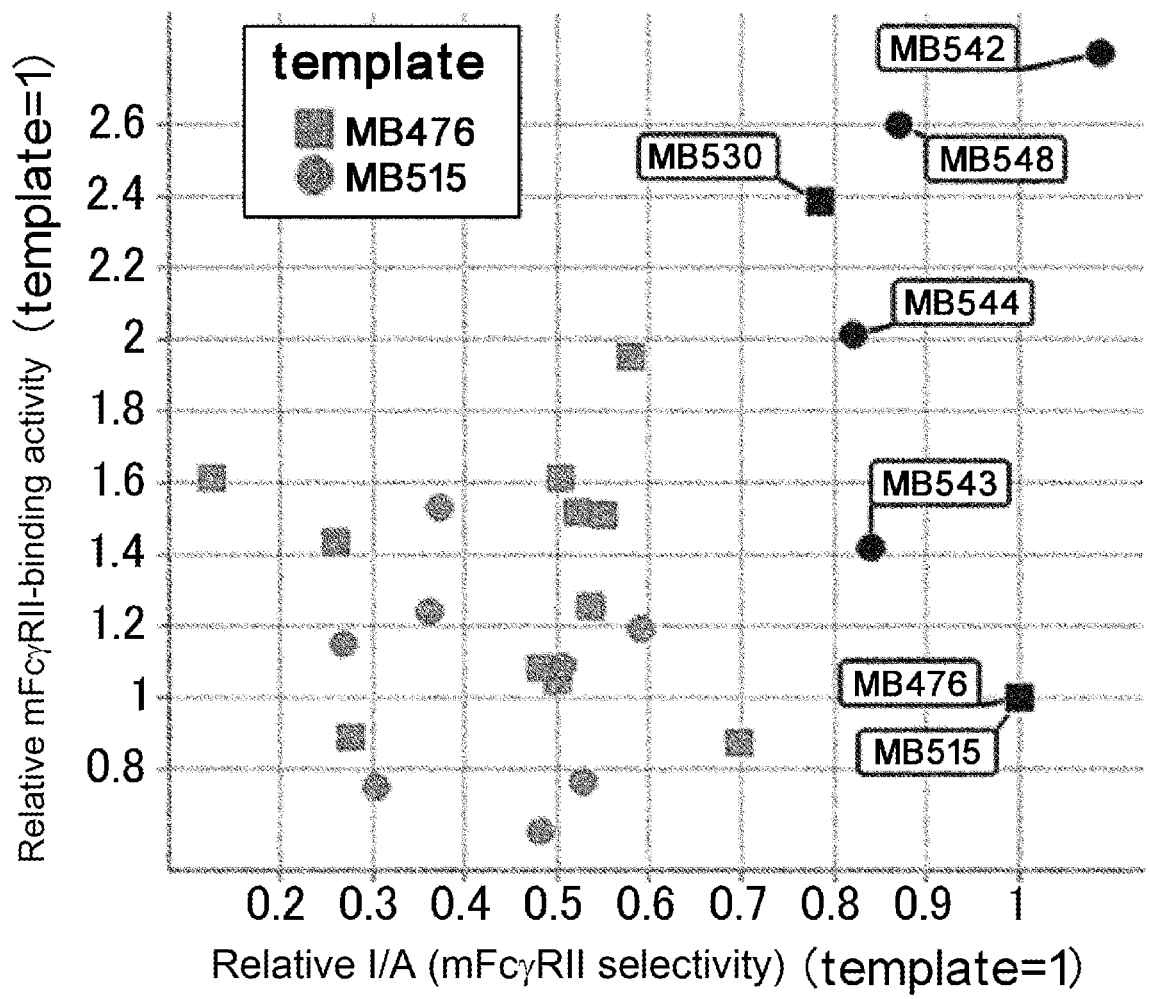
Figure 14:
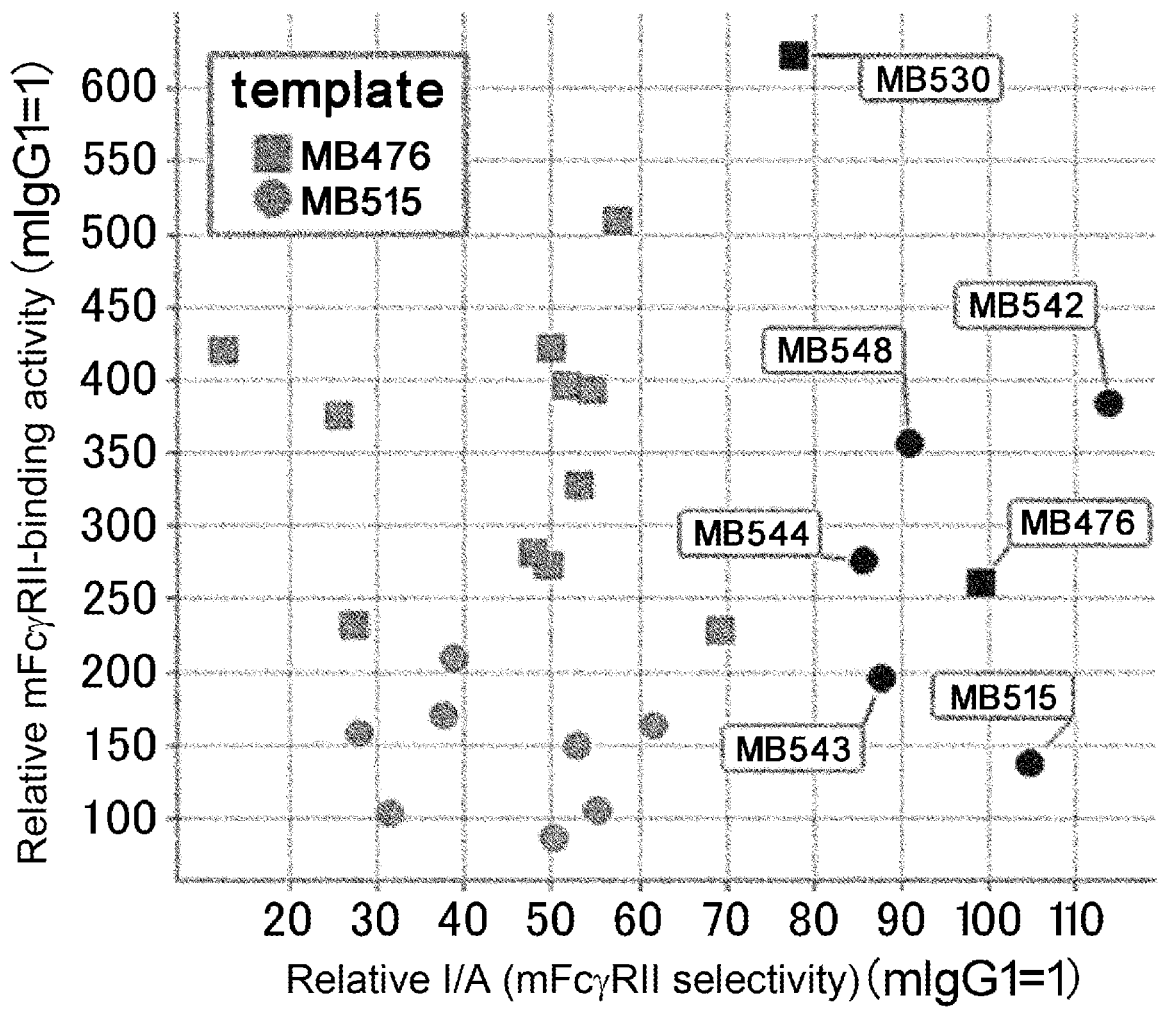
FIG. 14 is a diagram showing results of comparing binding to mFcγRII and selectivity between mFcγRII and mFcγRIII. Each variant having 70-fold or more relative I/A compared with that of H237-mIgG1/MRAL-k0 was labeled.

The results of analyzing interaction with each mFcγR were plotted according to the following method: the KD value of templated H237-MB476/MRAL-k0 or H237-MB515/MRAL-k0 for mFcγR was divided by the KD value of each corresponding variant for mFcγR, and the obtained value was used as an index for the relative binding activity for each mFcγR with the value of H237-MB476/MRAL-k0 or H237-MB515/MRAL-k0 as 1. Also, I/A (mFcγRII selectivity) which is a value determined by dividing the KD value of each variant for mFcγRIII by its KD value for mFcγRII was divided by I/A (mFcγRII selectivity) of H237-MB476/MRAL-k0 or H237-MB515/MRAL-k0, and the obtained value was used as an index for the relative I/A (mFcγRII selectivity) with the value of H237-MB476/MRAL-k0 or H237-MB515/MRAL-k0 as 1. The horizontal axis indicates the value of the relative I/A (mFcγRII selectivity) of each variant, and the vertical axis indicates the value of the relative binding activity of each variant for mFcγRII (FIG. 13). Likewise, the horizontal axis indicates the value of the relative I/A (mFcγRII selectivity) of each variant, and the vertical axis indicates the value of the relative binding activity of each variant for mFcγRII, with the values of unmutated H237-mIgG1/MRAL-k0 as 1 (FIG. 14).

Table 14 shows the relative binding activity against each mFcγR and relative I/A (mFcγRII selectivity) of all of the variants evaluated in this study with the values of H237-mIgG1/MRAL-k0 or each template (H237-MB476/MRAL-k0 or H237-MB515/MRAL-k0) as 1. "Name" in the table represents the name of the H chain constant region (CH) of each evaluated variant. As for alterations, "X000Z" represents the substitution of amino acid X at EU numbering position 000 by amino acid Z. In this context, X and Z represent the one-letter codes of the amino acid residues. The alterations described in Table 14 were alterations introduced to the H chain constant region (SEQ ID NO: 37) of the template MB476 or the H chain constant region (SEQ ID NO: 38) of the template MB515.

TABLE 14

| Name (CH) | template | Alteration added to template | Relative mFcγRII-binding activity (template = 1) | Relative mFcγRIII-binding activity (template = 1) | Relative I/A (mFcγRII selectivity) (template = 1) | Relative mFcγRII-binding activity (mIgG1 = 1) | Relative mFcγRIII-binding activity (mIgG1 = 1) | Relative I/A (mFcγRII selectivity) (mIgG1 = 1) |
|---|---|---|---|---|---|---|---|---|
| MB476 | MB476 | — | 1.00 | 1.00 | 1.00 | 261.2 | 2.6 | 99.0 |
| MB526 | | S298L | 0.89 | 3.23 | 0.28 | 232.4 | 8.5 | 27.3 |

TABLE 14-continued

| Name (CH) | template | Alteration added to template | Relative mFcγRII-binding activity (template = 1) | Relative mFcγRIII-binding activity (template = 1) | Relative I/A (mFcγRII selectivity) (template = 1) | Relative mFcγRII-binding activity (mIgG1 = 1) | Relative mFcγRIII-binding activity (mIgG1 = 1) | Relative I/A (mFcγRII selectivity) (mIgG1 = 1) |
|---|---|---|---|---|---|---|---|---|
| MG527 | | S298L/N324D | 1.05 | 2.09 | 0.50 | 273.3 | 5.5 | 49.5 |
| MB528 | | S298L/A326D | 1.44 | 5.52 | 0.26 | 375.3. | 14.6 | 25.7 |
| MB529 | | S298L/K334R | 1.08 | 2.24 | 0.48 | 281.9 | 5.9 | 47.7 |
| MB530 | | N324D/A326D | 2.38 | 3.04 | 0.78 | 622.6 | 8.0 | 77.6 |
| MB531 | | N324D/K334R | 0.88 | 1.25 | 0.70 | 228.8 | 3.3 | 69.1 |
| MB532 | | A326D/K334R | 1.26 | 2.35 | 0.54 | 328.6 | 6.2 | 53.0 |
| MB533 | | S298L/N324D/A326D | 1.51 | 2.74 | 0.55 | 393.6 | 7.2 | 54.5 |
| MB534 | | S298L/N324D/K334R | 1.61 | 12.79 | 0.13 | 420.7 | 33.8 | 12.5 |
| MB535 | | S298L/A326D/K334R | 1.61 | 3.21 | 0.50 | 421.7 | 8.5 | 49.8 |
| MB536 | | N324D/A326D/K334R | 1.52 | 2.90 | 0.52 | 396.0 | 7.7 | 51.7 |
| M6537 | | S298L/N324D/A326D/K334R | 1.95 | 3.36 | 0.58 | 510.1 | 8.9 | 57.4 |
| MB515 | MB515 | — | 1.00 | 1.00 | 1.00 | 137.3 | 1.3 | 104.4 |
| MB538 | | S298L | 0.63 | 1.30 | 0.48 | 86.2 | 1.7 | 50.3 |
| MB539 | | S298L/N324D | 0.77 | 1.45 | 0.53 | 105.1 | 1.9 | 55.0 |
| MB540 | | S298L/A326D | 1.09 | 2.15 | 0.51 | 149.4 | 2.8 | 52.7 |
| MB541 | | S298L/K334R | 0.75 | 2.48 | 0.30 | 103.0 | 3.3 | 31.6 |
| MB542 | | N324D/A326D | 2.80 | 2.57 | 1.09 | 384.2 | 3.4 | 113.7 |
| MB543 | | N324D/K334R | 1.42 | 1.69 | 0.84 | 195.3 | 2.2 | 87.7 |
| MB544 | | A326D/K334R | 2.01 | 2.45 | 0.82 | 276.2 | 3.2 | 85.6 |
| MB545 | | S298L/N324D/A326D | 1.19 | 2.02 | 0.59 | 163.4 | 2.7 | 61.6 |
| MB546 | | S298L/N324D/K334R | 1.15 | 4.28 | 0.27 | 158.1 | 5.6 | 28.1 |
| MB547 | | S298L/A326D/K334R | 1.24 | 3.43 | 0.36 | 170.3 | 4.5 | 37.7 |
| MB548 | | N324D/A326 1K334R | 2.60 | 2.99 | 0.87 | 356.7 | 3.9 | 90.9 |
| MB549 | | S298L/N324D/A326D/K334R | 1.53 | 4.11 | 0.37 | 210.0 | 5.4 | 38.9 |

(Relative binding activity: value determined by dividing the KD value of H237-mIgG1/MRAL-k0, H237-MB476/MRAL-k0, or H237-MB515/MRAL-k0 for each mFcγR by the KD value of each variant for each mFcγR,
Relative I/A (mFcγRII selectivity): value determined by dividing I/A (value determined by dividing the KD value for mFcγRIII by the KD value for mFcγRII) of each variant by I/A of H237-mIgG1/MRAL-k0, H237-MB476/M RAL-k0, or H237-MB515/MRAL-k0)

From these results (FIGS. 13 and 14 and Table 14), some variants in which one or two or more of the S298L, N324D, A326D, and K334R alterations were introduced were found to enhance binding activity against mFcγRII without largely reducing I/A (mFcγRII selectivity). Of them, H237-MB530/MRAL-k0 (N324D/A326D alterations were introduced in H237-MB476/MRAL-k0), H237-MB542/MRAL-k0 (N324D/A326D alterations were introduced in H237-MB515/MRAL-k0), H237-MB548/MRAL-k0 (N324D/A326D/K334R alterations were introduced in H237-MB515/MRAL-k0), H237-MB544/MRAL-k0 (A326D/K334R alterations were introduced in H237-MB515/MRAL-k0), and H237-MB543/MRAL-k0 (N324D/K334R alterations were introduced in H237-MB515/MRAL-k0) had relative mFcγRII-binding activity enhanced by 1.4 times or more, while maintaining 0.75-fold or more relative I/A (mFcγRII selectivity), with the values of each template as 1.

Particularly, H237-MB530/MRAL-k0, H237-MB542/MRAL-k0, and H237-MB548/MRAL-k0 exhibited 350-fold or more relative mFcγRII-binding activity and 70-fold or more relative I/A (mFcγRII selectivity) with the values of H237-mIgG1/MRAL-k0 as 1 and were much superior in I/A (mFcγRII selectivity) to the above-prepared variants having the same level of mFcγRII binding activity thereas.

(8-2) Study on Amino Acid Substitution at EU Numbering Position 239

As shown in Example 5, some variants with the amino acid substitution at EU numbering position 239 were found to maintain or improve I/A (mFcγRII selectivity). Thus, the substitution of this position by other amino acids that had not been studied in Example 5 was also studied.

The antibody H chain variable region used was the variable region H237 (SEQ ID NO: 1) of the H chain VH3-IgG1 of the anti-IL-6 receptor antibody Fv4-IgG1 described in WO2009/125825. The antibody L chain commonly used was the L chain MRAL-k0 (SEQ ID NO: 2) of the anti-IL-6 receptor antibody tocilizumab. The same 9 variants (all having Asp as the amino acid at EU numbering position 239) as those used in Example 5 were altered as templates to substitute the amino acid at EU numbering position 239 by Leu, Asn, Tyr, or Phe. Of the 9 templated variants, two templated variants H237-MB389/MRAL-k0 and H237-MB390/MRAL-k0 were also altered to substitute the amino acid at EU numbering position 239 by Ala, Gly, Val, Ile, Pro, Thr, Gln, Arg, or His. Of the 9 templated variants, the templated variant H237-MB432/MRAL-k0 was also altered to substitute the amino acid at EU numbering position 239 by Val or Ile. These variants were expressed and purified by the method of Reference Example 1 and evaluated for their binding to mFcγRII and mFcγRIII by the method of Reference Example 2 using Biacore T200.

Figure 15:
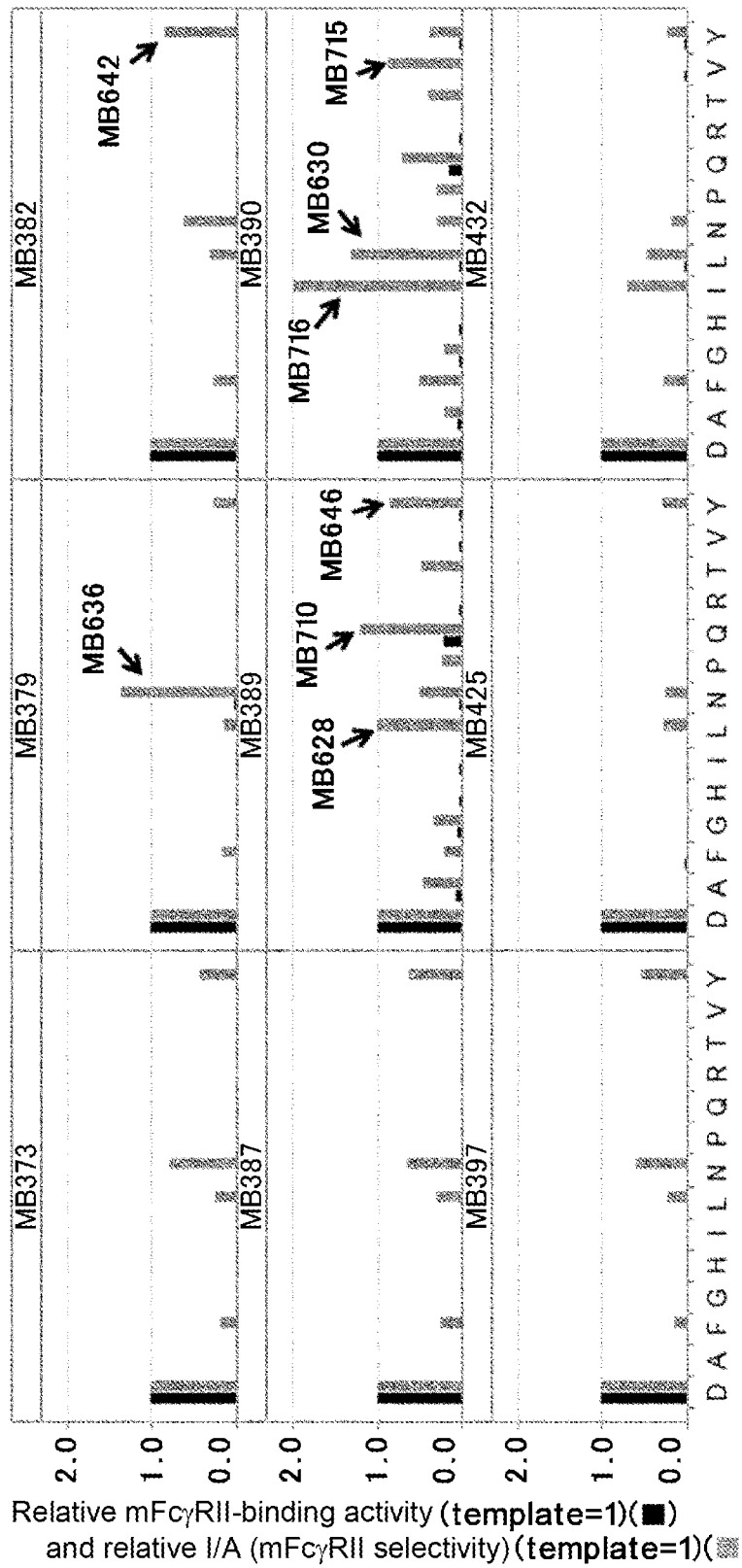
FIG. 15 is a diagram showing the results of comparing the effects of the type of an amino acid at EU numbering position 239 on each template in relation to binding to mFcγRII and selectivity between mFcγRII and mFcγRIII.

The results of analyzing interaction with each mFcγR were plotted according to the following method: in order to compare the effects of the types of the amino acid at EU numbering position 239 on each template, the KD value of each templated variant for mFcγR was divided by the KD value of each variant prepared from the templated variant for mFcγR, and the obtained value was used as an index for the relative binding activity for each mFcγR with the value of each templated variant as 1. Also, I/A (mFcγRII selectivity) which is a value determined by dividing the KD value of each variant for mFcγRIII by its KD value for mFcγRII was divided by I/A (mFcγRII selectivity) of its templated variant, and the obtained value was used as an index for the relative I/A (mFcγRII selectivity) with the value of each templated variant as 1. The horizontal axis indicates the type of the amino acid at EU numbering position 239, and the vertical axis indicates relative mFcγRII-binding activity (filled square) and relative I/A (mFcγRII selectivity) (open square) on a template basis (FIG. 15).

Table 15 shows the relative binding activity against each mFcγR and relative I/A (mFcγRII selectivity) of all of the variants evaluated in this study with the values of H237-mIgG1/MRAL-k0 as 1. "Name" in the table represents the name of the H chain constant region (CH) of each evaluated variant. As for alterations, "X000Z" represents the substitution of amino acid X at EU numbering position 000 by amino acid Z. In this context, X and Z represent the one-letter codes of the amino acid residues. All of the alterations described in Table 15 were alterations introduced to the H chain constant region (SEQ ID NO: 4) of mouse IgG1 (mIgG1).

TABLE 15

| Name (CH) | Alteration introduced to mIgG1 | template | Amino acid at EU numbering position 239 | Relative mFcγRII-binding activity (mIgG1 = 1) | Relative mFcγRIII-binding activity (mIgG1 = 1) | Relative I/A (mFcγRII selectivity) (mIgG1 = 1) |
|---|---|---|---|---|---|---|
| MB623 | T230E/V231A/P232Y/S238E/S239L | MB373 | L | 0.53 | 0.09 | 5.99 |
| MB624 | T230E/V231D/P232Y/S238E/S239L | MB382 | L | 0.80 | 0.10 | 8.14 |
| MB625 | T230E/V231N/P232Y/S238E/S239L | MB387 | L | 0.67 | 0.12 | 5.53 |
| MB626 | T230E/V231T/P232Y/S238E/S239L | MB397 | L | 0.81 | 0.12 | 6.78 |
| MB627 | T230E/P232Y/S238E/S239L | MB379 | L | 0.32 | 0.09 | 3.45 |
| MB628 | T230E/V231P/P232A/S238E/S239L | MB389 | L | 2.20 | 0.06 | 35.18 |
| MB629 | T230I/V231P/P232A/S238E/S239L | MB425 | L | 0.38 | 0.04 | 9.08 |
| MB630 | T230E/V231P/P232N/S238E/S239L | MB390 | L | 14.31 | 0.25 | 57.03 |
| MB631 | T230Q/V231P/P232N/S238E/S239L | MB432 | L | 4.29 | 0.28 | 15.32 |
| MB632 | T230E/V231A/P232Y/S238E/S239N | MB373 | N | 3.64 | 0.18 | 19.97 |
| MB633 | T230E/V231D/P232Y/S238E/S239N | MB382 | N | 2.77 | 0.17 | 16.12 |
| MB634 | T230E/V231N/P232Y/S238E/S239N | MB387 | N | 2.52 | 0.21 | 12.20 |
| MB635 | T230E/V231T/P232Y/S238E/S239N | MB397 | N | 5.06 | 0.29 | 17.54 |
| MB636 | T230E/P232Y/S238E/S239N | MB379 | N | 4.41 | 0.14 | 30.84 |
| MB637 | T230E/V231P/P232A/S238E/S239N | MB389 | N | 2.60 | 0.15 | 17.48 |
| MB638 | T230I/V231P/P232A/S238E/S239N | MB425 | N | 0.75 | 0.08 | 9.02 |
| MB639 | T230E/V231P/P232N/S238E/S239N | MB390 | N | 4.91 | 0.38 | 12.98 |
| MB640 | T230Q/V231P/P232N/S238E/S239N | MB432 | N | 1.06 | 0.18 | 5.87 |
| MB641 | T230E/V231A/P232Y/S238E/S239Y | MB373 | Y | 1.47 | 0.13 | 10.98 |
| MB642 | T230E/V231D/P232Y/S238E/S239Y | MB382 | Y | 1.87 | 0.08 | 22.12 |
| MB643 | T230E/V231N/P232Y/S238E/S239Y | MB387 | Y | 1.66 | 0.14 | 11.82 |
| MB644 | T230E/V231T/P232Y/S238E/S239Y | MB397 | Y | 4.55 | 0.30 | 15.32 |
| MB645 | T230E/P232Y/S238E/S239Y | MB379 | Y | 1.17 | 0.20 | 5.87 |
| MB646 | T230E/V231P/P232A/S238E/S239Y | MB389 | Y | 4.38 | 0.15 | 29.58 |
| MB647 | T230I/V231P/P232A/S238E/S239Y | MB425 | Y | 1.05 | 0.10 | 10.48 |
| MB648 | T230E/V231P/P232N/S238E/S239Y | MB390 | Y | 10.75 | 0.64 | 16.77 |
| MB649 | T230Q/V231P/P232N/S238E/S239Y | MB432 | Y | 3.89 | 0.51 | 7.63 |
| MB650 | T230E/V231A/P232Y/S238E/S239F | MB373 | F | 0.24 | 0.05 | 4.51 |
| MB651 | T230E/V231D/P232Y/S238E/S239F | MB382 | F | 0.30 | 0.04 | 6.85 |
| MB652 | T230E/V231N/P232Y/S238E/S239F | MB387 | F | 0.28 | 0.06 | 4.60 |
| MB653 | T230E/V231T/P232Y/S238E/S239F | MB397 | F | 0.41 | 0.10 | 3.95 |
| MB654 | T230E/P232Y/S238E/S239F | MB379 | F | 0.27 | 0.07 | 3.73 |
| MB655 | T230E/V231P/P232A/S238E/S239F | MB389 | F | 0.40 | 0.06 | 6.99 |
| MB656 | T230I/V231P/P232A/S238E/S239F | MB425 | F | N.B. | 0.02 | — |
| MB657 | T230E/V231P/P232N/S238E/S239F | MB390 | F | 1.77 | 0.08 | 21.92 |
| MB658 | T230Q/V231P/P232N/S238E/S239F | MB432 | F | 0.51 | 0.06 | 8.77 |
| MB704 | T230E/V231P/P232A/S238E/S239A | MB389 | A | 14.09 | 0.87 | 16.16 |
| MB705 | T230E/V231P/P232A/S238E/S239G | MB389 | G | 8.71 | 0.75 | 11.71 |
| MB706 | T230E/V231P/P232A/S238E/S239V | MB389 | V | 0.23 | N.B. | — |
| MB707 | T230E/V231P/P232A/S238E/S239I | MB389 | I | 0.37 | N.B. | — |
| MB708 | T230E/V231P/P232A/S238E/S239P | MB389 | P | 0.28 | 0.03 | 8.24 |
| MB709 | T230E/V231P/P232A/S238E/S239T | MB389 | T | 0.61 | 0.04 | 16.61 |
| MB710 | T230E/V231P/P232A/S238E/S239Q | MB389 | Q | 50.80 | 1.22 | 41.88 |
| MB711 | T230E/V231P/P232A/S238E/S239R | MB389 | R | 0.05 | N.B. | — |
| MB712 | T230E/V231P/P232A/S238E/S239H | MB389 | H | 0.16 | N.B. | — |
| MB713 | T230E/V231P/P232N/S238E/S239A | MB390 | A | 23.48 | 2.50 | 9.41 |
| MB714 | T230E/V231P/P232N/S238E/S239G | MB390 | G | 14.16 | 1.61 | 8.81 |
| MB715 | T230E/V231P/P232N/S238E/S239V | MB390 | V | 0.89 | 0.02 | 37.80 |
| MB716 | T230E/V231P/P232N/S238E/S239I | MB390 | I | 3.98 | 0.05 | 86.85 |
| MB717 | T230E/V231P/P232N/S238E/S239P | MB390 | P | 0.41 | 0.03 | 12.51 |
| MB718 | T230E/V231P/P232N/S238E/S239T | MB390 | T | 0.85 | 0.05 | 16.80 |
| MB719 | T230E/V231P/P232N/S238E/S239Q | MB390 | Q | 70.38 | 2.31 | 30.54 |
| MB720 | T230E/V231P/P232N/S238E/S239R | MB390 | R | 0.08 | N.B. | — |
| MB721 | T230E/V231P/P232N/S238E/S239H | MB390 | H | 0.30 | N.B. | — |
| MB792 | T230Q/V231P/P232N/S238E/S239V | MB432 | V | 0.31 | N.B. | — |
| MB793 | T230Q/V231P/P232N/S238E/S239I | MB432 | I | 1.17 | 0.05 | 22.87 |

(N.B.: although assay was conducted, binding was not observable because of being too weak, Relative binding activity: value determined by dividing the KD value of H237-mIgG1/MRAL-k0 for each mFcγR by the KD value of each variant for each mFcγR, Relative I/A (mFcγRII selectivity): value determined by dividing I/A (value determined by dividing the KD value for mFcγRIII by the KD value for mFcγRII) of each variant by I/A of H237-mIgG1/MRAL-k0)

As seen from the results of FIG. 15 and Table 15, mFcγRII-binding activity was largely reduced in all of the variants, whereas I/A (mFcγRII selectivity) was maintained or improved in some of the variants. In FIG. 15, variants having 0.8-fold or more relative I/A (mFcγRII selectivity) with the value of each templated variant as 1 were indicated by arrow with the name of CH. Of the variants with improved I/A (mFcγRII selectivity), H237-MB716/MRAL-k0, H237-MB630/MRAL-k0, and H237-MB710/MRAL-k0 had mFcγRII selectivity as high as 40-fold or more relative I/A (mFcγRII selectivity) with the value of H237-mIgG1/MRAL-k0 as 1. The introduction of, for example, the additional alterations shown in Example 6 or 8-1 to these variants as templates is expected to be able to prepare variants with further enhanced binding activity against mFcγRII while maintaining high mFcγRII selectivity.

(8-3) Study on Additional Alteration to H237-MB630/MRAL-k0

The study of Example 8-2 newly obtained variants having high mFcγRII selectivity. Of them, one variant (H237-MB630/MRAL-k0) was examined for further amino acid substitution for the purpose of enhancing mFcγRII-binding activity.

The antibody H chain variable region used was the variable region H237 (SEQ ID NO: 1) of the H chain VH3-IgG1 of the anti-IL-6 receptor antibody Fv4-IgG1 described in WO2009/125825. The antibody L chain commonly used was the L chain MRAL-k0 (SEQ ID NO: 2) of the anti-IL-6 receptor antibody tocilizumab. H237-MB630/MRAL-k0 found in Example 8-2 was used as a template to introduce the alterations studied in Example 6, etc. These variants were expressed and purified by the method of Reference Example 1 and evaluated for their binding to mFcγRII and mFcγRIII by the method of Reference Example 2 using Biacore T200.

For the results of analyzing interaction with each mFcγR, the KD value of H237-MB630/MRAL-k0 or H237-mIgG1/MRAL-k0 for mFcγR was divided by the KD value of each variant for mFcγR, and the obtained value was used as an index for the relative binding activity for each mFcγR with the value of H237-MB630/MRAL-k0 or H237-mIgG1/MRAL-k0 as 1. Also, I/A (mFcγRII selectivity) which is a value determined by dividing the KD value of each variant for mFcγRIII by its KD value for mFcγRII was divided by I/A (mFcγRII selectivity) of H237-MB716/MRAL-k0 or H237-mIgG1/MRAL-k0, and the obtained value was used as an index for the relative I/A (mFcγRII selectivity) with the value of H237-MB716/MRAL-k0 or H237-mIgG1/MRAL-k0 as 1. The horizontal axis indicates the value of the relative binding activity of each variant against mFcγRIII with the value of H237-MB630/MRAL-k0 as 1, and the vertical axis indicates the value of the relative binding activity of each variant against mFcγRII with the value of H237-MB630/MRAL-k0 as 1 (FIG. 16).

Table 16 shows the relative binding activity against each mFcγR and relative I/A (mFcγRII selectivity) of all of the variants evaluated in this study with the values of H237-MB630/MRAL-k0 or H237-mIgG1/MRAL-k0 as 1. "Name" in the table represents the name of the H chain constant region (CH) of each evaluated variant. As for alterations, "X000Z" represents the substitution of amino acid X at EU numbering position 000 by amino acid Z. In this context, X and Z represent the one-letter codes of the amino acid residues. All of the alterations described in Table 16 were alterations introduced to the H chain constant region (SEQ ID NO: 39) of MB630.

TABLE 16

| Name (CH) | Alteration added to MB630 | Relative mFcγRII-binding activity (MB630 = 1) | Relative mFcγRIII-binding activity (MB630 = 1) | Relative I/A (mFcγRII selectivity) (MB630 = 1) | Relative mFcγRII-binding activity (mIgG1 = 1) | Relative mFcγRIII-binding activity (mIgG1 = 1) | Relative I/A (mFcγRII selectivity) (mIgG1 = 1) |
|---|---|---|---|---|---|---|---|
| MB748 | S267A | 0.70 | 0.70 | 1.00 | 11.7 | 0.14 | 85.8 |
| MB749 | Q295L | 1.52 | 1.96 | 0.78 | 25.3 | 0.38 | 66.5 |
| MB750 | A326D | 1.77 | 2.06 | 0.86 | 29.4 | 0.40 | 73.8 |
| MB751 | K334R | 1.53 | 1.63 | 0.94 | 25.4 | 0.32 | 80.5 |
| MB752 | S298L | 0.36 | 0.44 | 0.81 | 6.0 | 0.09 | 69.7 |
| MB753 | S298M | 0.34 | 0.34 | 1.01 | 5.7 | 0.07 | 86.4 |
| MB754 | N324D | 1.26 | 1.28 | 0.99 | 21.0 | 0.25 | 84.5 |
| MB755 | S298L/N324D | 0.45 | 0.58 | 0.78 | 7.6 | 0.11 | 67.1 |
| MB756 | S298L/K334R | 0.64 | 1.09 | 0.59 | 10.6 | 0.21 | 50.3 |
| MB757 | S298M/N324D | 0.46 | 0.45 | 1.01 | 7.6 | 0.09 | 86.8 |
| MB758 | S298M/K334R | 0.59 | 0.69 | 0.86 | 9.8 | 0.13 | 73.4 |
| MB759 | N324D/K334R | 2.03 | 2.25 | 0.91 | 33.8 | 0.44 | 77.6 |
| MB760 | S298L/N324D/K334R | 0.85 | 1.42 | 0.60 | 14.1 | 0.28 | 51.2 |
| MB761 | S298M/N324D/K334R | 0.81 | 0.92 | 0.87 | 13.4 | 0.18 | 74.9 |
| MB762 | F296E | 0.40 | 0.51 | 0.79 | 4.4 | 0.09 | 49.9 |
| MB763 | F296N | 0.31 | 0.41 | 0.76 | 3.4 | 0.07 | 47.9 |
| MB764 | F296T | 0.23 | 0.32 | 0.71 | 2.5 | 0.05 | 45.3 |
| MB765 | N324L | 0.49 | 0.64 | 0.76 | 5.3 | 0.11 | 48.3 |
| MB766 | N324M | 1.29 | 1.55 | 0.83 | 14.0 | 0.27 | 52.8 |
| MB767 | A330G | 0.16 | 0.19 | 0.88 | 1.8 | 0.03 | 55.9 |
| MB768 | A330Q | 0.50 | 0.81 | 0.61 | 5.4 | 0.14 | 38.9 |
| MB769 | P331D | 0.31 | 0.38 | 0.82 | 3.3 | 0.06 | 51.7 |
| MB770 | P331F | 1.23 | 1.40 | 0.88 | 13.3 | 0.24 | 55.5 |
| MB771 | P331Y | 1.27 | 1.53 | 0.83 | 13.8 | 0.26 | 52.7 |
| MB772 | E333N | 0.32 | 0.42 | 0.76 | 3.5 | 0.07 | 47.9 |
| MB773 | E333Y | 1.17 | 1.25 | 0.93 | 12.7 | 0.22 | 59.2 |
| MB774 | E333V | 0.87 | 1.05 | 0.83 | 9.4 | 0.18 | 52.4 |
| MB775 | T335N | 0.84 | 1.02 | 0.82 | 9.1 | 0.18 | 52.0 |
| MB776 | T335Y | 1.04 | 1.15 | 0.90 | 11.3 | 0.20 | 57.1 |
| MB777 | S337I | 0.74 | 0.72 | 1.02 | 9.7 | 0.17 | 58.2 |
| MB778 | S337K | 0.57 | 0.65 | 0.88 | 6.1 | 0.11 | 55.4 |
| MB779 | S337W | 0.92 | 1.02 | 0.91 | 10.0 | 0.18 | 57.3 |

TABLE 16-continued

| Name (CH) | Alteration added to MB630 | Relative mFcγRII-binding activity (MB630 = 1) | Relative mFcγRIII-binding activity (MB630 = 1) | Relative I/A (mFcγRII selectivity) (MB630 = 1) | Relative mFcγRII-binding activity (mIgG1 = 1) | Relative mFcγRIII-binding activity (mIgG1 = 1) | Relative I/A (mFcγRII selectivity) (mIgG1 = 1) |
|---|---|---|---|---|---|---|---|
| MB780 | A327G | 1.86 | 2.29 | 0.81 | 20.2 | 0.39 | 51.4 |
| MB781 | A330K | 0.48 | 0.77 | 0.62 | 5.2 | 0.13 | 39.1 |
| MB782 | Q295L/N324D | 1.96 | 2.89 | 0.68 | 21.3 | 0.50 | 42.9 |
| MB783 | Q295L/A326D | 2.82 | 4.34 | 0.65 | 30.6 | 0.75 | 41.2 |
| MB784 | Q295L/K334R | 1.36 | 2.24 | 0.61 | 14.7 | 0.38 | 38.4 |
| MB785 | N324D/A326D | 2.29 | 2.85 | 0.81 | 24.9 | 0.49 | 51.1 |
| MB786 | A326D/K334R | 2.50 | 3.33 | 0.75 | 27.2 | 0.57 | 47.6 |
| MB787 | Q295L/N324D/A326D | 3.55 | 5.57 | 0.64 | 38.5 | 0.96 | 40.3 |
| MB788 | Q295L/N324D/K334R | 2.06 | 3.46 | 0.60 | 22.4 | 0.59 | 37.8 |
| MB789 | Q295L/A326D/K334R | 2.84 | 4.79 | 0.59 | 30.9 | 0.82 | 37.6 |
| MB790 | N324D/A326D/K334R | 3.08 | 4.09 | 0.75 | 33.5 | 0.70 | 47.8 |
| MB791 | Q295L/N324D/A326D/K334R | 3.70 | 6.43 | 0.58 | 40.1 | 1.10 | 36.4 |
| MB807 | Q295L/N324M | 1.67 | 2.11 | 0.79 | 21.9 | 0.49 | 45.1 |
| MB808 | Q295L/A327G | 2.22 | 3.40 | 0.65 | 29.2 | 0.78 | 37.3 |
| MB809 | Q295L/P331F | 1.44 | 1.92 | 0.75 | 19.0 | 0.44 | 43.0 |
| MB810 | Q295L/P331Y | 1.58 | 2.24 | 0.71 | 20.8 | 0.52 | 40.3 |
| MB811 | Q295L/E333Y | 1.69 | 1.87 | 0.90 | 22.2 | 0.43 | 51.6 |
| MB812 | N324D/A327G | 2.54 | 2.93 | 0.87 | 33.4 | 0.68 | 49.6 |
| MB813 | N324D/P331F | 1.24 | 1.29 | 0.96 | 16.3 | 0.30 | 55.0 |
| MB814 | N324D/P331Y | 1.37 | 1.48 | 0.93 | 18.0 | 0.34 | 52.9 |
| MB815 | N324D/E333Y | 1.34 | 1.30 | 1.02 | 17.6 | 0.30 | 58.5 |
| MB816 | N324M/A326D | 2.31 | 2.84 | 0.82 | 30.4 | 0.65 | 46.6 |
| MB817 | N324M/A327G | 2.17 | 2.27 | 0.95 | 28.5 | 0.52 | 54.6 |
| MB818 | N324M/P331F | 1.19 | 1.25 | 0.95 | 15.6 | 0.29 | 54.3 |
| MB819 | N324M/P331Y | 1.38 | 1.40 | 0.98 | 18.1 | 0.32 | 56.1 |
| MB820 | N324M/E333Y | 1.49 | 1.43 | 1.04 | 19.5 | 0.33 | 59.3 |
| MB821 | N324M/K334R | 1.86 | 1.96 | 0.95 | 24.4 | 0.45 | 54.3 |
| MB822 | A326D/A327G | 3.33 | 4.02 | 0.83 | 43.8 | 0.93 | 47.4 |
| MB823 | A326D/P331F | 1.90 | 2.13 | 0.90 | 25.0 | 0.49 | 51.2 |
| MB824 | A326D/P331Y | 2.13 | 2.45 | 0.87 | 28.0 | 0.56 | 49.6 |
| MB825 | A326D/E333Y | 2.16 | 2.17 | 1.00 | 28.4 | 0.50 | 57.0 |
| MB826 | A327G/P331F | 1.41 | 1.48 | 0.95 | 18.5 | 0.34 | 54.5 |
| MB827 | A327G/P331Y | 1.63 | 1.64 | 0.99 | 21.5 | 0.38 | 56.8 |
| MB828 | A327G/E333Y | 2.16 | 2.14 | 1.01 | 28.4 | 0.49 | 57.6 |
| MB829 | A327G/K334R | 2.57 | 2.75 | 0.93 | 33.8 | 0.63 | 53.4 |
| MB830 | P331F/E333Y | 0.37 | 0.36 | 1.01 | 4.8 | 0.08 | 57.7 |
| MB831 | P331F/K334R | 1.70 | 1.71 | 0.99 | 22.3 | 0.39 | 56.8 |
| MB832 | P331Y/E333Y | 0.40 | 0.40 | 0.99 | 5.2 | 0.09 | 56.3 |
| MB833 | P331Y/K334R | 1.92 | 1.94 | 0.99 | 25.3 | 0.45 | 56.5 |
| MB834 | E333Y/K334R | 1.29 | 1.25 | 1.03 | 17.0 | 0.29 | 58.9 |
| MB835 | K268D | 2.00 | 3.05 | 0.66 | 26.3 | 0.70 | 37.4 |
| MB846 | K268D/A326D/A327G | 6.80 | 11.57 | 0.59 | 72.1 | 2.12 | 34.1 |
| MB847 | Q295L/A326D/A327G | 4.12 | 7.24 | 0.57 | 43.7 | 1.33 | 33.0 |
| MB848 | N324D/A326D/A327G | 4.33 | 5.00 | 0.86 | 45.8 | 0.92 | 50.1 |
| MB849 | A326D/A327G/P331Y | 2.97 | 3.54 | 0.84 | 31.4 | 0.65 | 48.6 |
| MB850 | A326D/A327G/E333Y | 4.12 | 4.30 | 0.96 | 43.7 | 0.79 | 55.5 |
| MB851 | A326D/A327G/K334R | 4.13 | 5.23 | 0.79 | 43.8 | 0.96 | 45.9 |
| MB852 | Q295L/N324D/A326D/A327G | 5.76 | 10.02 | 0.58 | 61.0 | 1.83 | 33.4 |
| MB853 | Q295L/A326D/A327G/P331Y | 3.31 | 6.20 | 0.53 | 35.0 | 1.13 | 31.0 |
| MB854 | Q295L/A326D/A327G/E333Y | 4.77 | 6.84 | 0.70 | 50.6 | 1.25 | 40.5 |
| MB855 | Q295L/A326D/A327G/K334R | 3.41 | 6.21 | 0.55 | 36.2 | 1.14 | 31.9 |
| MB856 | N324D/A326D/A327G/P331Y | 4.23 | 4.95 | 0.85 | 44.8 | 0.91 | 49.5 |
| MB857 | N324D/A326D/A327G/E333Y | 4.21 | 4.92 | 0.85 | 44.6 | 0.90 | 49.6 |
| MB858 | N324D/A326D/A327G/K334R | 5.86 | 6.92 | 0.85 | 62.0 | 1.27 | 49.1 |
| MB859 | A326D/A327G/P331Y/K334R | 3.22 | 3.90 | 0.83 | 34.2 | 0.71 | 48.0 |
| MB860 | A326D/A327G/E333Y/K334R | 3.74 | 4.07 | 0.92 | 39.6 | 0.75 | 53.3 |
| MB861 | K268D/N324D/A326D/A327G | 7.25 | 13.18 | 0.55 | 76.8 | 2.41 | 31.9 |
| MB862 | K268D/A326D/A327G/P331Y | 6.41 | 10.83 | 0.59 | 67.9 | 1.98 | 34.4 |
| MB863 | K268D/A326D/A327G/E333Y | 7.68 | 12.71 | 0.60 | 81.3 | 2.33 | 35.0 |
| MB864 | K268D/A326D/A327G/K334R | 10.42 | 19.86 | 0.52 | 110.4 | 3.63 | 30.4 |
| MB865 | K268D/Q295L/A326D/A327G | 7.91 | 18.26 | 0.43 | 83.8 | 3.34 | 25.1 |

(Relative binding activity: value determined by dividing the KD value of H237-MB630/MRAL-k0 or H237-mIgG1/MRAL-k0 for each mFcγR by the KD value of each variant for each mFcγR, Relative I/A (mFcγRII selectivity): value determined by dividing I/A (value determined by dividing the KD value for mFcγRIII by the KD value for mFcγRII) of each variant by I/A of H237-MB630/MRAL-k0 or H237-mIgG1/MRAL-k0)

From the results of FIG. 16 and Table 16, many specimens with amino acid substitution newly introduced in H237-MB630/MRAL-k0 were found to reduce mFcγRII selectivity, but to enhance mFcγRII-binding activity. In addition, some variants were found to enhance or reduce mFcγRII-binding activity while maintaining high mFcγRII selectivity.

(8-4) Study on Additional Alteration to H237-MB716/MRAL-k0

Additional amino acid substitution was also studied on H237-MB716/MRAL-k0 (having Ile as the amino acid at EU numbering position 239) shown in the study of Example 8-2 to have higher mFcγRII selectivity than that of H237-MB630/MRAL-k0 (having Leu as the amino acid at EU numbering position 239). 7 alterations (K268D, Q295L, N324D, A326D, A327G, E333Y, and K334R) were selected from among the alterations found to enhance mFcγRII-binding activity by introduction to H237-MB630/MRAL-k0 in Example 8-3. These alterations were introduced in various combinations and studied.

The antibody H chain variable region used was the variable region H237 (SEQ ID NO: 1) of the H chain VH3-IgG1 of the anti-IL-6 receptor antibody Fv4-IgG1 described in WO2009/125825. The antibody L chain commonly used was the L chain MRAL-k0 (SEQ ID NO: 2) of the anti-IL-6 receptor antibody tocilizumab. H237-MB716/MRAL-k0 was used as a template to introduce the alterations. These variants were expressed and purified by the method of Reference Example 1 and evaluated for their binding to mFcγRII and mFcγRIII by the method of Reference Example 2 using Biacore T200.

For the results of analyzing interaction with each mFcγR, the KD value of H237-MB716/MRAL-k0 or H237-mIgG1/MRAL-k0 for mFcγR was divided by the KD value of each variant for mFcγR, and the obtained value was used as an index for the relative binding activity for each mFcγR with the value of H237-MB716/MRAL-k0 or H237-mIgG1/MRAL-k0 as 1. Also, I/A (mFcγRII selectivity) which is a value determined by dividing the KD value of each variant for mFcγRIII by its KD value for mFcγRII was divided by I/A (mFcγRII selectivity) of H237-MB716/MRAL-k0 or H237-mIgG1/MRAL-k0, and the obtained value was used as an index for the relative I/A (mFcγRII selectivity) with the value of H237-MB716/MRAL-k0 or H237-mIgG1/MRAL-k0 as 1. The horizontal axis indicates the value of the relative binding activity of each variant against mFcγRIII with the value of H237-MB716/MRAL-k0 as 1, and the vertical axis indicates the value of the relative binding activity of each variant against mFcγRII with the value of H237-MB716/MRAL-k0 as 1 (FIG. 17).

Table 17 shows the relative binding activity against each mFcγR and relative I/A (mFcγRII selectivity) of all of the variants evaluated in this study with the values of H237-MB716/MRAL-k0 or H237-mIgG1/MRAL-k0 as 1. "Name" in the table represents the name of the H chain constant region (CH) of each evaluated variant. As for alterations, "X000Z" represents the substitution of amino acid X at EU numbering position 000 by amino acid Z. In this context, X and Z represent the one-letter codes of the amino acid residues. All of the alterations described in Table 17 were alterations introduced to the H chain constant region (SEQ ID NO: 47) of MB716.

TABLE 17

| Name (CH) | Alteration added to MB716 | Relative mFcγRII-binding activity (MB716 = 1) | Relative mFcγRII)-binding activity (MB716 = 1) | Relative I/A (mFcγRII selectivity) (MB716 = 1) | Relative mFcγRII-binding activity (mIgG1 = 1) | Relative mFcγRII)-binding activity (mIgG1 = 1) | Relative I/A (mFcγRll selectivity) (mIgG1 = 1) |
|---|---|---|---|---|---|---|---|
| MB866 | A326D/A327G | 3.0 | 3.02 | 0.99 | 12.96 | 0.18 | 72.42 |
| MB867 | K268D/A326D/A327G | 8.1 | 14.35 | 0.57 | 35.23 | 0.85 | 41.41 |
| MB868 | K268D/N324D/A326D/A327G | 8.4 | 14.45 | 0.58 | 36.63 | 0.86 | 42.76 |
| MB869 | K268D/A326D/A327G/E333Y | 9.4 | 15.85 | 0.60 | 41.01 | 0.94 | 43.65 |
| MB870 | K268D/A326D/A327G/K334R | 8.9 | 17.64 | 0.50 | 38.60 | 1.05 | 36.92 |
| MB871 | K268D/Q295L/A326D/A327G | 14.2 | 28.17 | 0.51 | 61.82 | 1.67 | 37.02 |
| MB875 | K268D/Q295L/N324D/A326D/A327G | 16.8 | 32.31 | 0.52 | 72.84 | 1.92 | 38.03 |
| MB876 | K268D/Q295L/A326D/A327G/E333Y | 13.5 | 24.85 | 0.54 | 58.66 | 1.48 | 39.81 |
| MB877 | K268D/N324D/A326D/A327G/K334R | 12.7 | 24.36 | 0.52 | 55.26 | 1.45 | 38.26 |

(Relative binding activity: value determined by dividing the KD value of H237-MB716/MRAL-k0 or H237-mIgG1/MRAL-k0 for each mFcγR by the KD value of each variant for each mFcγR, Relative I/A (mFcγRII selectivity): value determined by dividing I/A (value determined by dividing the KD value for mFcγRIII by the KD value for mFcγRII) of each variant by I/A of H237-MB716/MRAL-k0 or H237-mIgG1/MRAL-k0)

From the results of FIG. 17 and Table 17, as observed in Example 8-3, many specimens with amino acid substitution newly introduced in H237-MB716/MRAL-k0 were found to reduce mFcγRII selectivity, but to enhance mFcγRII-binding activity. In addition, some variants were found to enhance mFcγRII-binding activity while maintaining high mFcγRII selectivity.

As mentioned above, H237-MB716/MRAL-k0 had higher mFcγRII selectivity than that of H237-MB630/MRAL-k0. The H237-MB716/MRAL-k0-templated variants exhibited higher mFcγRII selectivity than that of the H237-MB630/MRAL-k0-templated variants. These results suggest that the introduction of various alterations to H237-MB716/MRAL-k0 as a template can yield many specimens having high mFcγRII selectivity.

[Example 9] Preparation of Variant that Keeps Binding Activity Against mFcγRII at Same Level as that of Naturally Occurring Fc and Exhibits Reduced Binding Activity Against mFcγRIII As described herein, immune complexes are formed through the binding of antibodies to multivalent antigens and seem to induce various adverse reactions by their interaction with activating FcγR. This might reduce the values of the antibodies as drugs. For circumventing this problem while maintaining the effects mediated by FcγRIIb, it is desirable to maintain binding to FcγRIIb and, at the same time, to selectively reduce binding to activating FcγR. Nonetheless, there has been no report on an Fc variant that has such features in relation to mouse FcγR. Accordingly, in this Example, study was conducted for the purpose of preparing an Fc variant with reduced binding activity against activating mFcγRIII while keeping binding activity against inhibitory mFcγRII at the same level as that of naturally occurring mIgG1.

(9-1) Study on Combined Alterations to Reduce Binding Activity Against mFcγRIII

From the results of analyzing the interaction of the variants having 1 amino acid mutation obtained in Example 2 with mFcγRII and mFcγRIII, alterations to selectively reduce binding activity against mFcγRIII were searched for, and 10 variants were selected therefrom. These variants were expressed and purified by the method of Reference Example 1 and evaluated for their binding to mFcγRII and mFcγRIII by the method of Reference Example 2 using Biacore T200.

For the results of analyzing interaction with each mFcγR, the KD value of H237-mIgG1/MRAL-k0 for mFcγR was divided by the KD value of each variant for mFcγR, and the obtained value was used as an index for the relative binding activity for each mFcγR with the value of H237-mIgG1/MRAL-k0 as 1. Also, I/A (mFcγRII selectivity) which is a value determined by dividing the KD value of each variant for mFcγRIII by its KD value for mFcγRII was divided by I/A (mFcγRII selectivity) of H237-mIgG1/MRAL-k0, and the obtained value was used as an index for the relative I/A (mFcγRII selectivity) with the value of H237-mIgG1/MRAL-k0 as 1.

Table 18 shows the relative binding activity against each mFcγR and relative I/A (mFcγRII selectivity) of all of the evaluated variants. "Name" in the table represents the name of the H chain constant region (CH) of each evaluated variant. As for alterations, "X000Z" represents the substitution of amino acid X at EU numbering position 000 by amino acid Z. In this context, X and Z represent the one-letter codes of the amino acid residues. All of the alterations described in Table 18 were alterations introduced to the H chain constant region (SEQ ID NO: 4) of mouse IgG1 (mIgG1).

TABLE 18

| Name (CH) | Alteration introduced to mIgG1 | Relative mFcγRII-binding activity (mIgG1 = 1) | Relative mFcγRIII-binding activity (mIgG1 = 1) | Relative I/A (mFcγRII selectivity) (mIgG1 = 1) |
|---|---|---|---|---|
| MB092 | S238D | 0.16 | 0.05 | 2.87 |
| MB093 | S238E | 2.48 | 0.61 | 4.05 |
| MB075 | V237E | 0.12 | 0.07 | 1.80 |
| MB112 | S239F | 0.47 | 0.27 | 1.77 |
| MB125 | S239W | 0.81 | 0.48 | 1.70 |
| MB146 | F241D | 0.85 | 0.21 | 4.09 |
| MB147 | F241E | 0.95 | 0.36 | 2.64 |
| MB159 | F241T | 0.37 | 0.28 | 1.33 |
| MB208 | S267M | 0.40 | 0.26 | 1.52 |
| MB258 | S298H | 0.37 | 0.32 | 1.17 |

(Relative binding activity: value determined by dividing the KD value of H237-mIgG1/MRAL-k0 for each mFcγR by the KD value of each variant for each mFcγR, Relative I/A (mFcγRII selectivity): value determined by dividing I/A (value determined by dividing the KD value for mFcγRIII) by the KD value for mFcγRII) of each variant by I/A of H237-mIgG1/MRAL-k0; the value of H237-mIgG1/MRAL-k0 used was a value obtained by the same assay run as that of each variant)

From the results of Table 18, all of the variants were confirmed to improve mFcγRII selectivity by reducing binding activity against mFcγRIII relative to mFcγRII. Thus, study was conducted on whether the combination of these alterations could yield a variant strongly effective for reducing binding activity against mFcγRIII to thereby improve mFcγRII selectivity.

The antibody H chain variable region used was the variable region H237 (SEQ ID NO: 1) of the H chain VH3-IgG1 of the anti-IL-6 receptor antibody Fv4-IgG1 described in WO2009/125825. The antibody L chain commonly used was the L chain MRAL-k0 (SEQ ID NO: 2) of the anti-IL-6 receptor antibody tocilizumab. H237-mIgG1/MRAL-k0 was used as a template to introduce the alterations. These variants were expressed and purified by the method of Reference Example 1 and evaluated for their binding to mFcγRII and mFcγRIII by the method of Reference Example 2 using Biacore T200.

For the results of analyzing interaction with each mFcγR, the KD value of H237-mIgG1/MRAL-k0 for mFcγR was divided by the KD value of each variant for mFcγR, and the obtained value was used as an index for the relative binding activity for each mFcγR with the value of H237-mIgG1/MRAL-k0 as 1. Also, I/A (mFcγRII selectivity) which is a value determined by dividing the KD value of each variant for mFcγRIII by its KD value for mFcγRII was divided by I/A (mFcγRII selectivity) of H237-mIgG1/MRAL-k0, and the obtained value was used as an index for the relative I/A (mFcγRII selectivity) with the value of H237-mIgG1/MRAL-k0 as 1.

Table 19 shows the relative binding activity against each mFcγR and relative I/A (mFcγRII selectivity) of all of the variants evaluated in this study with the values of H237-mIgG1/MRAL-k0 as 1. "Name" in the table represents the name of the H chain constant region (CH) of each evaluated variant. As for alterations, "X000Z" represents the substitution of amino acid X at EU numbering position 000 by amino acid Z. In this context, X and Z represent the one-letter codes of the amino acid residues. All of the alterations described in Table 19 were alterations introduced to the H chain constant region (SEQ ID NO: 4) of mouse IgG1 (mIgG1).

TABLE 19

| Name (CH) | Alteration introduced to mIgG1 | Relative mFcγRII-binding activity (mIgG1 = 1) | Relative mFcγRIII-binding activity (mIgG1 = 1) | Relative I/A (mFcγRII selectivity) (mIgG1 = 1) |
|---|---|---|---|---|
| MB561 | V237E/S238E | 0.48 | 0.07 | 7.08 |
| MB562 | S238E/S239F | 0.05 | 0.02 | 1.99 |
| MB563 | S238E/S239W | 0.20 | 0.08 | 2.54 |
| MB564 | S238E/F241D | 0.32 | 0.11 | 3.02 |
| MB565 | S238E/F241E | 0.66 | 0.23 | 2.88 |
| MB566 | S238E/F241T | 0.18 | 0.10 | 1.80 |
| MB567 | S238E/S267M | 0.21 | 0.07 | 2.82 |
| MB568 | S238E/S298H | 0.71 | 0.18 | 3.83 |
| MB571 | V237E/S239F | 0.22 | 0.05 | 4.34 |
| MB572 | V237E/S239W | 0.26 | 0.07 | 3.66 |
| MB573 | V237E/F241D | 0.43 | 0.06 | 6.81 |
| MB574 | V237E/F241E | 0.27 | 0.10 | 2.83 |
| MB575 | V237E/F241T | 0.08 | 0.05 | 1.67 |
| MB576 | S239F/F241D | 1.54 | 0.60 | 2.55 |
| MB577 | S239F/F241E | 2.51 | 1.19 | 2.10 |
| MB578 | S239F/F241T | 0.39 | 0.25 | 1.55 |
| MB579 | S239W/F241D | 0.89 | 0.34 | 2.60 |
| MB580 | S239W/F241E | 1.38 | 0.61 | 2.26 |
| MB581 | S239W/F241T | 0.69 | 0.42 | 1.65 |
| MB584 | V237E/S238D | 0.08 | 0.02 | 3.92 |
| MB585 | S238D/S239F | 0.06 | 0.03 | 1.84 |
| MB586 | S238D/S239W | 0.13 | 0.08 | 1.68 |
| MB587 | S238D/F241D | 1.33 | 0.60 | 2.22 |
| MB588 | S238D/F241E | 2.01 | 1.01 | 1.99 |
| MB589 | S238D/F241T | 0.23 | 0.19 | 1.24 |
| MB590 | S238D/S267M | N.B. | N.B. | — |
| MB591 | S238D/S298H | 0.08 | 0.02 | 4.61 |
| MB594 | T230E/V237E/S238E | 1.85 | 0.10 | 18.70 |
| MB595 | T230E/S238E/S239F | 0.09 | 0.05 | 1.64 |

TABLE 19-continued

| Name (CH) | Alteration introduced to mIgG1 | Relative mFcγRII-binding activity (mIgG1 = 1) | Relative mFcγRIII-binding activity (mIgG1 = 1) | Relative I/A (mFcγRII selectivity) (mIgG1 = 1) |
|---|---|---|---|---|
| MB596 | T230E/S238E/S239W | 0.55 | 0.17 | 3.25 |
| MB597 | T230E/S238E/F241D | 1.28 | 0.54 | 2.38 |
| MB598 | T230E/S238E/S267M | 0.41 | 0.08 | 5.31 |
| MB599 | T230E/V237E/S239F | 0.70 | 0.11 | 6.58 |
| MB600 | T230E/V237E/S239W | 1.24 | 0.25 | 4.95 |
| MB601 | T230E/V237E/F241D | 0.55 | 0.10 | 5.55 |
| MB602 | T230E/V237E/S238D | 0.26 | 0.05 | 4.80 |
| MB603 | T230E/S238D/S239F | 0.12 | 0.06 | 1.96 |
| MB604 | T230E/S238D/S239W | 0.34 | 0.16 | 2.13 |
| MB605 | T230E/S238D/F241D | 9.85 | 4.40 | 2.24 |
| MB606 | T230E/S238D/S267M | 0.05 | N.B. | — |
| MB607 | V237E/S238E/S239E | 3.14 | 0.18 | 17.40 |
| MB608 | S238E/S239E/F241D | 0.42 | 0.13 | 3.21 |
| MB609 | S238E/S239E/S267M | 2.66 | 0.32 | 8.22 |
| MB610 | V237E/S239E/F241D | 0.23 | N.B. | — |
| MB611 | V237E/S238D/S239E | 1.11 | 0.09 | 11.90 |
| MB612 | S238D/S239E/F241D | 0.81 | 0.30 | 2.72 |
| MB613 | S238D/S239E/S267M | 0.24 | 0.06 | 3.77 |
| MB614 | V237E/S238E/S239D | 10.90 | 0.84 | 12.94 |
| MB615 | S238E/S239D/F241D | 0.59 | 0.14 | 4.16 |
| MB616 | S238E/S239D/S267M | 4.06 | 0.57 | 7.15 |
| MB617 | V237E/S239D/F241D | 0.84 | 0.15 | 5.51 |
| MB619 | S238D/S239D/F241D | 0.62 | 0.16 | 3.91 |
| MB620 | S238D/S239D/S267M | 0.23 | 0.07 | 3.19 |
| MB621 | S238D/S239E | 3.15 | 0.23 | 13.70 |
| MB622 | S238D/S239D | 3.83 | 0.40 | 9.48 |
| MB618 | V237E/S238D/S239D | 1.63 | 0.13 | 12.23 |

(N.B.: although assay was conducted, binding was not observable because of being too weak, Relative binding activity: value determined by dividing the KD value of H237-mIgG1/MRAL-k0 for each mFcγR by the KD value of each variant for each mFcγR, Relative I/A (mFcγRII selectivity): value determined by dividing I/A (value determined by dividing the KD value for mFcγRIII by the KD value for mFcγRII) of each variant by I/A of H237-mIgG1/MRAL-k0; the value of H237-mIgG1/MRAL-k0 used was a value obtained by the same assay run as that of each variant)

From the results of Table 19, a plurality of variants having the combination of the alterations were found to have more reduced binding activity against mFcγRIII and improved mFcγRII selectivity. In addition, some variants were also found to keep binding activity against mFcγRII at the same level as that of naturally occurring mIgG1. Six variants (MB594, MB599, MB601, MB611, MB617, and MB618) were successfully obtained which differed in mFcγRII-binding activity by within 2 times from H237-mIgG1/MRAL-k0 (0.5-fold or more and 2.0-fold or less relative mFcγRII-binding activity with the value of H237-mIgG1/MRAL-k0 as 1) and had 5-fold or more relative I/A (mFcγRII selectivity) compared with that of H237-mIgG1/MRAL-k0.

(9-2) Study on Introduction of mFcγR Binding-Reducing Alteration to Variant with Selectively Enhanced mFcγRII-Binding Activity The variants with selectively enhanced binding to mFcγRII were altered as templates to reduce binding activity against all mFcγ receptors also including mFcγRII. The resulting variants were expected to keep binding activity against mFcγRII at the same level as that of mIgG1 while having reduced binding activity against mFcγRIII compared with that of mIgG1.

P232K and S239K were used as alterations to reduce binding activity against all mFcγ receptors. As in Example 5, 9 variants were used as templates and studied for the effects of the P232K and S239K alterations.

The antibody H chain variable region used was the variable region H237 (SEQ ID NO: 1) of the H chain VH3-IgG1 of the anti-IL-6 receptor antibody Fv4-IgG1 described in WO2009/125825. The antibody L chain commonly used was the L chain MRAL-k0 (SEQ ID NO: 2) of the anti-IL-6 receptor antibody tocilizumab. The same 9 variants (all having Asp as the amino acid at EU numbering position 239) as those used in Example 5 were used as templates to introduce the alterations. These variants were expressed and purified by the method of Reference Example 1 and evaluated for their binding to mFcγRII and mFcγRIII by the method of Reference Example 2 using Biacore T200.

For the results of analyzing interaction with each mFcγR, the KD value of H237-mIgG1/MRAL-k0 for mFcγR was divided by the KD value of each variant for mFcγR, and the obtained value was used as an index for the relative binding activity for each mFcγR with the value of H237-mIgG1/MRAL-k0 as 1. Also, I/A (mFcγRII selectivity) which is a value determined by dividing the KD value of each variant for mFcγRIII by its KD value for mFcγRII was divided by I/A (mFcγRII selectivity) of H237-mIgG1/MRAL-k0, and the obtained value was used as an index for the relative I/A (mFcγRII selectivity) with the value of H237-mIgG1/MRAL-k0 as 1.

Table 20 shows the relative binding activity against each mFcγR and relative I/A (mFcγRII selectivity) of all of the variants evaluated in this study with the values of H237-mIgG1/MRAL-k0 as 1. "Name" in the table represents the name of the H chain constant region (CH) of each evaluated variant. As for alterations, "X000Z" represents the substitution of amino acid X at EU numbering position 000 by amino acid Z. In this context, X and Z represent the one-letter codes of the amino acid residues. The alterations described in Table 20 were alterations introduced to the H chain constant region (SEQ ID NO: 40) of the template MB373, the H chain constant region (SEQ ID NO: 41) of the template MB382, the H chain constant region (SEQ ID NO: 42) of the template MB387, the H chain constant region (SEQ ID NO: 5) of the template MB397, the H chain constant region (SEQ ID NO: 43) of the template MB379, the H chain constant region (SEQ ID NO: 44) of the template MB389, the H chain constant region (SEQ ID NO: 45) of the template MB425, the H chain constant region (SEQ ID NO: 6) of the template MB390, or the H chain constant region (SEQ ID NO: 46) of the template MB432.

TABLE 20

| Name (CH) | template | Alteration added to template | Relative mFcγRII-binding activity (mIgG1 = 1) | Relative mFcγRIII-binding activity (mIgG1 = 1) | Relative I/A (mFcγRII selectivity) (mIgG1 = 1) |
|---|---|---|---|---|---|
| MB669 | MB373 | S239K | N.B. | 0.04 | — |
| MB670 | MB382 | | N.B. | 0.06 | — |
| MB671 | MB387 | | N.B. | 0.04 | — |
| MB672 | MB397 | | 0.30 | 0.07 | 4.35 |
| MB673 | MB379 | | N.B. | 0.04 | — |
| MB674 | MB389 | | N.B. | 0.06 | — |
| MB675 | MB425 | | N.B. | 0.01 | — |
| MB676 | MB390 | | 0.22 | 0.12 | 1.84 |
| MB677 | MB432 | | N.B. | 0.03 | — |
| MB364 | MB373 | P232K | 6.55 | 1.35 | 4.84 |
| MB678 | MB379 | | 8.03 | 2.01 | 4.00 |
| MB679 | MB382 | | 7.57 | 1.68 | 4.51 |
| MB680 | MB387 | | 8.97 | 1.75 | 5.13 |
| MB681 | MB389 | | 13.88 | 1.83 | 7.60 |
| MB682 | MB390 | | 14.01 | 2.14 | 6.55 |
| MB683 | MB397 | | 7.70 | 0.90 | 8.55 |
| MB684 | MB432 | | 5.37 | 1.02 | 5.28 |

(N.B.: although assay was conducted, binding activity was not observable because of being too weak, Relative binding activity: value determined by dividing the KD value of H237-mIgG1/MRAL-k0 for each mFcγR by the KD value of each variant for each mFcγR, Relative I/A (mFcγRII selectivity): value determined by dividing I/A (value determined by dividing the KD value for mFcγRIII by the KD value for mFcγRII) of each variant by I/A of H237-mIgG1/MRAL-k0; the value of H237-mIgG1/MRAL-k0 used was a value obtained by the same assay run as that of each variant)

As seen from the results of Table 20, some variants having the introduced P232K alteration maintained 5-fold or more relative I/A (mFcγRII selectivity), while their relative mFcγRII-binding activity was enhanced by approximately 5 to 15 times. These results implied that it is effective to decrease the number of alterations for enhancing binding activity against mFcγRII or to further combine therewith alterations to reduce binding to mFcγRIII as studied in Example 9-1.

On the other hand, the introduction of the S239K alteration remarkably reduced binding activity against mFcγRII. Since the 9 variants used as templates had approximately 200-fold to 600-fold relative mFcγRII-binding activity, the variants with more enhanced binding activity against mFcγRII as with H237-MB498/MRAL-k0 and H237-MB494/MRAL-k0 (having approximately 3300-fold and approximately 2100-fold relative mFcγRII-binding activity, respectively) found in Example 6 may be used as templates to keep binding activity against mFcγRII at the same level as that of mIgG1.

All of these 9 variants had the S239D alteration, which made a great contribution to enhancement in mFcγRII-binding activity. Alteration at this site therefore reduces its own enhancement itself in mFcγRII-binding activity. Accordingly, it may also be effective to adopt an alteration to reduce FcγR-binding activity at a site different from an already altered site. Such an alteration is possibly, for example, N297A alteration for eliminating N-linked sugar chains added to Asn 297 (EU numbering). Reportedly, antibodies exhibit significantly reduced binding to FcγR as a result of eliminating N-linked sugar chains added to Asn 297 (EU numbering) in their Fc regions (The Journal of Biological Chemistry, 2000, 276, 6591-6604).

(9-3) Study on Decrease of the Number of Alterations in Variant with Selectively Enhanced mFcγRII-Binding Activity Decrease of the number of introduced alterations from the variants with selectively enhanced binding to mFcγRII was expected to obtain variants with reduced binding activity against mFcγRIII compared with that of mIgG1 while keeping binding activity against mFcγRII at the same level as that of mIgG1.

Of the variants prepared in the foregoing Examples up to Example 9-1, 7 variants (H237-MB594/MRAL-k0, H237-MB628/MRAL-k0, H237-MB632/MRAL-k0, H237-MB636/MRAL-k0, H237-MB642/MRAL-k0, H237-MB646/MRAL-k0, and H237-MB657/MRAL-k0) were selected from among variants having 1-fold to 5-fold relative mFcγRII-binding activity and 15-fold or more relative I/A (mFcγRII selectivity) with the values of H237-mIgG1/MRAL-k0 as 1, and studied for decrease of the number of the alterations introduced therein.

The antibody H chain variable region used was the variable region H237 (SEQ ID NO: 1) of the H chain VH3-IgG1 of the anti-IL-6 receptor antibody Fv4-IgG1 described in WO2009/125825. The antibody L chain commonly used was the L chain MRAL-k0 (SEQ ID NO: 2) of the anti-IL-6 receptor antibody tocilizumab. The aforementioned 7 variants were used as templates to substitute the amino acids at the alteration sites by the amino acids before the alteration. These variants were expressed and purified by the method of Reference Example 1 and evaluated for their binding to mFcγRII and mFcγRIII by the method of Reference Example 2 using Biacore T200.

For the results of analyzing interaction with each mFcγR, the KD value of H237-mIgG1/MRAL-k0 for mFcγR was divided by the KD value of each variant for mFcγR, and the obtained value was used as an index for the relative binding activity for each mFcγR with the value of H237-mIgG1/MRAL-k0 as 1. Also, I/A (mFcγRII selectivity) which is a value determined by dividing the KD value of each variant for mFcγRIII by its KD value for mFcγRII was divided by I/A (mFcγRII selectivity) of H237-mIgG1/MRAL-k0, and the obtained value was used as an index for the relative I/A (mFcγRII selectivity) with the value of H237-mIgG1/MRAL-k0 as 1. The horizontal axis indicates the value of the relative binding activity of each variant (also including the 7 templated variants) against mFcγRIII, and the vertical axis indicates the value of relative binding activity of each variant (also including the 7 templated variants) against mFcγRII (FIG. 18).

Table 21 shows the relative binding activity against each mFcγR and relative I/A (mFcγRII selectivity) of all of the variants (also including the 7 templated variants) evaluated in this study with the values of H237-mIgG1/MRAL-k0 as 1. "Name" in the table represents the name of the H chain constant region (CH) of each evaluated variant. As for alterations, "X000Z" represents the substitution of amino acid X at EU numbering position 000 by amino acid Z. In this context, X and Z represent the one-letter codes of the amino acid residues. All of the alterations described in Table 21 were alterations introduced to the H chain constant region (SEQ ID NO: 4) of mouse IgG1 (mIgG1).

TABLE 21

| Name (CH) | Introduced alteration | Relative mFcγRII-binding activity (mIgG1 = 1) | Relative mFcγRIII-binding activity (mIgG1 = 1) | Relative I/A (mFcγRII selectivity) (mIgG1 = 1) |
|---|---|---|---|---|
| MB594 | T230E/V237E/S238E | 1.302 | 0.057 | 23.0 |
| MB628 | T230E/V231P/P232A/S23XE/S239L | 2.087 | 0.083 | 25.0 |
| MB632 | T230E/V231A/P232Y/S238E/S239N | 3.720 | 0.236 | 15.8 |
| MB636 | T230E/P232Y/S238E/S239N | 3.917 | 0.172 | 22.8 |
| MB642 | T230E/V231D/P232Y/S238E/S239Y | 1.647 | 0.100 | 16.5 |
| MB646 | T230E/V231P/P232A/S238E/S239Y | 3.804 | 0.176 | 21.7 |
| MB657 | T230E/V231P/P232N/S238E/S239F | 1.541 | 0.087 | 17.7 |
| MB645 | T230E/P232Y/S238E/S239Y | 1.058 | 0.217 | 4.9 |
| MB685 | V231P/P232A/S238E/S239L | 0.606 | 0.093 | 6.5 |
| MB686 | T230E/P232A/S238E/S239L | 0.167 | 0.052 | 3.2 |
| MB687 | T230E/P231P/S238E/S239L | 0.943 | 0.096 | 9.8 |
| MB688 | P232Y/S238E/S239N | 0.634 | 0.081 | 7.8 |
| MB689 | T230E/S238E/S239N | 0.413 | 0.075 | 5.5 |
| MB690 | V231P/P232A/S238E/S239Y | 1.597 | 0.188 | 8.5 |

TABLE 21-continued

| Name (CH) | Introduced alteration | Relative mFcγRII-binding activity (mIgG1 = 1) | Relative mFcγRIII-binding activity (mIgG1 = 1) | Relative I/A (mFcγRII selectivity) (mIgG1 = 1) |
|---|---|---|---|---|
| MB691 | T230E/P232A/S238E/S239Y | 0.582 | 0.071 | 8.2 |
| MB692 | T230E/V231P/S238E/S239Y | 1.747 | 0.115 | 15.2 |
| MB693 | V231D/P232Y/S238E/S239Y | 1.219 | 0.094 | 12.9 |
| MB694 | T230E/V231D/S238ES239Y | 0.544 | 0.031 | 17.5 |
| MB695 | V231P/P232N/S238E/S239F | 0.435 | 0.088 | 5.0 |
| MB696 | T230E/P232N/S238E/S239F | 0.400 | 0.094 | 4.3 |
| MB697 | T230E/V231P/S238E/S239F | 0.217 | N.B. | — |
| MB698 | T230E/V237E/S238E/S239L | 0.194 | 0.024 | 8.1 |
| MB699 | T230E/V237ES238E/S239N | 0.216 | 0.035 | 6.1 |
| MB700 | T230E/V237E/S238E/S239Y | 0.559 | 0.044 | 12.7 |
| MB701 | T230E/V237E/S238E/S239F | 0.187 | N.B. | — |
| MB702 | V231A/P232Y/S238E/S239N | 0.960 | 0.145 | 6.6 |
| MB703 | T230E/V231A/S238E/S239N | 0.943 | 0.104 | 9.1 |

(N.B.: although assay was conducted, binding was not observable because of being too weak, Relative binding activity: value determined by dividing the KD value of H237-mIgG1/MRAL-k0 mFcγR by the KD value of each variant for each mFcγR, Relative FA (mFcγRII selectivity): value determined by dividing I/A (value determined by dividing KD value for mFcγRIII by the KD value for mFcγRII) of each variant by I/A of H237-mIgG1/MRAL-k0; the value of H237-mIgG1/MRAL-k0 used was a value obtained by the same assay run as that variant)

As seen from the results of FIG. 18 and Table 21, decrease of the number of alterations from the 7 variants successfully reduced both mFcγRII-binding activity and mFcγRIII-binding activity. As a result, a large number of variants (MB594, MB642, MB657, MB685, MB687, MB688, MB690, MB691, MB692, MB693, MB694, MB700, MB702, and MB703) were successfully obtained which differed in mFcγRII-binding activity by within 2 times from H237-mIgG1/MRAL-k0 (0.5-fold or more and 2.0-fold or less relative mFcγRII-binding activity with the value of H237-mIgG1/MRAL-k0 as 1) and had 5-fold or more relative I/A (mFcγRII selectivity) compared with that of H237-mIgG1/MRAL-k0.

The relative mFcγRII-binding activity of H237-MB697/MRAL-k0, H237-MB701/MRAL-k0, or the like was reduced to approximately 0.2 times with the value of H237-mIgG1/MRAL-k0 as 1. However, their binding activity against mFcγRIII was reduced to an extent that is impossible to convert into a KD value. Accordingly, the introduction of an mFcγRII binding-enhancing alteration to these variants is also expected to obtain the variant of interest.

(9-4) Study on Introduction of V237E Alteration to Variant with Selectively Enhanced mFcγRII-Binding Activity The results of Example 9-1 revealed some alterations to reduce binding to mFcγRII and mFcγRIII while improving I/A (mFcγRII selectivity). Accordingly, the introduction of these alterations to the templated variants with selectively enhanced binding to mFcγRII was expected to obtain variants with reduced binding activity against mFcγRIII compared with that of mIgG1 while keeping binding activity against mFcγRII at the same level as that of mIgG1.

V237E was selected as an alteration to be introduced. The 9 variants used as templates in Example 5 and H237-MB628/MRAL-k0 and H237-MB630/MRAL-k0 prepared in Example 8-2 were used as the templated variants with selectively enhanced binding to mFcγRII. These 11 variants were used as templates and studied for the effects of the introduced V237E alteration.

The antibody H chain variable region used was the variable region H237 (SEQ ID NO: 1) of the H chain VH3-IgG1 of the anti-IL-6 receptor antibody Fv4-IgG1 described in WO2009/125825. The antibody L chain commonly used was the L chain MRAL-k0 (SEQ ID NO: 2) of the anti-IL-6 receptor antibody tocilizumab. The aforementioned 11 variants were used as templates to introduce the alteration. These variants were expressed and purified by the method of Reference Example 1 and evaluated for their binding to mFcγRII and mFcγRIII by the method of Reference Example 2 using Biacore T200.

For the results of analyzing interaction with each mFcγR, the KD value of H237-mIgG1/MRAL-k0 for mFcγR was divided by the KD value of each variant for mFcγR, and the obtained value was used as an index for the relative binding activity for each mFcγR with the value of H237-mIgG1/MRAL-k0 as 1. Also, I/A (mFcγRII selectivity) which is a value determined by dividing the KD value of each variant for mFcγRIII by its KD value for mFcγRII was divided by I/A (mFcγRII selectivity) of H237-mIgG1/MRAL-k0, and the obtained value was used as an index for the relative I/A (mFcγRII selectivity) with the value of H237-mIgG1/MRAL-k0 as 1. The horizontal axis indicates the value of the relative binding activity of each variant against mFcγRIII, and the vertical axis indicates the value of relative binding activity of each variant against mFcγRII (FIG. 19).

Table 22 shows the relative binding activity against each mFcγR and relative I/A (mFcγRII selectivity) of all of the variants evaluated in this study with the values of H237-mIgG1/MRAL-k0 as 1. "Name" in the table represents the name of the H chain constant region (CH) of each evaluated variant. As for alterations, "X000Z" represents the substitution of amino acid X at EU numbering position 000 by amino acid Z. In this context, X and Z represent the one-letter codes of the amino acid residues. All of the alterations described in Table 22 were alterations introduced to the H chain constant region (SEQ ID NO: 4) of mouse IgG1 (mIgG1).

TABLE 22

| Name (CH) | Alteration introduced to mIgG1 | Relative mFcγRII-binding activity (mIgG1 = 1) | Relative mFcγRIII-binding activity (mIgG1 = 1) | Relative I/A (mFcγRII selectivity) (mIgG1 = 1) |
|---|---|---|---|---|
| MB722 | T230E/V231A/P232Y/V237E/S238E/S239D | 33.34 | 1.35 | 24.65 |
| MB723 | T230E/V231D/P232Y/V237E/S238E/S239D | 14.08 | 0.72 | 19.67 |
| MB724 | T230E/V231N/P232Y/V237E/S238E/S239D | 20.79 | 1.19 | 17.43 |
| MB725 | T230E/V231T/P232Y/V237E/S238E/S239D | 24.34 | 1.39 | 17.53 |
| MB726 | T230E/P232Y/V237E/S238E/S239D | 35.66 | 2.08 | 17.14 |
| MB727 | T230E/V231P/P232A/V237E/S238E/S239D | 11.69 | 0.66 | 17.85 |
| MB728 | T230E/V231P/P232A/V237E/S238E/S239D | 16.44 | 0.90 | 18.19 |
| MB729 | T230E/V231P/P232N/V237E/S238E/S239D | 10.43 | 0.53 | 19.79 |
| MB730 | T230Q/V231P/P232N/V237E/S238E/S239D | 7.24 | 0.43 | 16.74 |
| MB731 | T230E/V231P/P232A/V237E/S238E/S239L | 7.13 | 0.03 | 37.46 |
| MB732 | T230E/V231P/P232N/V237E/S238E/S239L | 0.84 | 0.03 | 24.84 |

(Relative binding activity: value determined by dividing the KD value of H237-mIgG1/MRAL-k0 for each mFcγR by the KD value of each variant for each mFcγR, Relative I/A (mFcγRII selectivity): value determined by dividing I/A (value determined by dividing the KD value for mFcγRIII by the KD value for mFcγRII) of each variant by I/A of H237-mIgG1/MRAL-k0; the value of H237-mIgG1/MRAL-k0 used was a value obtained by the same assay run as that of each variant)

As seen from the results of FIG. 19 and Table 22, the introduction of the V237E alteration to the variants with selectively enhanced binding activity against mFcγRII successfully reduced both mFcγRII-binding activity and mFcγRIII-binding activity, while maintaining high relative I/A (mFcγRII selectivity). As a result, two new variants (MB731 and MB732) were obtained which differed in mFcγRII-binding activity by within 2 times from H237-mIgG1/MRAL-k0 (0.5-fold or more and 2.0-fold or less relative mFcγRII-binding activity with the value of H237-mIgG1/MRAL-k0 as 1) and had 5-fold or more relative I/A (mFcγRII selectivity) compared with that of H237-mIgG1/MRAL-k0. These 2 variants (H237-MB731/MRAL-k0 and H237-MB732/MRAL-k0) had excellent properties such that the variants differed in mFcγRII-binding activity by within 20% from H237-mIgG1/MRAL-k0 (0.8-fold or more and 1.2-fold or less relative mFcγRII-binding activity with the value of H237-mIgG1/MRAL-k0 as 1) and had binding activity against mFcγRIII reduced to 0.03 times that of H237-mIgG1/MRAL-k0.

Next, study was conducted on decrease of the number of the alteration introduced in these 2 variants.

The antibody H chain variable region used was the variable region H237 (SEQ ID NO: 1) of the H chain VH3-IgG1 of the anti-IL-6 receptor antibody Fv4-IgG1 described in WO2009/125825. The antibody L chain commonly used was the L chain MRAL-k0 (SEQ ID NO: 2) of the anti-IL-6 receptor antibody tocilizumab. H237-mIgG1/MRAL-k0 was altered as a template to remove one introduced alteration from H237-MB731/MRAL-k0 and H237-MB732/MRAL-k0. These variants were expressed and purified by the method of Reference Example 1 and evaluated for their binding to mFcγRII and mFcγRIII by the method of Reference Example 2 using Biacore T200.

For the results of analyzing interaction with each mFcγR, the KD value of H237-mIgG1/MRAL-k0 for mFcγR was divided by the KD value of each variant for mFcγR, and the obtained value was used as an index for the relative binding activity for each mFcγR with the value of H237-mIgG1/MRAL-k0 as 1. Also, I/A (mFcγRII selectivity) which is a value determined by dividing the KD value of each variant for mFcγRIII by its KD value for mFcγRII was divided by I/A (mFcγRII selectivity) of H237-mIgG1/MRAL-k0, and the obtained value was used as an index for the relative I/A (mFcγRII selectivity) with the value of H237-mIgG1/MRAL-k0 as 1.

Table 23 shows the relative binding activity against each mFcγR and relative I/A (mFcγRII selectivity) of all of the variants evaluated in this study with the values of H237-mIgG1/MRAL-k0 as 1. "Name" in the table represents the name of the H chain constant region (CH) of each evaluated variant. As for alterations, "X000Z" represents the substitution of amino acid X at EU numbering position 000 by amino acid Z. In this context, X and Z represent the one-letter codes of the amino acid residues. All of the alterations described in Table 23 were alterations introduced to the H chain constant region (SEQ ID NO: 4) of mouse IgG1 (mIgG1).

TABLE 23

| Name (CH) | Alteration introduced to mIgG1 | Relative mFcγRII-binding activity (mIgG1 = 1) | Relative mFcγRIII-binding activity (mIgG1 = 1) | Relative I/A (mFcγRII selectivity) (mIgG1 = 1) |
|---|---|---|---|---|
| MB878 | V231P/P232A/V237E/S238E/S239L | 0.47 | 0.03 | 14.23 |
| MB879 | V231P/P232N/V237E/S238E/S239L | 0.30 | N.B. | — |
| MB880 | T230E/P232A/V237E/S238E/S239L | 0.34 | N.B. | — |
| MB881 | T230E/P232N/V237E/S238E/S239L | 0.23 | N.B. | — |
| MB883 | T230E/V231P/P232A/V237E/S239L | 2.21 | 0.11 | 20.15 |
| MB884 | T230E/V231P/P232N/V237E/S239L | 2.46 | 0.09 | 26.73 |

TABLE 23-continued

| Name (CH) | Alteration introduced to mIgG1 | Relative mFcγRII-binding activity (mIgG1 = 1) | Relative mFcγRIII-binding activity (mIgG1 = 1) | Relative I/A (mFcγRII selectivity) (mIgG1 = 1) |
|---|---|---|---|---|
| MB885 | T230E/V231P/P232A/V237E/S238E | 3.29 | 0.13 | 26.21 |
| MB886 | T230E/V231P/P232N/V237E/S238E | 1.47 | 0.08 | 19.53 |

(N.B.: although assay was conducted, binding was not observable because of being too weak, Relative binding activity: value determined by dividing the KD value of H237-mIgG1/MRAL-k0 for each mFcγR by the KD value of each variant for each mFcγR, Relative I/A (mFcγRII selectivity): value determined by dividing I/A (value determined by dividing the KD value for mFcγRIII by the KD value for mFcγRII) of each variant by I/A of H237-mIgG1/MRAL-k0; the value of H237-mIgG1/MRAL-k0 used was a value obtained by the same assay run as that of each variant)

As seen from the results of Table 23, decrease of the alteration from H237-MB731/MRAL-k0 and H237-MB732/MRAL-k0 enhanced or reduced mFcγRII-binding activity and consequently expanded the difference from H237-mIgG1/MRAL-k0. However, many variants still maintained high mFcγRII selectivity. The further combination of these variants with an alteration to enhance or reduce binding activity against mFcγRII is also expected to obtain an variant having mFcγRII-binding activity at the same level as that of H237-mIgG1/MRAL-k0 and reduced binding activity against mFcγRIII compared with that of H237-mIgG1/MRAL-k0.

[Example 10] KD Values for Each mFcγR and I/a (mFcγRII Selectivity) of Variants Prepared in Examples 8 and 9

For reference, the KD values for each mFcγR and I/A (mFcγRII selectivity) of some of the variants prepared and evaluated in Examples 8 and 9 are shown in tables.

Table 24 shows variants having 200-fold or more relative mFcγRII-binding activity compared with that of H237-mIgG1/MRAL-k0. These variants are excellent in terms of remarkably enhanced relative binding activity against mFcγRII. Table 25 shows variants having 10-fold or more relative mFcγRII-binding activity and 25-fold or more relative I/A (mFcγRII selectivity) compared with those of H237-mIgG1/MRAL-k0. These variants are excellent in terms of enhanced relative binding activity against mFcγR and also high mFcγR selectivity. Table 26 shows variants having 0.5-fold to 2-fold relative mFcγRII-binding activity and 5-fold or more relative I/A (mFcγRII selectivity) compared with those of H237-mIgG1/MRAL-k0. These variants exhibit selectively reduced binding activity against mFcγRIII, while maintaining binding activity against mFcγR, and as such, can be used for evaluating effects derived only from binding to mFcγRII. Particularly, by virtue of the absence of enhancement in effects on mFcγRII, these variants are excellent in terms of achieving the evaluation of the effects of binding to mFcγRII at the same level as that of mIgG1. Table 27 shows variants having 0.8-fold or more relative mFcγRII-binding activity, 0.2-fold or less relative mFcγRIII-binding activity, and 5-fold or more relative I/A (mFcγRII selectivity) compared with those of H237-mIgG1/MRAL-k0. These variants are similarly excellent in that the variants can be used for evaluating effects derived only from binding to mFcγRII. "Name" in each table represents the name of the H chain constant region of each evaluated variant. As for alterations, "X000Z" represents the substitution of amino acid X at EU numbering position 000 by amino acid Z. In this context, X and Z represent the one-letter codes of the amino acid residues. All of the alterations described in Tables 24 to 27 were alterations introduced to the H chain constant region (SEQ ID NO: 4) of mouse IgG1 (mIgG1).

TABLE 24

| Name (CH) | Alteration introduced to mIgG1 | Relative mFcγRII-binding activity (mIgG1 = 1) | Relative mFcγRIII-binding activity (mIgG1 = 1) | Relative I/A (mFcγRII selectivity) (mIgG1 = 1) | KD (mFcγRII) | KD (mFcγRIII) | I/A (mFcγRII selectivity) |
|---|---|---|---|---|---|---|---|
| MB530 | T230Q/V231P/P232N/S238E/S239E/N324D/A326D | 622.6 | 8.0 | 77.6 | 3.37E−10 | 3.51E−08 | 103.9 |
| MB537 | T230Q/V231P/P232N/S238E/S239E/S298L/N324D/A326D/K334R | 510.1 | 8.9 | 57.4 | 4.12E−10 | 3.17E−08 | 76.9 |
| MB535 | T230Q/V231P/P232N/S238E/S239E/S298L/A326D/K334R | 421.7 | 8.5 | 49.8 | 4.98E−10 | 3.32E−08 | 66.7 |
| MB534 | T230Q/V231P/P232N/S238E/S239E/S298L/N324D/K334R | 420.7 | 33.8 | 12.5 | 4.99E−10 | 8.34E−09 | 16.7 |
| MB536 | T230Q/V231P/P232N/S238E/S239E/N324D/A326D/K334R | 396.0 | 7.7 | 51.7 | 5.30E−10 | 3.68E−08 | 69.3 |
| MB533 | T230Q/V231P/P232N/S238E/S239E/S298L/N324D/A326D | 393.6 | 7.2 | 54.5 | 5.34E−10 | 3.90E−08 | 73.0 |

TABLE 24-continued

| Name (CH) | Alteration introduced to mIgG1 | Relative mFcγRII-binding activity (mIgG1 = 1) | Relative mFcγRIII-binding activity (mIgG1 = 1) | Relative I/A (mFcγRII selectivity) (mIgG1 = 1) | KD (mFcγRII) | KD (mFcγRIII) | I/A (mFcγRII selectivity) |
|---|---|---|---|---|---|---|---|
| MB542 | T230E/V231P/P232N/ S238E/S239M/N324D/ A326D | 384.2 | 3.4 | 113.7 | 5.47E−10 | 8.33E−08 | 152.3 |
| MB528 | T230Q/V231P/P232N/ S238E/S239E/S298L/ A326D | 375.3 | 14.6 | 25.7 | 5.60E−10 | 1.93E−08 | 34.5 |
| MB548 | T230E/V231P/P232N/ S238E/S239M/N324D/ A326D/K334R | 356.7 | 3.9 | 90.9 | 5.89E−10 | 7.17E−08 | 121.7 |
| MB532 | T230Q/V231P/P232N/ S238E/S239E/A326D/ K334R | 328.6 | 6.2 | 53.0 | 6.39E−10 | 4.54E−08 | 71.0 |
| MB529 | T230Q/V231P/P232N/ S238E/S239E/S298L/ K334R | 281.9 | 5.9 | 47.7 | 7.45E−10 | 4.76E−08 | 63.9 |
| MB544 | T230E/V231P/P232N/ S238E/S239M/A326D/ K334R | 276.2 | 3.2 | 85.6 | 7.60E−10 | 8.72E−08 | 114.7 |
| MB527 | T230Q/V231P/P232N/ S238E/S239E/S298L/ N324D | 273.3 | 5.5 | 49.5 | 7.68E−10 | 5.10E−08 | 66.3 |
| MB476 | T230Q/V231P/P232N/ S238E/S239E | 261.2 | 2.6 | 99.0 | 8.04E−10 | 1.07E−07 | 132.6 |
| MB526 | T230Q/V231P/P232N/ S238E/S239E/S298L | 232.4 | 8.5 | 27.3 | 9.04E−10 | 3.30E−08 | 36.5 |
| MB531 | T230Q/V231P/P232N/ S238E/S239E/N324D/ K334R | 228.8 | 3.3 | 69.1 | 9.18E−10 | 8.50E−08 | 92.6 |
| MB549 | T230E/V231P/P232N/ S238E/S239M/S298L/ N324D/A326D/K334R | 210.0 | 5.4 | 38.9 | 1.00E−09 | 5.21E−08 | 52.1 |

(I/A (mFcγRII selectivity): value determined by dividing the KD value of each variant for mFcγRIII by its KD value for mFcγRII, Relative binding activity: value determined by dividing the KD value of H237-mIgG1/MRAL-k0 for each mFcγR by the KD value of each variant for each mFcγR, Relative I/A (mFcγRII selectivity): value determined by dividing I/A (value determined by dividing the KD value for mFcγRIII by the KD value for mFcγRII) of each variant by I/A of H237-mIgG1/MRAL-k0)

TABLE 25

| Name (CH) | Alteration introduced to mIgG1 | Relative mFcγRII-binding activity (mIgG1 = 1) | Relative mFcγRIII-binding activity (mIgG1 = 1) | Relative I/A (mFcγRII selectivity) (mIgG1 = 1) | KD (mFcγRII) | KD (mFcγRIII) | I/A (mFcγRII selectivity) |
|---|---|---|---|---|---|---|---|
| MB542 | T230E/V231P/P232N/ S238E/S239M/N324D/ A326D | 384.2 | 3.4 | 113.7 | 5.47E−10 | 8.33E−08 | 152.3 |
| MB515 | T230E/V231P/P232N/ S238E/S239M | 137.3 | 1.3 | 104.4 | 1.53E−09 | 2.14E−07 | 140.0 |
| MB476 | T230Q/V231P/P232N/ S238E/S239E | 261.2 | 2.6 | 99.0 | 8.04E−10 | 1.07E−07 | 132.6 |
| MB548 | T230E/V231P/P232N/ S238E/S239M/N324D/ A326D/K334R | 356.7 | 3.9 | 90.9 | 5.89E−10 | 7.17E−08 | 121.7 |
| MB543 | T230E/V231P/P232N/ S238E/S239M/N324D/ K334R | 195.3 | 2.2 | 87.7 | 1.08E−09 | 1.26E−07 | 117.6 |
| MB748 | T230E/V231P/P232N/ S238E/S239L/S267A | 11.7 | 0.1 | 85.8 | 1.79E−08 | 2.06E−06 | 115.0 |
| MB544 | T230E/V231P/P232N/ S238E/S239M/A326D/ K334R | 276.2 | 3.2 | 85.6 | 7.60E−10 | 8.72E−08 | 114.7 |
| MB754 | T230E/V231P/P232N/ S238E/S239L/N324D | 21.0 | 0.2 | 84.5 | 1.00E−08 | 1.13E−06 | 113.3 |
| MB751 | T230E/V231P/P232N/ S238E/S239L/K334R | 25.4 | 0.3 | 80.5 | 8.25E−09 | 8.90E−07 | 107.8 |
| MB759 | T230E/V231P/P232N/ S238E/S239L/N324D/ K334R | 33.8 | 0.4 | 77.6 | 6.21E−09 | 6.46E−07 | 104.0 |

TABLE 25-continued

| Name (CH) | Alteration introduced to mIgG1 | Relative mFcγRII-binding activity (mIgG1 = 1) | Relative mFcγRIII-binding activity (mIgG1 = 1) | Relative I/A (mFcγRII selectivity) (mIgG1 = 1) | KD (mFcγRII) | KD (mFcγRIII) | I/A (mFcγRII selectivity) |
|---|---|---|---|---|---|---|---|
| MB530 | T230Q/V231P/P232N/S238E/S239E/N324D/A326D | 622.6 | 8.0 | 77.6 | 3.37E−10 | 3.51E−08 | 103.9 |
| MB761 | T230E/V231P/P232N/S238E/S239L/S298M/N324D/K334R | 13.4 | 0.2 | 74.9 | 1.57E−08 | 1.57E−06 | 100.3 |
| MB750 | T230E/V231P/P232N/S238E/S239L/A326D | 29.4 | 0.4 | 73.8 | 7.13E−09 | 7.05E−07 | 98.8 |
| MB866 | T230E/V231P/P232N/S238E/S239I/A326D/A327G | 13.0 | 0.2 | 72.4 | 1.62E−08 | 1.57E−06 | 97.0 |
| MB531 | T230Q/V231P/P232N/S238E/S239E/N324D/K334R | 228.8 | 3.3 | 69.1 | 9.18E−10 | 8.50E−08 | 92.6 |
| MB749 | T230E/V231P/P232N/S238E/S239L/Q295L | 25.3 | 0.4 | 66.5 | 8.30E−09 | 7.40E−07 | 89.1 |
| MB545 | T230E/V231P/P232N/S238E/S239M/S298L/N324D/A326D | 163.4 | 2.7 | 61.6 | 1.29E−09 | 1.06E−07 | 82.6 |
| MB820 | T230E/V231P/P232N/S238E/S239L/N324M/E333Y | 19.5 | 0.3 | 59.3 | 1.08E−08 | 8.54E−07 | 79.4 |
| MB773 | T230E/V231P/P232N/S238E/S239L/E333Y | 12.7 | 0.2 | 59.2 | 1.65E−08 | 1.31E−06 | 79.3 |
| MB834 | T230E/V231P/P232N/S238E/S239L/E333Y/K334R | 17.0 | 0.3 | 58.9 | 1.24E−08 | 9.76E−07 | 78.9 |
| MB815 | T230E/V231P/P232N/S238E/S239L/N324D E333Y | 17.6 | 0.3 | 58.5 | 1.20E−08 | 9.38E−07 | 78.5 |
| MB828 | T230E/V231P/P232N/S238E/S239L/A327G/E333Y | 28.4 | 0.5 | 57.6 | 7.40E−09 | 5.71E−07 | 77.2 |
| MB537 | T230Q/V231P/P232N/S238E/S239E/S298L/N324D/A326D/K334R | 510.1 | 8.9 | 57.4 | 4.12E−10 | 3.17E−08 | 76.9 |
| MB779 | T230E/V231P/P232N/S238E/S239L/S337W | 10.0 | 0.2 | 57.3 | 2.10E−08 | 1.61E−06 | 76.8 |
| MB776 | T230E/V231P/P232N/S238E/S239L/T335Y | 11.3 | 0.2 | 57.1 | 1.86E−08 | 1.43E−06 | 76.5 |
| MB630 | T230E/V231P/P232N/S238E/S239L | 14.3 | 0.3 | 57.0 | 1.47E−08 | 1.12E−06 | 76.4 |
| MB825 | T230E/V231P/P232N/S238E/S239L/A326D/E333Y | 28.4 | 0.5 | 57.0 | 7.38E−09 | 5.64E−07 | 76.4 |
| MB831 | T230E/V231P/P232N/S23BE/S239L/P331F/K334R | 22.3 | 0.4 | 56.8 | 9.40E−09 | 7.16E−07 | 76.1 |
| MB827 | T230E/V231P/P232N/S238E/S239L/A327G/P331Y | 21.5 | 0.4 | 56.8 | 9.77E−09 | 7.44E−07 | 76.1 |
| MB833 | T230E/V231P/P232N/S238E/S239L/P331Y/K334R | 25.3 | 0.4 | 56.5 | 8.31E−09 | 6.30E−07 | 75.8 |
| MB819 | T230E/V231P/P232N/S238E/S239L/N324M/P331Y | 18.1 | 0.3 | 56.1 | 1.16E−08 | 8.72E−07 | 75.2 |
| MB850 | T230E/V231P/P232N/S238E/S239L/A326D/A327G/E333Y | 43.7 | 0.8 | 55.5 | 4.81E−09 | 3.58E−07 | 74.4 |
| MB770 | T230E/V231P/P232N/S238E/S239L/P331F | 13.3 | 0.2 | 55.5 | 1.57E−D8 | 1.17E−06 | 74.3 |
| MB539 | T230E/V231P/P232N/S238E/S239M/S298L/N324D | 105.1 | 1.9 | 55.0 | 2.00E−09 | 1.47E−07 | 73.7 |
| MB813 | T230E/V231P/P232N/S238E/S239L/N324D/P331F | 16.3 | 0.3 | 55.0 | 1.29E−08 | 9.51E−07 | 73.7 |
| MB817 | T230E/V231P/P232N/S238E/S239L/N324M/A327O | 28.5 | 0.5 | 54.6 | 7.38E−09 | 5.39E−07 | 73.1 |

TABLE 25-continued

| Name (CH) | Alteration introduced to mIgG1 | Relative mFcγRII-binding activity (mIgG1 = 1) | Relative mFcγRIII-binding activity (mIgG1 = 1) | Relative I/A (mFcγRII selectivity) (mIgG1 = 1) | KD (mFcγRII) | KD (mFcγRIII) | I/A (mFcγRII selectivity) |
|---|---|---|---|---|---|---|---|
| MB533 | T230Q/V231P/P232N/S238E/S239E/S298L/N324D/A326D | 393.6 | 7.2 | 54.5 | 5.34E−10 | 3.90E−08 | 73.0 |
| MB826 | T230E/V231P/P232N/S238E/S239L/A327G/P331F | 18.5 | 0.3 | 54.5 | 1.14E−08 | 8.29E−07 | 73.0 |
| MB818 | T230E/V231P/P232N/S238E/S239L/N324M/P331F | 15.6 | 0.3 | 54.3 | 1.35E−08 | 9.79E−07 | 72.7 |
| MB821 | T230E/V231P/P232N/S238E/S239L/N324M/K334R | 24.4 | 0.5 | 54.3 | 8.60E−09 | 6.25E−07 | 72.7 |
| MB829 | T230E/V231P/P232N/S238E/S239L/A327G/K334R | 33.8 | 0.6 | 53.4 | 6.22E−09 | 4.45E−07 | 71.6 |
| MB860 | T230E/V231P/P232N/S238E/S239L/A326D/A327G/E333Y/K334R | 39.6 | 0.7 | 53.3 | 5.30E−09 | 3.79E−07 | 71.4 |
| MB532 | T230Q/V231P/P232N/S238E/S239E/A326D/K334R | 328.6 | 6.2 | 53.0 | 6.39E−10 | 4.54E−08 | 71.0 |
| MB814 | T230E/V231P/P232N/S238E/S239L/N324D/P331Y | 18.0 | 0.3 | 52.9 | 1.17E−08 | 8.26E−07 | 70.9 |
| MB766 | T230E/V231P/P232N/S238E/S239L/N324M | 14.0 | 0.3 | 52.8 | 1.50E−08 | 1.06E−06 | 70.8 |
| MB540 | T230E/V231P/P232N/S238E/S239M/S298L/A326D | 149.4 | 2.8 | 52.7 | 1.41E−09 | 9.94E−08 | 70.7 |
| MB771 | T230E/V231P/P232N/S238E/S239L/P331Y | 13.8 | 0.3 | 52.7 | 1.52E−08 | 1.07E−06 | 70.6 |
| MB536 | T230Q/V231P/P232N/S238E/S239E/N324D/A326D/K334R | 396.0 | 7.7 | 51.7 | 5.30E−10 | 3.68E−08 | 69.3 |
| MB811 | T230E/V231P/P232N/S238E/S239L/Q295L/E333Y | 22.2 | 0.4 | 51.6 | 9.45E−09 | 6.54E−07 | 69.2 |
| MB780 | T230E/V231P/P232N/S238E/S239L/A327G | 20.2 | 0.4 | 51.4 | 1.04E−08 | 7.16E−07 | 68.9 |
| MB760 | T230E/V231P/P232N/S238E/S239L/S298L/N324D/K334R | 14.1 | 0.3 | 51.2 | 1.49E−08 | 1.02E−06 | 68.6 |
| MB823 | T230E/V231P/P232N/S238E/S239L/A326D/P331F | 25.0 | 0.5 | 51.2 | 8.39E−09 | 5.75E−07 | 68.6 |
| MB785 | T230E/V231P/P232N/S238E/S239L/N324D/A326D | 24.9 | 0.5 | 51.1 | 8.43E−09 | 5.77E−07 | 68.4 |
| MB538 | T230E/V231P/P232N/S238E/S239M/S298L | 86.2 | 1.7 | 50.3 | 2.44E−09 | 1.64E−07 | 67.4 |
| MB756 | T230E/V231P/P232N/S238E/S239L/S298L/K334R | 10.6 | 0.2 | 50.3 | 1.98E−08 | 1.33E−06 | 67.4 |
| MB848 | T230E/V231P/P232N/S238E/S239L/N324D/A326D/A327G | 45.8 | 0.9 | 50.1 | 4.58E−09 | 3.08E−07 | 67.2 |
| MB535 | T230Q/V231P/P232N/S238E/S239E/S298L/A326D/K334R | 421.7 | 8.5 | 49.8 | 4.98E−10 | 3.32E−08 | 66.7 |
| MB824 | T230E/V231P/P232N/S238E/S239L/A326D/P331Y | 28.0 | 0.6 | 49.6 | 7.51E−09 | 5.00E−07 | 66.5 |
| MB812 | T230E/V231P/P232N/S238E/S239L/N324D/A327G | 33.4 | 0.7 | 49.6 | 6.28E−09 | 4.18E−07 | 66.5 |
| MB857 | T230E/V231P/P232N/S238E/S239L/N324D/A326D/A327G/E333Y | 44.6 | 0.9 | 49.6 | 4.71E−09 | 3.13E−07 | 66.5 |
| MB527 | T230Q/V231P/P232N/S238E/S239E/S298L/N324D | 273.3 | 5.5 | 49.5 | 7.68E−10 | 5.10E−08 | 66.3 |

TABLE 25-continued

| Name (CH) | Alteration introduced to mIgG1 | Relative mFcγRII-binding activity (mIgG1 = 1) | Relative mFcγRIII-binding activity (mIgG1 = 1) | Relative I/A (mFcγRII selectivity) (mIgG1 = 1) | KD (mFcγRII) | KD (mFcγRIII) | I/A (mFcγRII selectivity) |
|---|---|---|---|---|---|---|---|
| MB856 | T230E/V231P/P232N/8238E/S239L/N324D/A326D/A327G/P331Y | 44.8 | 0.9 | 49.5 | 4.69E−09 | 3.11E−07 | 66.3 |
| MB858 | T230E/V231P/P232N/S238E/S239L/N324D/A326D/A327G/K334R | 62.0 | 1.3 | 49.1 | 3.39E−09 | 2.23E−07 | 65.8 |
| MB849 | T230E/V231P/P232N/S238E/S239L/A326D/A327G/P331Y | 31.4 | 0.6 | 48.6 | 6.68E−09 | 4.36E−07 | 65.2 |
| MB859 | T230E/V231P/P232N/S238E/S239L/A326D/A327G/P331Y/K334R | 34.2 | 0.7 | 48.0 | 6.15E−09 | 3.96E−07 | 64.3 |
| MB790 | T230E/V231P/P232N/S238E/S239L/N324D/A326D/K334R | 33.5 | 0.7 | 47.8 | 6.28E−09 | 4.02E−07 | 64.0 |
| MB529 | T2300/V231P/P232N/S238E/S239E/S298L/K334R | 281.9 | 5.9 | 47.7 | 7.45E−10 | 4.76E−08 | 63.9 |
| MB786 | T230E/V231P/P232N/S238E/S239L/A326D/K334R | 27.2 | 0.6 | 47.6 | 7.73E−09 | 4.93E−07 | 63.7 |
| MB822 | T230E/V231P/P232N/8238E/S239L/A326D/A327G | 43.8 | 0.9 | 47.4 | 4.80E−09 | 3.04E−07 | 63.5 |
| MB816 | T230E/V231P/P232N/S238E/S239L/N324M/A326D | 30.4 | 0.7 | 46.6 | 6.90E−09 | 4.31E−07 | 62.5 |
| MB851 | T230E/V231P/P232N/S238E/S239L/A326D/A327G/K334R | 43.8 | 1.0 | 45.9 | 4.79E−09 | 2.95E−07 | 61.5 |
| MB807 | T230E/V231P/P232N/S238E/S239L/Q295L/N324M | 21.9 | 0.5 | 45.1 | 9.58E−09 | 5.79E−07 | 60.4 |
| MB869 | T230E/V231P/P232N/S238E/S2391/K268D/A326D/A327G/E333Y | 41.0 | 0.9 | 43.6 | 5.12E−09 | 3.00E−07 | 58.5 |
| MB809 | T230E/V231P/P232N/S238E/S239L/Q295L/P331F | 19.0 | 0.4 | 43.0 | 1.11E−08 | 6.38E−07 | 57.6 |
| MB782 | T230E/V231P/P232N/S238E/S239L/Q295L/N324D | 21.3 | 0.5 | 42.9 | 9.88E−09 | 5.67E−07 | 57.4 |
| MB868 | T230E/V231P/P232N/S238E/S2391/K268D/N324D/A326D/A327G | 36.6 | 0.9 | 42.8 | 5.73E−09 | 3.29E−07 | 57.3 |
| MB710 | T230E/V231P/P232N S238E/S239Q | 50.8 | 1.2 | 41.9 | 4.13E−09 | 2.32E−07 | 56.1 |
| MB867 | T230E/V231P/P232N/S238E/S2391/K268D/A326D/A327G | 35.2 | 0.9 | 41.4 | 5.96E−09 | 3.31E−07 | 55.5 |
| MB783 | T230E/V231P/P232N/S238E/S239L/Q295L/A3260 | 30.6 | 0.7 | 41.2 | 6.85E−09 | 3.78E−07 | 55.2 |
| MB854 | T230E/V231P/P232N/S238E/S239L/Q295L/A326D/A327G/E333Y | 50.6 | 1.3 | 40.5 | 4.15E−09 | 2.25E−07 | 54.2 |
| MB787 | T230E/V231P/P232N/S238E/S239L/Q295L/N324D/A326D | 38.5 | 1.0 | 40.3 | 5.45E−09 | 2.95E−07 | 54.1 |
| MB810 | T230E/V231P/P232N/S238E/S239L/Q295L/P331Y | 20.8 | 0.5 | 40.3 | 1.01E−08 | 5.46E−07 | 54.0 |
| MB876 | T230E/V231P/P232N/S238E/S2391/K268D/Q295L/A326D/A327G/E333Y | 58.7 | 1.5 | 39.8 | 3.58E−09 | 1.91E−07 | 53.4 |
| MB549 | T230E/V231P/P232N/S238E/S239M/S298L/N324D/A326D/K334R | 210.0 | 5.4 | 38.9 | 1.00E−09 | 5.21E−08 | 52.1 |
| MB784 | T230E/V231P/P232N/S238E/S239L/Q295L/K334R | 14.7 | 0.4 | 38.4 | 1.43E−08 | 7.34E−07 | 51.5 |

TABLE 25-continued

| Name (CH) | Alteration introduced to mIgG1 | Relative mFcγRII-binding activity (mIgG1 = 1) | Relative mFcγRIII-binding activity (mIgG1 = 1) | Relative I/A (mFcγRII selectivity) (mIgG1 = 1) | KD (mFcγRII) | KD (mFcγRIII) | I/A (mFcγRII selectivity) |
|---|---|---|---|---|---|---|---|
| MB877 | T230E/V231P/P232N/S238E/S2391/K268D/N324D/A326D/A327G/K334R | 55.3 | 1.4 | 38.3 | 3.80E−09 | 1.95E−07 | 51.3 |
| MB875 | T230E/V231P/P232N/S238E/S239I/K268D/Q295L/N324D/A326D/A327G | 72.8 | 1.9 | 38.0 | 2.88E−09 | 1.47E−07 | 51.0 |
| MB788 | T230E/V231P/P232N/S238E/S239L/Q295L/N324D/K334R | 22.4 | 0.6 | 37.8 | 9.38E−09 | 4.75E−07 | 50.6 |
| MB547 | T230E/V231P/P232N/S238E/S239M/S298L/A326D/K334R | 170.3 | 4.5 | 37.7 | 1.23E−09 | 6.23E−08 | 50.6 |
| MB789 | T230E/V231P/P232N/S238E/S239L/Q295L/A326D/K334R | 30.9 | 0.8 | 37.6 | 6.80E−09 | 3.43E−07 | 50.3 |
| MB835 | T230E/V231P/P232N/S238E/S239L/K268D | 26.3 | 0.7 | 37.4 | 8.00E−09 | 4.01E−07 | 50.2 |
| MB808 | T230E/V231P/P232N/S238E/S239L/Q295L/A327G | 29.2 | 0.8 | 37.3 | 7.19E−09 | 3.59E−07 | 50.0 |
| MB871 | T230E/V231P/P232N/S238E/S239I/K268D/Q295L/A326D/A327G | 61.8 | 1.7 | 37.0 | 3.40E−09 | 1.69E−07 | 49.6 |
| MB870 | T230E/V231P/P232N/S238E/S239I/K268D/A326D/A327G/K334R | 38.6 | 1.0 | 36.9 | 5.44E−09 | 2.69E−07 | 49.5 |
| MB791 | T230E/V231P/P232N/S238E/S239L/Q295L/N324D/A326D/K334R | 40.1 | 1.1 | 36.4 | 5.23E−09 | 2.56E−07 | 48.8 |
| MB863 | T230E/V231P/P232N/S238E/S239L/K268D/A326D/A327G/E333Y | 81.3 | 2.3 | 35.0 | 2.58E−09 | 1.21E−07 | 46.9 |
| MB862 | T230E/V231P/P232N/S238E/S239L/K268D/A326D/A327G/P331Y | 67.9 | 2.0 | 34.4 | 3.09E−09 | 1.42E−07 | 46.0 |
| MB846 | T230E/V231P/P232N/S238E/S239L/K268D/A326D/A327G | 72.1 | 2.1 | 34.1 | 2.91E−09 | 1.33E−07 | 45.7 |
| MB852 | T230E/V231P/P232N/S238E/S239L/Q295L/N324D/A326D/A327G | 61.0 | 1.8 | 33.4 | 3.44E−09 | 1.54E−07 | 44.7 |
| MB847 | T230E/V231P/P232N/S238E/S239L/Q295L/A326D/A327G | 43.7 | 1.3 | 33.0 | 4.81E−09 | 2.13E−07 | 44.3 |
| MB855 | T230E/V231P/P232N/S238E/S239L/Q295L/A326D/A327G/K334R | 36.2 | 1.1 | 31.9 | 5.81E−09 | 2.48E−07 | 42.8 |
| MB861 | T230E/V231P/P232N/S238E/S239L/K268D/N324D/A326D/A327G | 76.8 | 2.4 | 31.9 | 2.74E−09 | 1.17E−07 | 42.7 |
| MB722 | T230E/V231A/P232Y/V237E/S238E/S239D | 26.1 | 0.8 | 31.7 | 8.04E−09 | 3.41E−07 | 42.5 |
| MB541 | T230E/V231P/P232N/S238E/S239M/S298L/K334R | 103.0 | 3.3 | 31.6 | 2.04E−09 | 8.64E−08 | 42.3 |
| MB853 | T230E/V231P/P232N/S238E/S239L/Q295L/A326D/A327G/P331Y | 35.0 | 1.1 | 31.0 | 5.99E−09 | 2.49E−07 | 41.5 |
| MB719 | T230E/V231P/P232N/S238E/S239Q | 70.4 | 2.3 | 30.5 | 2.98E−09 | 1.22E−07 | 40.9 |
| MB864 | T230E/V231P/P232N/S238E/S239L/K268D/A326D/A327G/K334R | 110.4 | 3.6 | 30.4 | 1.90E−09 | 7.76E−08 | 40.8 |
| MB546 | T230E/V231P/P232N/S238E/S239M/S298I/N324D/K334R | 158.1 | 5.6 | 28.1 | 1.33E−09 | 5.00E−08 | 37.6 |
| MB526 | T230Q/V231P/P232N/S238E/S239E/S298L | 232.4 | 8.5 | 27.3 | 9.04E−10 | 3.30E−08 | 36.5 |
| MB528 | T230Q/V231P/P232N/S238E/S239E/S298L/A326D | 375.3 | 14.6 | 25.7 | 5.60E−10 | 1.93E−08 | 34.5 |

TABLE 25-continued

| Name (CH) | Alteration introduced to mIgG1 | Relative mFcγRII-binding activity (mIgG1 = 1) | Relative mFcγRIII-binding activity (mIgG1 = 1) | Relative I/A (mFcγRII selectivity) (mIgG1 = 1) | KD (mFcγRII) | KD (mFcγRIII) | I/A (mFcγRII selectivity) |
|---|---|---|---|---|---|---|---|
| MB723 | T230E/V231D/P232Y/V237E/S238E/S239D | 11.0 | 0.4 | 25.3 | 1.90E−08 | 6.45E−07 | 33.9 |
| MB865 | T230E/V231P/P232N/S238E/S239L/K268D/Q295L/A326D/A327G | 83.8 | 3.3 | 25.1 | 2.51E−09 | 8.44E−08 | 33.7 |

(I/A (mFcγRII selectivity): value determined by dividing the KD value of each variant for mFcγRIII by its KD value for mFcγRII, Relative binding activity: value determined by dividing the KD value of H237-mIgG1/MRAL-k0 for each mFcγR by the KD value of each variant for each mFcγR, Relative I/A (mFcγRII selectivity): value determined by dividing I/A (value determined by dividing the KD value for mFcγRIII by the KD value for mFcγRII) of each variant by I/A of H237-mIgG1/MRAL-k0)

TABLE 26

| Name (CH) | Alteration introduced to mIgG1 | Relative mFcγRII-binding activity (mIgG1 = 1) | Relative mFcγRIII-binding activity (mIgG1 = 1) | Relative I/A (mFcγRII selectivity) (mIgG1 = 1) | KD (mFcγRII) | KD (mFcγRIII) | I/A (mFcγRII selectivity) |
|---|---|---|---|---|---|---|---|
| MB657 | T230E/V231P/P232N/S238E/S239F | 1.95 | 0.09 | 20.9 | 1.18E−07 | 3.48E−06 | 29.4 |
| MB594 | T230E/V237E/S238E | 1.85 | 0.10 | 18.7 | 1.15E−07 | 3.23E−06 | 28.0 |
| MB643 | T230E/V231N/P232Y/S238E/S239Y | 1.83 | 0.16 | 11.3 | 1.26E−07 | 2.00E−06 | 15.8 |
| MB692 | T230E/V231P/S238E/S239Y | 1.75 | 0.12 | 15.2 | 1.86E−07 | 4.44E−06 | 23.8 |
| MB642 | T230E/V231D/P232Y/S238E/S239Y | 1.65 | 0.10 | 16.5 | 1.97E−07 | 5.11E−06 | 25.9 |
| MB618 | V237E/S238D/S239D | 1.63 | 0.13 | 12.2 | 1.56E−07 | 2.73E−06 | 17.6 |
| MB641 | T230E/V231A/P232Y/S238E/S239Y | 1.62 | 0.15 | 10.5 | 1.43E−07 | 2.10E−06 | 14.7 |
| MB690 | V231P/P232A/S238E/S239Y | 1.60 | 0.19 | 8.5 | 2.04E−07 | 2.71E−06 | 13.3 |
| MB657 | T230E/V231P/P232N/S238E/S239F | 1.54 | 0.09 | 17.7 | 2.11E−07 | 5.87E−06 | 27.8 |
| MB886 | T230E/V231P/P232N/V237E/S238E | 1.47 | 0.08 | 19.5 | 2.46E−07 | 7.22E−06 | 29.3 |
| MB793 | T230Q/V231P/P232N/S238E/S239I | 1.37 | 0.07 | 19.1 | 1.79E−07 | 5.50E−06 | 30.6 |
| MB594 | T230E/V237E/S238E | 1.30 | 0.06 | 23.0 | 2.50E−07 | 9.03E−06 | 36.2 |
| MB645 | T230E/P232Y/S238E/S239Y | 1.29 | 0.23 | 5.6 | 1.80E−07 | 1.42E−06 | 7.9 |
| MB600 | T230E/V237E/S239W | 1.24 | 0.25 | 5.0 | 1.71E−07 | 1.27E−06 | 7.4 |
| MB693 | V231D/P232Y/S238E/S239Y | 1.22 | 0.09 | 12.9 | 2.67E−07 | 5.41E−06 | 20.3 |
| MB640 | T230Q/V231P/P232N/S238E/S239N | 1.17 | 0.21 | 5.6 | 1.97E−07 | 1.55E−06 | 7.9 |
| MB647 | T230I/V231P/P232A/S238E/S239Y | 1.16 | 0.12 | 10.0 | 2.00E−07 | 2.80E−06 | 14.0 |
| MB715 | T230E/V231P/P232N/S238E/S239V | 1.14 | 0.04 | 29.4 | 2.36E−07 | 1.19E−05 | 50.7 |
| MB731 | T230E/V231P/P232A/V237E/S238E/S239L | 1.13 | 0.03 | 37.5 | 2.38E−07 | 1.53E−05 | 64.5 |
| MB611 | V237E/S238D/S239E | 1.11 | 0.09 | 11.9 | 1.92E−07 | 3.42E−06 | 17.8 |
| MB718 | T230E/V231P/P232N/S238E/S239T | 1.08 | 0.08 | 13.1 | 2.47E−07 | 5.56E−06 | 22.5 |
| MB645 | T230E/P232Y/S238E/S239Y | 1.06 | 0.22 | 4.9 | 3.07E−07 | 2.36E−06 | 7.7 |
| MB702 | V231A/P232Y/S238E/S239N | 0.96 | 0.14 | 6.6 | 3.39E−07 | 3.52E−06 | 10.4 |
| MB703 | T230E/V231A/S238E/S239N | 0.94 | 0.10 | 9.1 | 3.45E−07 | 4.90E−06 | 14.2 |
| MB687 | T230E/V231P/S238E/S239L | 0.94 | 0.10 | 9.8 | 3.45E−07 | 5.32E−06 | 15.4 |
| MB626 | T230E/V231T/P232Y/S238E/S239L | 0.89 | 0.14 | 6.5 | 2.61E−07 | 2.37E−06 | 9.1 |
| MB624 | T230E/V231D/P232Y/S238E/S239L | 0.88 | 0.11 | 7.8 | 2.63E−07 | 2.87E−06 | 10.9 |
| MB617 | V237E/S239D/F241D | 0.84 | 0.15 | 5.5 | 2.55E−07 | 2.10E−06 | 8.2 |
| MB732 | T230E/V231P/P232N/V237E/S238E/S239L | 0.84 | 0.03 | 24.8 | 3.21E−07 | 1.37E−05 | 42.8 |

TABLE 26-continued

| Name (CH) | Alteration introduced to mIgG1 | Relative mFcγRII-binding activity (mIgG1 = 1) | Relative mFcγRIII-binding activity (mIgG1 = 1) | Relative I/A (mFcγRII selectivity) (mIgG1 = 1) | KD (mFcγRII) | KD (mFcγRIII) | I/A (mFcγRII selectivity) |
|---|---|---|---|---|---|---|---|
| MB638 | T2301/V231P/P232A/S238E/S239N | 0.83 | 0.10 | 8.6 | 2.80E−07 | 3.38E−06 | 12.1 |
| MB709 | T230E/V231P/P232A/S238E/S239T | 0.78 | 0.06 | 12.9 | 3.45E−07 | 7.69E−06 | 22.3 |
| MB625 | T230E/V231N/P232Y/S238E/S239L | 0.74 | 0.14 | 5.3 | 3.12E−07 | 2.31E−06 | 7.4 |
| MB599 | T230E/V237E/S239F | 0.70 | 0.11 | 6.6 | 3.06E−07 | 3.02E−06 | 9.9 |
| MB688 | P232Y/S238E/S239N | 0.63 | 0.08 | 7.8 | 5.13E−07 | 6.30E−06 | 12.3 |
| MB685 | V231P/P232A/S238E/S239L | 0.61 | 0.09 | 6.5 | 5.37E−07 | 5.49E−06 | 10.2 |
| MB623 | T230E/V231A/P232Y/S238E/S239L | 0.59 | 0.10 | 5.7 | 3.95E−07 | 3.17E−06 | 8.0 |
| MB691 | T230E/P232A/S238E/S239Y | 0.58 | 0.07 | 8.2 | 5.59E−07 | 7.18E−06 | 12.8 |
| MB700 | T230E/V237E/S238E/S239Y | 0.56 | 0.04 | 12.7 | 5.82E−07 | 1.16E−05 | 19.9 |
| MB658 | T230Q/V231P/P232N/S238E/S239F | 0.56 | 0.07 | 8.4 | 4.15E−07 | 4.88E−06 | 11.7 |
| MB601 | T230E/V237E/F241D | 0.55 | 0.10 | 5.5 | 3.89E−07 | 3.23E−06 | 8.3 |
| MB694 | T230E/V231D/S238E/S239Y | 0.54 | 0.03 | 17.5 | 5.98E−07 | 1.64E−05 | 27.5 |
| MB717 | T230E/V231P/P232N/S238E/S239P | 0.52 | 0.05 | 9.7 | 5.14E−07 | 8.62E−06 | 16.8 |

(I/A (mFcγRII selectivity): value determined by dividing the KD value of each variant for mFcγRIII by its KD value for mFcγRII, Relative binding activity: value determined by dividing the KD value of H237-mIgG1/MRAL-k0 for each mFcγR by the KD value of each variant for each mFcγR, Relative I/A (mFcγRII selectivity): value determined by dividing I/A (value determined by dividing the KD value for mFcγRIII by the KD value for mFcγRII) of each variant by I/A of H237-mIgG1/MRAL-k0; the value of H237-mIgG1/MRAL-k0 used was a value obtained by the same assay run as that of each variant)

TABLE 27

| Name (CH) | Alteration introduced to mIgG1 | Relative mFcγRII-binding activity (mIgG1 = 1) | Relative mFcγRIII-binding activity (mIgG1 = 1) | Relative I/A (mFcγRII selectivity) (mIgG1 = 1) | KD (mFcγRII) | KD (mFcγRIII) | I/A (mFcγRII selectivity) |
|---|---|---|---|---|---|---|---|
| MB633 | T230E/V231D/P232Y/S238E/S239N | 3.05 | 0.20 | 15.4 | 7.58E−08 | 1.64E−06 | 21.6 |
| MB768 | T230E/V231P/P232N/S238E/S239L/A330Q | 6.34 | 0.20 | 32.5 | 3.89E−08 | 2.03E−06 | 52.1 |
| MB690 | V231P/P232A/S238E/S239Y | 1.60 | 0.19 | 8.5 | 2.04E−07 | 2.71E−06 | 13.3 |
| MB781 | T230E/V231P/P232N/S238E/S239L/A330K | 6.08 | 0.19 | 32.7 | 4.05E−08 | 2.12E−06 | 52.4 |
| MB607 | V237E/S238E/S239E | 3.14 | 0.18 | 17.4 | 6.79E−08 | 1.77E−06 | 26.1 |
| MB748 | T230E/V231P/P232N/S238E/S239L/S267A | 10.27 | 0.18 | 57.4 | 1.79E−08 | 2.06E−06 | 115.0 |
| MB646 | T230E/V231P/P232A/S238E/S239Y | 3.80 | 0.18 | 21.7 | 8.55E−08 | 2.91E−06 | 34.0 |
| MB758 | T230E/V231P/P232N/S238E/S239L/S298M/K334R | 8.57 | 0.17 | 49.1 | 2.15E−08 | 2.11E−06 | 98.4 |
| MB637 | T230E/V231P/P232A/S238E/S239N | 2.87 | 0.17 | 16.7 | 8.07E−08 | 1.89E−06 | 23.4 |
| MB636 | T230E/P232Y/S238E/S239N | 3.92 | 0.17 | 22.8 | 8.30E−08 | 2.98E−06 | 35.9 |
| MB646 | T230E/V231P/P232A/S238E/S239Y | 4.82 | 0.17 | 28.2 | 4.80E−08 | 1.90E−06 | 39.6 |
| MB636 | T230E/P232Y/S238E/S239N | 4.86 | 0.17 | 29.4 | 4.76E−08 | 1.97E−06 | 41.3 |
| MB643 | T230E/V231N/P232Y/S238E/S239Y | 1.83 | 0.16 | 11.3 | 1.26E−07 | 2.00E−06 | 15.8 |
| MB778 | T230E/V231P/P232N/S238E/S239L/S337K | 7.21 | 0.16 | 46.3 | 3.42E−08 | 2.54E−06 | 74.3 |
| MB641 | T230E/V231A/P232Y/S238E/S239Y | 1.62 | 0.15 | 10.5 | 1.43E−07 | 2.10E−06 | 14.7 |
| MB765 | T230E/V231P/P232N/S238E/S239L/N324L | 6.23 | 0.15 | 40.4 | 3.96E−08 | 2.56E−06 | 64.8 |
| MB617 | V237E/S239D/F241D | 0.84 | 0.15 | 5.5 | 2.55E−07 | 2.10E−06 | 8.2 |

TABLE 27-continued

| Name (CH) | Alteration introduced to mIgG1 | Relative mFcγRII-binding activity (mIgG1 = 1) | Relative mFcγRIII-binding activity (mIgG1 = 1) | Relative I/A (mFcγRII selectivity) (mIgG1 = 1) | KD (mFcγRII) | KD (mFcγRIII) | I/A (mFcγRII selectivity) |
|---|---|---|---|---|---|---|---|
| MB755 | T230E/V231P/P232N/S238E/S239L/S298L/N324D | 6.62 | 0.15 | 44.9 | 2.78E−08 | 2.50E−06 | 90.0 |
| MB702 | V231A/P232Y/S238E/S239N | 0.96 | 0.14 | 6.6 | 3.39E−07 | 3.52E−06 | 10.4 |
| MB626 | T230E/V231T/P232Y/S238E/S239L | 0.89 | 0.14 | 6.5 | 2,61E−07 | 2.37E−06 | 9.1 |
| MB618 | V237E/3238D/S239D | 1.63 | 0.13 | 12.2 | 1.56E−07 | 2.73E−06 | 17.6 |
| MB885 | T230E/V231P/P232A/V237E/S238E | 3.29 | 0.13 | 26.2 | 1.11E−07 | 4.35E−06 | 39.3 |
| MB762 | T230E/V231P/P232N/S238E/S239L/F296E | 5.12 | 0.12 | 41.7 | 4.81E−08 | 3.22E−06 | 66.8 |
| MB647 | T230I/V231P/P232A/S238E/S239Y | 1.16 | 0.12 | 10.0 | 2.00E−07 | 2.80E−06 | 14.0 |
| MB832 | T230E/V231P/P232N/S238E/S239L/P331Y/E333Y | 5.16 | 0.12 | 44.8 | 4.04E−08 | 3.05E−06 | 75.5 |
| MB692 | T230E/V231P/S238E/S239Y | 1.75 | 0.12 | 15.2 | 1.86E−07 | 4.44E−06 | 23.8 |
| MB757 | T230E/V231P/P232N/S238E/S239L/S298M/N324D | 6.63 | 0.11 | 58.0 | 2.78E−08 | 3.23E−06 | 116.3 |
| MB624 | T230E/V231D/P232Y/S238E/S239L | 0.88 | 0.11 | 7.8 | 2.63E−07 | 2.87E−06 | 10.9 |
| MB752 | T230E/V231P/P232N/S238E/S239L/S298L | 5.24 | 0.11 | 46.6 | 3.51E−08 | 3.28E−06 | 93.4 |
| MB883 | T230E/V231P/P232A/V237E/S239L | 2.21 | 0.11 | 20.1 | 1.64E−07 | 4.96E−06 | 30.2 |
| MB830 | T230E/V231P/P232N/S238E/S239L/P331F/E333Y | 4.78 | 0.10 | 45.9 | 4.36E−08 | 3.38E−06 | 77.4 |
| MB703 | T230E/V231A/S238E/S239N | 0.94 | 0.10 | 9.1 | 3.45E−07 | 4.90E−06 | 14.2 |
| MB772 | T230E/V231P/P232N/S238E/S239L/E333N | 4.07 | 0.10 | 40.0 | 6.05E−08 | 3.89E−06 | 64.2 |
| MB642 | T230E/V231D/P232Y/S238E/S239Y | 1.65 | 0.10 | 16.5 | 1.97E−07 | 5.11E−06 | 25.9 |
| MB763 | T230E/V231P/P232N/S238E/S239L/F296N | 3.98 | 0.10 | 40.0 | 6.19E−08 | 3.97E−06 | 64.2 |
| MB594 | T230E/V237E/S238E | 1.85 | 0.10 | 18.7 | 1.15E−07 | 3.23E−06 | 28.0 |
| MB642 | T230E/V231D/P232Y/S238E/S239Y | 2.06 | 0.10 | 21.1 | 1.12E−07 | 3.32E−06 | 29.6 |
| MB687 | T230E/V231P/S238E/S239L | 0.94 | 0.10 | 9.8 | 3.45E−07 | 5.32E−06 | 15.4 |
| MB638 | T230I/V231P/P232A/S238E/S239N | 0.83 | 0.10 | 8.6 | 2.80E−07 | 3.38E06 | 12.1 |
| MB693 | V231D/P232Y/S238E/S239Y | 1.22 | 0.09 | 12.9 | 2.67E−07 | 5.41E−06 | 20.3 |
| MB657 | T230E/V231P/P232N/S238E/S239F | 1.95 | 0.09 | 20.9 | 1.18E−07 | 3.48E−06 | 29.4 |
| MB611 | V237E/S238D/S239E | 1.11 | 0.09 | 11.9 | 1.92E−07 | 3.42E−06 | 17.8 |
| MB884 | T230E/V231P/P232N/V237E/S239L | 2.46 | 0.09 | 26.7 | 1.48E−07 | 5.91E−06 | 40.1 |
| MB769 | T230E/V231P/P232N/S238E/S239L/P331D | 3.90 | 0.09 | 43.2 | 6.32E−08 | 4.38E−06 | 69.3 |
| MB657 | T230E/V231P/P232N/S238E/S239F | 1.54 | 0.09 | 17.7 | 2.11E−07 | 5.87E−06 | 27.8 |
| MB753 | T230E/V231P/P232N/S238E/S239L/S298M | 5.00 | 0.09 | 57.8 | 3.68E−08 | 4.26E−06 | 115.8 |
| MB628 | T230E/V231P/P232A/S238E/S239L | 2.09 | 0.08 | 25.0 | 1.56E−07 | 6.13E−06 | 39.3 |
| MB718 | T230E/V231P/P232N/S238E/S239T | 1.08 | 0.08 | 13.1 | 2.47E−07 | 5.56E−06 | 22.5 |
| MB764 | T230E/V231P/P232N/S238E/S239L/F296T | 2.90 | 0.08 | 37.8 | 8.49E−08 | 5.15E−06 | 60.7 |
| MB886 | T230E/V231P/P232N/V237E/S238E | 1.47 | 0.08 | 19.5 | 2.46E−07 | 7.22E−06 | 29.3 |
| MB716 | T230E/V231P/P232N/S238E/S239I | 5.07 | 0.08 | 67.6 | 5.28E−08 | 6.15E−06 | 116.4 |
| MB628 | T230E/V231P/P232A/S238E/S239L | 2.42 | 0.07 | 33.6 | 9.56E−08 | 4.50E−06 | 47.1 |
| MB793 | T230Q/V231P/P232N/S238E/S239I | 1.37 | 0.07 | 19.1 | 1.79E−07 | 5.50E−06 | 30.6 |

TABLE 27-continued

| Name (CH) | Alteration introduced to mIgG1 | Relative mFcγRII-binding activity (mIgG1 = 1) | Relative mFcγRIII-binding activity (mIgG1 = 1) | Relative I/A (mFcγRII selectivity) (mIgG1 = 1) | KD (mFcγRII) | KD (mFcγRIII) | I/A (mFcγRII selectivity) |
|---|---|---|---|---|---|---|---|
| MB594 | T230E/V237E/S238E | 1.30 | 0.06 | 23.0 | 2.50E−07 | 9.03E−06 | 36.2 |
| MB767 | T230E/V231P/P232N/S238E/S239L/A330G | 2.10 | 0.04 | 46.7 | 1.17E−07 | 8.79E−06 | 74.9 |
| MB715 | T230E/V231P/P232N/S238E/S239V | 1.14 | 0.04 | 29.4 | 2.36E−07 | 1.19E−05 | 50.7 |
| MB732 | T230E/V231P/P232N/V237E/S238E/S239L | 0.84 | 0.03 | 24.8 | 3.21E−07 | 1.37E−05 | 42.8 |
| MB731 | T230E/V231P/P232A/V237E/S238E/S239L | 1.13 | 0.03 | 37.5 | 2.38E−07 | 1.53E−05 | 64.5 |

(I/A (mFcγRII selectivity): value determined by dividing the KD value of each variant for mFcγRIII by its KD value for mFcγRII, Relative binding activity: value determined by dividing the KD value of H237-mIgG1/MRAL-k0 for each mFcγR by the KD value of each variant for each mFcγR, Relative I/A (mFcγRII selectivity): value determined by dividing I/A (value determined by dividing the KD value for mFcγRIII by the KD value for mFcγRII) of each variant by I/A of H237-mIgG1/MRAL-k0; the value of H237-mIgG1/MRAL-k0 used was a value obtained by the same assay run as that of each variant)

[Example 11] In Vivo Evaluation of an Antibody Having Fc Variant with Selectively Enhanced Binding Activity Against mFcγRII In the foregoing Examples, the antibodies having the Fc variants with selectively enhanced binding activity against mFcγRII were obtained. WO2013/047752 has showed in normal mice that an antigen-binding molecule that binds to a soluble antigen in a pH-dependent manner and has an Fc variant with selectively enhanced binding activity against mFcγRII can efficiently cause the disappearance of the soluble antigen in plasma when administered into an organism. In this Example, the following test was conducted using normal mice in order to test whether this antigen disappearance effect would correlate with the degree of enhancement in binding activity against mFcγRII.

(11-1) mFcγR-Binding Activity of Antibody Having Fc Variant with Selectively Enhanced Binding Activity Against mFcγRII From among the variants prepared and evaluated in the foregoing Examples, H237-MB477/MRAL-k0 and H237-MB492/MRAL-k0 were selected as variants that exhibited selectively enhanced binding activity against mFcγRII and differed in the degree of enhancement. Table 28 shows the KD values for each mFcγR and I/A (mFcγRII selectivity) of these 2 variants and H237-mIgG1/MRAL-k0. "Name" in the table represents the name of the H chain constant region of each evaluated variant. As for alterations, "X000Z" represents the substitution of amino acid X at EU numbering position 000 by amino acid Z. In this context, X and Z represent the one-letter codes of the amino acid residues. All of the alterations described in Table 28 were alterations introduced to the H chain constant region (SEQ ID NO: 4) of mouse IgG1 (mIgG1).

TABLE 28

| Name (CH) | Alteration introduced to mIgG1 | Relative mFcγRII-binding activity (mIgG1 = 1) | Relative mFcγRIII-binding activity (mIgG1 = 1) | Relative I/A (mFcγRIII selectivity) (mIgG1 = 1) | KD (mFcγRII) | KD (mFcγRIII) | I/A (mFcγRII selectivity) |
|---|---|---|---|---|---|---|---|
| mIgG1 | — | 1.0 | 1.0 | 1.0 | 2.10E−07 | 2.82E−07 | 1.3 |
| MB477 | T230E/V231P/P232N/S238E/S239D/S267A | 195.7 | 3.0 | 65.3 | 1.07E−09 | 9.40E−08 | 87.6 |
| MB492 | T230E/V231P/P232N/S238E/S239D/N324D | 621.5 | 10.9 | 57.0 | 3.38E−10 | 2.58E−08 | 76.3 |

(I/A (mFcγRII selectivity): value determined by dividing the KD value of each variant for mFcγRIII by its KD value for mFcγRII, Relative binding activity: value determined by dividing the KD value of H237-mIgG1/MRAL-k0 for each mFcγR by the KD value of each variant for each mFcγR, Relative I/A (mFcγRII selectivity): value determined by dividing I/A (value determined by dividing the KD value for mFcγRIII by the KD value for mFcγRII) of each variant by I/A of H237-mIgG1/MRAL-k0)

(11-2) In Vivo Test Using Normal Mouse

A soluble human IL-6 receptor (prepared in Reference Example 3) was administered simultaneously with an anti-human IL-6 receptor mouse antibody to each normal mouse (C57BL/6J mouse, Charles River Laboratories Japan, Inc.). Then, the anti-human IL-6 receptor mouse antibody and the soluble human IL-6 receptor were evaluated for their disposition. The soluble human IL-6 receptor solution (5 μg/mL) or the mixed solution of the soluble human IL-6 receptor and the anti-human IL-6 receptor mouse antibody was administered to the tail vein at a dose of 10 mL/kg. The doses of the antibody and the soluble human IL-6 receptor were set to 1 mg/kg and 50 μg/kg, respectively. The anti-human IL-6 receptor mouse antibody used was H237-MB477/L104-mk1 and H237-MB492/L104-mk1 derived from the aforementioned H237-MB477/MRAL-k0 and H237-MB492/MRAL-k0, respectively, by the replacement of t L chain with L104-mk1 (SEQ ID NO: 32) comprised of the variable region L104 of the L chain VL3-CK of the anti-human IL-6 receptor antibody Fv4-IgG1 described in WO2009/125825 and the constant region mk1 of the mouse κ chain. After a lapse of 5 minutes, 2 hours, 7 hours, 1 day, 2 days, 3 days, 7 days, 14 days, 21 days, and 28 days after the administration of the anti-human IL-6 receptor mouse antibody, blood was collected from the mouse. However, the blood collection 2 hours after the administration of the antibody may not be performed. The collected blood was immediately centrifuged at 15,000 rpm at 4° C. for 15 minutes to obtain plasma. The separated plasma was stored in a refrigerator set to −20° C. or lower until measurement.

(11-3) Measurement of Soluble Human IL-6 Receptor Concentration in Plasma by Electrochemiluminescent Method The soluble human IL-6 receptor concentration in the mouse plasma was measured by the electrochemiluminescent method. Soluble human IL-6 receptor calibration curve samples having a plasma concentration adjusted to 12.5, 6.25, 3.13, 1.56, 0.781, 0.391, or 0.195 ng/mL, and mouse plasma assay samples diluted 50-fold or more were prepared. Monoclonal Anti-human IL-6R Antibody (R&D Systems, Inc.) conjugated with ruthenium using SULFO-TAG NHS Ester (Meso Scale Discovery), Biotinylated Anti-human IL-6 R Antibody (R&D Systems, Inc.), and a tocilizumab solution were mixed and reacted with the samples overnight at 37° C. Then, the reaction solutions were dispensed to wells of Streptavidin Gold Multi-ARRAY Plate (Meso Scale Discovery) blocked overnight at 5° C. with a PBS-Tween solution containing 0.5% BSA (w/v). After further reaction at room temperature for 2 hours and washing, Read Buffer T (×2) (Meso Scale Discovery) was dispensed to the wells. Immediately thereafter, assay was conducted using SECTOR Imager 2400 (Meso Scale Discovery). The soluble human IL-6 receptor concentration was calculated using analysis software SOFTmax PRO (Molecular Devices, LLC) from the response of the calibration curve. The results are shown in FIG. 20.

(11-4) Measurement of Anti-Human IL-6 Receptor Mouse Antibody Concentration in Plasma by ELISA The anti-human IL-6 receptor mouse antibody concentration in the mouse plasma was measured by ELISA. First, a soluble human IL-6 receptor was dispensed to wells of Nunc-Immuno Plate, MaxiSoup (Nalge Nunc International). The plate was left standing overnight at 4° C. to prepare a soluble human IL-6 receptor-immobilized plate. Calibration curve samples containing the anti-human IL-6 receptor mouse antibody at a plasma concentration of 2.50, 1.25, 0.625, 0.313, 0.156, 0.078, or 0.039 µg/mL, and mouse plasma assay samples diluted 100-fold or more were prepared. These calibration curve samples and plasma assay samples were dispensed at a concentration of 100 µL/well to the soluble human IL-6 receptor-immobilized plate, followed by stirring at room temperature for 2 hours. Then, the plate was reacted with Anti-Mouse IgG-Peroxidase antibody (Sigma-Aldrich Corp.) at room temperature for 2 hours. The chromogenic reaction of the reaction solution in each well was performed using TMB One Component HRP Microwell Substrate (BioFX Laboratories, Inc.) as a substrate. The reaction was stopped by the addition of 1 N sulfuric acid (Showa Chemical Industry Co., Ltd.). The absorbance of the reaction solution in each well was measured at 450 nm using a microplate reader. The antibody concentration in the mouse plasma was calculated using analysis software SOFTmax PRO (Molecular Devices, LLC) from the absorbance of the calibration curve. The results are shown in FIG. 21.

The results of FIG. 20 showed that, when administered to normal mice, the antibodies H237-MB477/L104-mkt (having approximately 200-fold relative mFcγRII-binding activity with the value of H237-mIgG1/L104-mk1 as 1) and H237-MB492/L104-mk1 (having approximately 620-fold relative mFcγRII-binding activity with the value of H237-mIgG1/L104-mk1 as 1) having Fc with selectively enhanced binding activity against mFcγRII exert the enhanced effect of antigen disappearance from plasma depending on the degree of enhancement in the binding activity of the antibody Fc against mFcγRII. Specifically, the concentration of the target antigen was lower in the mouse that received H237-MB492/L104-mk1 having approximately 620-fold relative mFcγRII-binding activity than in the mouse that received H237-MB477/L104-mk1 having approximately 200-fold relative mFcγRII-binding activity. The concentration of the target antigen was lower in the mouse that received H237-MB477/L104-mk1 having approximately 200-fold relative mFcγRII-binding activity than in the mouse that received H237-mIgG1/L104-mk1.

The results of FIG. 21 showed that H237-MB477/L104-mk1, in spite of its approximately 200-fold relative mFcγRII-binding activity, exhibited time-dependent change in plasma antibody concentration substantially equivalent to that of H237-mIgG1/L104-mk1. H237-MB492/L104-mk1 having approximately 620-fold relative mFcγRII-binding activity had slightly lower plasma antibody concentration than that of H237-mIgG1/L104-mk1. At 1 day after the administration, the antibody concentration of H237-MB492/L104-mk1 was substantially equivalent to that of H237-mIgG1/L104-mk1. Nonetheless, the soluble human IL-6 receptor concentration was decreased by approximately 10 times in the mouse that received H237-MB492/L104-mk1. This demonstrated that H237-MB492/L104-mk1 exhibits only slight reduction in antibody concentration, but can significantly reduce the concentration of the target antigen.

[Reference Example 1] Preparation of Antibody Expression Vector and Expression and Purification of Antibody The full-length genes having nucleotide sequences encoding antibody H and L chain variable regions were synthesized using assembly PCR or the like and prepared by a method generally known to those skilled in the art. Amino acid substitution was introduced by a method generally known to those skilled in the art using PCR or the like. The obtained plasmid fragments were inserted to vectors for expression in animal cells to prepare H chain and L chain expression vectors. The obtained expression vectors were sequenced by a method generally known to those skilled in the art. The prepared plasmids were transiently transferred to human embryonic kidney cancer cell-derived HEK293H line (Invitrogen Corp.) or FreeStyle 293 cells (Invitrogen Corp.) to express antibodies. The obtained culture supernatant was recovered and then passed through a 0.22-µm filter MILLEX(R)-GV (Millipore Corp.) or a 0.45-nm filter MILLEX(R)-GV (Millipore Corp.) to obtain a culture supernatant. Each antibody was purified from the obtained culture supernatant by a method generally known to those skilled in the art using rProtein A Sepharose Fast Flow (GE Healthcare Japan Corp.) or Protein G Sepharose 4 Fast Flow (GE Healthcare Japan Corp.). As for the concentration of the purified antibody, the absorbance was measured at 280 nm using a spectrophotometer, and the antibody concentration was calculated by use of an extinction coefficient calculated from the obtained value by a method such as PACE (Protein Science 1995, 4, 2411-2423).

[Reference Example 2] Method for Preparing mFcγR and Method for Analyzing Interaction Between Altered Antibody and mFcγR The extracellular domain of mouse FcγR was prepared by the following method: first, the gene of the FcγR extracellular domain was synthesized by a method generally known to those skilled in the art. For this synthesis, the sequence of each FcγR was prepared on the basis of the information registered in NCBI. Specifically, mFcγRI was prepared on the basis of the sequence of NCBI Reference Sequence: NP_034316.1; mFcγRII was prepared on the basis of the sequence of NCBI Reference Sequence: NP_034317.1; mFcγRIII was prepared on the basis of the sequence of NCBI Reference Sequence: NP_034318.2; and mFcγRIV was prepared on the basis of the sequence of NCBI Reference Sequence: NP_653142.2. Each of these sequences was C-terminally tagged with a His tag.

Each obtained gene fragment was inserted to vectors for expression in animal cells to prepare expression vectors. The prepared expression vectors were transiently transferred to human embryonic kidney cancer cell-derived FreeStyle 293 cells (Invitrogen Corp.) to express the protein of interest. The obtained culture supernatant was recovered and then passed through a 0.22-μm filter to obtain a culture supernatant. The obtained culture supernatant was purified, as a rule, by the following 4 steps: ion-exchanged column chromatography as step 1, affinity column chromatography for the His tag (HisTrap HP) as step 2, gel filtration column chromatography (Superdex 200) as step 3, and sterile filtration as step 4. The ion-exchanged column chromatography of step 1 was carried out using Q Sepharose HP for mFcγR1, SP Sepharose FF for mFcγRII and mFcγRIV, and SP Sepharose HP for mFcγRIII. D-PBS(-) was used as a solvent in step 3 or later, while D-PBS(-) containing 0.1 M arginine was used for mFcγRIII. The absorbance was measured for each purified protein at 280 nm using a spectrophotometer, and the concentration of the purified protein was calculated by use of an extinction coefficient calculated from the obtained value by a method such as PACE (Protein Science 1995; 4: 2411-2423).

Each altered antibody was analyzed for its interaction with each Fcγ receptor prepared above using Biacore T100 (GE Healthcare Japan Corp.), Biacore T200 (GE Healthcare Japan Corp.), Biacore A100, or Biacore 4000. The running buffer used was HBS-EP+(0.01 M HEPES pH 7.4, 0.15 M NaCl, 3 mM ethylene diamine tetraacetic acid (EDTA), 0.05% polysorbate 20) (GE Healthcare Japan Corp.). The assay temperature was set to 25° C. The sensor chips used were chips prepared by immobilizing Protein L (ACTIGEN or BioVision) onto Series S Sensor Chip CM5 (GE Healthcare Japan Corp.) or Series S Sensor Chip CM4 (GE Healthcare Japan Corp.) by the amine coupling method.

The antibody of interest was captured onto any of these sensor chips and allowed to interact with mFcγR diluted with a running buffer. The amount bound to the antibody was measured and compared among antibodies. Since the amount of mFcγR bound depends on the amount of the captured antibody, a correction value determined by dividing the amount of mFcγR bound by the amount of each captured antibody was used in the comparison. The antibody captured on the sensor chip was washed off through the reaction of 10 mM glycine-HCl (pH 1.5) to regenerate the sensor chip, which was repetitively used.

In order to calculate the KD value of each altered antibody for FcγR, kinetic analysis was conducted according to the following method: first, the antibody of interest was captured onto any of these chips and allowed to interact with mFcγR diluted with a running buffer. For the obtained sensorgram, the assay results were globally fit into the 1:1 Langmuir binding model using Biacore Evaluation Software to calculate an association rate constant ka (L/mol/s) and a dissociation rate constant kd (1/s). From these values, the dissociation constant KD (mol/L) was calculated.

[Reference Example 3] Preparation of Soluble Human IL-6 Receptor (hsIL-6R)

A recombinant human IL-6 receptor of the human IL-6 receptor as an antigen was prepared as follows: a CHO strain constantly expressing a soluble human IL-6 receptor (hereinafter, referred to as hsIL-6R) comprised of an amino acid sequence from the 1st (N-terminal) to 357th positions as reported in J Immunol 152, 4958-4968 (1994) was constructed by a method generally known to those skilled in the art, cultured, and allowed to express hsIL-6R. From the obtained culture supernatant, hsIL-6R was purified by 2 steps involving Blue Sepharose 6 FF column chromatography and gel filtration column chromatography. A fraction eluted as a main peak in the final step was used as a final purified product.

INDUSTRIAL APPLICABILITY

The present invention provides a polypeptide comprising an Fc variant selectively binding to mouse FcγRII relative to mouse FcγRIII. This polypeptide is very useful in achieving use of mice to predict the effects of a polypeptide comprising an Fc variant selectively binding to human FcγRIIb relative to human FcγRIIa on humans. Specifically, the polypeptide is useful in, for example, (i) predicting a therapeutic or preventive effect on a disease in a human, (ii) selecting a human disease suitable for treatment or prevention, (iii) selecting a target antigen suitable for the treatment or prevention of a disease in a human, (iv) selecting an antigen-binding region suitable for the treatment or prevention of a disease in a human, (v) predicting safety or toxicity in a human; and (vi) predicting pharmacokinetics in a human.

The invention claimed is:

1. A polypeptide comprising a full-length Fc region that is a variant of a full-length, naturally occurring mouse Fc region, wherein the amino acid sequence of the variant Fc region differs from the amino acid sequence of the naturally occurring mouse Fc region at two to six positions, wherein the binding selectivity of the variant Fc region for mouse FcγRII relative to mouse FcγRIII is at least 5 times greater than that of the naturally occurring Fc region, wherein the amino acid at position 239 of the variant Fc region is Asp, and wherein at least one of the two to six positions of the variant Fc region is selected from the following group and is substituted with the indicated amino acid:
- position 230, substituted with Glu;
- position 231, substituted with Asp;
- position 232, substituted with Glu; and
- position 238, substituted with Glu (all positions by EU numbering).

2. The polypeptide of claim 1, wherein the variant Fc region binds mouse FcγRII with a KD of 20 nM or less, as measured by a surface plasmon resonance technique in which a polypeptide comprising the variant Fc region is immobilized, an extracellular domain of the mouse FcγRII serves as analyte, the temperature is set at 25° C., and the running buffer is HBS-EP+ (0.01 M HEPES pH 7.4, 0.15 M NaCl, 3 mM ethylene diamine tetraacetic acid (EDTA), 0.05% polysorbate 20).

3. The polypeptide of claim 1, wherein the FcγRII-binding activity of the variant Fc region is at least 10 times greater than that of the naturally occurring Fc region.

4. The polypeptide of claim 1, wherein the variant Fc region binds mouse FcγRIII with a KD of at least 1 μM, as measured by a surface plasmon resonance technique in which a polypeptide comprising the variant Fc region is immobilized, an extracellular domain of the mouse FcγRIII serves as analyte, the temperature is set at 25° C., and the running buffer is HBS-EP+ (0.01 M HEPES pH 7.4, 0.15 M NaCl, 3 mM EDTA, 0.05% polysorbate 20).

5. The polypeptide of claim 1, wherein the FcγRIII-binding activity of the variant Fc region is no more than 0.25 times that of the naturally occurring Fc region.

6. The polypeptide of claim 1, wherein the naturally occurring Fc region is the Fc region of mouse IgG1.

7. The polypeptide of claim 1, wherein the polypeptide is an antibody.

8. The polypeptide of claim 1, wherein position 240 in the variant Fc region is either Glu or His.

9. The polypeptide of claim 1, wherein the amino acid sequence of the variant Fc region differs from the amino acid sequence of the naturally occurring mouse Fc region at just two positions.

10. The polypeptide of claim 1, wherein at least two of the following positions in the variant Fc region are substituted with the indicated amino acid:
- position 230, substituted with Glu;
- position 231, substituted with Asp;
- position 232, substituted with Glu; and
- position 238, substituted with Glu (all positions by EU numbering).

11. The polypeptide of claim 1, wherein at least three of the following positions in the variant Fc region are substituted with the indicated amino acid:
- position 230, substituted with Glu;
- position 231, substituted with Asp;
- position 232, substituted with Glu; and
- position 238, substituted with Glu (all positions by EU numbering).

12. The polypeptide of claim 1, wherein the amino acid sequence of the variant Fc region includes the following five substitutions compared to the amino acid sequence of the naturally occurring mouse Fc region: 230E, 231D, 232E, 238E, and 239D (all positions by EU numbering).

13. The polypeptide of claim 12, wherein position 240 in the variant Fc region is either Glu or His.

14. A method of producing a polypeptide comprising a variant Fc region, the method comprising:
- selecting a first nucleotide sequence encoding a first polypeptide comprising a first Fc region, wherein the amino acid sequence of the first Fc region is identical to the amino acid sequence of a full-length, naturally occurring mouse Fc region;
- providing a nucleic acid molecule comprising a second nucleotide sequence encoding a second polypeptide comprising the variant Fc region, wherein the variant Fc region is a full-length Fc region that differs from the first Fc region at two to six positions;
- expressing the nucleic acid molecule in vitro, thereby producing the second polypeptide; and
- collecting the produced second polypeptide comprising the variant Fc region, wherein the binding selectivity of the second polypeptide for mouse FcγRII relative to mouse FcγRIII is at least 5 times greater than that of the first polypeptide, wherein the amino acid at position 239 is Asp, and wherein at least one of the two to six positions of the variant Fc region is selected from the following group and is substituted with the indicated amino acid:
- position 230, substituted with Glu;
- position 231, substituted with Asp;
- position 232, substituted with Glu; and
- position 238, substituted with Glu (all positions by EU numbering).

15. The method of claim 14, wherein the naturally occurring mouse Fc region is the Fc region of mouse IgG1.

16. The method of claim 14, wherein the produced second polypeptide is part of an antibody.

17. The method of claim 14, wherein position 240 in the variant Fc region is either Glu or His.

18. The method of claim 14, wherein the amino acid sequence of the variant Fc region includes the following five substitutions compared to the amino acid sequence of the naturally occurring mouse Fc region: 230E, 231P, 232N, 238E, and 239D (all positions by EU numbering).

* * * * *

SEQUENCE LISTING

```
<160> NUMBER OF SEQ ID NOS: 47

<210> SEQ ID NO 1
<211> LENGTH: 119
<212> TYPE: PRT
<213> ORGANISM: Artificial Sequence
<220> FEATURE:
<223> OTHER INFORMATION: an artificially synthesized sequence

<400> SEQUENCE: 1

Gln Val Gln Leu Gln Glu Ser Gly Pro Gly Leu Val Lys Pro Ser Glu
1               5                   10                  15
```

```
Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser
            115

<210> SEQ ID NO 2
<211> LENGTH: 214
<212> TYPE: PRT
<213> ORGANISM: Artificial Sequence
<220> FEATURE:
<223> OTHER INFORMATION: an artificially synthesized sequence

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Ser Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Gly Asn Thr Leu Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 3
<211> LENGTH: 330
<212> TYPE: PRT
<213> ORGANISM: Homo sapiens
```

<400> SEQUENCE: 3

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 4
<211> LENGTH: 324
<212> TYPE: PRT
<213> ORGANISM: Mus musculus

<400> SEQUENCE: 4

Ala Lys Thr Thr Pro Pro Ser Val Tyr Pro Leu Ala Pro Gly Ser Ala
1               5                   10                  15

Ala Gln Thr Asn Ser Met Val Thr Leu Gly Cys Leu Val Lys Gly Tyr
            20                  25                  30
```

Phe Pro Glu Pro Val Thr Val Thr Trp Asn Ser Gly Ser Leu Ser Ser
            35                  40                  45

Gly Val His Thr Phe Pro Ala Val Leu Gln Ser Asp Leu Tyr Thr Leu
 50                  55                  60

Ser Ser Ser Val Thr Val Pro Ser Ser Thr Trp Pro Ser Glu Thr Val
 65                  70                  75                  80

Thr Cys Asn Val Ala His Pro Ala Ser Ser Thr Lys Val Asp Lys Lys
                    85                  90                  95

Ile Val Pro Arg Asp Cys Gly Cys Lys Pro Cys Ile Cys Thr Val Pro
                100                 105                 110

Glu Val Ser Ser Val Phe Ile Phe Pro Pro Lys Pro Lys Asp Val Leu
            115                 120                 125

Thr Ile Thr Leu Thr Pro Lys Val Thr Cys Val Val Val Asp Ile Ser
130                 135                 140

Lys Asp Asp Pro Glu Val Gln Phe Ser Trp Phe Val Asp Asp Val Glu
145                 150                 155                 160

Val His Thr Ala Gln Thr Gln Pro Arg Glu Glu Gln Phe Asn Ser Thr
                165                 170                 175

Phe Arg Ser Val Ser Glu Leu Pro Ile Met His Gln Asp Trp Leu Asn
            180                 185                 190

Gly Lys Glu Phe Lys Cys Arg Val Asn Ser Ala Ala Phe Pro Ala Pro
        195                 200                 205

Ile Glu Lys Thr Ile Ser Lys Thr Lys Gly Arg Pro Lys Ala Pro Gln
    210                 215                 220

Val Tyr Thr Ile Pro Pro Pro Lys Glu Gln Met Ala Lys Asp Lys Val
225                 230                 235                 240

Ser Leu Thr Cys Met Ile Thr Asp Phe Phe Pro Glu Asp Ile Thr Val
                245                 250                 255

Glu Trp Gln Trp Asn Gly Gln Pro Ala Glu Asn Tyr Lys Asn Thr Gln
            260                 265                 270

Pro Ile Met Asp Thr Asp Gly Ser Tyr Phe Val Tyr Ser Lys Leu Asn
        275                 280                 285

Val Gln Lys Ser Asn Trp Glu Ala Gly Asn Thr Phe Thr Cys Ser Val
    290                 295                 300

Leu His Glu Gly Leu His Asn His His Thr Glu Lys Ser Leu Ser His
305                 310                 315                 320

Ser Pro Gly Lys

<210> SEQ ID NO 5
<211> LENGTH: 324
<212> TYPE: PRT
<213> ORGANISM: Artificial Sequence
<220> FEATURE:
<223> OTHER INFORMATION: an artificially synthesized sequence

<400> SEQUENCE: 5

Ala Lys Thr Thr Pro Pro Ser Val Tyr Pro Leu Ala Pro Gly Ser Ala
1               5                   10                  15

Ala Gln Thr Asn Ser Met Val Thr Leu Gly Cys Leu Val Lys Gly Tyr
            20                  25                  30

Phe Pro Glu Pro Val Thr Val Thr Trp Asn Ser Gly Ser Leu Ser Ser
        35                  40                  45

Gly Val His Thr Phe Pro Ala Val Leu Gln Ser Asp Leu Tyr Thr Leu
 50                  55                  60

```
Ser Ser Ser Val Thr Val Pro Ser Ser Thr Trp Pro Ser Glu Thr Val
 65                  70                  75                  80

Thr Cys Asn Val Ala His Pro Ala Ser Ser Thr Lys Val Asp Lys Lys
                 85                  90                  95

Ile Val Pro Arg Asp Cys Gly Cys Lys Pro Cys Ile Cys Glu Thr Tyr
            100                 105                 110

Glu Val Glu Asp Val Phe Ile Phe Pro Pro Lys Pro Lys Asp Val Leu
        115                 120                 125

Thr Ile Thr Leu Thr Pro Lys Val Thr Cys Val Val Val Asp Ile Ser
    130                 135                 140

Lys Asp Asp Pro Glu Val Gln Phe Ser Trp Phe Val Asp Asp Val Glu
145                 150                 155                 160

Val His Thr Ala Gln Thr Gln Pro Arg Glu Glu Gln Phe Asn Ser Thr
                165                 170                 175

Phe Arg Ser Val Ser Glu Leu Pro Ile Met His Gln Asp Trp Leu Asn
            180                 185                 190

Gly Lys Glu Phe Lys Cys Arg Val Asn Ser Ala Ala Phe Pro Ala Pro
        195                 200                 205

Ile Glu Lys Thr Ile Ser Lys Thr Lys Gly Arg Pro Lys Ala Pro Gln
    210                 215                 220

Val Tyr Thr Ile Pro Pro Lys Glu Gln Met Ala Lys Asp Lys Val
225                 230                 235                 240

Ser Leu Thr Cys Met Ile Thr Asp Phe Phe Pro Glu Asp Ile Thr Val
                245                 250                 255

Glu Trp Gln Trp Asn Gly Gln Pro Ala Glu Asn Tyr Lys Asn Thr Gln
            260                 265                 270

Pro Ile Met Asp Thr Asp Gly Ser Tyr Phe Val Tyr Ser Lys Leu Asn
        275                 280                 285

Val Gln Lys Ser Asn Trp Glu Ala Gly Asn Thr Phe Thr Cys Ser Val
    290                 295                 300

Leu His Glu Gly Leu His Asn His His Thr Glu Lys Ser Leu Ser His
305                 310                 315                 320

Ser Pro Gly Lys

<210> SEQ ID NO 6
<211> LENGTH: 324
<212> TYPE: PRT
<213> ORGANISM: Artificial Sequence
<220> FEATURE:
<223> OTHER INFORMATION: an artificially synthesized sequence

<400> SEQUENCE: 6

Ala Lys Thr Thr Pro Pro Ser Val Tyr Pro Leu Ala Pro Gly Ser Ala
 1               5                  10                  15

Ala Gln Thr Asn Ser Met Val Thr Leu Gly Cys Leu Val Lys Gly Tyr
                20                  25                  30

Phe Pro Glu Pro Val Thr Val Thr Trp Asn Ser Gly Ser Leu Ser Ser
            35                  40                  45

Gly Val His Thr Phe Pro Ala Val Leu Gln Ser Asp Leu Tyr Thr Leu
        50                  55                  60

Ser Ser Ser Val Thr Val Pro Ser Ser Thr Trp Pro Ser Glu Thr Val
 65                  70                  75                  80

Thr Cys Asn Val Ala His Pro Ala Ser Ser Thr Lys Val Asp Lys Lys
                 85                  90                  95

Ile Val Pro Arg Asp Cys Gly Cys Lys Pro Cys Ile Cys Glu Pro Asn
```

```
                100                 105                 110
Glu Val Glu Asp Val Phe Ile Phe Pro Pro Lys Pro Lys Asp Val Leu
            115                 120                 125
Thr Ile Thr Leu Thr Pro Lys Val Thr Cys Val Val Val Asp Ile Ser
        130                 135                 140
Lys Asp Asp Pro Glu Val Gln Phe Ser Trp Phe Val Asp Asp Val Glu
145                 150                 155                 160
Val His Thr Ala Gln Thr Gln Pro Arg Glu Glu Gln Phe Asn Ser Thr
                165                 170                 175
Phe Arg Ser Val Ser Glu Leu Pro Ile Met His Gln Asp Trp Leu Asn
            180                 185                 190
Gly Lys Glu Phe Lys Cys Arg Val Asn Ser Ala Ala Phe Pro Ala Pro
        195                 200                 205
Ile Glu Lys Thr Ile Ser Lys Thr Lys Gly Arg Pro Lys Ala Pro Gln
210                 215                 220
Val Tyr Thr Ile Pro Pro Lys Glu Gln Met Ala Lys Asp Lys Val
225                 230                 235                 240
Ser Leu Thr Cys Met Ile Thr Asp Phe Phe Pro Glu Asp Ile Thr Val
                245                 250                 255
Glu Trp Gln Trp Asn Gly Gln Pro Ala Glu Asn Tyr Lys Asn Thr Gln
            260                 265                 270
Pro Ile Met Asp Thr Asp Gly Ser Tyr Phe Val Tyr Ser Lys Leu Asn
        275                 280                 285
Val Gln Lys Ser Asn Trp Glu Ala Gly Asn Thr Phe Thr Cys Ser Val
290                 295                 300
Leu His Glu Gly Leu His Asn His His Thr Glu Lys Ser Leu Ser His
305                 310                 315                 320
Ser Pro Gly Lys

<210> SEQ ID NO 7
<211> LENGTH: 443
<212> TYPE: PRT
<213> ORGANISM: Artificial Sequence
<220> FEATURE:
<223> OTHER INFORMATION: an artificially synthesized sequence

<400> SEQUENCE: 7

Gln Val Gln Leu Gln Glu Ser Gly Pro Gly Leu Val Lys Pro Ser Glu
1               5                   10                  15
Thr Leu Ser Leu Thr Cys Ala Val Ser Gly His Ser Ile Ser His Asp
            20                  25                  30
His Ala Trp Ser Trp Val Arg Gln Pro Pro Gly Glu Gly Leu Glu Trp
        35                  40                  45
Ile Gly Phe Ile Ser Tyr Ser Gly Ile Thr Asn Tyr Asn Pro Ser Leu
    50                  55                  60
Gln Gly Arg Val Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg Ser Leu Ala Arg Thr Thr Ala Met Asp Tyr Trp Gly Glu Gly
            100                 105                 110
Thr Leu Val Thr Val Ser Ser Ala Lys Thr Thr Pro Pro Ser Val Tyr
        115                 120                 125
Pro Leu Ala Pro Gly Ser Ala Ala Gln Thr Asn Ser Met Val Thr Leu
    130                 135                 140
```

Gly Cys Leu Val Lys Gly Tyr Phe Pro Glu Pro Val Thr Val Thr Trp
145                 150                 155                 160

Asn Ser Gly Ser Leu Ser Ser Gly Val His Thr Phe Pro Ala Val Leu
            165                 170                 175

Gln Ser Asp Leu Tyr Thr Leu Ser Ser Val Thr Val Pro Ser Ser
        180                 185                 190

Thr Trp Pro Ser Glu Thr Val Thr Cys Asn Val Ala His Pro Ala Ser
            195                 200                 205

Ser Thr Lys Val Asp Lys Lys Ile Val Pro Arg Asp Cys Gly Cys Lys
        210                 215                 220

Pro Cys Ile Cys Thr Val Pro Glu Val Ser Ser Val Phe Ile Phe Pro
225                 230                 235                 240

Pro Lys Pro Lys Asp Val Leu Thr Ile Thr Leu Thr Pro Lys Val Thr
            245                 250                 255

Cys Val Val Val Asp Ile Ser Lys Asp Asp Pro Glu Val Gln Phe Ser
            260                 265                 270

Trp Phe Val Asp Asp Val Glu Val His Thr Ala Gln Thr Gln Pro Arg
        275                 280                 285

Glu Glu Gln Phe Asn Ser Thr Phe Arg Ser Val Ser Glu Leu Pro Ile
290                 295                 300

Met His Gln Asp Trp Leu Asn Gly Lys Glu Phe Lys Cys Arg Val Asn
305                 310                 315                 320

Ser Ala Ala Phe Pro Ala Pro Ile Glu Lys Thr Ile Ser Lys Thr Lys
            325                 330                 335

Gly Arg Pro Lys Ala Pro Gln Val Tyr Thr Ile Pro Pro Lys Glu
        340                 345                 350

Gln Met Ala Lys Asp Lys Val Ser Leu Thr Cys Met Ile Thr Asp Phe
        355                 360                 365

Phe Pro Glu Asp Ile Thr Val Glu Trp Gln Trp Asn Gly Gln Pro Ala
        370                 375                 380

Glu Asn Tyr Lys Asn Thr Gln Pro Ile Met Asp Thr Asp Gly Ser Tyr
385                 390                 395                 400

Phe Val Tyr Ser Lys Leu Asn Val Gln Lys Ser Asn Trp Glu Ala Gly
            405                 410                 415

Asn Thr Phe Thr Cys Ser Val Leu His Glu Gly Leu His Asn His His
            420                 425                 430

Thr Glu Lys Ser Leu Ser His Ser Pro Gly Lys
        435                 440

<210> SEQ ID NO 8
<211> LENGTH: 443
<212> TYPE: PRT
<213> ORGANISM: Artificial Sequence
<220> FEATURE:
<223> OTHER INFORMATION: an artificially synthesized sequence

<400> SEQUENCE: 8

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

```
Gln Gly Arg Val Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Ser Leu Ala Arg Thr Thr Ala Met Asp Tyr Trp Gly Glu Gly
            100                 105                 110

Thr Leu Val Thr Val Ser Ser Ala Lys Thr Thr Pro Pro Ser Val Tyr
        115                 120                 125

Pro Leu Ala Pro Gly Ser Ala Ala Gln Thr Asn Ser Met Val Thr Leu
130                 135                 140

Gly Cys Leu Val Lys Gly Tyr Phe Pro Glu Pro Val Thr Val Thr Trp
145                 150                 155                 160

Asn Ser Gly Ser Leu Ser Ser Gly Val His Thr Phe Pro Ala Val Leu
                165                 170                 175

Gln Ser Asp Leu Tyr Thr Leu Ser Ser Ser Val Thr Val Pro Ser Ser
            180                 185                 190

Thr Trp Pro Ser Glu Thr Val Thr Cys Asn Val Ala His Pro Ala Ser
        195                 200                 205

Ser Thr Lys Val Asp Lys Lys Ile Val Pro Arg Asp Cys Gly Cys Lys
210                 215                 220

Pro Cys Ile Cys Glu Ala Asn Glu Val Glu Asp Val Phe Ile Phe Pro
225                 230                 235                 240

Pro Lys Pro Lys Asp Val Leu Thr Ile Thr Leu Thr Pro Lys Val Thr
                245                 250                 255

Cys Val Val Val Asp Ile Ser Lys Asp Asp Pro Glu Val Gln Phe Ser
            260                 265                 270

Trp Phe Val Asp Asp Val Glu Val His Thr Ala Gln Thr Gln Pro Arg
        275                 280                 285

Glu Glu Gln Phe Asn Ser Thr Phe Arg Ser Val Ser Glu Leu Pro Ile
290                 295                 300

Met His Gln Asp Trp Leu Asn Gly Lys Glu Phe Lys Cys Arg Val Asn
305                 310                 315                 320

Ser Ala Ala Phe Pro Ala Pro Ile Glu Lys Thr Ile Ser Lys Thr Lys
                325                 330                 335

Gly Arg Pro Lys Ala Pro Gln Val Tyr Thr Ile Pro Pro Lys Glu
            340                 345                 350

Gln Met Ala Lys Asp Lys Val Ser Leu Thr Cys Met Ile Thr Asp Phe
        355                 360                 365

Phe Pro Glu Asp Ile Thr Val Glu Trp Gln Trp Asn Gly Gln Pro Ala
370                 375                 380

Glu Asn Tyr Lys Asn Thr Gln Pro Ile Met Asp Thr Asp Gly Ser Tyr
385                 390                 395                 400

Phe Val Tyr Ser Lys Leu Asn Val Gln Lys Ser Asn Trp Glu Ala Gly
                405                 410                 415

Asn Thr Phe Thr Cys Ser Val Leu His Glu Gly Leu His Asn His His
            420                 425                 430

Thr Glu Lys Ser Leu Ser His Ser Pro Gly Lys
        435                 440

<210> SEQ ID NO 9
<211> LENGTH: 443
<212> TYPE: PRT
<213> ORGANISM: Artificial Sequence
<220> FEATURE:
```

<223> OTHER INFORMATION: an artificially synthesized sequence

<400> SEQUENCE: 9

```
Gln Val Gln Leu Gln Glu Ser Gly Pro Gly Leu Val Lys Pro Ser Glu
 1               5                  10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Lys Thr Thr Pro Pro Ser Val Tyr
        115                 120                 125

Pro Leu Ala Pro Gly Ser Ala Ala Gln Thr Asn Ser Met Val Thr Leu
    130                 135                 140

Gly Cys Leu Val Lys Gly Tyr Phe Pro Glu Pro Val Thr Val Thr Trp
145                 150                 155                 160

Asn Ser Gly Ser Leu Ser Ser Gly Val His Thr Phe Pro Ala Val Leu
                165                 170                 175

Gln Ser Asp Leu Tyr Thr Leu Ser Ser Val Thr Val Pro Ser Ser
            180                 185                 190

Thr Trp Pro Ser Glu Thr Val Thr Cys Asn Val Ala His Pro Ala Ser
        195                 200                 205

Ser Thr Lys Val Asp Lys Lys Ile Val Pro Arg Asp Cys Gly Cys Lys
    210                 215                 220

Pro Cys Ile Cys Thr Val Pro Glu Val Ser Asp Val Phe Ile Phe Pro
225                 230                 235                 240

Pro Lys Pro Lys Asp Val Leu Thr Ile Thr Leu Thr Pro Lys Val Thr
                245                 250                 255

Cys Val Val Val Asp Ile Ser Lys Asp Asp Pro Glu Val Gln Phe Ser
            260                 265                 270

Trp Phe Val Asp Asp Val Glu Val His Thr Ala Gln Thr Gln Pro Arg
        275                 280                 285

Glu Glu Gln Phe Asn Ser Thr Phe Arg Ser Val Ser Glu Leu Pro Ile
    290                 295                 300

Met His Gln Asp Trp Leu Asn Gly Lys Glu Phe Lys Cys Arg Val Asn
305                 310                 315                 320

Ser Ala Asp Phe Pro Ala Pro Ile Glu Lys Thr Ile Ser Lys Thr Lys
                325                 330                 335

Gly Arg Pro Lys Ala Pro Gln Val Tyr Thr Ile Pro Pro Pro Lys Glu
            340                 345                 350

Gln Met Ala Lys Asp Lys Val Ser Leu Thr Cys Met Ile Thr Asp Phe
        355                 360                 365

Phe Pro Glu Asp Ile Thr Val Glu Trp Gln Trp Asn Gly Gln Pro Ala
    370                 375                 380

Glu Asn Tyr Lys Asn Thr Gln Pro Ile Met Asp Thr Asp Gly Ser Tyr
385                 390                 395                 400
```

```
Phe Val Tyr Ser Lys Leu Asn Val Gln Lys Ser Asn Trp Glu Ala Gly
                405                 410                 415

Asn Thr Phe Thr Cys Ser Val Leu His Glu Gly Leu His Asn His His
            420                 425                 430

Thr Glu Lys Ser Leu Ser His Ser Pro Gly Lys
        435                 440

<210> SEQ ID NO 10
<211> LENGTH: 1125
<212> TYPE: DNA
<213> ORGANISM: Homo sapiens

<400> SEQUENCE: 10
atgtggttct tgacaactct gctcctttgg gttccagttg atgggcaagt ggacaccaca      60
aaggcagtga tcactttgca gcctccatgg gtcagcgtgt tccaagagga aaccgtaacc     120
ttgcactgtg aggtgctcca tctgcctggg agcagctcta cacagtggtt tctcaatggc     180
acagccactc agacctcgac ccccagctac agaatcacct tgccagtgt caatgacagt      240
ggtgaataca ggtgccagag aggtctctca gggcgaagtg accccataca gctggaaatc     300
cacagaggct ggctactact gcaggtctcc agcagagtct tcacggaagg agaacctctg     360
gccttgaggt gtcatgcgtg gaaggataag ctggtgtaca atgtgcttta ctatcgaaat     420
ggcaaagcct ttaagttttt ccactggaat tctaacctca ccattctgaa aaccaacata     480
agtcacaatg gcacctacca ttgctcaggc atgggaaagc atcgctacac atcagcagga     540
atatctgtca ctgtgaaaga gctatttcca gctccagtgc tgaatgcatc tgtgacatcc     600
ccactcctgg aggggaatct ggtcaccctg agctgtgaaa caaagttgct cttgcagagg     660
cctggtttgc agctttactt ctccttctac atgggcagca gaccctgcg aggcaggaac     720
acatcctctg aataccaaat actaactgct agaagagaag actctgggtt atactggtgc     780
gaggctgcca cagaggatgg aaatgtcctt aagcgcagcc tgagttgga gcttcaagtg     840
cttggcctcc agttaccaac tcctgtctgg tttcatgtcc ttttctatct ggcagtggga     900
ataatgtttt tagtgaacac tgttctctgg gtgacaatac gtaaagaact gaaaagaaag     960
aaaaagtggg atttagaaat ctctttggat tctggtcatg agaagaaggt aatttccagc    1020
cttcaagaag acagacattt agaagaagag ctgaaatgtc aggaacaaaa agaagaacag    1080
ctgcaggaag gggtgcaccg gaaggagccc caggggggcca cgtag                   1125

<210> SEQ ID NO 11
<211> LENGTH: 374
<212> TYPE: PRT
<213> ORGANISM: Homo sapiens

<400> SEQUENCE: 11

Met Trp Phe Leu Thr Thr Leu Leu Leu Trp Val Pro Val Asp Gly Gln
1               5                   10                  15

Val Asp Thr Thr Lys Ala Val Ile Thr Leu Gln Pro Pro Trp Val Ser
            20                  25                  30

Val Phe Gln Glu Glu Thr Val Thr Leu His Cys Glu Val Leu His Leu
        35                  40                  45

Pro Gly Ser Ser Ser Thr Gln Trp Phe Leu Asn Gly Thr Ala Thr Gln
    50                  55                  60

Thr Ser Thr Pro Ser Tyr Arg Ile Thr Ser Ala Ser Val Asn Asp Ser
65                  70                  75                  80

Gly Glu Tyr Arg Cys Gln Arg Gly Leu Ser Gly Arg Ser Asp Pro Ile
```

```
                85                  90                  95
Gln Leu Glu Ile His Arg Gly Trp Leu Leu Gln Val Ser Ser Arg
            100                 105                 110

Val Phe Thr Glu Gly Glu Pro Leu Ala Leu Arg Cys His Ala Trp Lys
        115                 120                 125

Asp Lys Leu Val Tyr Asn Val Leu Tyr Tyr Arg Asn Gly Lys Ala Phe
130                 135                 140

Lys Phe Phe His Trp Asn Ser Asn Leu Thr Ile Leu Lys Thr Asn Ile
145                 150                 155                 160

Ser His Asn Gly Thr Tyr His Cys Ser Gly Met Gly Lys His Arg Tyr
                165                 170                 175

Thr Ser Ala Gly Ile Ser Val Thr Val Lys Glu Leu Phe Pro Ala Pro
            180                 185                 190

Val Leu Asn Ala Ser Val Thr Ser Pro Leu Leu Glu Gly Asn Leu Val
        195                 200                 205

Thr Leu Ser Cys Glu Thr Lys Leu Leu Leu Gln Arg Pro Gly Leu Gln
    210                 215                 220

Leu Tyr Phe Ser Phe Tyr Met Gly Ser Lys Thr Leu Arg Gly Arg Asn
225                 230                 235                 240

Thr Ser Ser Glu Tyr Gln Ile Leu Thr Ala Arg Arg Glu Asp Ser Gly
                245                 250                 255

Leu Tyr Trp Cys Glu Ala Ala Thr Glu Asp Gly Asn Val Leu Lys Arg
            260                 265                 270

Ser Pro Glu Leu Glu Leu Gln Val Leu Gly Leu Gln Leu Pro Thr Pro
        275                 280                 285

Val Trp Phe His Val Leu Phe Tyr Leu Ala Val Gly Ile Met Phe Leu
    290                 295                 300

Val Asn Thr Val Leu Trp Val Thr Ile Arg Lys Glu Leu Lys Arg Lys
305                 310                 315                 320

Lys Lys Trp Asp Leu Glu Ile Ser Leu Asp Ser Gly His Glu Lys Lys
                325                 330                 335

Val Ile Ser Ser Leu Gln Glu Asp Arg His Leu Glu Glu Glu Leu Lys
            340                 345                 350

Cys Gln Glu Gln Lys Glu Glu Gln Leu Gln Glu Gly Val His Arg Lys
        355                 360                 365

Glu Pro Gln Gly Ala Thr
    370

<210> SEQ ID NO 12
<211> LENGTH: 951
<212> TYPE: DNA
<213> ORGANISM: Homo sapiens

<400> SEQUENCE: 12
atgactatgg agacccaaat gtctcagaat gtatgtccca gaaacctgtg gctgcttcaa      60
ccattgacag ttttgctgct gctggcttct gcagacagtc aagctgctcc cccaaaggct     120
gtgctgaaac ttgagccccc gtggatcaac gtgctccagg aggactctgt gactctgaca     180
tgccaggggg ctcgcagccc tgagagcgac tccattcagt ggttccacaa tgggaatctc     240
attcccaccc acacgcagcc cagctacagg ttcaaggcca caacaatga cagcggggag     300 tacacgtgcc agactggcca gaccagcctg agcgaccctg tgcatctgac tgtgctttcc     360
gaatggctgg tgctccagac ccctcacctg gagttccagg gggagaaaac catcatgctg     420
aggtgccaca gctggaagga caagcctctg gtcaaggtca cattcttcca gaatggaaaa     480
```

```
tcccagaaat tctcccattt ggatcccacc ttctccatcc cacaagcaaa ccacagtcac    540
agtggtgatt accactgcac aggaaacata ggctacacgc tgttctcatc caagcctgtg    600
accatcactg tccaagtgcc cagcatgggc agctcttcac caatgggggt cattgtggct    660
gtggtcattg cgactgctgt agcagccatt gttgctgctg tagtggcctt gatctactgc    720
aggaaaaagc ggatttcagc caattccact gatcctgtga aggctgccca atttgagcca    780
cctggacgtc aaatgattgc catcagaaag agacaacttg aagaaaccaa caatgactat    840
gaaacagctg acggcggcta catgactctg aaccccaggg cacctactga cgatgataaa    900
aacatctacc tgactcttcc tcccaacgac catgtcaaca gtaataacta a             951
```

<210> SEQ ID NO 13
<211> LENGTH: 316
<212> TYPE: PRT
<213> ORGANISM: Homo sapiens

<400> SEQUENCE: 13

```
Met Thr Met Glu Thr Gln Met Ser Gln Asn Val Cys Pro Arg Asn Leu
1               5                   10                  15

Trp Leu Leu Gln Pro Leu Thr Val Leu Leu Leu Leu Ala Ser Ala Asp
            20                  25                  30

Ser Gln Ala Ala Pro Pro Lys Ala Val Leu Lys Leu Glu Pro Pro Trp
        35                  40                  45

Ile Asn Val Leu Gln Glu Asp Ser Val Thr Leu Thr Cys Gln Gly Ala
    50                  55                  60

Arg Ser Pro Glu Ser Asp Ser Ile Gln Trp Phe His Asn Gly Asn Leu
65                  70                  75                  80

Ile Pro Thr His Thr Gln Pro Ser Tyr Arg Phe Lys Ala Asn Asn Asn
                85                  90                  95

Asp Ser Gly Glu Tyr Thr Cys Gln Thr Gly Gln Thr Ser Leu Ser Asp
            100                 105                 110

Pro Val His Leu Thr Val Leu Ser Glu Trp Leu Val Leu Gln Thr Pro
        115                 120                 125

His Leu Glu Phe Gln Glu Gly Glu Thr Ile Met Leu Arg Cys His Ser
    130                 135                 140

Trp Lys Asp Lys Pro Leu Val Lys Val Thr Phe Phe Gln Asn Gly Lys
145                 150                 155                 160

Ser Gln Lys Phe Ser His Leu Asp Pro Thr Phe Ser Ile Pro Gln Ala
                165                 170                 175

Asn His Ser His Ser Gly Asp Tyr His Cys Thr Gly Asn Ile Gly Tyr
            180                 185                 190

Thr Leu Phe Ser Ser Lys Pro Val Thr Ile Thr Val Gln Val Pro Ser
        195                 200                 205

Met Gly Ser Ser Ser Pro Met Gly Val Ile Val Ala Val Val Ile Ala
    210                 215                 220

Thr Ala Val Ala Ala Ile Val Ala Ala Val Val Ala Leu Ile Tyr Cys
225                 230                 235                 240

Arg Lys Lys Arg Ile Ser Ala Asn Ser Thr Asp Pro Val Lys Ala Ala
                245                 250                 255

Gln Phe Glu Pro Pro Gly Arg Gln Met Ile Ala Ile Arg Lys Arg Gln
            260                 265                 270

Leu Glu Glu Thr Asn Asn Asp Tyr Glu Thr Ala Asp Gly Gly Tyr Met
        275                 280                 285
```

```
Thr Leu Asn Pro Arg Ala Pro Thr Asp Asp Asp Lys Asn Ile Tyr Leu
        290                 295                 300

Thr Leu Pro Pro Asn Asp His Val Asn Ser Asn Asn
305                 310                 315

<210> SEQ ID NO 14
<211> LENGTH: 876
<212> TYPE: DNA
<213> ORGANISM: Homo sapiens

<400> SEQUENCE: 14
atgggaatcc tgtcattctt acctgtcctt gccactgaga gtgactgggc tgactgcaag      60 tcccccagc cttggggtca tatgcttctg tggacagctg tgctattcct ggctcctgtt     120
gctgggacac ctgcagctcc cccaaaggct gtgctgaaac tcgagcccca gtggatcaac     180
gtgctccagg aggactctgt gactctgaca tgccggggga ctcacagccc tgagagcgac     240
tccattcagt ggttccacaa tgggaatctc attcccaccc acacgcagcc cagctacagg     300
ttcaaggcca acaacaatga cagcggggag tacacgtgcc agactggcca gaccagcctc     360
agcgaccctg tgcatctgac tgtgctttct gagtggctgg tgctccagac ccctcacctg     420
gagttccagg agggagaaac catcgtgctg aggtgccaca gctggaagga caagcctctg     480
gtcaaggtca cattcttcca gaatggaaaa tccaagaaat tttcccgttc ggatcccaac     540
ttctccatcc acaagcaaa ccacagtcac agtggtgatt accactgcac aggaaacata     600
ggctacacgc tgtactcatc caagcctgtg accatcactg tccaagctcc cagctcttca     660
ccgatgggga tcattgtggc tgtggtcact gggattgctg tagcggccat tgttgctgct     720
gtagtggcct tgatctactg caggaaaaag cggatttcag ccaatcccac taatcctgat     780
gaggctgaca agttggggc tgagaacaca atcacctatt cacttctcat gcacccggat     840
gctctggaag agcctgatga ccagaaccgt atttag                              876

<210> SEQ ID NO 15
<211> LENGTH: 291
<212> TYPE: PRT
<213> ORGANISM: Homo sapiens

<400> SEQUENCE: 15

Met Gly Ile Leu Ser Phe Leu Pro Val Leu Ala Thr Glu Ser Asp Trp
1               5                   10                  15

Ala Asp Cys Lys Ser Pro Gln Pro Trp Gly His Met Leu Leu Trp Thr
            20                  25                  30

Ala Val Leu Phe Leu Ala Pro Val Ala Gly Thr Pro Ala Ala Pro Pro
        35                  40                  45

Lys Ala Val Leu Lys Leu Glu Pro Gln Trp Ile Asn Val Leu Gln Glu
    50                  55                  60

Asp Ser Val Thr Leu Thr Cys Arg Gly Thr His Ser Pro Glu Ser Asp
65                  70                  75                  80

Ser Ile Gln Trp Phe His Asn Gly Asn Leu Ile Pro Thr His Thr Gln
                85                  90                  95

Pro Ser Tyr Arg Phe Lys Ala Asn Asn Asn Asp Ser Gly Glu Tyr Thr
            100                 105                 110

Cys Gln Thr Gly Gln Thr Ser Leu Ser Asp Pro Val His Leu Thr Val
        115                 120                 125

Leu Ser Glu Trp Leu Val Leu Gln Thr Pro His Leu Glu Phe Gln Glu
    130                 135                 140
```

```
Gly Glu Thr Ile Val Leu Arg Cys His Ser Trp Lys Asp Lys Pro Leu
145                 150                 155                 160

Val Lys Val Thr Phe Phe Gln Asn Gly Lys Ser Lys Lys Phe Ser Arg
            165                 170                 175

Ser Asp Pro Asn Phe Ser Ile Pro Gln Ala Asn His Ser His Ser Gly
            180                 185                 190

Asp Tyr His Cys Thr Gly Asn Ile Gly Tyr Thr Leu Tyr Ser Ser Lys
            195                 200                 205

Pro Val Thr Ile Thr Val Gln Ala Pro Ser Ser Pro Met Gly Ile
            210                 215                 220

Ile Val Ala Val Val Thr Gly Ile Ala Val Ala Ala Ile Val Ala Ala
225                 230                 235                 240

Val Val Ala Leu Ile Tyr Cys Arg Lys Lys Arg Ile Ser Ala Asn Pro
            245                 250                 255

Thr Asn Pro Asp Glu Ala Asp Lys Val Gly Ala Glu Asn Thr Ile Thr
            260                 265                 270

Tyr Ser Leu Leu Met His Pro Asp Ala Leu Glu Glu Pro Asp Asp Gln
            275                 280                 285

Asn Arg Ile
    290
```

<210> SEQ ID NO 16
<211> LENGTH: 765
<212> TYPE: DNA
<213> ORGANISM: Homo sapiens

<400> SEQUENCE: 16

```
atgtggcagc tgctcctccc aactgctctg ctacttctag tttcagctgg catgcggact    60
gaagatctcc caaaggctgt ggtgttcctg agcctcaat ggtacagggt gctcgagaag   120
gacagtgtga ctctgaagtg ccagggagcc tactcccctg aggacaattc cacacagtgg   180
tttcacaatg agagcctcat ctcaagccag gcctcgagct acttcattga cgctgccaca   240
gttgacgaca gtggagagta caggtgccag acaaacctct ccaccctcag tgacccggtg   300
cagctagaag tccatatcgg ctggctgttg ctccaggccc ctcggtgggt gttcaaggag   360
gaagaccta ttcacctgag gtgtcacagc tggaagaaca ctgctctgca taaggtcaca   420
tatttacaga tggcaaagg caggaagtat tttcatcata attctgactt ctacattcca   480
aaagccacac tcaaagacag cggctcctac ttctgcaggg ggcttgttgg gagtaaaaat   540
gtgtcttcag agactgtgaa catcaccatc actcaaggtt tgtcagtgtc aaccatctca   600
tcattctttc cacctgggta ccaagtctct ttctgcttgg tgatggtact ccttttttgca  660
gtggacacag gactatattt ctctgtgaag acaaacattc gaagctcaac aagagactgg   720
aaggaccata aatttaaatg gagaaaggac cctcaagaca aatga                   765
```

<210> SEQ ID NO 17
<211> LENGTH: 254
<212> TYPE: PRT
<213> ORGANISM: Homo sapiens

<400> SEQUENCE: 17

```
Met Trp Gln Leu Leu Leu Pro Thr Ala Leu Leu Leu Leu Val Ser Ala
1               5                   10                  15

Gly Met Arg Thr Glu Asp Leu Pro Lys Ala Val Val Phe Leu Glu Pro
            20                  25                  30

Gln Trp Tyr Arg Val Leu Glu Lys Asp Ser Val Thr Leu Lys Cys Gln
```

|                 |                 |                 |                 |                 |                 |                 |                 |                 |                 |                 |                 |
|-----------------|-----------------|-----------------|-----------------|-----------------|-----------------|-----------------|-----------------|-----------------|-----------------|-----------------|-----------------|
|                 |                 |                 | 35              |                 |                 |                 | 40              |                 |                 |                 | 45              |
| Gly             | Ala             | Tyr             | Ser             | Pro             | Glu             | Asp             | Asn             | Ser             | Thr             | Gln             | Trp             | Phe | His | Asn | Glu |
| 50              |                 |                 |                 |                 | 55              |                 |                 |                 |                 | 60              |

Ser Leu Ile Ser Ser Gln Ala Ser Ser Tyr Phe Ile Asp Ala Ala Thr
65                      70                      75                      80

Val Asp Asp Ser Gly Glu Tyr Arg Cys Gln Thr Asn Leu Ser Thr Leu
                    85                      90                      95

Ser Asp Pro Val Gln Leu Glu Val His Ile Gly Trp Leu Leu Leu Gln
                100                     105                     110

Ala Pro Arg Trp Val Phe Lys Glu Glu Asp Pro Ile His Leu Arg Cys
            115                     120                     125

His Ser Trp Lys Asn Thr Ala Leu His Lys Val Thr Tyr Leu Gln Asn
        130                     135                     140

Gly Lys Gly Arg Lys Tyr Phe His His Asn Ser Asp Phe Tyr Ile Pro
145                     150                     155                     160

Lys Ala Thr Leu Lys Asp Ser Gly Ser Tyr Phe Cys Arg Gly Leu Val
                165                     170                     175

Gly Ser Lys Asn Val Ser Ser Glu Thr Val Asn Ile Thr Ile Thr Gln
                180                     185                     190

Gly Leu Ser Val Ser Thr Ile Ser Ser Phe Phe Pro Pro Gly Tyr Gln
            195                     200                     205

Val Ser Phe Cys Leu Val Met Val Leu Leu Phe Ala Val Asp Thr Gly
210                     215                     220

Leu Tyr Phe Ser Val Lys Thr Asn Ile Arg Ser Ser Thr Arg Asp Trp
225                     230                     235                     240

Lys Asp His Lys Phe Lys Trp Arg Lys Asp Pro Gln Asp Lys
                245                     250

<210> SEQ ID NO 18
<211> LENGTH: 702
<212> TYPE: DNA
<213> ORGANISM: Homo sapiens

<400> SEQUENCE: 18

| atgtggcagc tgctcctccc aactgctctg ctacttctag tttcagctgg catgcggact | 60 |
| gaagatctcc caaaggctgt ggtgttcctg gagcctcaat ggtacagcgt gcttgagaag | 120 |
| gacagtgtga ctctgaagtg ccagggagcc tactcccctg aggacaattc acacagtgg | 180 |
| tttcacaatg agagcctcat ctcaagccag gcctcgagct acttcattga cgctgccaca | 240 |
| gtcaacgaca gtggagagta caggtgccag acaaacctct ccaccctcag tgacccggtg | 300 |
| cagctagaag tccatatcgg ctggctgttg ctccaggccc ctcggtgggt gttcaaggag | 360 |
| gaagacccta ttcacctgag gtgtcacagc tggaagaaca ctgctctgca taaggtcaca | 420 |
| tatttacaga atggcaaaga caggaagtat tttcatcata attctgactt ccacattcca | 480 |
| aaagccacac tcaaagatag cggctcctac ttctgcaggg ggcttgttgg agtaaaaat | 540 |
| gtgtcttcag agactgtgaa catcaccatc actcaaggtt tggcagtgtc aaccatctca | 600 |
| tcattctctc cacctgggta ccaagtctct ttctgcttgg tgatggtact cctttttgca | 660 |
| gtggacacag gactatattt ctctgtgaag acaaacattt ga | 702 |

<210> SEQ ID NO 19
<211> LENGTH: 233
<212> TYPE: PRT
<213> ORGANISM: Homo sapiens

<400> SEQUENCE: 19

```
Met Trp Gln Leu Leu Leu Pro Thr Ala Leu Leu Leu Val Ser Ala
1               5                   10                  15

Gly Met Arg Thr Glu Asp Leu Pro Lys Ala Val Val Phe Leu Glu Pro
            20                  25                  30

Gln Trp Tyr Ser Val Leu Glu Lys Asp Ser Val Thr Leu Lys Cys Gln
        35                  40                  45

Gly Ala Tyr Ser Pro Glu Asp Asn Ser Thr Gln Trp Phe His Asn Glu
    50                  55                  60

Ser Leu Ile Ser Ser Gln Ala Ser Ser Tyr Phe Ile Asp Ala Ala Thr
65                  70                  75                  80

Val Asn Asp Ser Gly Glu Tyr Arg Cys Gln Thr Asn Leu Ser Thr Leu
                85                  90                  95

Ser Asp Pro Val Gln Leu Glu Val His Ile Gly Trp Leu Leu Leu Gln
            100                 105                 110

Ala Pro Arg Trp Val Phe Lys Glu Glu Asp Pro Ile His Leu Arg Cys
        115                 120                 125

His Ser Trp Lys Asn Thr Ala Leu His Lys Val Thr Tyr Leu Gln Asn
    130                 135                 140

Gly Lys Asp Arg Lys Tyr Phe His His Asn Ser Asp Phe His Ile Pro
145                 150                 155                 160

Lys Ala Thr Leu Lys Asp Ser Gly Ser Tyr Phe Cys Arg Gly Leu Val
                165                 170                 175

Gly Ser Lys Asn Val Ser Ser Glu Thr Val Asn Ile Thr Ile Thr Gln
            180                 185                 190

Gly Leu Ala Val Ser Thr Ile Ser Ser Phe Ser Pro Pro Gly Tyr Gln
        195                 200                 205

Val Ser Phe Cys Leu Val Met Val Leu Leu Phe Ala Val Asp Thr Gly
    210                 215                 220

Leu Tyr Phe Ser Val Lys Thr Asn Ile
225                 230
```

<210> SEQ ID NO 20
<211> LENGTH: 404
<212> TYPE: PRT
<213> ORGANISM: Mus musculus

<400> SEQUENCE: 20

```
Met Ile Leu Thr Ser Phe Gly Asp Asp Met Trp Leu Leu Thr Thr Leu
1               5                   10                  15

Leu Leu Trp Val Pro Val Gly Gly Glu Val Val Asn Ala Thr Lys Ala
            20                  25                  30

Val Ile Thr Leu Gln Pro Pro Trp Val Ser Ile Phe Gln Lys Glu Asn
        35                  40                  45

Val Thr Leu Trp Cys Glu Gly Pro His Leu Pro Gly Asp Ser Ser Thr
    50                  55                  60

Gln Trp Phe Ile Asn Gly Thr Ala Val Gln Ile Ser Thr Pro Ser Tyr
65                  70                  75                  80

Ser Ile Pro Glu Ala Ser Phe Gln Asp Ser Gly Glu Tyr Arg Cys Gln
                85                  90                  95

Ile Gly Ser Ser Met Pro Ser Asp Pro Val Gln Leu Gln Ile His Asn
            100                 105                 110

Asp Trp Leu Leu Leu Gln Ala Ser Arg Arg Val Leu Thr Glu Gly Glu
        115                 120                 125
```

```
Pro Leu Ala Leu Arg Cys His Gly Trp Lys Asn Lys Leu Val Tyr Asn
130                 135                 140

Val Val Phe Tyr Arg Asn Gly Lys Ser Phe Gln Phe Ser Ser Asp Ser
145                 150                 155                 160

Glu Val Ala Ile Leu Lys Thr Asn Leu Ser His Ser Gly Ile Tyr His
                165                 170                 175

Cys Ser Gly Thr Gly Arg His Arg Tyr Thr Ser Ala Gly Val Ser Ile
            180                 185                 190

Thr Val Lys Glu Leu Phe Thr Thr Pro Val Leu Arg Ala Ser Val Ser
        195                 200                 205

Ser Pro Phe Pro Glu Gly Ser Leu Val Thr Leu Asn Cys Glu Thr Asn
210                 215                 220

Leu Leu Leu Gln Arg Pro Gly Leu Gln Leu His Phe Ser Phe Tyr Val
225                 230                 235                 240

Gly Ser Lys Ile Leu Glu Tyr Arg Asn Thr Ser Ser Glu Tyr His Ile
                245                 250                 255

Ala Arg Ala Glu Arg Glu Asp Ala Gly Phe Tyr Trp Cys Glu Val Ala
            260                 265                 270

Thr Glu Asp Ser Ser Val Leu Lys Arg Ser Pro Glu Leu Glu Leu Gln
        275                 280                 285

Val Leu Gly Pro Gln Ser Ser Ala Pro Val Trp Phe His Ile Leu Phe
290                 295                 300

Tyr Leu Ser Val Gly Ile Met Phe Ser Leu Asn Thr Val Leu Tyr Val
305                 310                 315                 320

Lys Ile His Arg Leu Gln Arg Glu Lys Lys Tyr Asn Leu Glu Val Pro
                325                 330                 335

Leu Val Ser Glu Gln Gly Lys Lys Ala Asn Ser Phe Gln Gln Val Arg
            340                 345                 350

Ser Asp Gly Val Tyr Glu Glu Val Thr Ala Thr Ala Ser Gln Thr Thr
        355                 360                 365

Pro Lys Glu Ala Pro Asp Gly Pro Arg Ser Ser Val Gly Asp Cys Gly
370                 375                 380

Pro Glu Gln Pro Glu Pro Leu Pro Pro Ser Asp Ser Thr Gly Ala Gln
385                 390                 395                 400

Thr Ser Gln Ser

<210> SEQ ID NO 21
<211> LENGTH: 293
<212> TYPE: PRT
<213> ORGANISM: Mus musculus

<400> SEQUENCE: 21

Met Gly Ile Leu Pro Phe Leu Leu Ile Pro Met Glu Ser Asn Trp Thr
1               5                   10                  15

Val His Val Phe Ser Arg Thr Leu Cys His Met Leu Leu Trp Thr Ala
                20                  25                  30

Val Leu Asn Leu Ala Ala Gly Thr His Asp Leu Pro Lys Ala Val Val
            35                  40                  45

Lys Leu Glu Pro Pro Trp Ile Gln Val Leu Lys Glu Asp Thr Val Thr
        50                  55                  60

Leu Thr Cys Glu Gly Thr His Asn Pro Gly Asn Ser Ser Thr Gln Trp
65                  70                  75                  80

Phe His Asn Gly Arg Ser Ile Arg Ser Gln Val Gln Ala Ser Tyr Thr
                85                  90                  95
```

```
Phe Lys Ala Thr Val Asn Asp Ser Gly Glu Tyr Arg Cys Gln Met Glu
                100                 105                 110

Gln Thr Arg Leu Ser Asp Pro Val Asp Leu Gly Val Ile Ser Asp Trp
            115                 120                 125

Leu Leu Leu Gln Thr Pro Gln Leu Val Phe Leu Glu Gly Glu Thr Ile
        130                 135                 140

Thr Leu Arg Cys His Ser Trp Arg Asn Lys Leu Leu Asn Arg Ile Ser
145                 150                 155                 160

Phe Phe His Asn Glu Lys Ser Val Arg Tyr His His Tyr Ser Ser Asn
                165                 170                 175

Phe Ser Ile Pro Lys Ala Asn His Ser His Ser Gly Asp Tyr Tyr Cys
            180                 185                 190

Lys Gly Ser Leu Gly Arg Thr Leu His Gln Ser Lys Pro Val Thr Ile
        195                 200                 205

Thr Val Gln Gly Pro Lys Ser Ser Arg Ser Leu Pro Val Leu Thr Ile
210                 215                 220

Val Ala Ala Val Thr Gly Ile Ala Val Ala Ala Ile Val Ile Ile Leu
225                 230                 235                 240

Val Ser Leu Val Tyr Leu Lys Lys Lys Gln Val Pro Asp Asn Pro Pro
                245                 250                 255

Asp Leu Glu Glu Ala Ala Lys Thr Glu Ala Glu Asn Thr Ile Thr Tyr
            260                 265                 270

Ser Leu Leu Lys His Pro Glu Ala Leu Asp Glu Glu Thr Glu His Asp
        275                 280                 285

Tyr Gln Asn His Ile
        290

<210> SEQ ID NO 22
<211> LENGTH: 267
<212> TYPE: PRT
<213> ORGANISM: Mus musculus

<400> SEQUENCE: 22

Met Thr Leu Asp Thr Gln Met Phe Gln Asn Ala His Ser Gly Ser Gln
1               5                   10                  15

Trp Leu Leu Pro Pro Leu Thr Ile Leu Leu Phe Ala Phe Ala Asp
                20                  25                  30

Arg Gln Ser Ala Ala Leu Pro Lys Ala Val Val Lys Leu Asp Pro Pro
            35                  40                  45

Trp Ile Gln Val Leu Lys Glu Asp Met Val Thr Leu Met Cys Glu Gly
        50                  55                  60

Thr His Asn Pro Gly Asn Ser Ser Thr Gln Trp Phe His Asn Trp Ser
65                  70                  75                  80

Ser Ile Arg Ser Gln Val Gln Ser Ser Tyr Thr Phe Lys Ala Thr Val
                85                  90                  95

Asn Asp Ser Gly Glu Tyr Arg Cys Gln Met Glu Gln Thr Arg Leu Ser
            100                 105                 110

Asp Pro Val Asp Leu Gly Val Ile Ser Asp Trp Leu Leu Leu Gln Thr
        115                 120                 125

Pro Gln Arg Val Phe Leu Glu Gly Glu Thr Ile Thr Leu Arg Cys His
    130                 135                 140

Ser Trp Arg Asn Lys Leu Leu Asn Arg Ile Ser Phe Phe His Asn Glu
145                 150                 155                 160

Lys Ser Val Arg Tyr His His Tyr Lys Ser Asn Phe Ser Ile Pro Lys
                165                 170                 175
```

```
Ala Asn His Ser His Ser Gly Asp Tyr Tyr Cys Lys Gly Ser Leu Gly
            180                 185                 190

Ser Thr Gln His Gln Ser Lys Pro Val Thr Ile Thr Val Gln Asp Pro
        195                 200                 205

Ala Thr Thr Ser Ser Ile Ser Leu Val Trp Tyr His Thr Ala Phe Ser
210                 215                 220

Leu Val Met Cys Leu Leu Phe Ala Val Asp Thr Gly Leu Tyr Phe Tyr
225                 230                 235                 240

Val Arg Arg Asn Leu Gln Thr Pro Arg Asp Tyr Trp Arg Lys Ser Leu
                245                 250                 255

Ser Ile Arg Lys His Gln Ala Pro Gln Asp Lys
            260                 265

<210> SEQ ID NO 23
<211> LENGTH: 249
<212> TYPE: PRT
<213> ORGANISM: Mus musculus

<400> SEQUENCE: 23

Met Trp Gln Leu Leu Pro Thr Ala Leu Val Leu Thr Ala Phe Ser
1               5                   10                  15

Gly Ile Gln Ala Gly Leu Gln Lys Ala Val Asn Leu Asp Pro Lys
            20                  25                  30

Trp Val Arg Val Leu Glu Glu Asp Ser Val Thr Leu Arg Cys Gln Gly
        35                  40                  45

Thr Phe Ser Pro Glu Asp Asn Ser Ile Lys Trp Phe His Asn Glu Ser
50                  55                  60

Leu Ile Pro His Gln Asp Ala Asn Tyr Val Ile Gln Ser Ala Arg Val
65                  70                  75                  80

Lys Asp Ser Gly Met Tyr Arg Cys Gln Thr Ala Leu Ser Thr Ile Ser
                85                  90                  95

Asp Pro Val Gln Leu Glu Val His Met Gly Trp Leu Leu Leu Gln Thr
            100                 105                 110

Thr Lys Trp Leu Phe Gln Glu Gly Asp Pro Ile His Leu Arg Cys His
        115                 120                 125

Ser Trp Gln Asn Arg Pro Val Arg Lys Val Thr Tyr Leu Gln Asn Gly
130                 135                 140

Lys Gly Lys Lys Tyr Phe His Glu Asn Ser Glu Leu Leu Ile Pro Lys
145                 150                 155                 160

Ala Thr His Asn Asp Ser Gly Ser Tyr Phe Cys Arg Gly Leu Ile Gly
                165                 170                 175

His Asn Asn Lys Ser Ser Ala Ser Phe Arg Ile Ser Leu Gly Asp Pro
            180                 185                 190

Gly Ser Pro Ser Met Phe Pro Pro Trp His Gln Ile Thr Phe Cys Leu
        195                 200                 205

Leu Ile Gly Leu Leu Phe Ala Ile Asp Thr Val Leu Tyr Phe Ser Val
210                 215                 220

Arg Arg Gly Leu Gln Ser Pro Val Ala Asp Tyr Glu Glu Pro Lys Ile
225                 230                 235                 240

Gln Trp Ser Lys Glu Pro Gln Asp Lys
                245

<210> SEQ ID NO 24
<211> LENGTH: 324
<212> TYPE: PRT
```

<213> ORGANISM: Mus musculus

<400> SEQUENCE: 24

```
Ala Lys Thr Thr Pro Pro Ser Val Tyr Pro Leu Ala Pro Gly Ser Ala
1               5                   10                  15
Ala Gln Thr Asn Ser Met Val Thr Leu Gly Cys Leu Val Lys Gly Tyr
            20                  25                  30
Phe Pro Glu Pro Val Thr Val Thr Trp Asn Ser Gly Ser Leu Ser Ser
        35                  40                  45
Gly Val His Thr Phe Pro Ala Val Leu Gln Ser Asp Leu Tyr Thr Leu
    50                  55                  60
Ser Ser Ser Val Thr Val Pro Ser Ser Thr Trp Pro Ser Glu Thr Val
65                  70                  75                  80
Thr Cys Asn Val Ala His Pro Ala Ser Ser Thr Lys Val Asp Lys Lys
                85                  90                  95
Ile Val Pro Arg Asp Cys Gly Cys Lys Pro Cys Ile Cys Thr Val Pro
            100                 105                 110
Glu Val Ser Ser Val Phe Ile Phe Pro Pro Lys Pro Lys Asp Val Leu
        115                 120                 125
Thr Ile Thr Leu Thr Pro Lys Val Thr Cys Val Val Asp Ile Ser
    130                 135                 140
Lys Asp Asp Pro Glu Val Gln Phe Ser Trp Phe Val Asp Asp Val Glu
145                 150                 155                 160
Val His Thr Ala Gln Thr Gln Pro Arg Glu Glu Gln Phe Asn Ser Thr
                165                 170                 175
Phe Arg Ser Val Ser Glu Leu Pro Ile Met His Gln Asp Trp Leu Asn
            180                 185                 190
Gly Lys Glu Phe Lys Cys Arg Val Asn Ser Ala Ala Phe Pro Ala Pro
        195                 200                 205
Ile Glu Lys Thr Ile Ser Lys Thr Lys Gly Arg Pro Lys Ala Pro Gln
    210                 215                 220
Val Tyr Thr Ile Pro Pro Lys Glu Gln Met Ala Lys Asp Lys Val
225                 230                 235                 240
Ser Leu Thr Cys Met Ile Thr Asp Phe Phe Pro Glu Asp Ile Thr Val
                245                 250                 255
Glu Trp Gln Trp Asn Gly Gln Pro Ala Glu Asn Tyr Lys Asn Thr Gln
            260                 265                 270
Pro Ile Met Asp Thr Asp Gly Ser Tyr Phe Val Tyr Ser Lys Leu Asn
        275                 280                 285
Val Gln Lys Ser Asn Trp Glu Ala Gly Asn Thr Phe Thr Cys Ser Val
    290                 295                 300
Leu His Glu Gly Leu His Asn His His Thr Glu Lys Ser Leu Ser His
305                 310                 315                 320
Ser Pro Gly Lys
```

<210> SEQ ID NO 25
<211> LENGTH: 330
<212> TYPE: PRT
<213> ORGANISM: Mus musculus

<400> SEQUENCE: 25

```
Ala Lys Thr Thr Ala Pro Ser Val Tyr Pro Leu Ala Pro Val Cys Gly
1               5                   10                  15
Asp Thr Thr Gly Ser Ser Val Thr Leu Gly Cys Leu Val Lys Gly Tyr
            20                  25                  30
```

```
Phe Pro Glu Pro Val Thr Leu Thr Trp Asn Ser Gly Ser Leu Ser Ser
            35                  40                  45

Gly Val His Thr Phe Pro Ala Val Leu Gln Ser Asp Leu Tyr Thr Leu
        50                  55                  60

Ser Ser Ser Val Thr Val Thr Ser Ser Thr Trp Pro Ser Gln Ser Ile
 65                  70                  75                  80

Thr Cys Asn Val Ala His Pro Ala Ser Ser Thr Lys Val Asp Lys Lys
                    85                  90                  95

Ile Glu Pro Arg Gly Pro Thr Ile Lys Pro Cys Pro Pro Cys Lys Cys
                100                 105                 110

Pro Ala Pro Asn Leu Leu Gly Gly Pro Ser Val Phe Ile Phe Pro Pro
                115                 120                 125

Lys Ile Lys Asp Val Leu Met Ile Ser Leu Ser Pro Ile Val Thr Cys
                130                 135                 140

Val Val Val Asp Val Ser Glu Asp Asp Pro Asp Val Gln Ile Ser Trp
145                 150                 155                 160

Phe Val Asn Asn Val Glu Val His Thr Ala Gln Thr Gln Thr His Arg
                165                 170                 175

Glu Asp Tyr Asn Ser Thr Leu Arg Val Val Ser Ala Leu Pro Ile Gln
                180                 185                 190

His Gln Asp Trp Met Ser Gly Lys Glu Phe Lys Cys Lys Val Asn Asn
                195                 200                 205

Lys Asp Leu Pro Ala Pro Ile Glu Arg Thr Ile Ser Lys Pro Lys Gly
                210                 215                 220

Ser Val Arg Ala Pro Gln Val Tyr Val Leu Pro Pro Pro Glu Glu Glu
225                 230                 235                 240

Met Thr Lys Lys Gln Val Thr Leu Thr Cys Met Val Thr Asp Phe Met
                245                 250                 255

Pro Glu Asp Ile Tyr Val Glu Trp Thr Asn Asn Gly Lys Thr Glu Leu
                260                 265                 270

Asn Tyr Lys Asn Thr Glu Pro Val Leu Asp Ser Asp Gly Ser Tyr Phe
                275                 280                 285

Met Tyr Ser Lys Leu Arg Val Glu Lys Lys Asn Trp Val Glu Arg Asn
                290                 295                 300

Ser Tyr Ser Cys Ser Val Val His Glu Gly Leu His Asn His His Thr
305                 310                 315                 320

Thr Lys Ser Phe Ser Arg Thr Pro Gly Lys
                325                 330

<210> SEQ ID NO 26
<211> LENGTH: 336
<212> TYPE: PRT
<213> ORGANISM: Mus musculus

<400> SEQUENCE: 26

Ala Lys Thr Thr Pro Pro Ser Val Tyr Pro Leu Ala Pro Gly Cys Gly
 1                   5                  10                  15

Asp Thr Thr Gly Ser Ser Val Thr Ser Gly Cys Leu Val Lys Gly Tyr
                 20                  25                  30

Phe Pro Glu Pro Val Thr Val Thr Trp Asn Ser Gly Ser Leu Ser Ser
             35                  40                  45

Ser Val His Thr Phe Pro Ala Leu Leu Gln Ser Gly Leu Tyr Thr Met
         50                  55                  60

Ser Ser Ser Val Thr Val Pro Ser Ser Thr Trp Pro Ser Gln Thr Val
```

```
                65                  70                  75                  80
        Thr Cys Ser Val Ala His Pro Ala Ser Thr Thr Val Asp Lys Lys
                        85                  90                  95

Leu Glu Pro Ser Gly Pro Ile Ser Thr Ile Asn Pro Cys Pro Cys
                        100                 105                 110

Lys Glu Cys His Lys Cys Pro Ala Pro Asn Leu Glu Gly Pro Ser
                        115                 120                 125

Val Phe Ile Phe Pro Pro Asn Ile Lys Asp Val Leu Met Ile Ser Leu
        130                 135                 140

Thr Pro Lys Val Thr Cys Val Val Asp Val Ser Glu Asp Asp Pro
        145                 150                 155                 160

Asp Val Gln Ile Ser Trp Phe Val Asn Asn Val Glu Val His Thr Ala
                        165                 170                 175

Gln Thr Gln Thr His Arg Glu Asp Tyr Asn Ser Thr Ile Arg Val Val
                        180                 185                 190

Ser Thr Leu Pro Ile Gln His Gln Asp Trp Met Ser Gly Lys Glu Phe
                        195                 200                 205

Lys Cys Lys Val Asn Asn Lys Asp Leu Pro Ser Pro Ile Glu Arg Thr
                        210                 215                 220

Ile Ser Lys Ile Lys Gly Leu Val Arg Ala Pro Gln Val Tyr Thr Leu
        225                 230                 235                 240

Pro Pro Pro Ala Glu Gln Leu Ser Arg Lys Asp Val Ser Leu Thr Cys
                        245                 250                 255

Leu Val Val Gly Phe Asn Pro Gly Asp Ile Ser Val Glu Trp Thr Ser
                        260                 265                 270

Asn Gly His Thr Glu Glu Asn Tyr Lys Asp Thr Ala Pro Val Leu Asp
                        275                 280                 285

Ser Asp Gly Ser Tyr Phe Ile Tyr Ser Lys Leu Asn Met Lys Thr Ser
                        290                 295                 300

Lys Trp Glu Lys Thr Asp Ser Phe Ser Cys Asn Val Arg His Glu Gly
        305                 310                 315                 320

Leu Lys Asn Tyr Tyr Leu Lys Lys Thr Ile Ser Arg Ser Pro Gly Lys
                        325                 330                 335

<210> SEQ ID NO 27
<211> LENGTH: 330
<212> TYPE: PRT
<213> ORGANISM: Mus musculus

<400> SEQUENCE: 27

Ala Thr Thr Thr Ala Pro Ser Val Tyr Pro Leu Val Pro Gly Cys Ser
1               5                   10                  15

Asp Thr Ser Gly Ser Ser Val Thr Leu Gly Cys Leu Val Lys Gly Tyr
                20                  25                  30

Phe Pro Glu Pro Val Thr Val Lys Trp Asn Tyr Gly Ala Leu Ser Ser
                35                  40                  45

Gly Val Arg Thr Val Ser Ser Val Leu Gln Ser Gly Phe Tyr Ser Leu
            50                  55                  60

Ser Ser Leu Val Thr Val Pro Ser Ser Thr Trp Pro Ser Gln Thr Val
65                  70                  75                  80

Ile Cys Asn Val Ala His Pro Ala Ser Lys Thr Glu Leu Ile Lys Arg
                85                  90                  95

Ile Glu Pro Arg Ile Pro Lys Pro Ser Thr Pro Pro Gly Ser Ser Cys
                100                 105                 110
```

-continued

Pro Pro Gly Asn Ile Leu Gly Gly Pro Ser Val Phe Ile Phe Pro Pro
            115                 120                 125

Lys Pro Lys Asp Ala Leu Met Ile Ser Leu Thr Pro Lys Val Thr Cys
130                 135                 140

Val Val Val Asp Val Ser Glu Asp Asp Pro Asp Val His Val Ser Trp
145                 150                 155                 160

Phe Val Asp Asn Lys Glu Val His Thr Ala Trp Thr Gln Pro Arg Glu
                165                 170                 175

Ala Gln Tyr Asn Ser Thr Phe Arg Val Val Ser Ala Leu Pro Ile Gln
            180                 185                 190

His Gln Asp Trp Met Arg Gly Lys Glu Phe Lys Cys Lys Val Asn Asn
        195                 200                 205

Lys Ala Leu Pro Ala Pro Ile Glu Arg Thr Ile Ser Lys Pro Lys Gly
210                 215                 220

Arg Ala Gln Thr Pro Gln Val Tyr Thr Ile Pro Pro Arg Glu Gln
225                 230                 235                 240

Met Ser Lys Lys Lys Val Ser Leu Thr Cys Leu Val Thr Asn Phe Phe
                245                 250                 255

Ser Glu Ala Ile Ser Val Glu Trp Glu Arg Asn Gly Glu Leu Glu Gln
            260                 265                 270

Asp Tyr Lys Asn Thr Pro Pro Ile Leu Asp Ser Asp Gly Thr Tyr Phe
        275                 280                 285

Leu Tyr Ser Lys Leu Thr Val Asp Thr Asp Ser Trp Leu Gln Gly Glu
290                 295                 300

Ile Phe Thr Cys Ser Val Val His Glu Ala Leu His Asn His His Thr
305                 310                 315                 320

Gln Lys Asn Leu Ser Arg Ser Pro Gly Lys
                325                 330

<210> SEQ ID NO 28
<211> LENGTH: 330
<212> TYPE: PRT
<213> ORGANISM: Homo sapiens

<400> SEQUENCE: 28

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

```
Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 29
<211> LENGTH: 326
<212> TYPE: PRT
<213> ORGANISM: Homo sapiens

<400> SEQUENCE: 29

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
```

```
              195                 200                 205
Ala Pro Ile Glu Lys Thr Ile Ser Lys Thr Lys Gly Gln Pro Arg Glu
210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
                275                 280                 285

Leu Thr Val Asp Lys Ser Arg Trp Gln Gln Gly Asn Val Phe Ser Cys
            290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 30
<211> LENGTH: 377
<212> TYPE: PRT
<213> ORGANISM: Homo sapiens

<400> SEQUENCE: 30

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Cys Pro Arg
        115                 120                 125

Cys Pro Glu Pro Lys Ser Cys Asp Thr Pro Pro Cys Pro Arg Cys
    130                 135                 140

Pro Glu Pro Lys Ser Cys Asp Thr Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
        195                 200                 205

Val Asp Gly Val Glu Val His Asn Ala Lys Thr Lys Pro Arg Glu Glu
    210                 215                 220

Gln Tyr Asn Ser Thr Phe Arg Val Val Ser Val Leu Thr Val Leu His
225                 230                 235                 240
```

```
Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Thr Lys Gly Gln
            260                 265                 270

Pro Arg Glu Pro Gln Val Tyr Thr Leu Pro Pro Ser Arg Glu Glu Met
        275                 280                 285

Thr Lys Asn Gln Val Ser Leu Thr Cys Leu Val Lys Gly Phe Tyr Pro
    290                 295                 300

Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
            340                 345                 350

Phe Ser Cys Ser Val Met His Glu Ala Leu His Asn Arg Phe Thr Gln
        355                 360                 365

Lys Ser Leu Ser Leu Ser Pro Gly Lys
    370                 375

<210> SEQ ID NO 31
<211> LENGTH: 327
<212> TYPE: PRT
<213> ORGANISM: Homo sapiens

<400> SEQUENCE: 31

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240
```

```
Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
            275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 32
<211> LENGTH: 214
<212> TYPE: PRT
<213> ORGANISM: Artificial Sequence
<220> FEATURE:
<223> OTHER INFORMATION: an artificially synthesized sequence

<400> SEQUENCE: 32

Asp Ile Gln Met Thr Gln Ser Pro Ser Ser Leu Ser Ala Ser Val Gly
1               5                   10                  15

Asp Ser Val Thr Ile Thr Cys Gln Ala Ser Thr Asp Ile Ser Ser His
            20                  25                  30

Leu Asn Trp Tyr Gln Gln Lys Pro Gly Lys Ala Pro Glu Leu Leu Ile
        35                  40                  45

Tyr Tyr Gly Ser His Leu Leu Ser Gly Val Pro Ser Arg Phe Ser Gly
    50                  55                  60

Ser Gly Ser Gly Thr Asp Phe Thr Phe Thr Ile Ser Ser Leu Glu Ala
65                  70                  75                  80

Glu Asp Ala Ala Thr Tyr Tyr Cys Gly Gln Gly Asn Arg Leu Pro Tyr
                85                  90                  95

Thr Phe Gly Gln Gly Thr Lys Val Glu Ile Glu Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210

<210> SEQ ID NO 33
<211> LENGTH: 1215
<212> TYPE: DNA
<213> ORGANISM: Mus musculus

<400> SEQUENCE: 33
```

```
atgattctta ccagctttgg agatgacatg tggcttctaa caactctgct actttgggtt      60
ccagtcggtg gggaagtggt taatgccacc aaggctgtga tcaccttgca gcctccatgg     120
gtcagtattt tccagaagga aaatgtcact ttatggtgtg aggggcctca cctgcctgga     180
gacagttcca cacaatggtt tatcaacgga acagccgttc agatctccac gcctagttat     240
agcatcccag aggccagttt tcaggacagt ggcgaataca ggtgtcagat aggttcctca     300
atgccaagtg accctgtgca gttgcaaatc acaatgatt ggctgctact ccaggcctcc      360
cgcagagtcc tcacagaagg agaacccctg gccttgaggt gtcacggatg gaagaataaa     420
ctggtgtaca atgtggtttt ctatagaaat ggaaaatcct ttcagttttc ttcagattcg     480
gaggtcgcca ttctgaaaac caacctgagt cacagcggca tctaccactg ctcaggcacg     540
ggaagacacc gctacacatc tgcaggagtg tccatcacgg tgaaagagct gtttaccacg     600
ccagtgctga gagcatccgt gtcatctccc ttcccggagg ggagtctggt caccctgaac     660
tgtgagacga atttgctcct gcagagaccc ggcttacagc ttcacttctc cttctacgtg     720
ggcagcaaga tcctggagta caggaacaca tcctcagagt accatatagc aagggcggaa     780
agagaagatg ctggattcta ctggtgtgag gtagccacgg aggacagcag tgtccttaag     840
cgcagccctg agttggagct ccaagtgctt ggtccccagt catcagctcc tgtctggttt     900
cacatcctgt tttatctgtc agtgggaata atgttttcgt tgaacacggt tctctatgtg     960
aaaatacaca ggctgcagag agagaagaaa tacaacttag aagtcccttt ggtttctgag    1020
cagggaaaga aagcaaattc ctttcagcaa gttagaagcg atggcgtgta tgaagaagta    1080
acagccactg cgagccagac cacaccaaaa gaagcgcccg atggacctcg aagctcagtg    1140
ggtgactgtg gacccgagca gcctgaaccc cttcctccca gtgacagtac tggggcacaa    1200
acttcccaaa gttga                                                     1215
```

<210> SEQ ID NO 34
<211> LENGTH: 882
<212> TYPE: DNA
<213> ORGANISM: Mus musculus

<400> SEQUENCE: 34

```
atgggaatcc tgccgttcct actgatcccc atggagagca actggactgt ccatgtgttc      60
tcacggactt tgtgccatat gctactgtgg acagccgtgc taaatcttgc tgctgggact     120
catgatcttc caaaggctgt ggtcaaactc gagcccccgt ggatccaggt gctcaaggaa     180
gacacggtga cactgacatg cgaagggacc cacaaccctg gaactcttc tacccagtgg     240
ttccacaatg ggaggtccat ccggagccag gtccaagcca gctacacgtt taaggccaca     300
gtcaatgaca gtgagaata tcggtgtcaa atggagcaga cccgcctcag cgaccctgta     360
gatctgggag tgatttctga ctggctgctg ctccagaccc ctcagctggt gtttctggaa     420
ggggaaacca tcacgctaag gtgccatagc tggaggaaca aactactgaa caggatctcg     480
ttcttccata tgaaaaatc cgtgaggtat catcactaca gtagtaattt ctctatccca     540
aaagccaacc acagtcacag tggggactac tactgcaaag aagtctagg aaggacactg    600
caccagtcca agcctgtcac catcactgtc caagggccca gtccagcag tctcttacca    660
gtattgacaa ttgtggctgc tgtcactggg attgctgtcg cagccattgt tattatccta    720
gtatccttgg tctatctcaa gaaaagcag gttccagaca atcctcctga tctggaagaa    780
gctgccaaaa ctgaggctga gaatacgatc acctactcac ttctcaagca tcccgaagcc    840
ctggatgaag aaacagagca tgattaccag aaccacattt ag                        882
```

<210> SEQ ID NO 35
<211> LENGTH: 804
<212> TYPE: DNA
<213> ORGANISM: Mus musculus

<400> SEQUENCE: 35

```
atgactttgg acacccagat gtttcagaat gcacactctg gaagccaatg gctacttcca      60
ccactgacaa ttctgctgct gtttgctttt gcagacaggc agagtgcagc tcttccgaag     120
gctgtggtga aactggaccc cccatggatc caggtgctca aggaagacat ggtgacactg     180
atgtgcgaag ggacccacaa ccctgggaac tcttctactc agtggttcca caactggagt     240
tccatccgga gccaggtcca atccagctac acgtttaagg ccacagtcaa tgacagtgga     300
gaatatcggt gtcaaatgga gcagacccgc ctcagcgacc ctgtagatct gggagtgatt     360
tctgactggc tgctgctcca gacccctcag cgggtgtttc tggaagggga aaccatcacg     420
ctaaggtgcc atagctggag gaacaaacta ctgaacagga tctcgttctt ccataatgaa     480
aaatccgtga ggtatcatca ctacaaaagt aatttctcta tcccaaaagc caaccacagt     540
cacagtgggg actactactg caaaggaagt ctaggaagta cacagcacca gtccaagcct     600
gtcaccatca ctgtccaaga cccagcaact acatcctcca tctctctagt ctggtaccac     660
actgctttct ccctagtgat gtgcctcctg tttgcagtgg acacgggcct ttatttctat     720
gtacggagaa atcttcaaac cccgagggat tactggagga agtccctgtc aatcagaaag     780
caccaggctc ctcaagacaa gtga                                            804
```

<210> SEQ ID NO 36
<211> LENGTH: 750
<212> TYPE: DNA
<213> ORGANISM: Mus musculus

<400> SEQUENCE: 36

```
atgtggcagc tactactacc aacagctctg gtacttacag ctttctctgg cattcaagct      60
ggtctccaaa aggctgtggt gaacctagac cccaagtggg tcagggtgct tgaggaagac     120
agcgtgaccc tcagatgcca aggcactttc tcccccgagg acaattctat caagtggttc     180
cataacgaaa gcctcatccc acaccaggat gccaactatg tcatccaaag tgccagagtt     240
aaggacagtg aatgtacag gtgccagaca gccctctcca cgatcagtga cccagtgcaa     300
ctagaggtcc atatgggctg gctattgctt cagaccacta gtggctgtt ccaggagggg     360
gacccccattc atctgagatg ccacagttgg caaaacagac tgtacggaa ggtcacctat     420
ttacagaacg gcaaaggcaa gaagtatttc catgaaaatt ctgaattact cattccaaaa     480
gctacacaca atgacagtgg ctcctacttc tgcagagggc tcattggaca caacaacaaa     540
tcttcagcat cctttcgtat aagcctaggc gatccagggt ctccatccat gtttccaccg     600
tggcatcaaa tcacattctg cctgctgata ggactcttgt ttgcaataga cagtgctg     660
tatttctctg tgcggagggg tcttcaaagt cctgtggctg actatgagga acccaagatt     720
caatggagca aggaacctca ggacaagtga                                     750
```

<210> SEQ ID NO 37
<211> LENGTH: 324
<212> TYPE: PRT
<213> ORGANISM: Artificial Sequence
<220> FEATURE:
<223> OTHER INFORMATION: an artificially synthesized sequence

<400> SEQUENCE: 37

```
Ala Lys Thr Thr Pro Pro Ser Val Tyr Pro Leu Ala Pro Gly Ser Ala
1               5                   10                  15

Ala Gln Thr Asn Ser Met Val Thr Leu Gly Cys Leu Val Lys Gly Tyr
            20                  25                  30

Phe Pro Glu Pro Val Thr Val Thr Trp Asn Ser Gly Ser Leu Ser Ser
        35                  40                  45

Gly Val His Thr Phe Pro Ala Val Leu Gln Ser Asp Leu Tyr Thr Leu
    50                  55                  60

Ser Ser Ser Val Thr Val Pro Ser Ser Thr Trp Pro Ser Glu Thr Val
65                  70                  75                  80

Thr Cys Asn Val Ala His Pro Ala Ser Ser Thr Lys Val Asp Lys Lys
                85                  90                  95

Ile Val Pro Arg Asp Cys Gly Cys Lys Pro Cys Ile Cys Gln Pro Asn
            100                 105                 110

Glu Val Glu Glu Val Phe Ile Phe Pro Pro Lys Pro Lys Asp Val Leu
        115                 120                 125

Thr Ile Thr Leu Thr Pro Lys Val Thr Cys Val Val Val Asp Ile Ser
130                 135                 140

Lys Asp Asp Pro Glu Val Gln Phe Ser Trp Phe Val Asp Asp Val Glu
145                 150                 155                 160

Val His Thr Ala Gln Thr Gln Pro Arg Glu Glu Gln Phe Asn Ser Thr
                165                 170                 175

Phe Arg Ser Val Ser Glu Leu Pro Ile Met His Gln Asp Trp Leu Asn
            180                 185                 190

Gly Lys Glu Phe Lys Cys Arg Val Asn Ser Ala Ala Phe Pro Ala Pro
        195                 200                 205

Ile Glu Lys Thr Ile Ser Lys Thr Lys Gly Arg Pro Lys Ala Pro Gln
    210                 215                 220

Val Tyr Thr Ile Pro Pro Lys Glu Gln Met Ala Lys Asp Lys Val
225                 230                 235                 240

Ser Leu Thr Cys Met Ile Thr Asp Phe Phe Pro Glu Asp Ile Thr Val
                245                 250                 255

Glu Trp Gln Trp Asn Gly Gln Pro Ala Glu Asn Tyr Lys Asn Thr Gln
            260                 265                 270

Pro Ile Met Asp Thr Asp Gly Ser Tyr Phe Val Tyr Ser Lys Leu Asn
        275                 280                 285

Val Gln Lys Ser Asn Trp Glu Ala Gly Asn Thr Phe Thr Cys Ser Val
    290                 295                 300

Leu His Glu Gly Leu His Asn His His Thr Glu Lys Ser Leu Ser His
305                 310                 315                 320

Ser Pro Gly Lys
```

<210> SEQ ID NO 38
<211> LENGTH: 324
<212> TYPE: PRT
<213> ORGANISM: Artificial Sequence
<220> FEATURE:
<223> OTHER INFORMATION: an artificially synthesized sequence

<400> SEQUENCE: 38

```
Ala Lys Thr Thr Pro Pro Ser Val Tyr Pro Leu Ala Pro Gly Ser Ala
1               5                   10                  15

Ala Gln Thr Asn Ser Met Val Thr Leu Gly Cys Leu Val Lys Gly Tyr
            20                  25                  30
```

```
Phe Pro Glu Pro Val Thr Val Thr Trp Asn Ser Gly Ser Leu Ser Ser
            35                  40                  45

Gly Val His Thr Phe Pro Ala Val Leu Gln Ser Asp Leu Tyr Thr Leu
     50                  55                  60

Ser Ser Ser Val Thr Val Pro Ser Ser Thr Trp Pro Ser Glu Thr Val
 65              70                  75                  80

Thr Cys Asn Val Ala His Pro Ala Ser Ser Thr Lys Val Asp Lys Lys
                     85                  90                  95

Ile Val Pro Arg Asp Cys Gly Cys Lys Pro Cys Ile Cys Glu Pro Asn
                100                 105                 110

Glu Val Glu Met Val Phe Ile Phe Pro Pro Lys Pro Lys Asp Val Leu
            115                 120                 125

Thr Ile Thr Leu Thr Pro Lys Val Thr Cys Val Val Val Asp Ile Ser
        130                 135                 140

Lys Asp Asp Pro Glu Val Gln Phe Ser Trp Phe Val Asp Asp Val Glu
145                 150                 155                 160

Val His Thr Ala Gln Thr Gln Pro Arg Glu Glu Gln Phe Asn Ser Thr
                165                 170                 175

Phe Arg Ser Val Ser Glu Leu Pro Ile Met His Gln Asp Trp Leu Asn
            180                 185                 190

Gly Lys Glu Phe Lys Cys Arg Val Asn Ser Ala Ala Phe Pro Ala Pro
        195                 200                 205

Ile Glu Lys Thr Ile Ser Lys Thr Lys Gly Arg Pro Lys Ala Pro Gln
    210                 215                 220

Val Tyr Thr Ile Pro Pro Lys Glu Gln Met Ala Lys Asp Lys Val
225                 230                 235                 240

Ser Leu Thr Cys Met Ile Thr Asp Phe Phe Pro Glu Asp Ile Thr Val
                245                 250                 255

Glu Trp Gln Trp Asn Gly Gln Pro Ala Glu Asn Tyr Lys Asn Thr Gln
            260                 265                 270

Pro Ile Met Asp Thr Asp Gly Ser Tyr Phe Val Tyr Ser Lys Leu Asn
        275                 280                 285

Val Gln Lys Ser Asn Trp Glu Ala Gly Asn Thr Phe Thr Cys Ser Val
    290                 295                 300

Leu His Glu Gly Leu His Asn His His Thr Glu Lys Ser Leu Ser His
305                 310                 315                 320

Ser Pro Gly Lys

<210> SEQ ID NO 39
<211> LENGTH: 324
<212> TYPE: PRT
<213> ORGANISM: Artificial Sequence
<220> FEATURE:
<223> OTHER INFORMATION: an artificially synthesized sequence

<400> SEQUENCE: 39

Ala Lys Thr Thr Pro Pro Ser Val Tyr Pro Leu Ala Pro Gly Ser Ala
 1               5                  10                  15

Ala Gln Thr Asn Ser Met Val Thr Leu Gly Cys Leu Val Lys Gly Tyr
            20                  25                  30

Phe Pro Glu Pro Val Thr Val Thr Trp Asn Ser Gly Ser Leu Ser Ser
            35                  40                  45

Gly Val His Thr Phe Pro Ala Val Leu Gln Ser Asp Leu Tyr Thr Leu
     50                  55                  60
```

```
Ser Ser Ser Val Thr Val Pro Ser Ser Thr Trp Pro Ser Glu Thr Val
 65                  70                  75                  80

Thr Cys Asn Val Ala His Pro Ala Ser Ser Thr Lys Val Asp Lys Lys
                 85                  90                  95

Ile Val Pro Arg Asp Cys Gly Cys Lys Pro Cys Ile Cys Glu Pro Asn
            100                 105                 110

Glu Val Glu Leu Val Phe Ile Phe Pro Pro Lys Pro Lys Asp Val Leu
        115                 120                 125

Thr Ile Thr Leu Thr Pro Lys Val Thr Cys Val Val Asp Ile Ser
    130                 135                 140

Lys Asp Asp Pro Glu Val Gln Phe Ser Trp Phe Val Asp Asp Val Glu
145                 150                 155                 160

Val His Thr Ala Gln Thr Gln Pro Arg Glu Glu Gln Phe Asn Ser Thr
                165                 170                 175

Phe Arg Ser Val Ser Glu Leu Pro Ile Met His Gln Asp Trp Leu Asn
            180                 185                 190

Gly Lys Glu Phe Lys Cys Arg Val Asn Ser Ala Ala Phe Pro Ala Pro
        195                 200                 205

Ile Glu Lys Thr Ile Ser Lys Thr Lys Gly Arg Pro Lys Ala Pro Gln
    210                 215                 220

Val Tyr Thr Ile Pro Pro Lys Glu Gln Met Ala Lys Asp Lys Val
225                 230                 235                 240

Ser Leu Thr Cys Met Ile Thr Asp Phe Phe Pro Glu Asp Ile Thr Val
                245                 250                 255

Glu Trp Gln Trp Asn Gly Gln Pro Ala Glu Asn Tyr Lys Asn Thr Gln
            260                 265                 270

Pro Ile Met Asp Thr Asp Gly Ser Tyr Phe Val Tyr Ser Lys Leu Asn
        275                 280                 285

Val Gln Lys Ser Asn Trp Glu Ala Gly Asn Thr Phe Thr Cys Ser Val
    290                 295                 300

Leu His Glu Gly Leu His Asn His His Thr Glu Lys Ser Leu Ser His
305                 310                 315                 320

Ser Pro Gly Lys

<210> SEQ ID NO 40
<211> LENGTH: 324
<212> TYPE: PRT
<213> ORGANISM: Artificial Sequence
<220> FEATURE:
<223> OTHER INFORMATION: an artificially synthesized sequence

<400> SEQUENCE: 40

Ala Lys Thr Thr Pro Pro Ser Val Tyr Pro Leu Ala Pro Gly Ser Ala
 1               5                  10                  15

Ala Gln Thr Asn Ser Met Val Thr Leu Gly Cys Leu Val Lys Gly Tyr
                20                  25                  30

Phe Pro Glu Pro Val Thr Val Thr Trp Asn Ser Gly Ser Leu Ser Ser
            35                  40                  45

Gly Val His Thr Phe Pro Ala Val Leu Gln Ser Asp Leu Tyr Thr Leu
        50                  55                  60

Ser Ser Ser Val Thr Val Pro Ser Ser Thr Trp Pro Ser Glu Thr Val
 65                  70                  75                  80

Thr Cys Asn Val Ala His Pro Ala Ser Ser Thr Lys Val Asp Lys Lys
                 85                  90                  95

Ile Val Pro Arg Asp Cys Gly Cys Lys Pro Cys Ile Cys Glu Ala Tyr
            100                 105                 110
```

-continued

```
                100                 105                 110
Glu Val Glu Asp Val Phe Ile Phe Pro Pro Lys Pro Lys Asp Val Leu
            115                 120                 125
Thr Ile Thr Leu Thr Pro Lys Val Thr Cys Val Val Val Asp Ile Ser
            130                 135                 140
Lys Asp Asp Pro Glu Val Gln Phe Ser Trp Phe Val Asp Val Glu
145                 150                 155                 160
Val His Thr Ala Gln Thr Gln Pro Arg Glu Glu Gln Phe Asn Ser Thr
                165                 170                 175
Phe Arg Ser Val Ser Glu Leu Pro Ile Met His Gln Asp Trp Leu Asn
            180                 185                 190
Gly Lys Glu Phe Lys Cys Arg Val Asn Ser Ala Ala Phe Pro Ala Pro
            195                 200                 205
Ile Glu Lys Thr Ile Ser Lys Thr Lys Gly Arg Pro Lys Ala Pro Gln
            210                 215                 220
Val Tyr Thr Ile Pro Pro Pro Lys Glu Gln Met Ala Lys Asp Lys Val
225                 230                 235                 240
Ser Leu Thr Cys Met Ile Thr Asp Phe Phe Pro Glu Asp Ile Thr Val
                245                 250                 255
Glu Trp Gln Trp Asn Gly Gln Pro Ala Glu Asn Tyr Lys Asn Thr Gln
            260                 265                 270
Pro Ile Met Asp Thr Asp Gly Ser Tyr Phe Val Tyr Ser Lys Leu Asn
            275                 280                 285
Val Gln Lys Ser Asn Trp Glu Ala Gly Asn Thr Phe Thr Cys Ser Val
            290                 295                 300
Leu His Glu Gly Leu His Asn His His Thr Glu Lys Ser Leu Ser His
305                 310                 315                 320
Ser Pro Gly Lys

<210> SEQ ID NO 41
<211> LENGTH: 324
<212> TYPE: PRT
<213> ORGANISM: Artificial Sequence
<220> FEATURE:
<223> OTHER INFORMATION: an artificially synthesized sequence

<400> SEQUENCE: 41

Ala Lys Thr Thr Pro Pro Ser Val Tyr Pro Leu Ala Pro Gly Ser Ala
1               5                   10                  15
Ala Gln Thr Asn Ser Met Val Thr Leu Gly Cys Leu Val Lys Gly Tyr
            20                  25                  30
Phe Pro Glu Pro Val Thr Val Thr Trp Asn Ser Gly Ser Leu Ser Ser
            35                  40                  45
Gly Val His Thr Phe Pro Ala Val Leu Gln Ser Asp Leu Tyr Thr Leu
        50                  55                  60
Ser Ser Ser Val Thr Val Pro Ser Ser Thr Trp Pro Ser Glu Thr Val
65                  70                  75                  80
Thr Cys Asn Val Ala His Pro Ala Ser Ser Thr Lys Val Asp Lys Lys
                85                  90                  95
Ile Val Pro Arg Asp Cys Gly Cys Lys Pro Cys Ile Cys Glu Asp Tyr
            100                 105                 110
Glu Val Glu Asp Val Phe Ile Phe Pro Pro Lys Pro Lys Asp Val Leu
            115                 120                 125
Thr Ile Thr Leu Thr Pro Lys Val Thr Cys Val Val Val Asp Ile Ser
            130                 135                 140
```

Lys Asp Asp Pro Glu Val Gln Phe Ser Trp Phe Val Asp Asp Val Glu
145                 150                 155                 160

Val His Thr Ala Gln Thr Gln Pro Arg Glu Glu Gln Phe Asn Ser Thr
                165                 170                 175

Phe Arg Ser Val Ser Glu Leu Pro Ile Met His Gln Asp Trp Leu Asn
            180                 185                 190

Gly Lys Glu Phe Lys Cys Arg Val Asn Ser Ala Ala Phe Pro Ala Pro
        195                 200                 205

Ile Glu Lys Thr Ile Ser Lys Thr Lys Gly Arg Pro Lys Ala Pro Gln
    210                 215                 220

Val Tyr Thr Ile Pro Pro Lys Glu Gln Met Ala Lys Asp Lys Val
225                 230                 235                 240

Ser Leu Thr Cys Met Ile Thr Asp Phe Phe Pro Glu Asp Ile Thr Val
                245                 250                 255

Glu Trp Gln Trp Asn Gly Gln Pro Ala Glu Asn Tyr Lys Asn Thr Gln
            260                 265                 270

Pro Ile Met Asp Thr Asp Gly Ser Tyr Phe Val Tyr Ser Lys Leu Asn
        275                 280                 285

Val Gln Lys Ser Asn Trp Glu Ala Gly Asn Thr Phe Thr Cys Ser Val
    290                 295                 300

Leu His Glu Gly Leu His Asn His His Thr Glu Lys Ser Leu Ser His
305                 310                 315                 320

Ser Pro Gly Lys

<210> SEQ ID NO 42
<211> LENGTH: 324
<212> TYPE: PRT
<213> ORGANISM: Artificial Sequence
<220> FEATURE:
<223> OTHER INFORMATION: an artificially synthesized sequence

<400> SEQUENCE: 42

Ala Lys Thr Thr Pro Pro Ser Val Tyr Pro Leu Ala Pro Gly Ser Ala
1               5                   10                  15

Ala Gln Thr Asn Ser Met Val Thr Leu Gly Cys Leu Val Lys Gly Tyr
                20                  25                  30

Phe Pro Glu Pro Val Thr Val Thr Trp Asn Ser Gly Ser Leu Ser Ser
            35                  40                  45

Gly Val His Thr Phe Pro Ala Val Leu Gln Ser Asp Leu Tyr Thr Leu
        50                  55                  60

Ser Ser Ser Val Thr Val Pro Ser Ser Thr Trp Pro Ser Glu Thr Val
65                  70                  75                  80

Thr Cys Asn Val Ala His Pro Ala Ser Ser Thr Lys Val Asp Lys Lys
                85                  90                  95

Ile Val Pro Arg Asp Cys Gly Cys Lys Pro Cys Ile Cys Glu Asn Tyr
            100                 105                 110

Glu Val Glu Asp Val Phe Ile Phe Pro Pro Lys Pro Lys Asp Val Leu
        115                 120                 125

Thr Ile Thr Leu Thr Pro Lys Val Thr Cys Val Val Val Asp Ile Ser
    130                 135                 140

Lys Asp Asp Pro Glu Val Gln Phe Ser Trp Phe Val Asp Asp Val Glu
145                 150                 155                 160

Val His Thr Ala Gln Thr Gln Pro Arg Glu Glu Gln Phe Asn Ser Thr
                165                 170                 175

```
Phe Arg Ser Val Ser Glu Leu Pro Ile Met His Gln Asp Trp Leu Asn
                180                 185                 190

Gly Lys Glu Phe Lys Cys Arg Val Asn Ser Ala Ala Phe Pro Ala Pro
            195                 200                 205

Ile Glu Lys Thr Ile Ser Lys Thr Lys Gly Arg Pro Lys Ala Pro Gln
        210                 215                 220

Val Tyr Thr Ile Pro Pro Lys Glu Gln Met Ala Lys Asp Lys Val
225                 230                 235                 240

Ser Leu Thr Cys Met Ile Thr Asp Phe Phe Pro Glu Asp Ile Thr Val
                245                 250                 255

Glu Trp Gln Trp Asn Gly Gln Pro Ala Glu Asn Tyr Lys Asn Thr Gln
            260                 265                 270

Pro Ile Met Asp Thr Asp Gly Ser Tyr Phe Val Tyr Ser Lys Leu Asn
        275                 280                 285

Val Gln Lys Ser Asn Trp Glu Ala Gly Asn Thr Phe Thr Cys Ser Val
    290                 295                 300

Leu His Glu Gly Leu His Asn His His Thr Glu Lys Ser Leu Ser His
305                 310                 315                 320

Ser Pro Gly Lys

<210> SEQ ID NO 43
<211> LENGTH: 324
<212> TYPE: PRT
<213> ORGANISM: Artificial Sequence
<220> FEATURE:
<223> OTHER INFORMATION: an artificially synthesized sequence

<400> SEQUENCE: 43

Ala Lys Thr Thr Pro Pro Ser Val Tyr Pro Leu Ala Pro Gly Ser Ala
1               5                   10                  15

Ala Gln Thr Asn Ser Met Val Thr Leu Gly Cys Leu Val Lys Gly Tyr
            20                  25                  30

Phe Pro Glu Pro Val Thr Val Thr Trp Asn Ser Gly Ser Leu Ser Ser
        35                  40                  45

Gly Val His Thr Phe Pro Ala Val Leu Gln Ser Asp Leu Tyr Thr Leu
    50                  55                  60

Ser Ser Ser Val Thr Val Pro Ser Ser Thr Trp Pro Ser Glu Thr Val
65                  70                  75                  80

Thr Cys Asn Val Ala His Pro Ala Ser Ser Thr Lys Val Asp Lys Lys
                85                  90                  95

Ile Val Pro Arg Asp Cys Gly Cys Lys Pro Cys Ile Cys Glu Val Tyr
            100                 105                 110

Glu Val Glu Asp Val Phe Ile Phe Pro Pro Lys Pro Lys Asp Val Leu
        115                 120                 125

Thr Ile Thr Leu Thr Pro Lys Val Thr Cys Val Val Val Asp Ile Ser
    130                 135                 140

Lys Asp Asp Pro Glu Val Gln Phe Ser Trp Phe Val Asp Val Glu
145                 150                 155                 160

Val His Thr Ala Gln Thr Gln Pro Arg Glu Glu Gln Phe Asn Ser Thr
                165                 170                 175

Phe Arg Ser Val Ser Glu Leu Pro Ile Met His Gln Asp Trp Leu Asn
            180                 185                 190

Gly Lys Glu Phe Lys Cys Arg Val Asn Ser Ala Ala Phe Pro Ala Pro
        195                 200                 205

Ile Glu Lys Thr Ile Ser Lys Thr Lys Gly Arg Pro Lys Ala Pro Gln
```

```
            210                 215                 220
Val Tyr Thr Ile Pro Pro Lys Glu Gln Met Ala Lys Asp Lys Val
225                 230                 235                 240

Ser Leu Thr Cys Met Ile Thr Asp Phe Phe Pro Glu Asp Ile Thr Val
                245                 250                 255

Glu Trp Gln Trp Asn Gly Gln Pro Ala Glu Asn Tyr Lys Asn Thr Gln
                260                 265                 270

Pro Ile Met Asp Thr Asp Gly Ser Tyr Phe Val Tyr Ser Lys Leu Asn
                275                 280                 285

Val Gln Lys Ser Asn Trp Glu Ala Gly Asn Thr Phe Thr Cys Ser Val
        290                 295                 300

Leu His Glu Gly Leu His Asn His His Thr Glu Lys Ser Leu Ser His
305                 310                 315                 320

Ser Pro Gly Lys

<210> SEQ ID NO 44
<211> LENGTH: 324
<212> TYPE: PRT
<213> ORGANISM: Artificial Sequence
<220> FEATURE:
<223> OTHER INFORMATION: an artificially synthesized sequence

<400> SEQUENCE: 44

Ala Lys Thr Thr Pro Pro Ser Val Tyr Pro Leu Ala Pro Gly Ser Ala
1               5                   10                  15

Ala Gln Thr Asn Ser Met Val Thr Leu Gly Cys Leu Val Lys Gly Tyr
                20                  25                  30

Phe Pro Glu Pro Val Thr Val Thr Trp Asn Ser Gly Ser Leu Ser Ser
                35                  40                  45

Gly Val His Thr Phe Pro Ala Val Leu Gln Ser Asp Leu Tyr Thr Leu
        50                  55                  60

Ser Ser Ser Val Thr Val Pro Ser Ser Thr Trp Pro Ser Glu Thr Val
65                  70                  75                  80

Thr Cys Asn Val Ala His Pro Ala Ser Ser Thr Lys Val Asp Lys Lys
                85                  90                  95

Ile Val Pro Arg Asp Cys Gly Cys Lys Pro Cys Ile Cys Glu Pro Ala
                100                 105                 110

Glu Val Glu Asp Val Phe Ile Phe Pro Pro Lys Pro Lys Asp Val Leu
            115                 120                 125

Thr Ile Thr Leu Thr Pro Lys Val Thr Cys Val Val Val Asp Ile Ser
        130                 135                 140

Lys Asp Asp Pro Glu Val Gln Phe Ser Trp Phe Val Asp Asp Val Glu
145                 150                 155                 160

Val His Thr Ala Gln Thr Gln Pro Arg Glu Glu Gln Phe Asn Ser Thr
                165                 170                 175

Phe Arg Ser Val Ser Glu Leu Pro Ile Met His Gln Asp Trp Leu Asn
                180                 185                 190

Gly Lys Glu Phe Lys Cys Arg Val Asn Ser Ala Ala Phe Pro Ala Pro
            195                 200                 205

Ile Glu Lys Thr Ile Ser Lys Thr Lys Gly Arg Pro Lys Ala Pro Gln
        210                 215                 220

Val Tyr Thr Ile Pro Pro Lys Glu Gln Met Ala Lys Asp Lys Val
225                 230                 235                 240

Ser Leu Thr Cys Met Ile Thr Asp Phe Phe Pro Glu Asp Ile Thr Val
                245                 250                 255
```

```
Glu Trp Gln Trp Asn Gly Gln Pro Ala Glu Asn Tyr Lys Asn Thr Gln
            260                 265                 270

Pro Ile Met Asp Thr Asp Gly Ser Tyr Phe Val Tyr Ser Lys Leu Asn
        275                 280                 285

Val Gln Lys Ser Asn Trp Glu Ala Gly Asn Thr Phe Thr Cys Ser Val
    290                 295                 300

Leu His Glu Gly Leu His Asn His His Thr Glu Lys Ser Leu Ser His
305                 310                 315                 320

Ser Pro Gly Lys

<210> SEQ ID NO 45
<211> LENGTH: 324
<212> TYPE: PRT
<213> ORGANISM: Artificial Sequence
<220> FEATURE:
<223> OTHER INFORMATION: an artificially synthesized sequence

<400> SEQUENCE: 45

Ala Lys Thr Thr Pro Pro Ser Val Tyr Pro Leu Ala Pro Gly Ser Ala
1               5                   10                  15

Ala Gln Thr Asn Ser Met Val Thr Leu Gly Cys Leu Val Lys Gly Tyr
            20                  25                  30

Phe Pro Glu Pro Val Thr Val Thr Trp Asn Ser Gly Ser Leu Ser Ser
        35                  40                  45

Gly Val His Thr Phe Pro Ala Val Leu Gln Ser Asp Leu Tyr Thr Leu
    50                  55                  60

Ser Ser Ser Val Thr Val Pro Ser Ser Thr Trp Pro Ser Glu Thr Val
65                  70                  75                  80

Thr Cys Asn Val Ala His Pro Ala Ser Ser Thr Lys Val Asp Lys Lys
                85                  90                  95

Ile Val Pro Arg Asp Cys Gly Cys Lys Pro Cys Ile Cys Ile Pro Ala
            100                 105                 110

Glu Val Glu Asp Val Phe Ile Phe Pro Pro Lys Pro Lys Asp Val Leu
        115                 120                 125

Thr Ile Thr Leu Thr Pro Lys Val Thr Cys Val Val Asp Ile Ser
    130                 135                 140

Lys Asp Asp Pro Glu Val Gln Phe Ser Trp Phe Val Asp Asp Val Glu
145                 150                 155                 160

Val His Thr Ala Gln Thr Gln Pro Arg Glu Glu Gln Phe Asn Ser Thr
                165                 170                 175

Phe Arg Ser Val Ser Glu Leu Pro Ile Met His Gln Asp Trp Leu Asn
            180                 185                 190

Gly Lys Glu Phe Lys Cys Arg Val Asn Ser Ala Ala Phe Pro Ala Pro
        195                 200                 205

Ile Glu Lys Thr Ile Ser Lys Thr Lys Gly Arg Pro Lys Ala Pro Gln
    210                 215                 220

Val Tyr Thr Ile Pro Pro Lys Glu Gln Met Ala Lys Asp Lys Val
225                 230                 235                 240

Ser Leu Thr Cys Met Ile Thr Asp Phe Phe Pro Glu Asp Ile Thr Val
                245                 250                 255

Glu Trp Gln Trp Asn Gly Gln Pro Ala Glu Asn Tyr Lys Asn Thr Gln
            260                 265                 270

Pro Ile Met Asp Thr Asp Gly Ser Tyr Phe Val Tyr Ser Lys Leu Asn
        275                 280                 285
```

Val Gln Lys Ser Asn Trp Glu Ala Gly Asn Thr Phe Thr Cys Ser Val
290                 295                 300

Leu His Glu Gly Leu His Asn His His Thr Glu Lys Ser Leu Ser His
305                 310                 315                 320

Ser Pro Gly Lys

<210> SEQ ID NO 46
<211> LENGTH: 324
<212> TYPE: PRT
<213> ORGANISM: Artificial Sequence
<220> FEATURE:
<223> OTHER INFORMATION: an artificially synthesized sequence

<400> SEQUENCE: 46

Ala Lys Thr Thr Pro Pro Ser Val Tyr Pro Leu Ala Pro Gly Ser Ala
1               5                   10                  15

Ala Gln Thr Asn Ser Met Val Thr Leu Gly Cys Leu Val Lys Gly Tyr
            20                  25                  30

Phe Pro Glu Pro Val Thr Val Thr Trp Asn Ser Gly Ser Leu Ser Ser
        35                  40                  45

Gly Val His Thr Phe Pro Ala Val Leu Gln Ser Asp Leu Tyr Thr Leu
    50                  55                  60

Ser Ser Ser Val Thr Val Pro Ser Ser Thr Trp Pro Ser Glu Thr Val
65                  70                  75                  80

Thr Cys Asn Val Ala His Pro Ala Ser Ser Thr Lys Val Asp Lys Lys
                85                  90                  95

Ile Val Pro Arg Asp Cys Gly Cys Lys Pro Cys Ile Cys Gln Pro Asn
            100                 105                 110

Glu Val Glu Asp Val Phe Ile Phe Pro Pro Lys Pro Lys Asp Val Leu
        115                 120                 125

Thr Ile Thr Leu Thr Pro Lys Val Thr Cys Val Val Val Asp Ile Ser
    130                 135                 140

Lys Asp Asp Pro Glu Val Gln Phe Ser Trp Phe Val Asp Asp Val Glu
145                 150                 155                 160

Val His Thr Ala Gln Thr Gln Pro Arg Glu Glu Gln Phe Asn Ser Thr
                165                 170                 175

Phe Arg Ser Val Ser Glu Leu Pro Ile Met His Gln Asp Trp Leu Asn
            180                 185                 190

Gly Lys Glu Phe Lys Cys Arg Val Asn Ser Ala Ala Phe Pro Ala Pro
        195                 200                 205

Ile Glu Lys Thr Ile Ser Lys Thr Lys Gly Arg Pro Lys Ala Pro Gln
    210                 215                 220

Val Tyr Thr Ile Pro Pro Pro Lys Glu Gln Met Ala Lys Asp Lys Val
225                 230                 235                 240

Ser Leu Thr Cys Met Ile Thr Asp Phe Phe Pro Glu Asp Ile Thr Val
                245                 250                 255

Glu Trp Gln Trp Asn Gly Gln Pro Ala Glu Asn Tyr Lys Asn Thr Gln
            260                 265                 270

Pro Ile Met Asp Thr Asp Gly Ser Tyr Phe Val Tyr Ser Lys Leu Asn
        275                 280                 285

Val Gln Lys Ser Asn Trp Glu Ala Gly Asn Thr Phe Thr Cys Ser Val
    290                 295                 300

Leu His Glu Gly Leu His Asn His His Thr Glu Lys Ser Leu Ser His
305                 310                 315                 320

Ser Pro Gly Lys

```
<210> SEQ ID NO 47
<211> LENGTH: 324
<212> TYPE: PRT
<213> ORGANISM: Artificial Sequence
<220> FEATURE:
<223> OTHER INFORMATION: an artificially synthesized sequence

<400> SEQUENCE: 47

Ala Lys Thr Thr Pro Pro Ser Val Tyr Pro Leu Ala Pro Gly Ser Ala
1               5                   10                  15

Ala Gln Thr Asn Ser Met Val Thr Leu Gly Cys Leu Val Lys Gly Tyr
            20                  25                  30

Phe Pro Glu Pro Val Thr Val Thr Trp Asn Ser Gly Ser Leu Ser Ser
        35                  40                  45

Gly Val His Thr Phe Pro Ala Val Leu Gln Ser Asp Leu Tyr Thr Leu
    50                  55                  60

Ser Ser Ser Val Thr Val Pro Ser Ser Thr Trp Pro Ser Glu Thr Val
65                  70                  75                  80

Thr Cys Asn Val Ala His Pro Ala Ser Ser Thr Lys Val Asp Lys Lys
                85                  90                  95

Ile Val Pro Arg Asp Cys Gly Cys Lys Pro Cys Ile Cys Glu Pro Asn
            100                 105                 110

Glu Val Glu Ile Val Phe Ile Phe Pro Pro Lys Pro Lys Asp Val Leu
        115                 120                 125

Thr Ile Thr Leu Thr Pro Lys Val Thr Cys Val Val Val Asp Ile Ser
130                 135                 140

Lys Asp Asp Pro Glu Val Gln Phe Ser Trp Phe Val Asp Asp Val Glu
145                 150                 155                 160

Val His Thr Ala Gln Thr Gln Pro Arg Glu Glu Gln Phe Asn Ser Thr
                165                 170                 175

Phe Arg Ser Val Ser Glu Leu Pro Ile Met His Gln Asp Trp Leu Asn
            180                 185                 190

Gly Lys Glu Phe Lys Cys Arg Val Asn Ser Ala Ala Phe Pro Ala Pro
        195                 200                 205

Ile Glu Lys Thr Ile Ser Lys Thr Lys Gly Arg Pro Lys Ala Pro Gln
    210                 215                 220

Val Tyr Thr Ile Pro Pro Lys Glu Gln Met Ala Lys Asp Lys Val
225                 230                 235                 240

Ser Leu Thr Cys Met Ile Thr Asp Phe Phe Pro Glu Asp Ile Thr Val
                245                 250                 255

Glu Trp Gln Trp Asn Gly Gln Pro Ala Glu Asn Tyr Lys Asn Thr Gln
            260                 265                 270

Pro Ile Met Asp Thr Asp Gly Ser Tyr Phe Val Tyr Ser Lys Leu Asn
        275                 280                 285

Val Gln Lys Ser Asn Trp Glu Ala Gly Asn Thr Phe Thr Cys Ser Val
    290                 295                 300

Leu His Glu Gly Leu His Asn His His Thr Glu Lys Ser Leu Ser His
305                 310                 315                 320

Ser Pro Gly Lys
```